(12) United States Patent
Panarese et al.

(10) Patent No.: US 11,058,678 B2
(45) Date of Patent: Jul. 13, 2021

(54) SUBSTITUTED HETEROCYCLES AS ANTIVIRAL AGENTS

(71) Applicant: Enanta Pharmaceuticals, Inc., Watertown, MA (US)

(72) Inventors: Joseph Panarese, Malden, MA (US); Samuel Bartlett, Brighton, MA (US); Katherine Chong, Belmont, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/251,386

(22) Filed: Jan. 18, 2019

(65) Prior Publication Data

US 2019/0224188 A1 Jul. 25, 2019

Related U.S. Application Data

(60) Provisional application No. 62/753,335, filed on Oct. 31, 2018, provisional application No. 62/620,292, filed on Jan. 22, 2018.

(51) Int. Cl.
*A61K 31/473* (2006.01)
*A61K 31/4355* (2006.01)
*A61K 31/501* (2006.01)
*A61K 31/506* (2006.01)
*A61P 31/20* (2006.01)

(52) U.S. Cl.
CPC ........ *A61K 31/473* (2013.01); *A61K 31/4355* (2013.01); *A61K 31/501* (2013.01); *A61K 31/506* (2013.01); *A61P 31/20* (2018.01)

(58) Field of Classification Search
CPC .............. A61K 31/473; A61K 31/4355; A61K 31/501; A61K 31/506; A61P 31/20
See application file for complete search history.

(56) References Cited

U.S. PATENT DOCUMENTS

| | | | |
|---|---|---|---|
| 3,385,756 A | 5/1968 | Early et al. |
| 3,975,532 A | 8/1976 | Miller et al. |
| 4,285,946 A | 8/1981 | Kampe et al. |
| 4,507,481 A | 3/1985 | Davidson et al. |
| 5,510,387 A | 4/1996 | Leonidov et al. |
| 5,656,644 A | 8/1997 | Adams et al. |
| 6,498,165 B1 | 12/2002 | Armstrong et al. |
| 6,503,913 B1 | 1/2003 | Goldmann et al. |
| 6,525,069 B1 | 2/2003 | Ko et al. |
| 6,667,342 B1 | 12/2003 | Clarke et al. |
| 7,232,825 B2 | 6/2007 | Chen et al. |
| 7,312,214 B2 | 12/2007 | Qiao et al. |
| 7,411,003 B1 | 8/2008 | Wen et al. |
| 7,615,569 B2 | 11/2009 | Fulp et al. |
| 7,741,494 B2 | 6/2010 | Bressi et al. |
| 8,101,643 B2 | 1/2012 | Qiu et al. |
| 8,202,876 B2 | 6/2012 | Albaugh et al. |
| 8,420,823 B2 | 4/2013 | Sato et al. |
| 9,447,086 B2 | 9/2016 | Liu et al. |
| 9,498,479 B2 | 11/2016 | Zhang et al. |
| 9,573,941 B2 | 2/2017 | Liu et al. |
| 9,617,252 B2 | 4/2017 | Liu |
| 9,845,325 B2 | 12/2017 | Fu et al. |
| 9,938,301 B2 | 4/2018 | He et al. |
| 10,179,131 B2 | 1/2019 | Qiu et al. |
| 10,189,846 B2 | 1/2019 | Qiu et al. |
| 10,253,030 B2 | 4/2019 | He et al. |

(Continued)

FOREIGN PATENT DOCUMENTS

| CN | 106810548 A | 6/2017 |
|---|---|---|
| CN | 106928215 A | 7/2017 |

(Continued)

OTHER PUBLICATIONS

Li, X. et al., 8 ACS Medicinal Chemistry Letters, 8, 2017, 969-974.

(Continued)

*Primary Examiner* — Timothy R Rozof
(74) *Attorney, Agent, or Firm* — Edgar A. Harlan; Carolyn S. Elmore; Elmore Patent Law Group, P.C.

(57) ABSTRACT

The present invention discloses compounds of Formula (I), and pharmaceutically acceptable salts thereof:

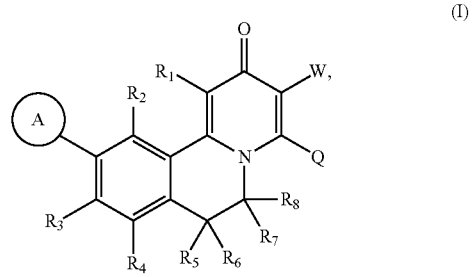

(I)

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

21 Claims, No Drawings

(56) References Cited

U.S. PATENT DOCUMENTS

| | | | |
|---|---|---|---|
| 10,428,070 B2 | 10/2019 | Qiu et al. | |
| 2002/0068838 A1 | 6/2002 | Demassey et al. | |
| 2003/0232842 A1 | 12/2003 | Goldmann et al. | |
| 2004/0209930 A1 | 10/2004 | Carboni et al. | |
| 2005/0113450 A1 | 5/2005 | Atli et al. | |
| 2005/0203119 A1 | 9/2005 | Ono et al. | |
| 2006/0100233 A1 | 5/2006 | Villa et al. | |
| 2007/0219239 A1 | 9/2007 | Mjalli et al. | |
| 2007/0225373 A1 | 9/2007 | Chen et al. | |
| 2009/0023740 A1 | 1/2009 | Fulp et al. | |
| 2011/0009622 A1 | 1/2011 | Jitsuoka et al. | |
| 2011/0165118 A1 | 7/2011 | Chan et al. | |
| 2011/0281950 A1 | 11/2011 | Baiocchi et al. | |
| 2012/0009142 A1 | 1/2012 | Karp et al. | |
| 2013/0251673 A1 | 9/2013 | Hartman et al. | |
| 2013/0267517 A1 | 10/2013 | Guo et al. | |
| 2014/0343032 A1 | 11/2014 | Zhu et al. | |
| 2014/0357858 A1 | 12/2014 | Ushioda et al. | |
| 2015/0005295 A1 | 1/2015 | Haché et al. | |
| 2015/0119362 A1 | 4/2015 | Gurney et al. | |
| 2015/0133428 A1 | 5/2015 | Velaparthi et al. | |
| 2015/0152073 A1 | 6/2015 | Hartman et al. | |
| 2015/0152096 A1 | 6/2015 | Zhang et al. | |
| 2015/0197493 A1 | 7/2015 | Hartman et al. | |
| 2015/0210682 A1* | 7/2015 | Han | A61K 31/4745 514/233.2 |
| 2015/0252057 A1 | 9/2015 | Zhu et al. | |
| 2015/0266890 A1 | 9/2015 | Vandyck et al. | |
| 2015/0274653 A1 | 10/2015 | Verschueren et al. | |
| 2016/0185777 A1 | 6/2016 | Hartman et al. | |
| 2016/0206616 A1 | 7/2016 | Zhang et al. | |
| 2016/0237078 A9 | 8/2016 | Guo et al. | |
| 2016/0264562 A1 | 9/2016 | Liu et al. | |
| 2016/0264563 A1 | 9/2016 | Ren et al. | |
| 2016/0289212 A1 | 10/2016 | Gao et al. | |
| 2016/0296515 A1 | 10/2016 | Han et al. | |
| 2016/0332996 A1 | 11/2016 | Gao et al. | |
| 2016/0347746 A1 | 12/2016 | Zhang | |
| 2017/0014408 A1 | 1/2017 | Gao et al. | |
| 2017/0022150 A1 | 1/2017 | Gao et al. | |
| 2017/0197986 A1 | 7/2017 | He et al. | |
| 2017/0217974 A1 | 8/2017 | Gao et al. | |
| 2017/0240548 A1 | 8/2017 | Fu et al. | |
| 2017/0253609 A1 | 9/2017 | Gao et al. | |
| 2017/0354641 A1 | 12/2017 | Bastian et al. | |
| 2017/0355701 A1 | 12/2017 | Qiu et al. | |
| 2017/0355712 A1 | 12/2017 | Campbell et al. | |
| 2018/0312507 A1 | 11/2018 | Fu et al. | |
| 2018/0312512 A1 | 11/2018 | He et al. | |
| 2019/0060258 A1 | 2/2019 | Qiu et al. | |
| 2019/0084994 A1 | 3/2019 | Qiu et al. | |
| 2019/0119288 A1 | 4/2019 | Qiu et al. | |
| 2019/0177316 A1 | 6/2019 | Qiu et al. | |
| 2019/0177320 A1 | 6/2019 | Qiu et al. | |
| 2019/0224188 A1 | 7/2019 | Panarese et al. | |
| 2019/0298865 A1 | 10/2019 | Cuthbertson et al. | |
| 2019/0321360 A1 | 10/2019 | Qiu et al. | |
| 2019/0337903 A1 | 11/2019 | Khan | |

FOREIGN PATENT DOCUMENTS

| | | |
|---|---|---|
| CN | 106928245 A | 7/2017 |
| CN | 108727378 A | 11/2018 |
| EP | 2280001 A1 | 2/2011 |
| WO | 8702367 A2 | 4/1987 |
| WO | 9504046 A1 | 2/1995 |
| WO | 0168641 A1 | 9/2001 |
| WO | 0168647 A1 | 9/2001 |
| WO | 2004018414 A2 | 3/2004 |
| WO | 2004052852 A1 | 6/2004 |
| WO | 2006033995 A2 | 3/2006 |
| WO | 2008120759 A1 | 10/2008 |
| WO | 2009158473 A1 | 12/2009 |
| WO | 2013006394 A1 | 1/2013 |
| WO | 2013096744 A1 | 6/2013 |
| WO | 2013130703 A2 | 9/2013 |
| WO | 2013144129 A1 | 10/2013 |
| WO | 2013181584 A2 | 12/2013 |
| WO | 2014106019 A2 | 7/2014 |
| WO | 2014184350 A1 | 11/2014 |
| WO | 2014184365 A1 | 11/2014 |
| WO | 2015005295 A1 | 1/2015 |
| WO | 2015074546 A1 | 5/2015 |
| WO | 2015108631 A1 | 7/2015 |
| WO | 2015113990 A1 | 8/2015 |
| WO | 2015173164 A1 | 11/2015 |
| WO | 2015180631 A1 | 12/2015 |
| WO | 2016016370 A1 | 2/2016 |
| WO | 2016023877 A1 | 2/2016 |
| WO | 2016025933 A2 | 2/2016 |
| WO | 2016071215 A1 | 5/2016 |
| WO | 2016107832 A1 | 7/2016 |
| WO | 2016128335 A1 | 8/2016 |
| WO | 2016177655 A1 | 11/2016 |
| WO | 2017013046 A1 | 1/2017 |
| WO | 2017017042 A1 | 2/2017 |
| WO | 2017017043 A1 | 2/2017 |
| WO | 2017061466 A1 | 4/2017 |
| WO | 2017140821 A1 | 8/2017 |
| WO | 2017153919 A1 | 9/2017 |
| WO | 2017205115 A1 | 11/2017 |
| WO | 2017216391 A1 | 12/2017 |
| WO | 2017216685 A1 | 12/2017 |
| WO | 2017216686 A1 | 12/2017 |
| WO | 2018001944 A1 | 1/2018 |
| WO | 2018001952 A1 | 1/2018 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018083081 A1 | 5/2018 |
| WO | 2018083106 A1 | 5/2018 |
| WO | 2018083136 A1 | 5/2018 |
| WO | 2018085619 A1 | 5/2018 |
| WO | 2018087345 A1 | 5/2018 |
| WO | 2018130152 A1 | 7/2018 |
| WO | 2018144605 A1 | 8/2018 |
| WO | 2018154466 A1 | 8/2018 |
| WO | WO2018/154466 * | 8/2018 |
| WO | 2018161960 A1 | 9/2018 |
| WO | 2018181883 A1 | 10/2018 |
| WO | 2018196805 A1 | 11/2018 |
| WO | 2018198079 A1 | 11/2018 |
| WO | 2018219356 A1 | 12/2018 |
| WO | 2019069293 A1 | 4/2019 |
| WO | 2019097479 A1 | 5/2019 |
| WO | 2019100735 A1 | 5/2019 |
| WO | 2019110352 A1 | 6/2019 |
| WO | 2019123285 A1 | 6/2019 |
| WO | 2019129681 A1 | 7/2019 |
| WO | 2019166951 A1 | 9/2019 |

OTHER PUBLICATIONS

Noguchi, Chiemi et al., "G to A Hypermutation of Hepatitis B Virus", Hepatology, vol. 41, No. 3, 2005, 2005, 626-633.

CAS Abstract and Indexed Compounds WO 01/68647 (2001), 2001.

PubChem SID 79456770 CID 10880307, 2009.

"N-[4-(cyanomethyl)phenyl]-5-(hexyhydro-1-H-azepine-1-yl)sulfonyl]-2-methoxy-benzamid e", Database Registry [Online] Chemical Abstracts Service, Columbus, Ohio, US; May 6, 2011 (May 6, 2011), XP55358935,accession No. RN: 1291044-81-9.

Das, Jagabandhu et al., "Discovery of 2-Amino-heteroaryl-benzothiazole-6-anilides as Potent p56lck Inhibitors", Biorganic & Medicinal Chemistry Letters, 13, 2587-2590 (2003), 2003, 2587-2590.

El-Hamouly, Wageeh S. et al., "Synthesis and Antimicrobial Activity of New 3, 4-Dihydropyrimidinones", International Journal of Pharmaceutical Sciences and Research, vol. 2, 1054-1062 (2011), 2011, 1054-1062.

(56) References Cited

OTHER PUBLICATIONS

Qiu, Zongxing et al., "Design and Synthesis of Orally Bioavailable 4-Methyl Heteroaryldihydropyrimidine Based Hepatitis B Virus (HBV) Capsid Inhibitors", Journal of Medicinal Chemistry, 2016.
Chemical Abstract Service STN CAplus [online database], Accession No. 2003:1014580. (Year: 2003).
Chemical Abstract Service STN Database Registry No. 1578268-77-5 [online][Entered STN: Apr. 1, 2014].
Chemical Abstracts Registry No. 1026741-09-2, indexed in the Registry file on Jun. 9, 2008.
Chemical Abstracts Registry No. 115280-56-3, indexed in the Registry file on STN CAS Online Jul. 16, 1988.
Chemical Abstracts Registry No. 1269203-67-9, indexed in the Registry file on STN CAS Online Mar. 21, 2011.
Chemical Abstracts Registry No. 1350251-34-1, indexed in the Registry file on STN CAS Online Dec. 7, 2011.
Chemical Abstracts Registry No. 397288-41-1, indexed in the Registry file on Mar. 1 (Year: 2002).
Chemical Abstracts Registry No. 792901-47-4, indexed in the Registry file on STN CAS Online Dec. 6, 2004.
Chemical Abstracts Registry No. 92555-24-3, indexed in the Registry file on Dec. 17, 1984.
Chemical Abstracts Registry No. 950067-32-0, indexed in the Registry file on Oct. 10, 2007.
PubChem CID 57036978, National Center for Biotechnology Information. PubChem Compound Database; CID=57036978, https://pubchem.ncbi.nlm.nih.gov/ compound/57036978 (accessed May 19, 2017), create date Jun. 13, 2012.
PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.
PubChem CI D 10194182, National Center for Biotechnology Information. PubChem Compound Database; CI 0=10194182, https://pubchem.ncbi.nlm.nih.gov/ compound/10194182 (accessed May 19, 2017), create date Oct. 25, 2006.
Pubchem-'428' Create Date: Sep. 11, 2005 (Sep. 11, 2005) Date Accessed: Jun. 17, 2016.
Pubchem—CID 23201920, Create Date: Dec. 5, 2007, p. 3.
Pubchem—CID 63186259, Create Date: Oct. 22, 2012 (Oct. 22, 2012) p. 3.
Pubchem—SID 15224030 Deposit Date: Oct. 25, 2006.
Pubchern—57224610 ('610') Create Date: Jun. 14, 2012 (Jun. 14, 2012) Date Accessed: Jun. 17, 2016.
U.S. Appl. No. 16/194,608, filed Nov. 19, 2018.
U.S. Appl. No. 16/210,472, filed Dec. 5, 2018.
Ballatore, C. et al., "Carboxylic Acid (Bio)Isosteres in Drug Design", ChemMedChem., vol. 8, No. 3, 2013, 385-395.
Clark, M. T. et al., "5-(aLKYLSULFONYL)Salicylanilides As Potential Dental Antiplaque Agents", Journal of Medicinal Chemistry, 29(1), 1986, 25-29.
Janetka, J. W. et al., "Discovery of a novel class of 2-ureido thiophene carboxamide checkpoint kinase inhibitors", Bioorganic & Medicinal Chemistry Letters, 18, 2008, 4242-4248.
Yang, et al., "Enzyme-mediated hydrolytic activation of prodrugs", Acta Pharmaceutica Sinica B., vol. 1(3), Sep. 9, 2011, 143-159.
U.S. Appl. No. 16/689,448, filed Nov. 20, 2019.
"8-Tert-butyl-4-[(1 E)-1-(difluoromethoxy)buta-1, 3-dienyl]-5-ethyl-12-oxo-6, 9-diazatricyclo[7.4.0.02,6]trideca-1(13),2,4, 10-tetraene-11-carboxylic acid", PubChem-CID-134460393, CreateDate: Jun. 23, 2018 (Jun. 23, 2018), p. 2, Fig.
Chowshury, Chinmay et al., "A rapid and facile method for the general synthesis of 3-aryl substituted 4,5,6,7-tetrahydro[1,2,3]triazolo[1,5-a]pyrazines and their ring fused analogues", Organic & Biomolecular Chemistry, vol. 9, 2011, 5856-5862.
Teuber, Hans et al., "Simple indolo[2,3-a]quinolizine synthesis", Tetrahedron Letters, vol. 5 (7), pp. 325-329, 1964.

* cited by examiner

SUBSTITUTED HETEROCYCLES AS ANTIVIRAL AGENTS

RELATED APPLICATIONS

This application claims the benefit of U.S. Provisional Application No. 62/620,292, filed on Jan. 22, 2018, and 62/753,335, filed on Oct. 31, 2018. The entire teachings of the above applications are incorporated herein by reference.

TECHNICAL FIELD

The present invention relates generally to compounds and pharmaceutical compositions useful as hepatitis virus replication inhibitors. Specifically, the present invention relates to tetracyclic pyridone compounds that are useful in treating viral infections such as hepatitis B virus (HBV). The invention provides novel tetracyclic pyridone compounds as disclosed herein, pharmaceutical compositions containing such compounds, and methods of using these compounds and compositions in the treatment and prevention of HBV infections.

BACKGROUND OF THE INVENTION

Over 240 million people throughout the world are chronically infected with hepatitis B virus (HBV). Out of this patient population, at least 2 million reside in the United States. For those that are chronically infected, many will develop complications of liver disease from cirrhosis or hepatocellular carcinoma (HCC).

HBV is a member of the Hepadnavirus family, and it is able to replicate through the reverse transcription of an RNA intermediate. The 3.2-kb HBV genome exists in a circular, partially doublestranded DNA conformation (rcDNA) that has four overlapping open reading frames (ORF). These encode for the core, polymerase, envelope, and X proteins of the virus. rcDNA must be converted into covalently closed circular DNA (cccDNA) in cells prior to the transcription of viral RNAs. As rcDNA is transcriptionally inert, cccDNA is the only template for HBV transcription, and its existence is required for infection.

The HBV viral envelope contains a mixture of surface antigen proteins (HBsAg). The HBsAg coat contains three proteins that share a common region that includes the smallest of the three proteins (SHBsAg). The other two proteins, Medium HBsAg (MHBsAg) and Large HBsAg (LHBsAg), both contain a segment of SHBsAg with additional polypeptide segments. SHBsAg, MHBsAg, and LHBsAg can also assemble into a non-infectious subviral particle known as the 22-nm particle that contains the same proteins found around infectious viral particles. As the 22-nm particles contain the same antigenic surface proteins that exist around the infectious HBV virion, they can be used as a vaccine to produce neutralizing antibodies.

In chronically infected patients, the non-infectious 22-nm particles are found in much greater abundance than the infectious virions. As a result, the 22-nm particles are thought to be able to protect the infectious virions from the infected host's immune response. Not only can they serve as infectious decoys, but they also suppress normal functioning of immune cells thereby impairing the host's immune response to HBV. Therefore, reducing the level of subviral particles is a feasible therapeutic approach to treating HBV infections. (Refer to WO2015/13990).

In the clinical setting, a diagnostic marker of chronic HBV infection is high serum levels of HBsAg. In recent years, data have suggested that sustained virologic response (SVR) corresponds with HBsAg decline during early treatment, while sustained exposure to HBsAg and other viral antigens might lead to inept immunogenicity. Patients that display higher decreases in serum HBsAg reached a considerably higher SVR following treatment.

Current treatment options for chronically infected HBV patients are limited in number and scope. They include interferon therapy and nucleoside-based inhibitors of HBV DNA polymerase, namely entecavir and tenofovir. The current standard of care is dedicated to reducing the level of viremia and allowance of liver dysfunction, but is associated with negative side-effects and increase persistence of drug-resistant HBV mutants. A significant shortcoming of current therapies is that they are unable to eliminate hepatic reservoirs of cccDNA, prevent transcription of HBsAg from cccDNA, or limit the secretion of HBsAg into serum that will ultimately stifle the immune response. Although compounds have been reported to reduce serum HBsAg levels, they have not been approved as HBV therapies. (Refer to WO2015/113990, WO2015/173164, WO2016/023877, WO2016/071215, WO2016/128335, WO2017/140821, WO2017017042, WO2017216685, WO2017216686, WO2018019297, WO2018022282, WO2018085619, WO2018154466, WO2018219356, CN106928215, CN106928245, and U.S. Pat. No. 9,458,153).

More effective therapies for chronic HBV infections are needed due to this high unmet clinical need. This invention describes the methods to prepare and methods for use of compounds that are believed to suppress the secretion of subviral particles containing HBsAg. Compounds of this type might be used to treat HBV infections and decrease occurrence of liver disease complications such as cirrhosis or HCC.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention includes the process for the preparation of the said compounds.

The present invention provides compounds represented by Formula (I),

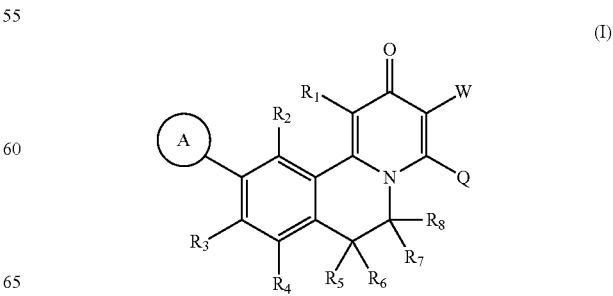

and pharmaceutically acceptable salts, esters and prodrugs thereof, wherein:

$R_1$ is hydrogen, halo, or optionally substituted $C_1$-$C_6$ alkyl;

$R_2$ is hydrogen, halo, CN, optionally substituted $C_1$-$C_6$ alkyl, or optionally substituted $C_1$-$C_6$ alkoxy;

A is optionally substituted $C_3$-$C_{12}$ cycloalkyl, optionally substituted $C_3$-$C_{12}$ cycloalkenyl, optionally substituted 3- to 12-membered heterocyclic, optionally substituted aryl, or optionally substituted heteroaryl;

$R_3$ is selected from $R_{11}$, —$OR_{11}$, —$SR_{11}$, and —$NRR_{11}$;

$R_4$ is halo, CN, $R_{11}$, —$OR_{11}$, —$SR_{11}$, or —$NRR_{11}$;

In one embodiment, $R_{11}$ at each occurrence is independently selected from hydrogen, optionally substituted $C_1$-$C_6$ alkyl, an optionally substituted $C_2$-$C_6$ alkenyl, optionally substituted $C_3$-$C_6$ cycloalkyl, an optionally substituted $C_3$-$C_7$ cycloalkenyl, and optionally substituted 3- to 7-membered heterocyclic; in another embodiment, $R_{11}$ at each occurrence is independently selected from hydrogen, optionally substituted $C_1$-$C_6$ alkyl, optionally substituted $C_3$-$C_6$ cycloalkyl, and optionally substituted 3- to 7-membered heterocyclic; preferably, $R_{11}$ is optionally substituted $C_1$-$C_4$ alkyl; optionally substituted oxetanyl, optionally substituted tetrahydrofuranyl, or optionally substituted tetrahydropyranyl;

R is selected from hydrogen and optionally substituted $C_1$-$C_6$ alkyl;

Alternatively, R and $R_{11}$ are taken together with the nitrogen atom to which they are attached to form an optionally substituted 3- to 7-membered heterocyclic;

Alternatively, $R_3$ and $R_4$ are taken together with the carbon atoms to which they are attached to form an optionally substituted $C_3$-$C_7$ cycloalkenyl, an optionally substituted 3- to 7-membered heterocyclic, optionally substituted aryl, or optionally substituted heteroaryl; or $R_3$ and $R_4$ are taken together with the carbon atoms to which they are attached to form an optionally substituted $C_3$-$C_7$ cycloalkenyl, or an optionally substituted 3- to 7-membered heterocyclic; or $R_3$ and $R_4$ together form an optionally substituted $C_1$-$C_5$-alkylene;

$R_5$ is hydrogen, halo, optionally substituted $C_1$-$C_6$ alkyl, or optionally substituted $C_1$-$C_6$ alkoxy;

$R_6$ is hydrogen, halo, optionally substituted $C_1$-$C_6$ alkyl, or optionally substituted $C_1$-$C_6$ alkoxy;

$R_7$ is hydrogen or optionally substituted $C_1$-$C_6$ alkyl;

$R_8$ is hydrogen, halo, optionally substituted $C_1$-$C_6$ alkyl, or optionally substituted $C_1$-$C_6$ alkoxy;

Alternatively, $R_8$ is taken together with $R_6$ and the carbon atoms to which they are attached to form a $C_3$-$C_7$ cycloalkyl ring or a 3- to 7-membered heterocyclic ring; or $R_8$ is taken together with $R_6$ and the carbon atoms to which they are attached to form a $C_4$-$C_7$ cycloalkenyl ring; wherein the cycloalkyl, cycloalkenyl or heterocyclic ring is optionally substituted with up to three groups selected from R, —OR, —$N(R)_2$, halo, CN, COOR, CON$(R)_2$, and oxo; or $R_8$ is taken together with $R_7$ and the carbon atom to which they are attached to form a $C_3$-$C_7$ cycloalkyl ring or a 3- to 7-membered heterocyclic ring; wherein the cycloalkyl or heterocyclic ring is optionally substituted with up to three groups selected from R, —OR, —$N(R)_2$, halo, CN, COOR, CON$(R)_2$, and oxo;

Q is hydrogen or optionally substituted methyl;

W is —$COOR_9$, —$C(O)NHSO_2R$, —$C(O)NHSO_2N(R)_2$, 5-tetrazolyl, or 1,2,4-oxadiazol-3-yl-5(4H)-one; and $R_9$ is hydrogen or optionally substituted $C_1$-$C_6$ alkyl that is optionally substituted with one or two groups selected from halo, —OR, oxo, CN, —$N(R)_2$, COOR, and CON$(R)_2$.

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

In certain embodiments, the present invention relates to compounds of Formula (I), and pharmaceutically acceptable salts thereof, wherein $R_1$ is hydrogen, Cl, F, —$CH_3$ or —$CF_3$.

In certain embodiments, the present invention relates to compounds of Formula (I), and pharmaceutically acceptable salts thereof, wherein $R_2$ is hydrogen, Cl or F.

In certain embodiments, the present invention relates to compounds of Formula (I), and pharmaceutically acceptable salts thereof, wherein A is optionally substituted aryl, or optionally substituted heteroaryl.

In certain embodiments, the present invention relates to compounds of Formula (I), and pharmaceutically acceptable salts thereof, wherein $R_3$ is $R_{11}$ or —$OR_{11}$, where $R_{11}$ is as previously defined.

In certain embodiments, the present invention relates to compounds of Formula (I), and pharmaceutically acceptable salts thereof, wherein $R_3$ is $R_{11}$ or —$OR_{11}$, and $R_{11}$ is hydrogen or optionally substituted $C_1$-$C_6$ alkyl. Preferably, $R_{11}$ is selected from —$CH_2R_{21}$, —$CH_2CH_2R_{21}$, —$CH_2CH_2CH_2R_{21}$, and —$CH_2CH_2CH_2CH_2R_{21}$, wherein $R_{21}$ is selected from —OH, —OMe, —OEt, phenyl,

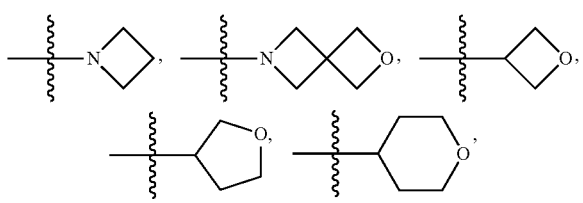

—OC(O)R, —C(O)OR, —C(O)NRR, —OC(O)OR, —OC(O)NRR, —NRR, —NRC(O)R, —NRC(O)OR, —NRC(O)—NRR, —S(O)R, —OS(O)$_2$R, —S(O)$_2$OR, —S(O)$_2$R, —S(O)$_2$NRR; —NRS(O)$_2$NRR; —OP(O)(OR)$_2$, —P(O)(OR)$_2$, —NRP(O)(OR)$_2$, and —P(O)(NRR)$_2$. In certain embodiments, $R_3$ is —O(CH$_2$)$_3$OCH$_3$.

In certain embodiments, the present invention relates to compounds of Formula (I), and pharmaceutically acceptable salts thereof, wherein $R_4$ is hydrogen, Cl or F.

In certain embodiments, the present invention relates to compounds of Formula (I), and pharmaceutically acceptable salts thereof, wherein $R_3$ and $R_4$ are taken together with the carbon atoms on phenyl ring to which they attached to form a ring selected from the groups below,

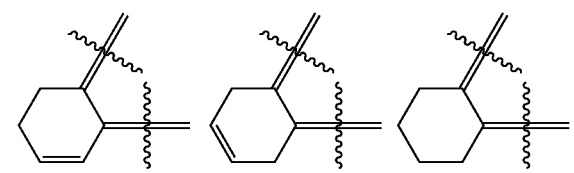

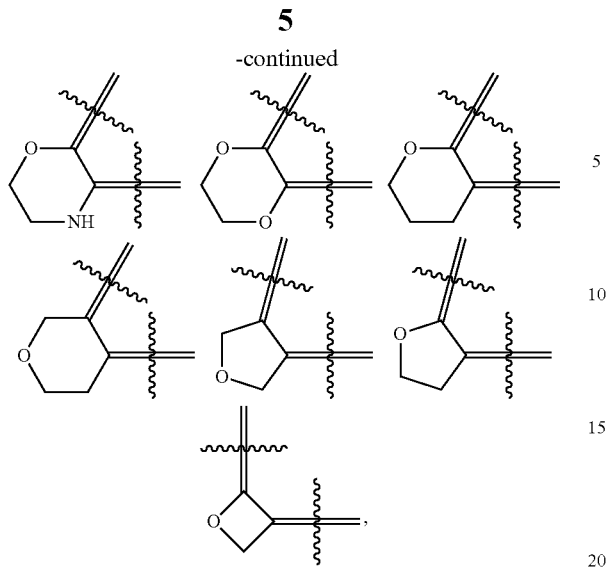

each of which is optionally substituted.

In certain embodiments, the present invention relates to compounds of Formula (I), and pharmaceutically acceptable salts thereof, wherein $R_5$ is hydrogen, Cl or F.

In certain embodiments, the present invention relates to compounds of Formula (I), and pharmaceutically acceptable salts thereof, wherein Q is hydrogen, or methyl optionally substituted with one or more halo, preferably fluoro. In certain embodiments, Q is difluoromethyl or trifluoromethyl.

In certain embodiments, the present invention relates to compounds of Formula (I), and pharmaceutically acceptable salts thereof, wherein W is —COOH or —C(O)NH—SO$_2$N(R)$_2$, wherein R is as previously defined.

In another embodiment, the compound of Formula (I) is represented by Formula (II), or a pharmaceutically acceptable salt thereof:

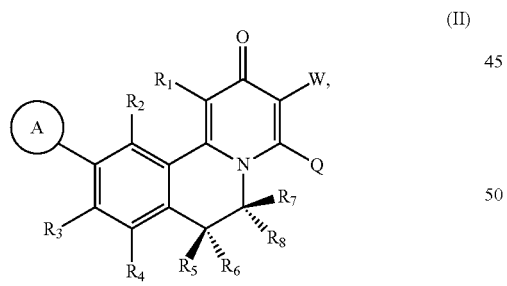

wherein $R_1$, $R_2$, A, $R_3$, $R_4$, $R_5$, $R_6$, $R_7$, $R_8$, Q and W are as previously defined. In certain embodiments, the compounds of the invention have the absolute stereochemistry illustrated in Formula (II). In certain embodiments, $R_7$ and $R_8$ are taken together with the carbon atom to which they are attached to form a spiro ring. In certain embodiments, $R_6$ and $R_8$ are taken together with the carbon atoms to which they are attached to form a cis-fused ring. In certain embodiments, $R_5$ and $R_7$ are both hydrogen.

In another embodiment, the compound of Formula (I) is represented by Formula (IIIa) or Formula (IIIb), or a pharmaceutically acceptable salt thereof:

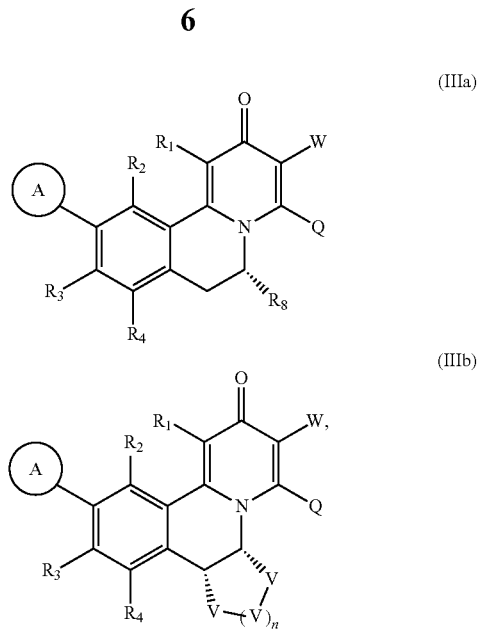

wherein one V is —O—, —C(O)—, —S—, —S(O)$_2$—, —NR$_{22}$— or —C(R$_{22}$)$_2$—, and the other Vs are independently —O—, —NR$_{22}$— or —C(R$_{22}$)$_2$—; each $R_{22}$ is independently hydrogen, optionally substituted —C$_1$-C$_6$ alkyl, optionally substituted —C$_2$-C$_6$ alkenyl, optionally substituted —C$_2$-C$_6$ alkynyl, optionally substituted C$_1$-C$_6$ alkoxy; optionally substituted —C$_3$-C$_7$ cycloalkyl, optionally substituted 3- to 7-membered heterocyclic, optionally substituted aryl or optionally substituted heteroaryl; n is 0, 1, 2 or 3; $R_1$, $R_2$, A, $R_3$, $R_4$, $R_8$, Q and W are as previously defined. In certain embodiments, each of two adjacent Vs is —C(R$_{22}$)$_2$—. In another embodiment, two adjacent Vs are taken together to form —C(R$_{22}$)=C(R$_{22}$)—.

In another embodiment, the compound of Formula (I) is represented by Formula (IIIb-1) or (IIIb-2), or a pharmaceutically acceptable salt thereof:

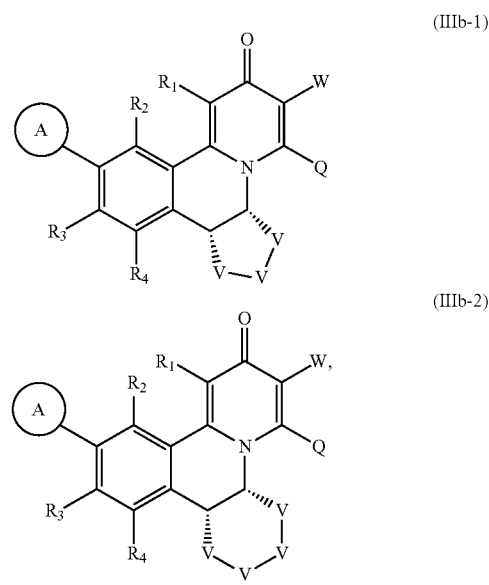

wherein $R_1$, $R_2$, A, $R_3$, $R_4$, V, Q and W are as previously defined. In certain embodiments, each of two adjacent Vs is —C(R$_{22}$)$_2$—. In another embodiment, two adjacent Vs are together to form —C(R$_{22}$)═C(R$_{22}$)—.

In another embodiment, the compound of Formula (I) is represented by Formula (IIIb-1a) or (IIIb-2a), or a pharmaceutically acceptable salt thereof:

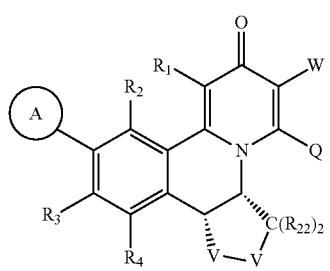
(IIIb-1a)

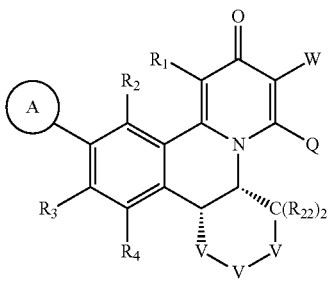
(IIIb-2a)

wherein R$_1$, R$_2$, A, R$_3$, R$_4$, V, R$_{22}$, Q and W are as previously defined. In certain embodiments, each V is —C(R$_{22}$)$_2$—. In certain embodiments, the two adjacent Vs together form —C(R$_{22}$)═C(R$_{22}$)—. In certain embodiments, each R$_{22}$ is independently hydrogen or methyl. In certain embodiments, each R$_{22}$ is methyl.

In another embodiment, the compound of Formula (I) is represented by Formula (IVa) or (IVb), or a pharmaceutically acceptable salt thereof:

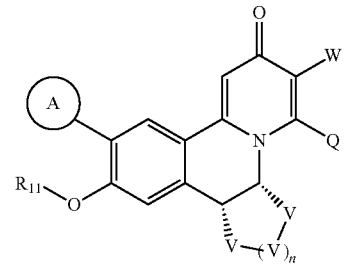
(IVa)

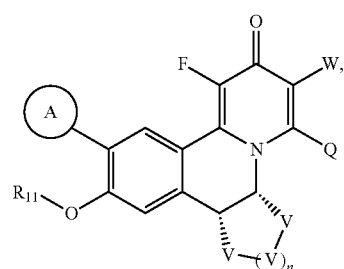
(IVb)

wherein A, R$_{11}$, V, Q, W, and n are as previously defined. In certain embodiments, each of two adjacent Vs is —C(R$_{22}$)$_2$—. In another embodiment, two adjacent Vs are taken together to form —C(R$_{22}$)═C(R$_{22}$)—.

In another embodiment, the compound of Formula (I) is represented by Formula (Va), or Formula (Vb), or a pharmaceutically acceptable salt thereof:

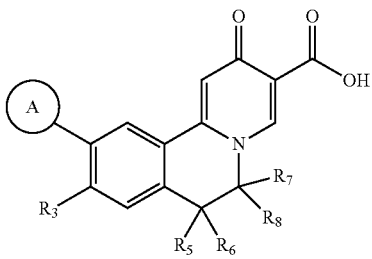
(Va)

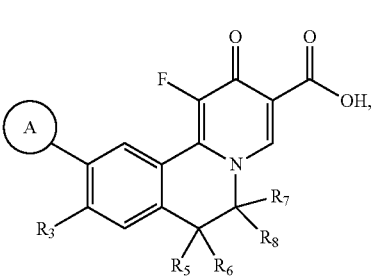
(Vb)

wherein A, R$_3$, R$_5$, R$_6$, R$_7$, and R$_8$ are as previously defined.

In another embodiment, the compound of Formula (I) is represented by Formula (VIa) or Formula (VIb), or a pharmaceutically acceptable salt thereof:

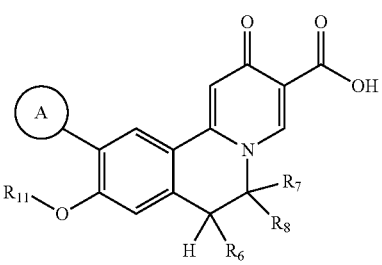
(VIa)

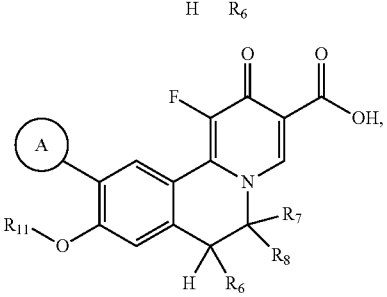
(VIb)

wherein A, R$_{11}$, R$_6$, R$_7$, and R$_8$ are as previously defined.

In another embodiment, the compound of Formula (I) is represented by Formula (VIIa), (VIIb), (VIIc), or (VIId), or a pharmaceutically acceptable salt thereof:

(VIIa)
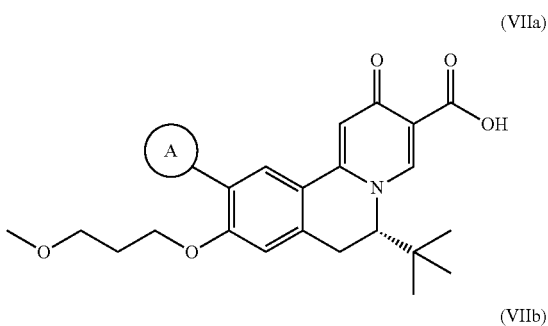

(VIIb)
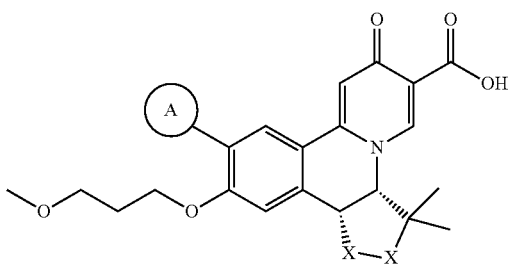

(VIIc)
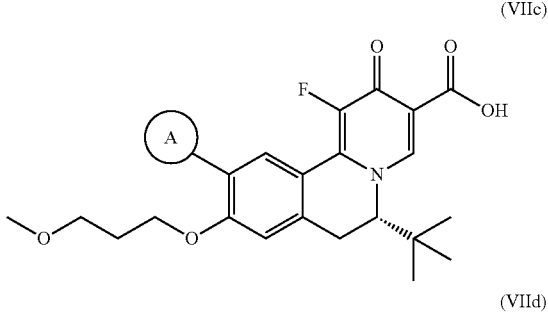

(VIId)
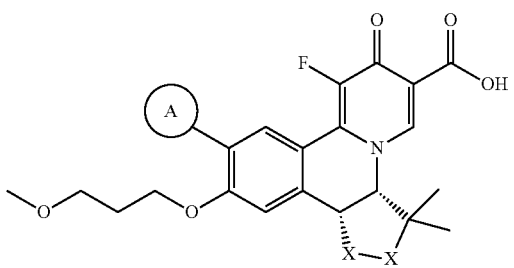

wherein one X is O or $CH_2$, and the other X is $CH_2$; A is previously defined.

In another embodiment, the compound of Formula (I) is represented by Formula (VIIIa) or (VIIIb), or a pharmaceutically acceptable salt thereof:

(VIIIa)
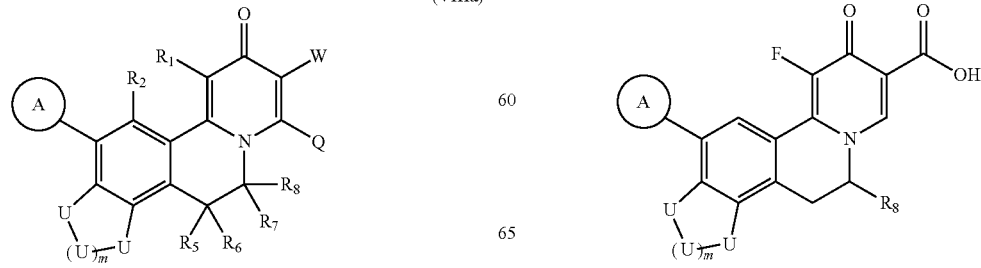

(VIIIb)
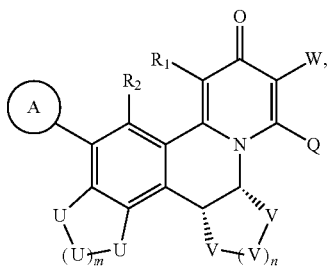

wherein one U is —O—, —C(O)—, —S—, —S(O)$_2$—, —NR$_{22}$— or —C(R$_{22}$)$_2$—, and the other Us are independently —O—, —NR$_{22}$— or —C(R$_{22}$)$_2$—; m is 0, 1, 2 or 3; and R$_1$, R$_2$, A, R$_5$, R$_6$, R$_7$, R$_8$, R$_{22}$, V, n, Q and W are as previously defined. Alternatively, two adjacent Vs together form —C(R$_{22}$)=C(R$_{22}$)—.

In another embodiment, the compound of Formula (I) is represented by Formula (IXa), (IXb), (IXc), or (IXd), or a pharmaceutically acceptable salt thereof:

(IXa)
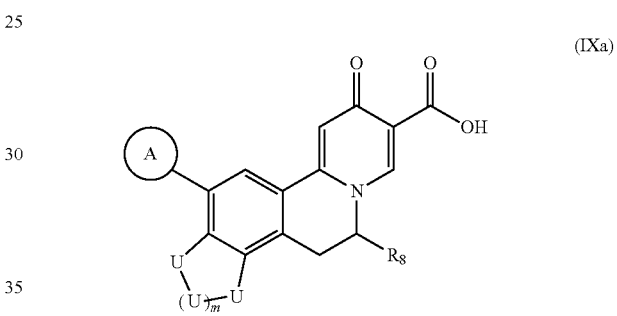

(IXb)
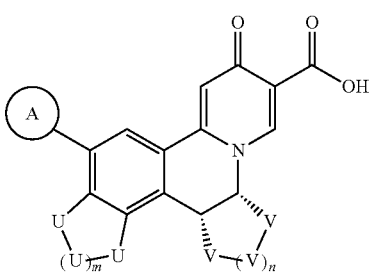

(IXc)

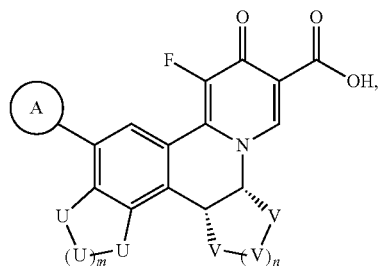
(IXd)
wherein U, m, V, n, A and $R_8$ are previously defined.
In another embodiment, the compound of Formula (I) is represented by one of Formulae (Xa-1)~(Xf-1), (Xa-2)~(Xf-2), or a pharmaceutically acceptable salt thereof:
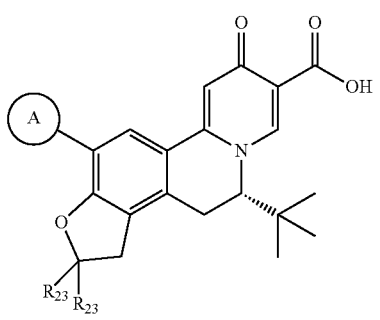
(Xa-1)

(Xb-1)
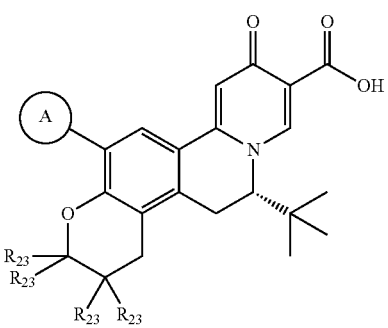
(Xc-1)
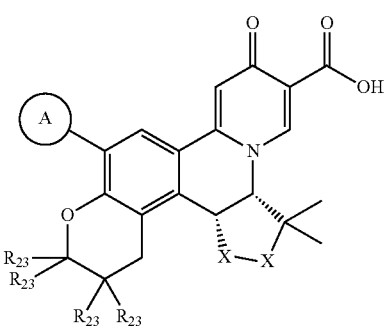
(Xd-1)
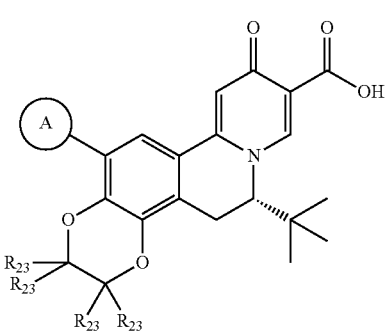
(Xe-1)
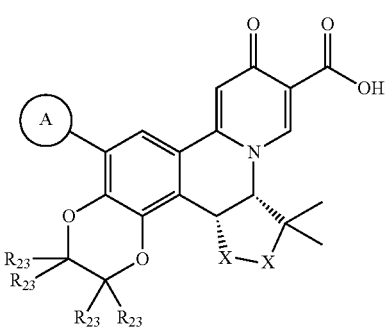
(Xf-1)
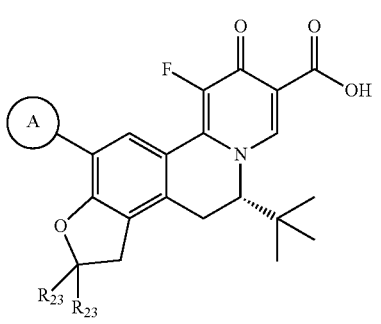
(Xa-2)
(Xb-2)

-continued

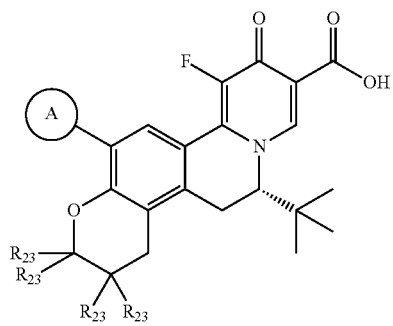
(Xc-2)

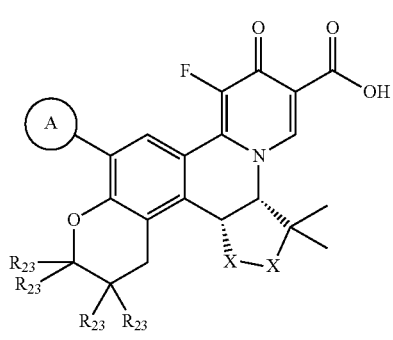
(Xd-2)

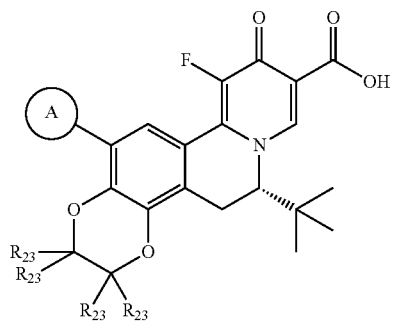
(Xe-2)

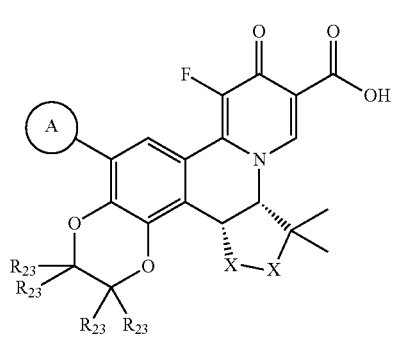
(Xf-2)

wherein each $R_{23}$ is independently hydrogen, optionally substituted —$C_1$-$C_6$ alkyl, optionally substituted —$C_2$-$C_6$ alkenyl, optionally substituted —$C_2$-$C_6$ alkynyl, optionally substituted —$C_1$-$C_6$ alkoxy; optionally substituted aryl or optionally substituted heteroaryl; X and A are as previously defined; alternatively, two adjacent $R_{23}$ groups together with the carbon atoms to which they are attached to form an olefinic double bond.

In another embodiment, the compound of Formula (I) is represented by one of Formulae (XIa-1)~(XIf-1), (XIa-2)~(XIf-2), or a pharmaceutically acceptable salt thereof:

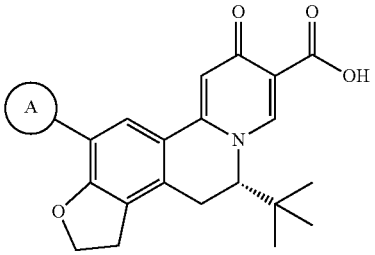
(XIa-1)

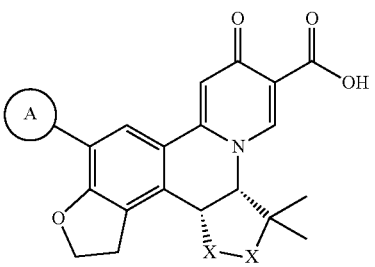
(XIb-1)

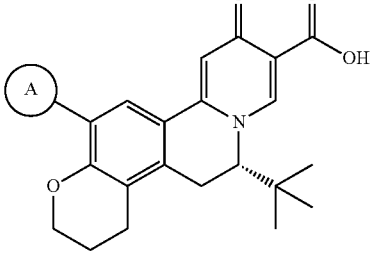
(XIc-1)

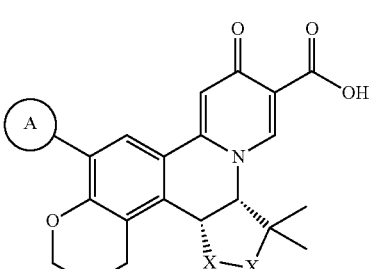
(XId-1)

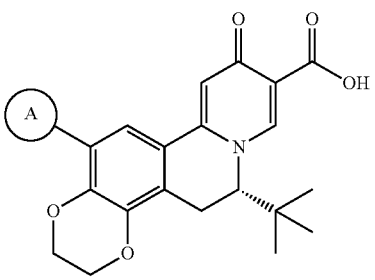
(XIe-1)

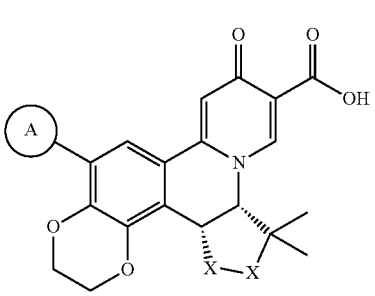
(XIf-1)

(XIa-2)
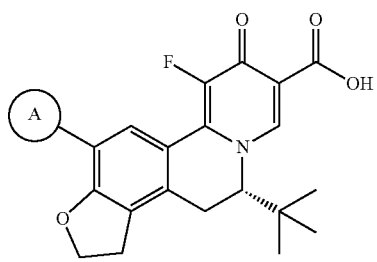
(XIb-2)
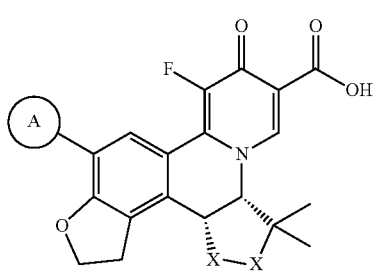
(XIc-2)
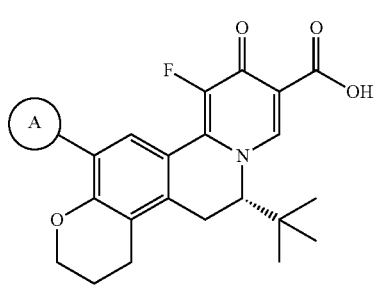
(XId-2)
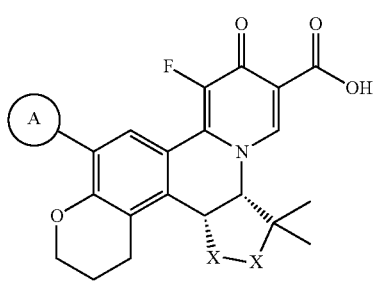
(XIe-2)
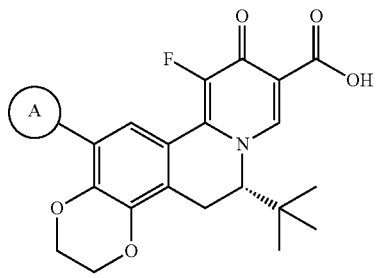
(XIf-2)
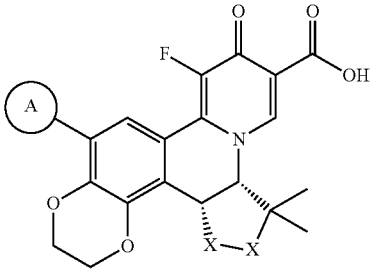
wherein X and A are previously defined.
In the compounds of the invention, A is preferably selected from one of the following by removal of a hydrogen atom:
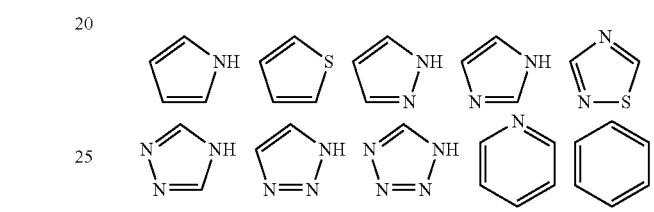
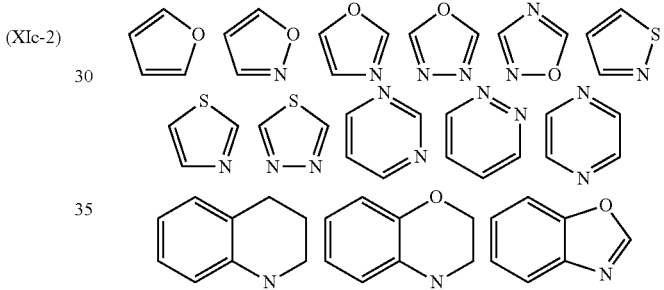
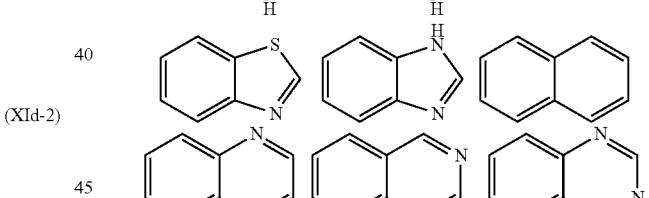

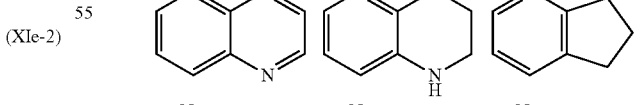
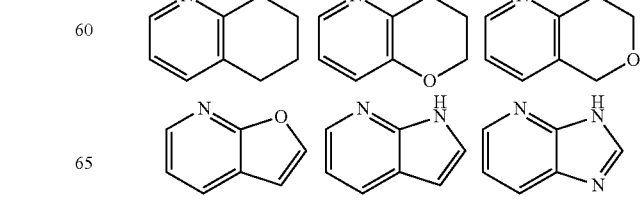

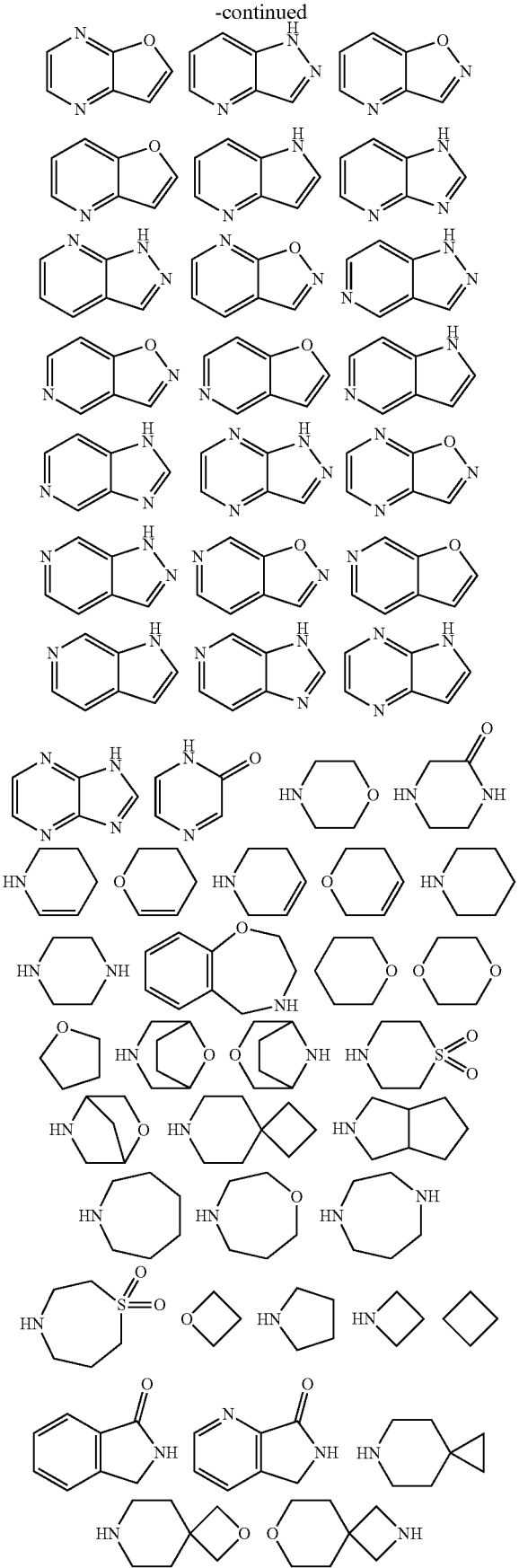

wherein each of these groups is optionally substituted with one to four groups selected from halo, CN, —OR, —N(R)$_2$, optionally substituted C$_1$-C$_6$ alkyl, and optionally substituted 3- to 7-membered heterocyclic. In certain embodiments, each of these groups is optionally substituted with one to four, preferably one or two, groups selected from fluoro, chloro, methyl, methoxy, trifluoromethyl and difluoromethyl.

In certain embodiments of the compounds of the invention, A is selected from the groups set forth below.

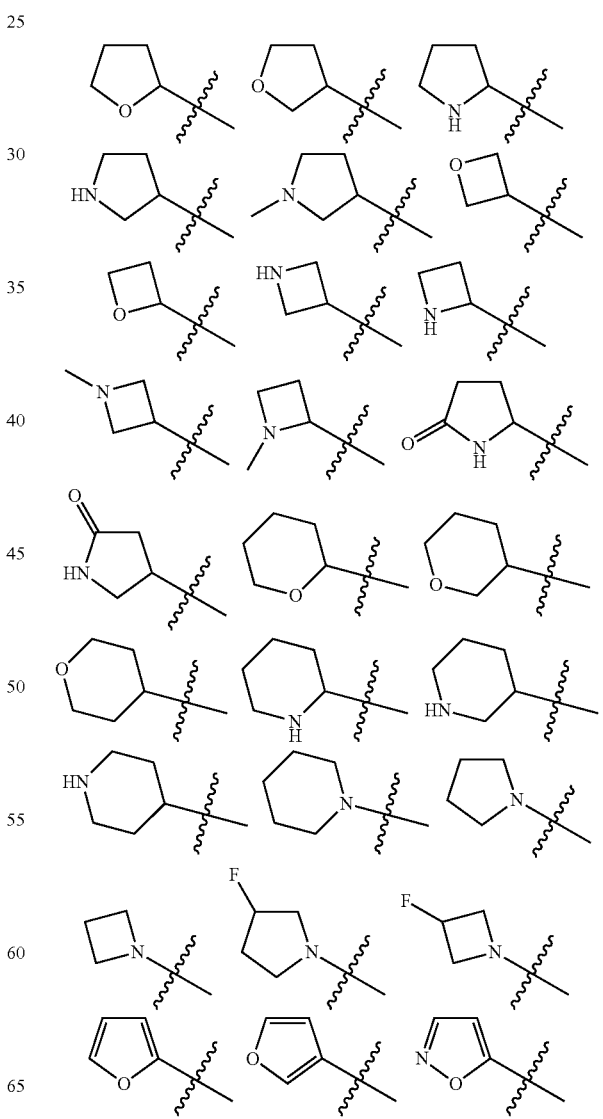

-continued
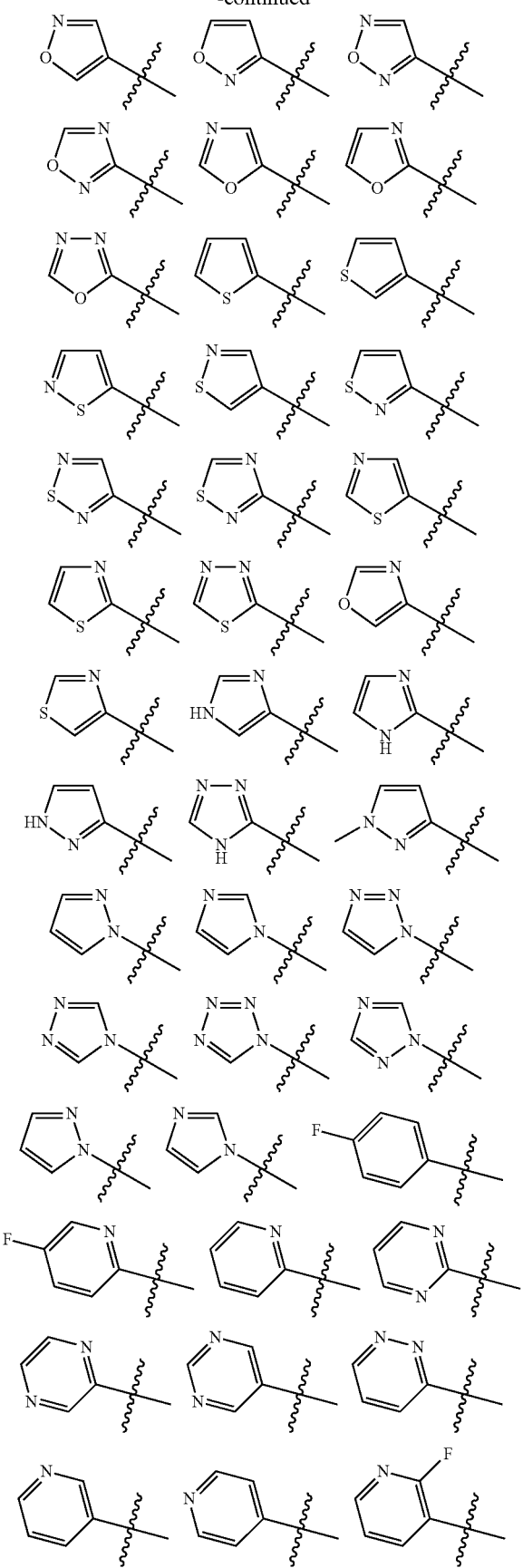
-continued
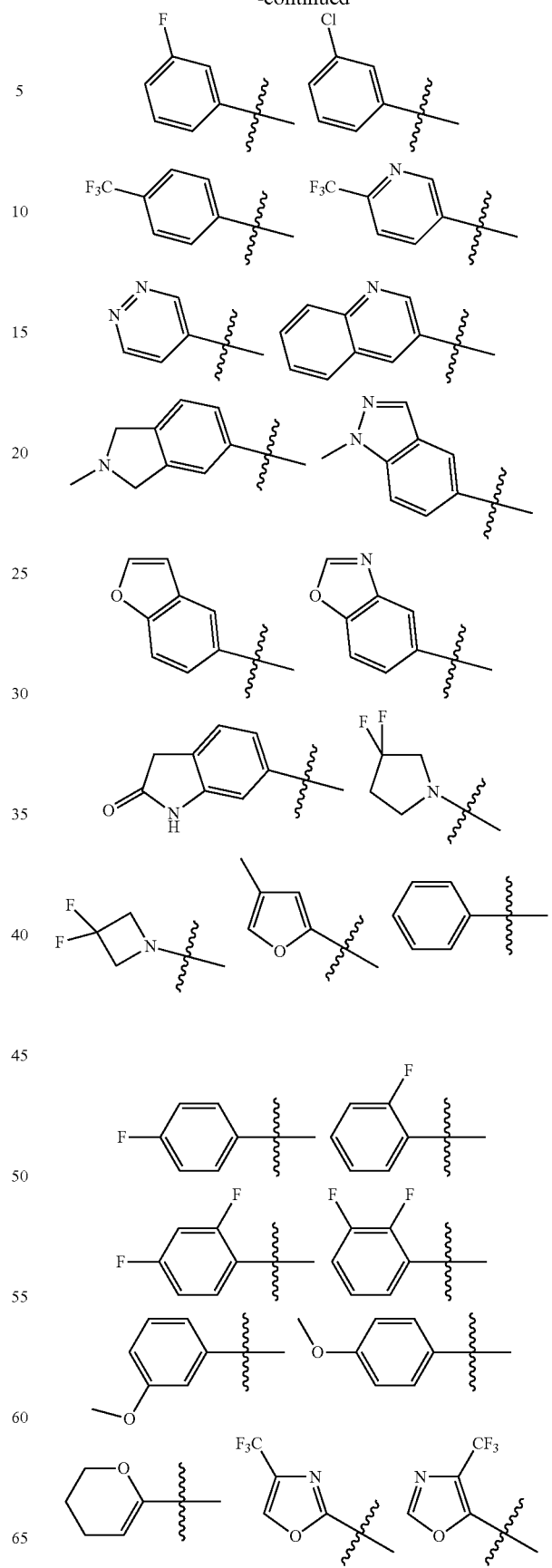

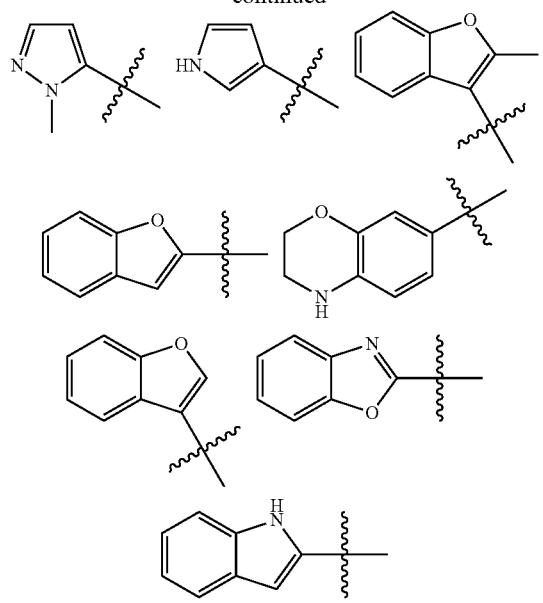
Representative compounds of the invention include, but are not limited to, the following compounds according to Formula (VIIb), (VIId), (XIb-1), (XId-1), (XIf-1), (XIb-2), (XId-2), and (XIf-2), and pharmaceutically acceptable salts thereof, wherein A and
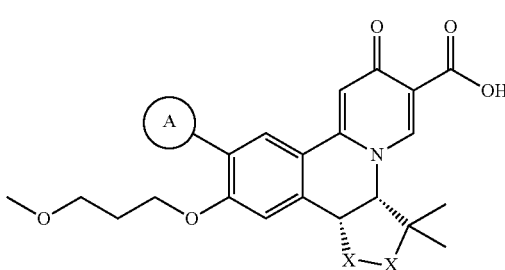
are delineated for each example in Table 1.
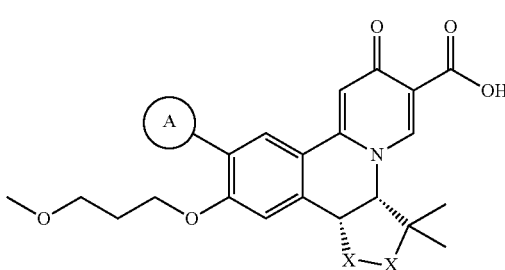
(VIIb)
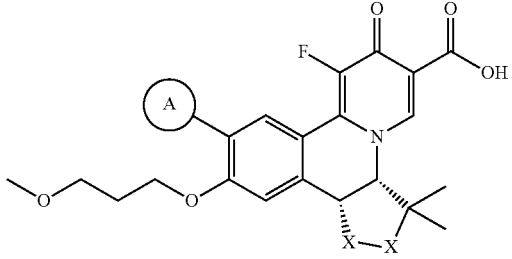
(VIId)
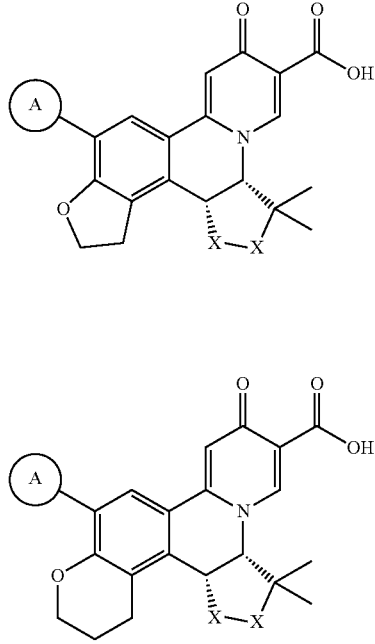
(XIb-1)
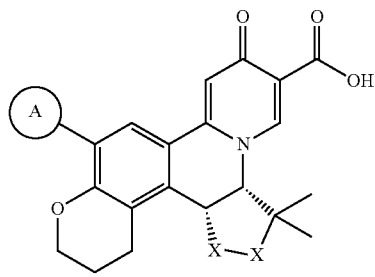
(XId-1)
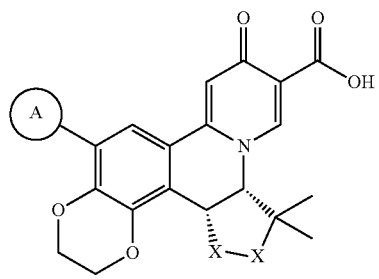
(XIf-1)
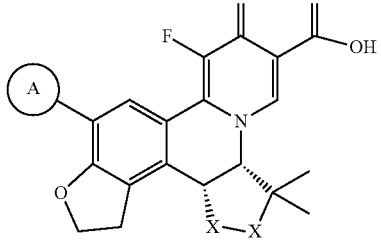
(XIb-2)
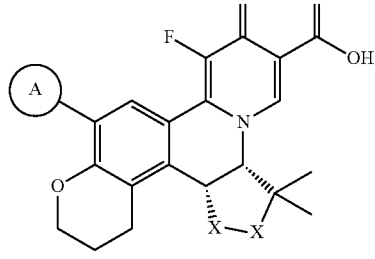
(XId-2)

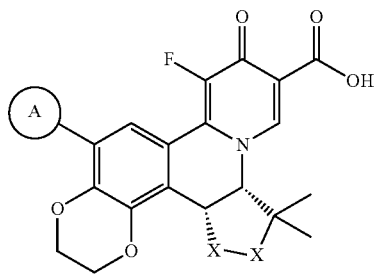
(XIf-2)
TABLE 1
| Entry | A | X—X |
|---|---|---|
| 1 | | |
| 2 | | |
| 3 | | |
| 4 | | |
| 5 | | |
| 6 | | |
TABLE 1-continued
| Entry | A | X—X |
|---|---|---|
| 7 | | |
| 8 | | |
| 9 | | |
| 10 | | |
| 11 | | |
| 12 | | |
| 13 | | |
| 14 | | |
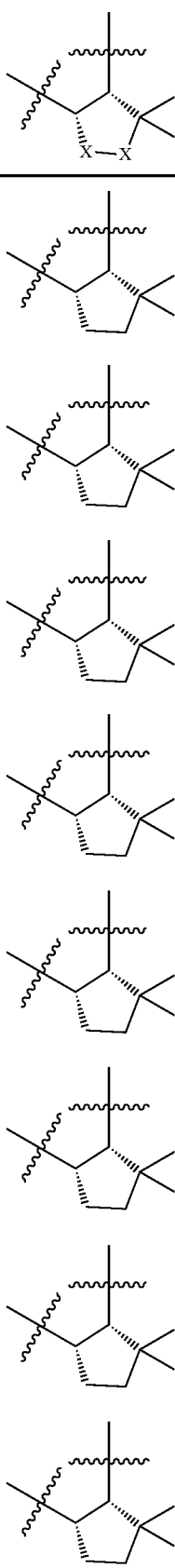

TABLE 1-continued
| Entry | A | 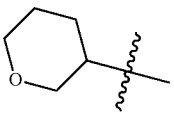 [SMILES: *C1CCCOC1] |
|---|---|---|
| 15 | 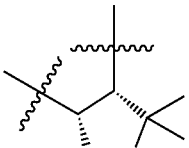 | 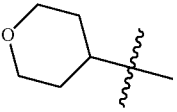 [SMILES: *C1CCOCC1] |
| 16 | 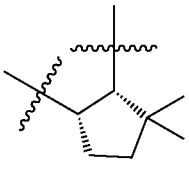 [SMILES: *[C@H]1CCC(C)(C)[C@H]1*] | 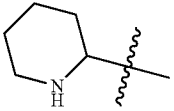 |
| 17 | 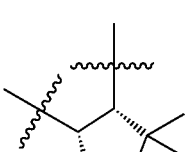 | 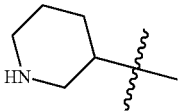 |
| 18 | 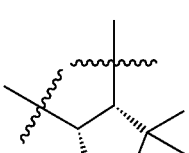 | 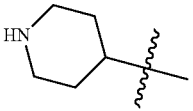 [SMILES: *C1CCNCC1] |
| 19 | 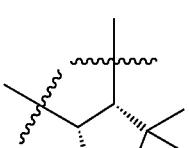 | 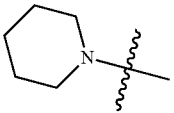 [SMILES: *N1CCCCC1] |
| 20 | 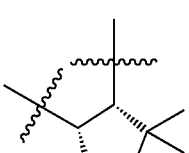 | 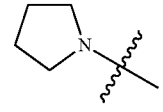 [SMILES: *N1CCCC1] |
| 21 | 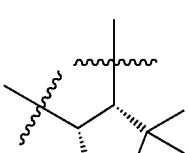 | 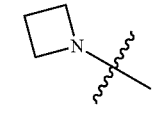 |
| 22 | 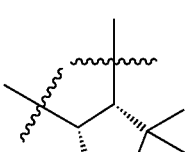 | 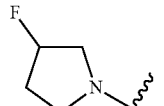 |
| 23 |  | 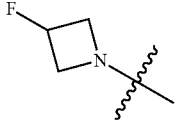 |
| 24 | 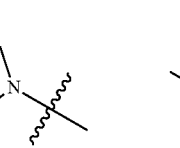 | 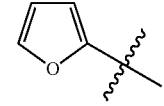 [SMILES: *c1ccco1] |
| 25 | 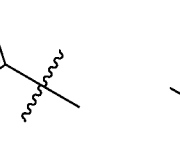 | 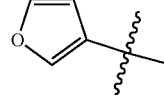 |
| 26 | 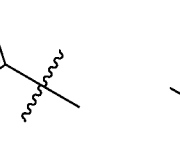 | 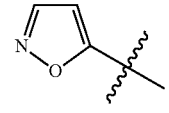 [SMILES: *c1ccno1] |
| 27 | 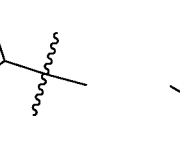 | 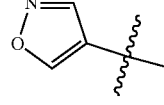 |
| 28 | 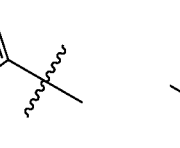 | 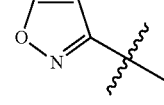 |
| 29 | 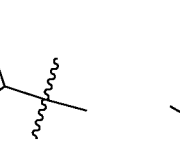 | 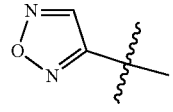 [SMILES: *c1cnon1] |
| 30 | 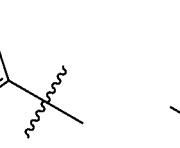 | 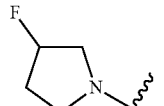 |

TABLE 1-continued

| Entry | A | X—X |
|---|---|---|
| 31 | 1,2,4-oxadiazol-3-yl | cyclopentane structure |
| 32 | isoxazol-5-yl | cyclopentane structure |
| 33 | oxazol-2-yl | cyclopentane structure |
| 34 | 1,3,4-oxadiazol-2-yl | cyclopentane structure |
| 35 | thiophen-2-yl | cyclopentane structure |
| 36 | thiophen-3-yl | cyclopentane structure |
| 37 | isothiazol-3-yl | cyclopentane structure |
| 38 | isothiazol-4-yl | cyclopentane structure |

TABLE 1-continued

| Entry | A | X—X |
|---|---|---|
| 39 | isothiazol-3-yl | cyclopentane structure |
| 40 | 1,2,3-thiadiazol-4-yl | cyclopentane structure |
| 41 | 1,3,4-thiadiazol-2-yl | cyclopentane structure |
| 42 | thiazol-5-yl | cyclopentane structure |
| 43 | thiazol-2-yl | cyclopentane structure |
| 44 | 1,3,4-thiadiazol-2-yl | cyclopentane structure |
| 45 | oxazol-4-yl | cyclopentane structure |
| 46 | 1,3,4-thiadiazol-4-yl | cyclopentane structure |

TABLE 1-continued

| Entry | A | X—X |
|---|---|---|
| 47 | 1H-imidazol-4-yl | cyclopentane (gem-dimethyl) |
| 48 | 1H-imidazol-2-yl | cyclopentane (gem-dimethyl) |
| 49 | 1H-pyrazol-3-yl | cyclopentane (gem-dimethyl) |
| 50 | 4H-1,2,4-triazol-3-yl | cyclopentane (gem-dimethyl) |
| 51 | 1-methyl-1H-pyrazol-3-yl | cyclopentane (gem-dimethyl) |
| 52 | 1H-pyrazol-1-yl | cyclopentane (gem-dimethyl) |
| 53 | 1H-imidazol-1-yl | cyclopentane (gem-dimethyl) |
| 54 | 1H-1,2,3-triazol-1-yl | cyclopentane (gem-dimethyl) |
| 55 | 1H-1,2,4-triazol-1-yl | cyclopentane (gem-dimethyl) |
| 56 | 1H-tetrazol-1-yl | cyclopentane (gem-dimethyl) |
| 57 | 4H-1,2,4-triazol-4-yl | cyclopentane (gem-dimethyl) |
| 58 | 1H-pyrazol-1-yl | cyclopentane (gem-dimethyl) |
| 59 | 1H-imidazol-1-yl | cyclopentane (gem-dimethyl) |
| 60 | 4-fluorophenyl | cyclopentane (gem-dimethyl) |
| 61 | 5-fluoropyridin-2-yl | cyclopentane (gem-dimethyl) |
| 62 | pyridazin-3-yl | cyclopentane (gem-dimethyl) |

TABLE 1-continued
| Entry | A | X—X |
|---|---|---|
| 63 | 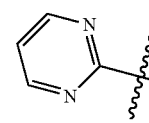 | 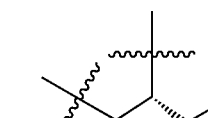 |
| 64 | 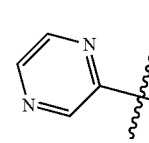 | 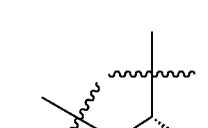 |
| 65 | 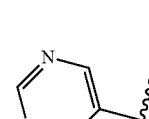 |  |
| 66 | 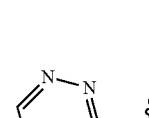 | 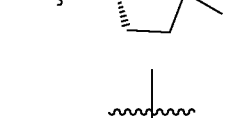 |
| 67 | 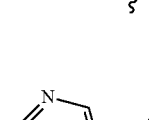 | 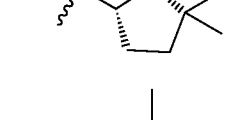 |
| 68 | 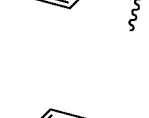 | 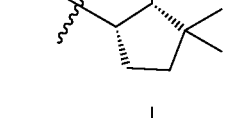 |
| 69 | 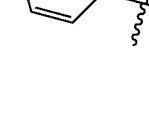 | 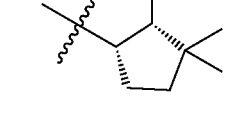 |
| 70 | 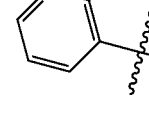 | 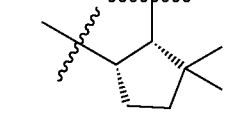 |
| 71 | 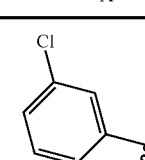 | |
| 72 | 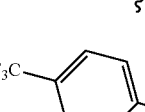 | |
| 73 | 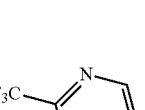 | |
| 74 | 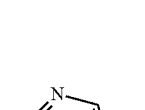 | |
| 75 | 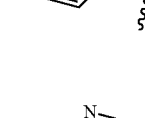 | |
| 76 | 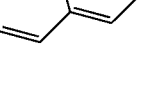 | |
| 77 | 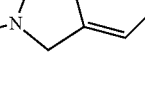 | |
| 78 | 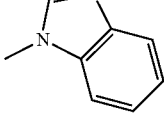 | |

TABLE 1-continued

| Entry | A | X—X |
|---|---|---|
| 79 | benzoxazol-5-yl | cyclopentane |
| 80 | 2-oxoindolin-6-yl | cyclopentane |
| 81 | tetrahydrofuran-2-yl | tetrahydrofuran |
| 82 | tetrahydrofuran-3-yl | tetrahydrofuran |
| 83 | pyrrolidin-2-yl | tetrahydrofuran |
| 84 | pyrrolidin-3-yl | tetrahydrofuran |
| 85 | 1-methylpyrrolidin-3-yl | tetrahydrofuran |
| 86 | oxetan-3-yl | tetrahydrofuran |

TABLE 1-continued

| Entry | A | X—X |
|---|---|---|
| 87 | oxetan-2-yl | tetrahydrofuran |
| 88 | azetidin-3-yl | tetrahydrofuran |
| 89 | azetidin-2-yl | tetrahydrofuran |
| 90 | 1-methylazetidin-3-yl | tetrahydrofuran |
| 91 | 1-methylazetidin-2-yl | tetrahydrofuran |
| 92 | 5-oxopyrrolidin-2-yl | tetrahydrofuran |
| 93 | 5-oxopyrrolidin-3-yl | tetrahydrofuran |
| 94 | tetrahydro-2H-pyran-2-yl | tetrahydrofuran |

TABLE 1-continued
| Entry | A | 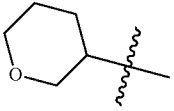 [SMILES: *C1CCCOC1] |
|---|---|---|
| 95 | 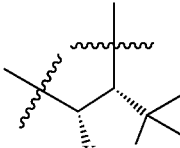 | 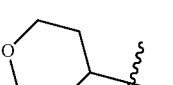 |
| 96 | 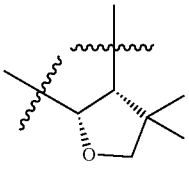 [SMILES: *[C@H]1OCC(C)(C)[C@H]1*] | 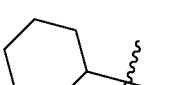 |
| 97 | 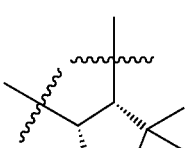 | 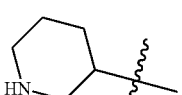 |
| 98 | 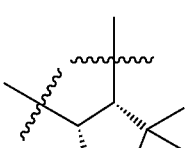 | 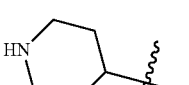 |
| 99 | 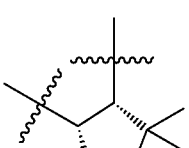 | 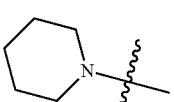 |
| 100 |  | 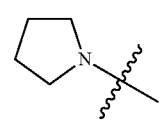 [SMILES: *N1CCCC1] |
| 101 | 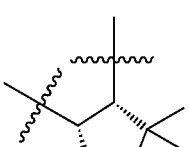 | 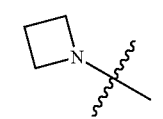 |
| 102 | 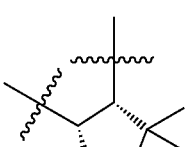 | |
TABLE 1-continued
| Entry | A | 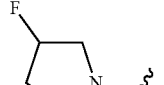 |
|---|---|---|
| 103 | 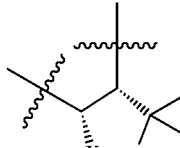 | 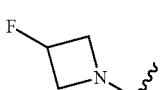 |
| 104 | 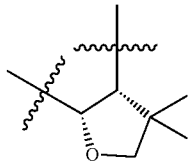 [SMILES: *[C@H]1OCC(C)(C)[C@H]1*] | 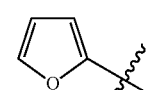 |
| 105 |  | 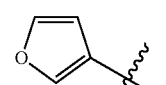 |
| 106 | 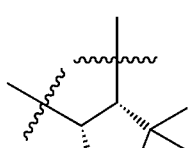 | 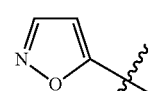 |
| 107 | 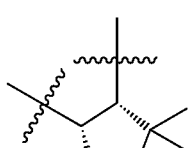 | 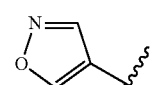 |
| 108 |  | 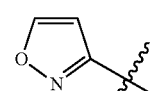 |
| 109 |  | 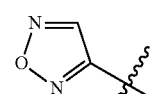 |
| 110 | 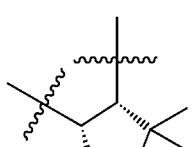 | |

TABLE 1-continued
| Entry | A | 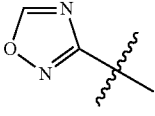 [SMILES: *c1ncon1] | Entry | A | 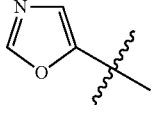 [SMILES: *c1cnco1] |
|---|---|---|---|---|---|
| 111 | 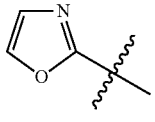 [SMILES: *c1ncco1] | 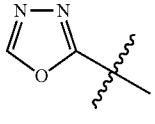 [SMILES: *c1nnco1] | 119 | 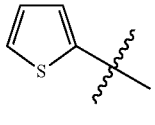 [SMILES: *c1cccs1] | 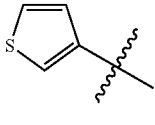 [SMILES: *c1ccsc1] |
| 112 | 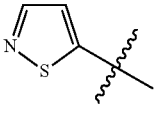 [SMILES: *c1ccns1] | 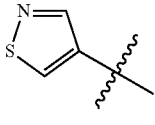 | 120 | 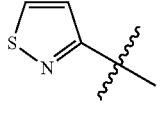 [SMILES: *c1ccsn1] | 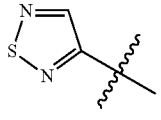 [SMILES: *c1cnsn1] |
| 113 | 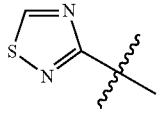 [SMILES: *c1ncsn1] | 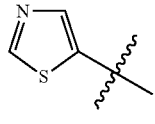 [SMILES: *c1cncs1] | 121 | 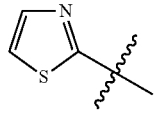 [SMILES: *c1nccs1] | 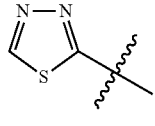 [SMILES: *c1nncs1] |
| 114 | 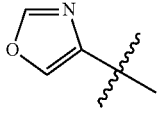 [SMILES: *c1cocn1] | 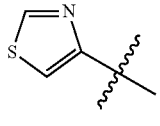 [SMILES: *c1cscn1] | 122 | | |
| 115 | | | 123 | | |
| 116 | | | 124 | | |
| 117 | | | 125 | | |
| 118 | | | 126 | | |

TABLE 1-continued
| Entry | A | 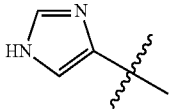 |
|---|---|---|
| 127 | 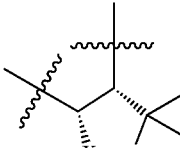 | 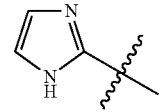 [SMILES: *c1ncc[nH]1] |
| 128 | 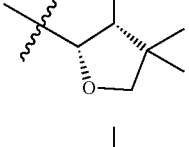 | 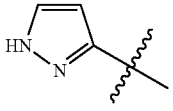 |
| 129 | 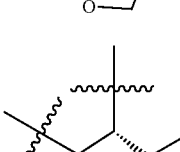 | 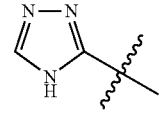 [SMILES: *c1nnc[nH]1] |
| 130 | 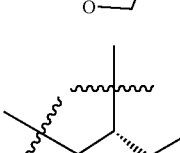 | 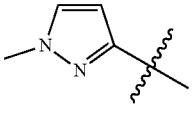 [SMILES: *c1ccn(C)n1] |
| 131 | 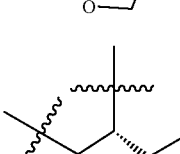 | 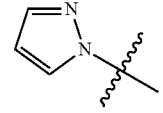 [SMILES: *n1cccn1] |
| 132 | 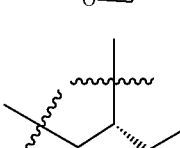 | 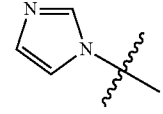 [SMILES: *n1ccnc1] |
| 133 | 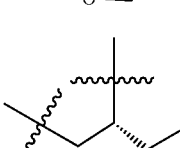 | 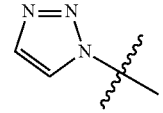 |
| 134 | 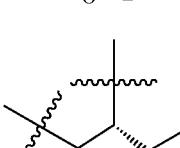 | 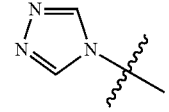 [SMILES: *n1cnnc1] |
TABLE 1-continued
| Entry | A | 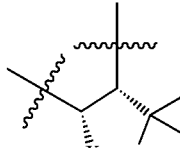 |
|---|---|---|
| 135 | 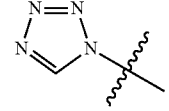 | 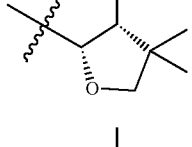 |
| 136 | 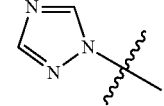 [SMILES: *n1cncn1] | 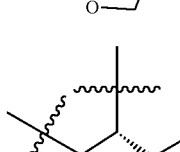 |
| 137 | 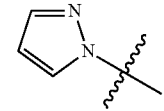 [SMILES: *n1cccn1] | 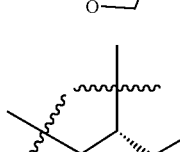 |
| 138 | 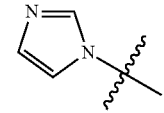 [SMILES: *n1ccnc1] | 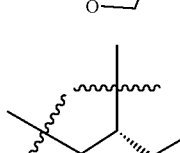 |
| 139 | 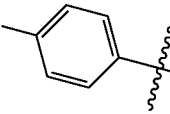 | 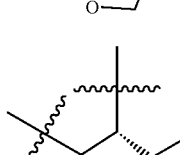 |
| 140 | 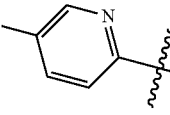 | 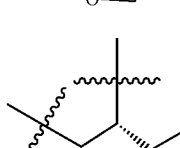 |
| 141 | 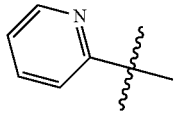 | 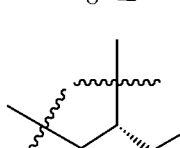 |
| 142 | | |

TABLE 1-continued

| Entry | A | X—X |
|---|---|---|
| 143 | pyrimidin-2-yl | tetrahydrofuran (gem-dimethyl, O) |
| 144 | pyrazin-2-yl | tetrahydrofuran (gem-dimethyl, O) |
| 145 | pyrimidin-5-yl | tetrahydrofuran (gem-dimethyl, O) |
| 146 | pyridazin-3-yl | tetrahydrofuran (gem-dimethyl, O) |
| 147 | pyridin-3-yl | tetrahydrofuran (gem-dimethyl, O) |
| 148 | pyridin-4-yl | tetrahydrofuran (gem-dimethyl, O) |
| 149 | 2-fluoropyridin-3-yl | tetrahydrofuran (gem-dimethyl, O) |
| 150 | 3-fluorophenyl | tetrahydrofuran (gem-dimethyl, O) |
| 151 | 3-chlorophenyl | tetrahydrofuran (gem-dimethyl, O) |
| 152 | 4-(trifluoromethyl)phenyl | tetrahydrofuran (gem-dimethyl, O) |
| 153 | 6-(trifluoromethyl)pyridin-3-yl | tetrahydrofuran (gem-dimethyl, O) |
| 154 | pyridazin-4-yl | tetrahydrofuran (gem-dimethyl, O) |
| 155 | quinolin-3-yl | tetrahydrofuran (gem-dimethyl, O) |
| 156 | 2-methylisoindolin-5-yl | tetrahydrofuran (gem-dimethyl, O) |
| 157 | 1-methyl-1H-indazol-5-yl | tetrahydrofuran (gem-dimethyl, O) |
| 158 | benzofuran-5-yl | tetrahydrofuran (gem-dimethyl, O) |

TABLE 1-continued
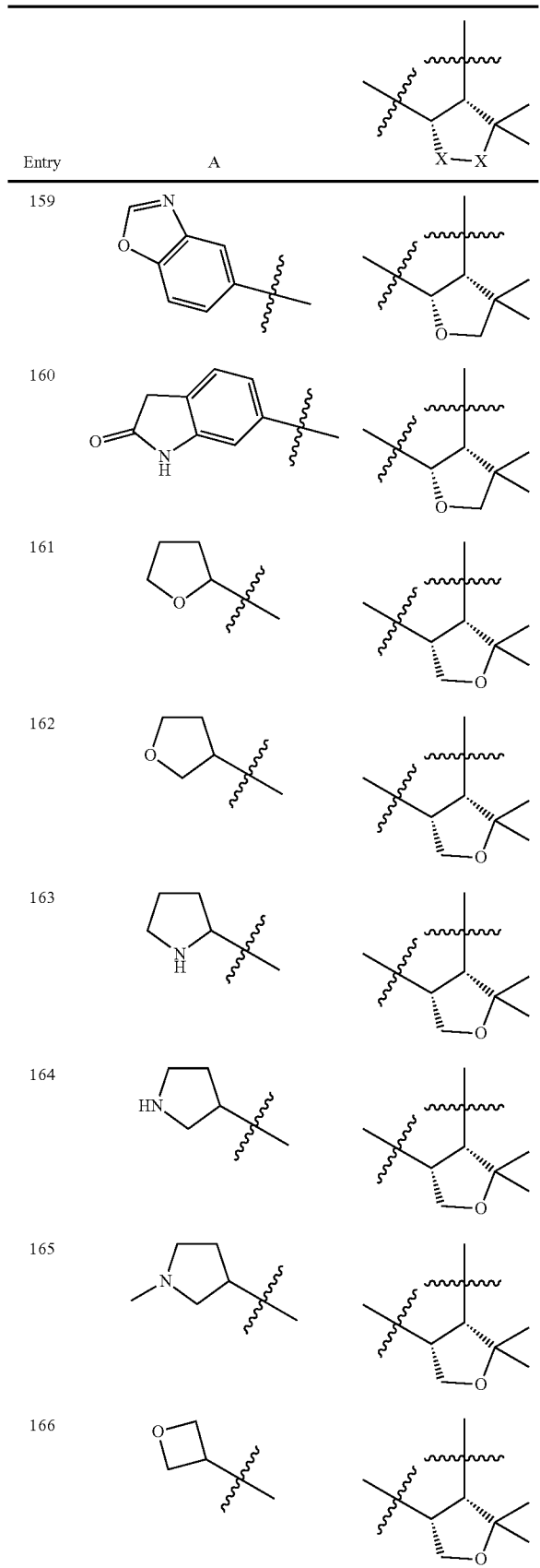
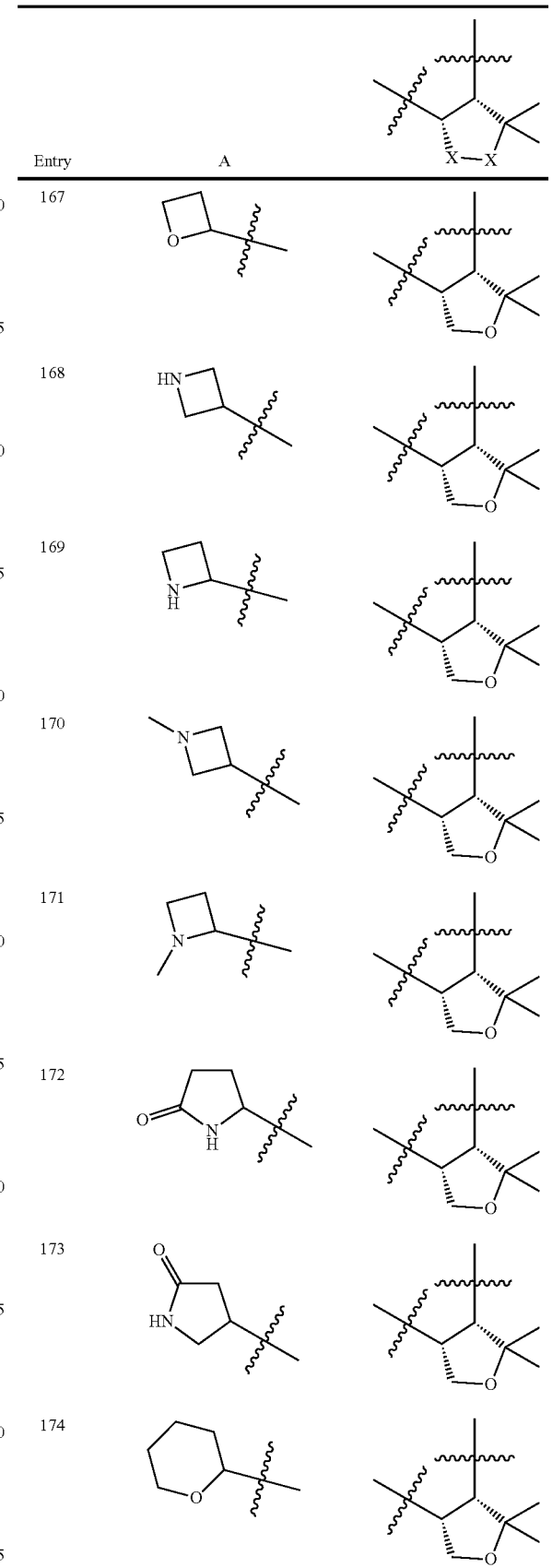

TABLE 1-continued
| Entry | A | X—X |
|---|---|---|
| 175 | 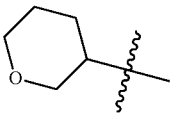 [SMILES: *C1CCCOC1] | 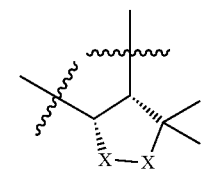 |
| 176 | 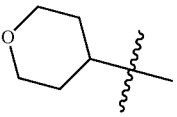 | 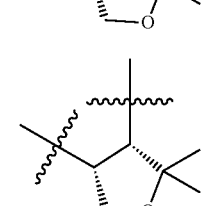 |
| 177 | 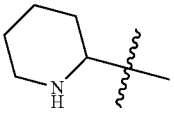 | 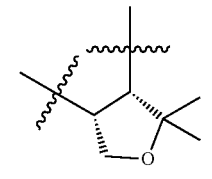 [SMILES: *[C@H]1COC(C)(C)[C@H]1*] |
| 178 | 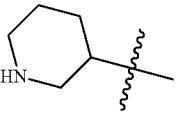 | 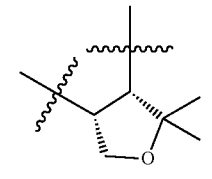 [SMILES: *[C@H]1COC(C)(C)[C@H]1*] |
| 179 | 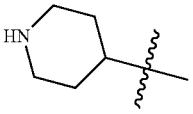 | 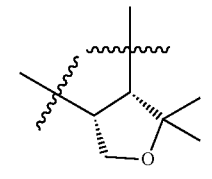 [SMILES: *[C@H]1COC(C)(C)[C@H]1*] |
| 180 | 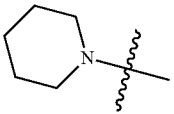 | 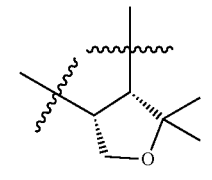 [SMILES: *[C@H]1COC(C)(C)[C@H]1*] |
| 181 | 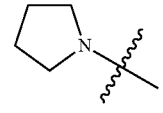 [SMILES: *N1CCCC1] | 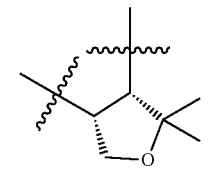 [SMILES: *[C@H]1COC(C)(C)[C@H]1*] |
| 182 | 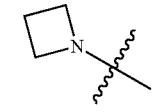 [SMILES: *N1CCC1] | 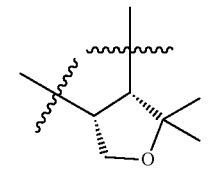 [SMILES: *[C@H]1COC(C)(C)[C@H]1*] |
| 183 | 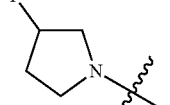 | 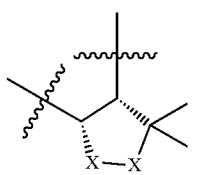 |
| 184 | 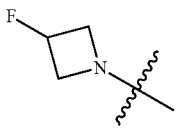 | 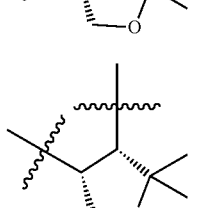 |
| 185 | 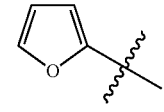 [SMILES: *c1ccco1] | 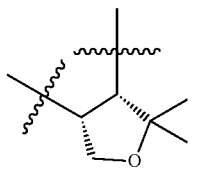 [SMILES: *[C@H]1COC(C)(C)[C@H]1*] |
| 186 | 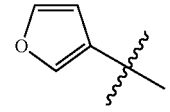 [SMILES: *c1ccoc1] | 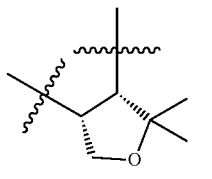 [SMILES: *[C@H]1COC(C)(C)[C@H]1*] |
| 187 | 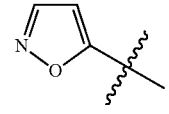 [SMILES: *c1ccno1] | 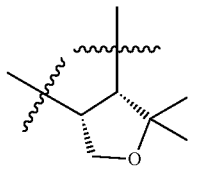 [SMILES: *[C@H]1COC(C)(C)[C@H]1*] |
| 188 | 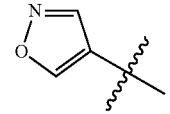 [SMILES: *c1cnoc1] | 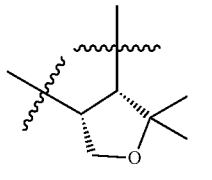 [SMILES: *[C@H]1COC(C)(C)[C@H]1*] |
| 189 | 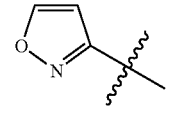 [SMILES: *c1ccon1] | 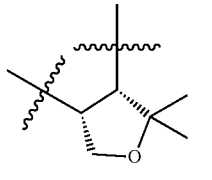 [SMILES: *[C@H]1COC(C)(C)[C@H]1*] |
| 190 | 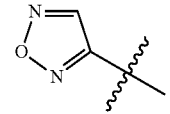 | 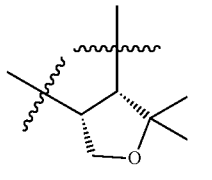 [SMILES: *[C@H]1COC(C)(C)[C@H]1*] |

TABLE 1-continued

| Entry | A | X—X |
|---|---|---|
| 191 | 1,2,4-oxadiazol-3-yl | tetrahydrofuran-gem-dimethyl |
| 192 | oxazol-5-yl | tetrahydrofuran-gem-dimethyl |
| 193 | oxazol-2-yl | tetrahydrofuran-gem-dimethyl |
| 194 | 1,3,4-oxadiazol-2-yl | tetrahydrofuran-gem-dimethyl |
| 195 | thien-2-yl | tetrahydrofuran-gem-dimethyl |
| 196 | thien-3-yl | tetrahydrofuran-gem-dimethyl |
| 197 | isothiazol-5-yl | tetrahydrofuran-gem-dimethyl |
| 198 | isothiazol-4-yl | tetrahydrofuran-gem-dimethyl |

TABLE 1-continued

| Entry | A | X—X |
|---|---|---|
| 199 | isothiazol-3-yl | tetrahydrofuran-gem-dimethyl |
| 200 | 1,2,3-thiadiazol-4-yl | tetrahydrofuran-gem-dimethyl |
| 201 | 1,3,4-thiadiazol-2-yl | tetrahydrofuran-gem-dimethyl |
| 202 | thiazol-5-yl | tetrahydrofuran-gem-dimethyl |
| 203 | thiazol-2-yl | tetrahydrofuran-gem-dimethyl |
| 204 | 1,3,4-thiadiazol-2-yl | tetrahydrofuran-gem-dimethyl |
| 205 | oxazol-4-yl | tetrahydrofuran-gem-dimethyl |
| 206 | thiazol-4-yl | tetrahydrofuran-gem-dimethyl |

TABLE 1-continued

| Entry | A | X—X |
|---|---|---|
| 207 | imidazole (4-yl) | tetrahydrofuran-gem-dimethyl |
| 208 | imidazol-2-yl | tetrahydrofuran-gem-dimethyl |
| 209 | pyrazol-3-yl (NH) | tetrahydrofuran-gem-dimethyl |
| 210 | 1,2,4-triazol-3-yl (NH) | tetrahydrofuran-gem-dimethyl |
| 211 | 1-methylpyrazol-3-yl | tetrahydrofuran-gem-dimethyl |
| 212 | pyrazol-1-yl | tetrahydrofuran-gem-dimethyl |
| 213 | imidazol-1-yl | tetrahydrofuran-gem-dimethyl |
| 214 | 1,2,3-triazol-1-yl | tetrahydrofuran-gem-dimethyl |
| 215 | 1,2,4-triazol-1-yl | tetrahydrofuran-gem-dimethyl |
| 216 | tetrazol-1-yl | tetrahydrofuran-gem-dimethyl |
| 217 | 1,2,4-triazol-1-yl (isomer) | tetrahydrofuran-gem-dimethyl |
| 218 | pyrazol-1-yl (isomer) | tetrahydrofuran-gem-dimethyl |
| 219 | imidazol-1-yl (isomer) | tetrahydrofuran-gem-dimethyl |
| 220 | 4-fluorophenyl | tetrahydrofuran-gem-dimethyl |
| 221 | 5-fluoropyridin-2-yl | tetrahydrofuran-gem-dimethyl |
| 222 | pyridazin-3-yl | tetrahydrofuran-gem-dimethyl |

TABLE 1-continued
| Entry | A | 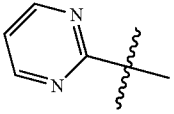 [SMILES: *c1ncccn1] |
|---|---|---|
| 223 | 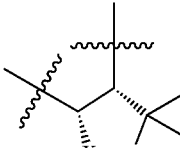 | 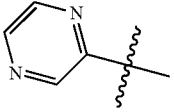 |
| 224 | 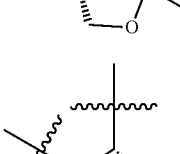 | 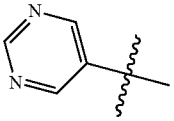 |
| 225 | 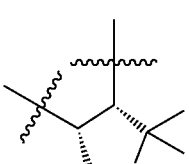 | 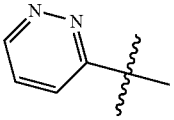 [SMILES: *c1cccnn1] |
| 226 | 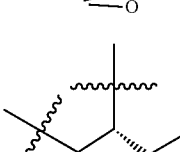 | 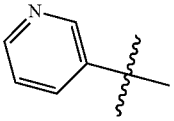 [SMILES: *c1cccnc1] |
| 227 | 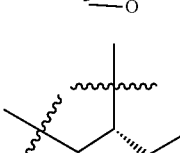 | 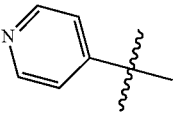 |
| 228 | 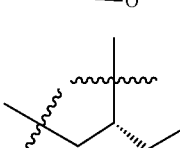 | 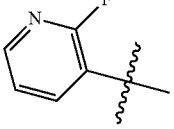 |
| 229 | 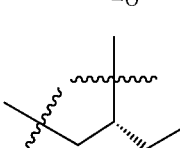 | 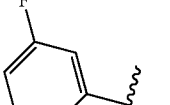 |
| 230 | 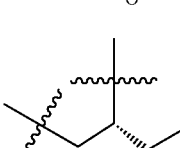 | 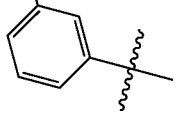 |
TABLE 1-continued
| Entry | A | 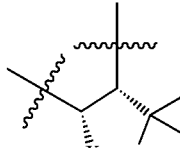 |
|---|---|---|
| 231 | 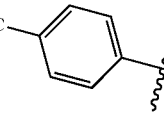 | 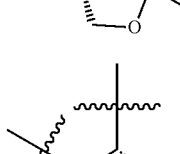 |
| 232 | 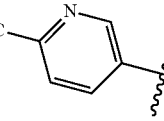 | 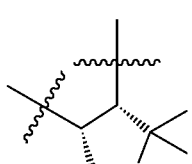 |
| 233 | 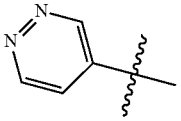 [SMILES: *c1ccnnc1] | 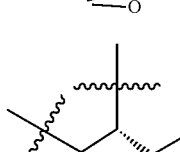 |
| 234 | 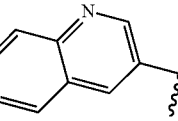 | 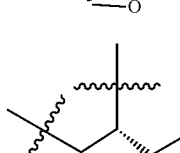 |
| 235 | 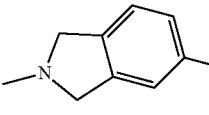 | 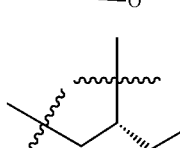 |
| 236 | 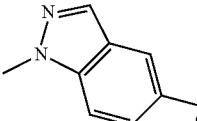 | 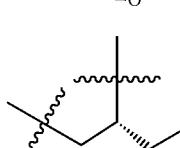 |
| 237 | 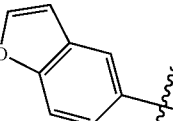 | 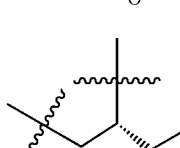 |
| 238 | | |

TABLE 1-continued

| Entry | A | X—X |
|---|---|---|
| 239 | benzoxazol-5-yl | tetrahydrofuran-gem-dimethyl |
| 240 | 2-oxoindolin-6-yl | tetrahydrofuran-gem-dimethyl |
| 241 | 3,3-difluoroazetidin-1-yl | cyclopentane-gem-dimethyl |
| 242 | 3,3-difluoroazetidin-1-yl | tetrahydrofuran-gem-dimethyl |
| 243 | 3,3-difluoroazetidin-1-yl | tetrahydrofuran-gem-dimethyl |
| 244 | 3,3-difluoropyrrolidin-1-yl | cyclopentane-gem-dimethyl |
| 245 | 3,3-difluoropyrrolidin-1-yl | tetrahydrofuran-gem-dimethyl |
| 246 | 3,3-difluoropyrrolidin-1-yl | tetrahydrofuran-gem-dimethyl |

Representative compounds of the invention include, but are not limited to, the following compounds according to Formula (VIIa), (VIIc), (XIa-1), (XIc-1), (XIe-1), (XIa-2), (XIc-2), and (XIe-2), and pharmaceutically acceptable salts thereof, wherein A is delineated for each example in Table 2.

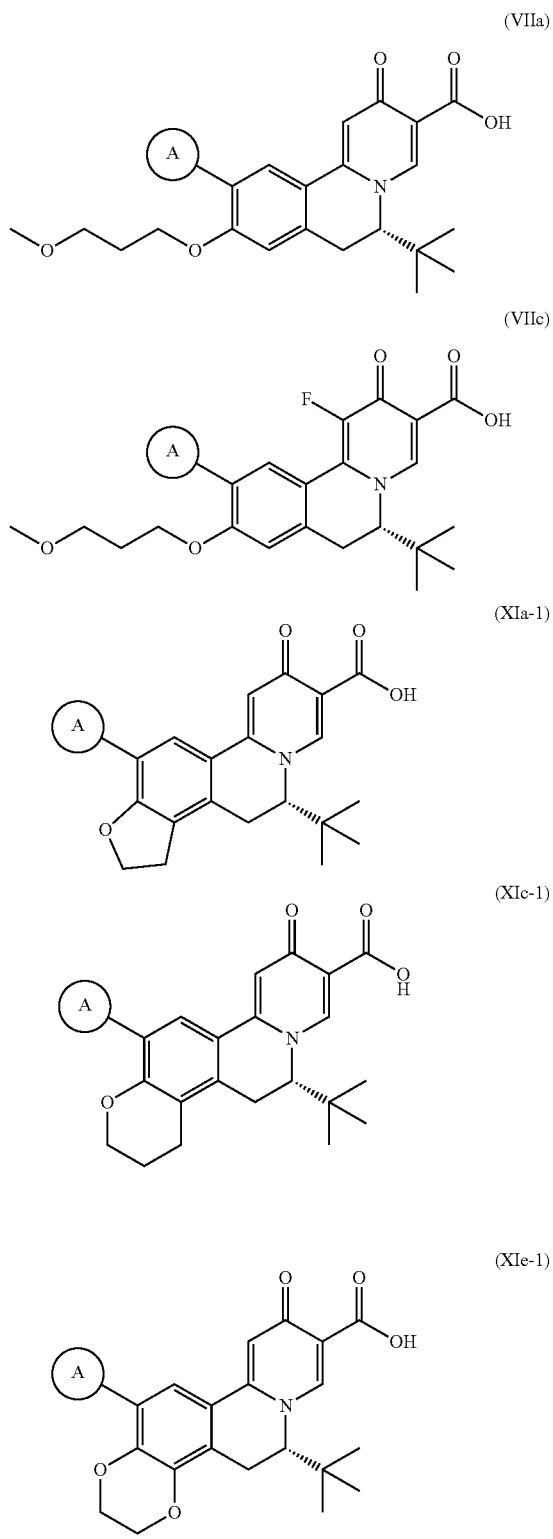

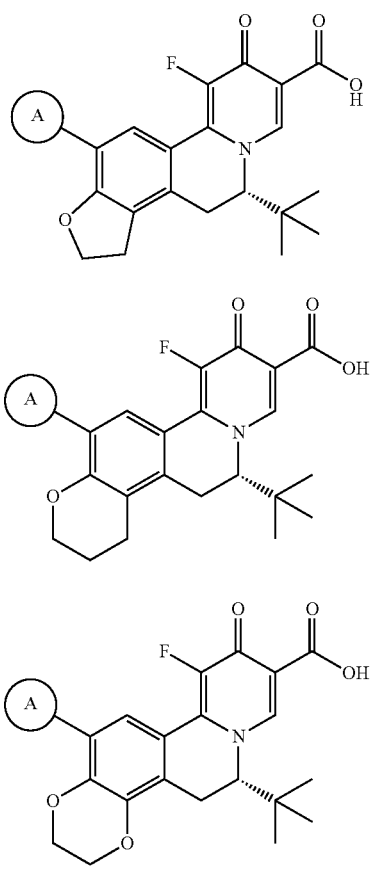
| TABLE 2 |  |
|---|---|
| Entry | A |
| 1 | tetrahydrofuran-2-yl |
| 2 | tetrahydrofuran-3-yl |
| 3 | pyrrolidin-2-yl |
| 4 | pyrrolidin-3-yl |
| 5 | 1-methylpyrrolidin-3-yl |
| 6 | oxetan-3-yl |
| 7 | oxetan-2-yl |
| 8 | azetidin-3-yl |
| 9 | azetidin-2-yl |
| 10 | 1-methylazetidin-3-yl |
| 11 | 1-methylazetidin-2-yl |
| 12 | 5-oxopyrrolidin-2-yl |
| 13 | 2-oxopyrrolidin-4-yl |
| 14 | tetrahydropyran-2-yl |
| 15 | tetrahydropyran-3-yl |
| 16 | tetrahydropyran-4-yl |
| 17 | piperidin-2-yl |

TABLE 2-continued

| Entry | A |
|---|---|
| 18 | 3-piperidinyl (HN) |
| 19 | 4-piperidinyl (HN) |
| 20 | piperidin-1-yl |
| 21 | pyrrolidin-1-yl |
| 22 | azetidin-1-yl |
| 23 | 3-fluoropyrrolidin-1-yl |
| 24 | 3-fluoroazetidin-1-yl |
| 25 | furan-2-yl |
| 26 | furan-3-yl |
| 27 | isoxazol-5-yl |
| 28 | isoxazol-4-yl |
| 29 | isoxazol-3-yl |
| 30 | 1,2,5-oxadiazol-3-yl |
| 31 | 1,3,4-oxadiazol-2-yl |
| 32 | oxazol-5-yl |
| 33 | oxazol-2-yl |
| 34 | 1,3,4-oxadiazol-2-yl |
| 35 | thiophen-2-yl |
| 36 | thiophen-3-yl |
| 37 | isothiazol-5-yl |
| 38 | isothiazol-4-yl |
| 39 | isothiazol-3-yl |
| 40 | 1,2,3-thiadiazol-4-yl |
| 41 | 1,3,4-thiadiazol-2-yl |
| 42 | thiazol-2-yl |

TABLE 2-continued

| Entry | A |
|---|---|
| 43 | thiazol-2-yl |
| 44 | 1,3,4-thiadiazol-2-yl |
| 45 | oxazol-4-yl |
| 46 | 1,3,4-thiadiazol-2-yl (isomer) |
| 47 | 1H-imidazol-4-yl |
| 48 | 1H-imidazol-2-yl |
| 49 | 1H-pyrazol-3-yl |
| 50 | 4H-1,2,4-triazol-3-yl |
| 51 | 1-methyl-1H-pyrazol-3-yl |
| 52 | 1H-pyrazol-1-yl |
| 53 | 1H-imidazol-1-yl |
| 54 | 1H-1,2,3-triazol-1-yl |
| 55 | 4H-1,2,4-triazol-4-yl |
| 56 | 1H-tetrazol-1-yl |
| 57 | 1H-1,2,4-triazol-1-yl |
| 58 | 1H-pyrazol-1-yl |
| 59 | 1H-imidazol-1-yl |
| 60 | 4-fluorophenyl |
| 61 | 5-fluoropyridin-2-yl |
| 62 | pyridin-2-yl |
| 63 | pyrimidin-2-yl |
| 64 | 1,2,4-triazin-3-yl |
| 65 | pyrazin-2-yl |
| 66 | pyridazin-3-yl |

TABLE 2-continued

| Entry | A |
|---|---|
| 67 | 3-pyridyl |
| 68 | 4-pyridyl |
| 69 | 2-fluoropyridin-3-yl |
| 70 | 3-fluorophenyl |
| 71 | 3-chlorophenyl |
| 72 | 4-(trifluoromethyl)phenyl |
| 73 | 6-(trifluoromethyl)pyridin-3-yl |
| 74 | pyridazin-4-yl |
| 75 | quinolin-3-yl |
| 76 | 2-methylisoindolin-5-yl |
| 77 | 1-methyl-1H-indazol-5-yl |
| 78 | benzofuran-5-yl |
| 79 | benzo[d]oxazol-5-yl |
| 80 | 2-oxoindolin-6-yl |
| 81 | 3,3-difluoroazetidin-1-yl |
| 82 | 3,3-difluoropyrrolidin-1-yl |

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from core inhibitor, which includes GLS4, GLS4JHS, JNJ-379, ABI-H0731, ABI-H2158, AB-423, AB-506, WX-066, and QL-OA6A; immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or STING (stimulator of interferon genes) modulator; or TLR modulators such as TLR-7 agonists, TLR-8 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein, or RNA interence (RNAi) or small interfering RNA (siRNA) such as ARC-520, ARC-521, ARB-1467, and ALN-HBV RNAi, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139, RG7834, and AB-452. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl]amino Imethyl)phenyl]acetate), GS-9620 (4-Amino-2-butoxy-8-[3-(1-pyrrolidinylmethyl)benzyl]-7,8-dihydro-6 (5H)-pteridinone), AL-034 (TQ-A3334), and RO6864018.

In another embodiment of the combination therapy, the TLR-8 agonist is GS-9688.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds.

Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs. For example, an alkyl group which has an open valence on two different carbon atoms can also be referred to as an alkylene group.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$-aryl, CO$_2$-heteroaryl, CO$_2$-heterocyloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-

$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; NH$_2$; $C_1$-$C_4$-alkylamino; di($C_1$-$C_4$-alkyl)amino; and NO$_2$. It is understood that the aryls, heteroaryls, alkyls, and the like can be further substituted. In some cases, each substituent in a substituted moiety is additionally optionally substituted when possible with one or more groups, each group being independently selected from $C_1$-$C_4$-alkyl; —CF$_3$, —OCH$_3$, —OCF$_3$, —F, —Cl, —Br, —I, —OH, —NO$_2$, —CN, and —NH$_2$. Preferably, a substituted alkyl group, such as a substituted methyl group, is substituted with one or more halogen atoms, more preferably one or more fluorine or chlorine atoms.

The term "halo" or "halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, Prodrugs, *Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2$^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Combination and Alternation Therapy

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), (3-D-dioxolanyl-guanine (DXG), P3-D-dioxolanyl-2,6-diaminopurine (DAPD), and (3-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluorophosphate; Brine for sodium chloride solution in water; BSA for N,O-bis(trimethylsilyl)acetamide; CDI for carbonyldiimidazole; DCM or CH$_2$Cl$_2$ for dichloromethane; CH$_3$ for methyl; CH$_3$CN or ACN for acetonitrile; Cs$_2$CO$_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-un-dec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylamino-pyridine; DCE for 1,2-dichloroethane; DMA for N,N-dimethylacetamide; DME for 1,2-dimethoxyethane; DMF for N,N-dimethylformamide; DMSO for dimethyl sulfoxide; DMT for di(p-methoxyphenyl)-phenylmethyl or dimethoxy-trityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc or EA for ethyl acetate; EtOH for ethanol; $Et_2O$ for diethyl ether; HATU for O-(7-azabenzotriazol-1-yl)-N,N,N',N'-tetramethyluronium Hexafluoro-phosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; DDQ for 2,3-dichloro-5,6-dicyano-1,4-benzoquinone; PhLi for phenyl lithium; LDA for lithium diisopropylamide; LiTMP for lithium 2,2,6,6-tetramethyl-piperidinate; mCPBA or m-CPBA for meta-chloroperbenzoic acid; MeOH for methanol; Mg for magnesium; MOM for methoxymethyl; Ms for mesyl or $-SO_2-CH_3$; $Ms_2O$ for methanesulfonic anhydride or mesyl-anhydride; MTBE for t-butyl methyl ether; $NaN(TMS)_2$ or NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMO for N-methylmorpholine N-oxide; $NaIO_4$ for sodium periodate; Ni for nickel; OH for hydroxyl; $OsO_4$ for osmium tetroxide; PPA for polyphosphoric acid; p-TSA or PTSA for p-toluenesulfonic acid; PPTS for pyridinium p-toluenesulfonate; $PhI(OPiv)_2$ for Bis(tert-butylcarbonyloxy)iodobenzene; $Rh_2(Esp)_2$ for Bis[rhodium($\alpha,\alpha,\alpha',\alpha'$-tetramethyl-1,3-benzenedipropionic acid)]; TBAF for tetrabutylammonium fluoride; TEA or $Et_3N$ for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or $PPh_3$ for triphenyl-phosphine; Troc for 2,2,2-trichloroethyl carbonyl; Ts for tosyl or $-SO_2-C_6H_4CH_3$; $Ts_2O$ for tolylsulfonic anhydride or tosyl-anhydride; TsOH for p-tolylsulfonic acid; Tf for triflate; LCMS for liquid chromatography mass spectrometry; TLC for thin layer chromatography; PE for petroleum ether; TFAA for trifluoroacetic anhydride; THP for tetrahydropyranyl; MS for mass spectrometry; ESI for electrospray ionization; RPHPLC for reverse phase high performance liquid chromatography; Pd for palladium; Ph for phenyl; POPd for dihydrogen dichlorobis(di-tert-butylphosphinito-KP)palladate(II); $Pd_2(dba)_3$ for tris(dibenzylideneacetone) dipalladium (0); $Pd(PPh_3)_4$ for tetrakis(triphenylphosphine)-palladium (0); $PdCl_2(PPh_3)_2$ for trans-dichlorobis(triphenylphosphine)palladium (II); Pt for platinum; Rh for rhodium; rt for room temperature; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

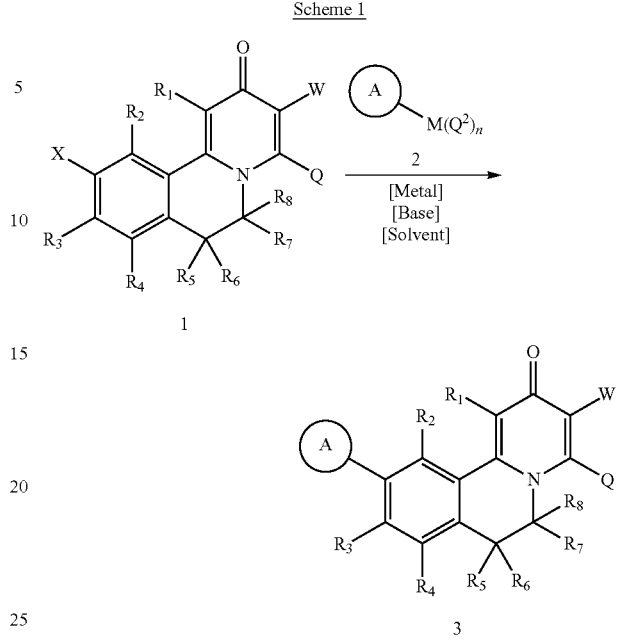

Scheme 1

Illustrated in Scheme 1, intermediate compounds such as 1 can be produced as described in U.S. Pat. No. 9,458,153; WO 2017/140821; WO 2017/017042; CN 106810548A; or Schemes 2a, 2b, 3a, 3b, 4a, 4b, 5a, 5b, 6a, or 6b. Compounds such as intermediate 1 ($R_1$, $R_2$, $R_3$, $R_4$, $R_5$, $R_6$, $R_7$, $R_8$, Q, and W as defined previously; X defined as —Cl, —Br, —I, or —OTf) can be reacted directly in a cross-coupling reaction with compounds such as intermediate 2 (A as defined previously; M defined as a boron, tin, or hydrogen atom; $Q^2$ defined as —OH, —OR, —R, or halogen; n equal to 0, 1, 2, or 3) whereby intermediate 2 is commercially available or can be prepared by those familiar with the skill of the arts. The stated cross-coupling reaction can be mediated by a metal-based reagent (denoted as [Metal] in Scheme 1) including, but not limited to: $Pd(OAc)_2$, $PdCl_2(dppf)$, $Pd(Ph_3P)_4$, $Pd_2(dba)_3$, PdRuPhos G2, or Pd$^t$BuXPhos G3. The stated cross-coupling reaction can also be mediated by a base (denoted as [Base] in Scheme 1) including, but not limited to: $Cs_2CO_3$, $K_2CO_3$, $Na_2CO_3$, CsF, KOAc, $K_3PO_4$, $Et_3N$, or DBU. The stated cross-coupling reaction can be performed in a solvent or a mixture of solvents (denoted as [Solvent] in Scheme 1) including, but not limited to: THF, toluene, benzene, DMF, DMA, 1,4-dioxane, or water. The stated cross-coupling reaction can be performed at a temperature range between 0° C. and 180° C. where appropriate.

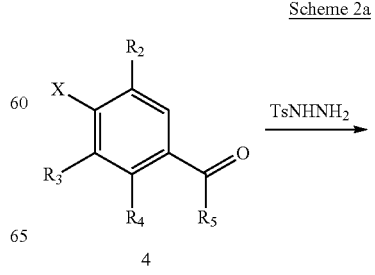

Scheme 2a

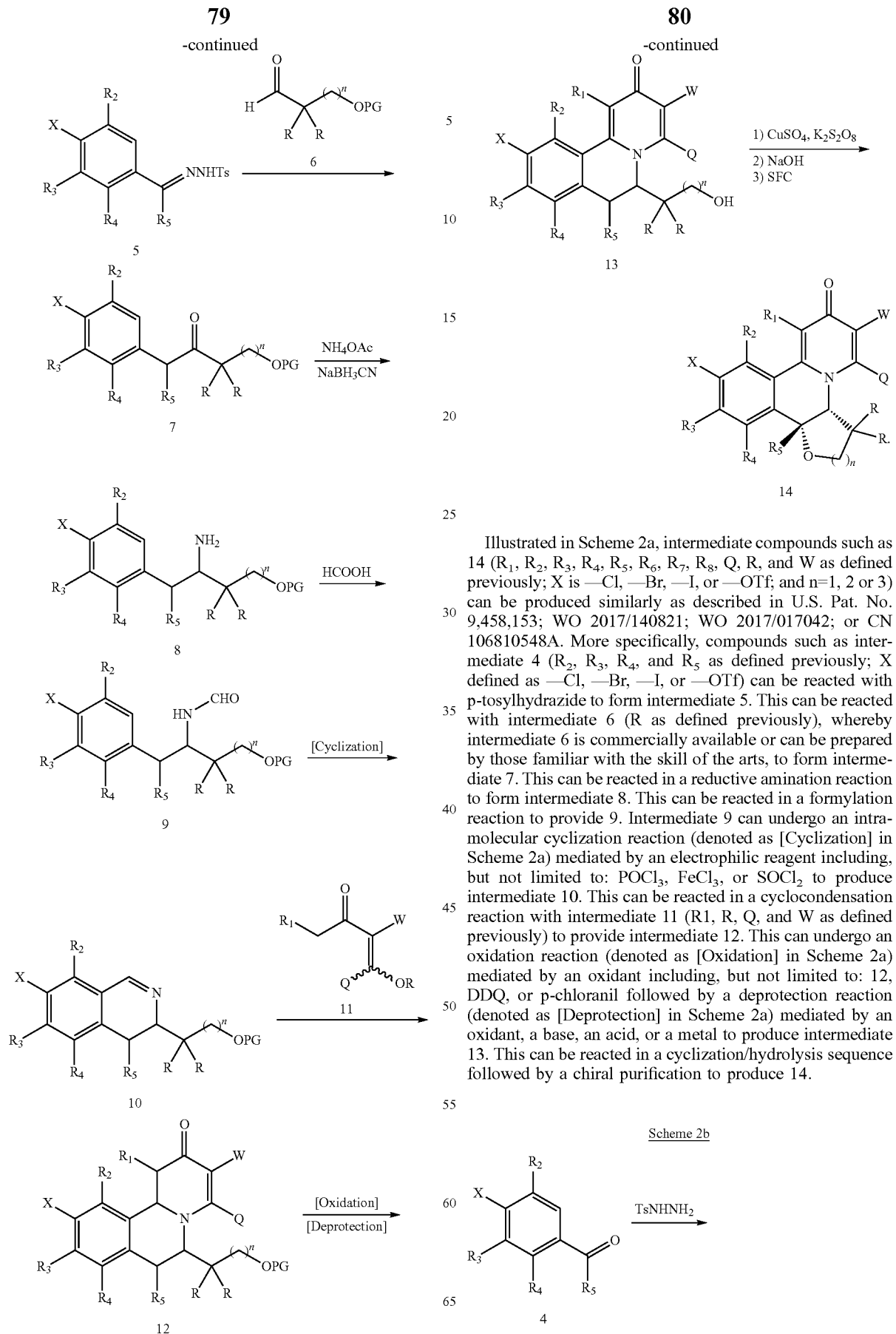

Illustrated in Scheme 2a, intermediate compounds such as 14 ($R_1$, $R_2$, $R_3$, $R_4$, $R_5$, $R_6$, $R_7$, $R_8$, Q, R, and W as defined previously; X is —Cl, —Br, —I, or —OTf; and n=1, 2 or 3) can be produced similarly as described in U.S. Pat. No. 9,458,153; WO 2017/140821; WO 2017/017042; or CN 106810548A. More specifically, compounds such as intermediate 4 ($R_2$, $R_3$, $R_4$, and $R_5$ as defined previously; X defined as —Cl, —Br, —I, or —OTf) can be reacted with p-tosylhydrazide to form intermediate 5. This can be reacted with intermediate 6 (R as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 2a) mediated by an electrophilic reagent including, but not limited to: $POCl_3$, $FeCl_3$, or $SOCl_2$ to produce intermediate 10. This can be reacted in a cyclocondensation reaction with intermediate 11 (R1, R, Q, and W as defined previously) to provide intermediate 12. This can undergo an oxidation reaction (denoted as [Oxidation] in Scheme 2a) mediated by an oxidant including, but not limited to: 12, DDQ, or p-chloranil followed by a deprotection reaction (denoted as [Deprotection] in Scheme 2a) mediated by an oxidant, a base, an acid, or a metal to produce intermediate 13. This can be reacted in a cyclization/hydrolysis sequence followed by a chiral purification to produce 14.

-continued

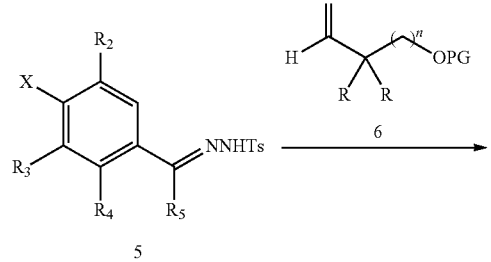

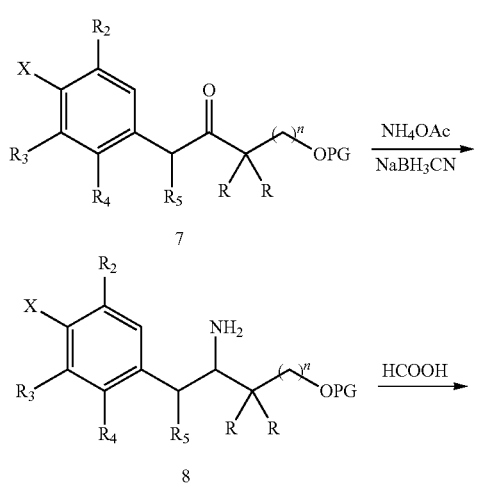

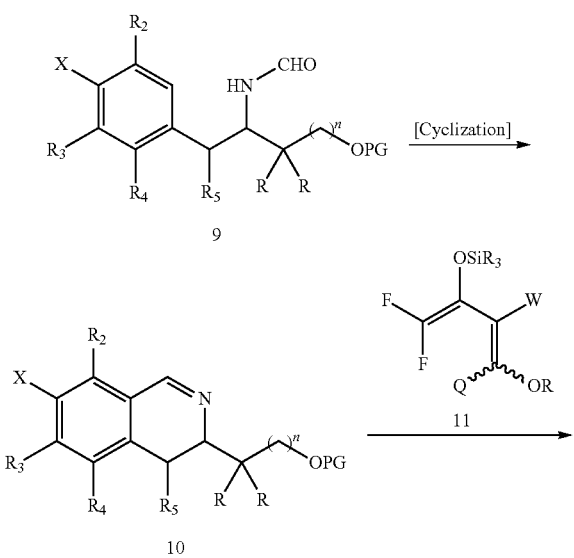

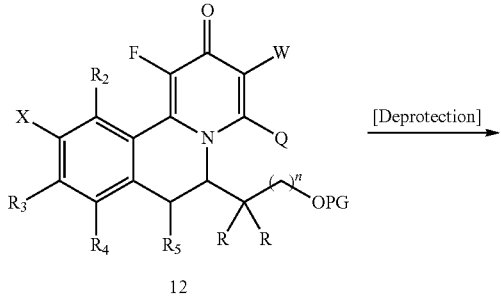

-continued

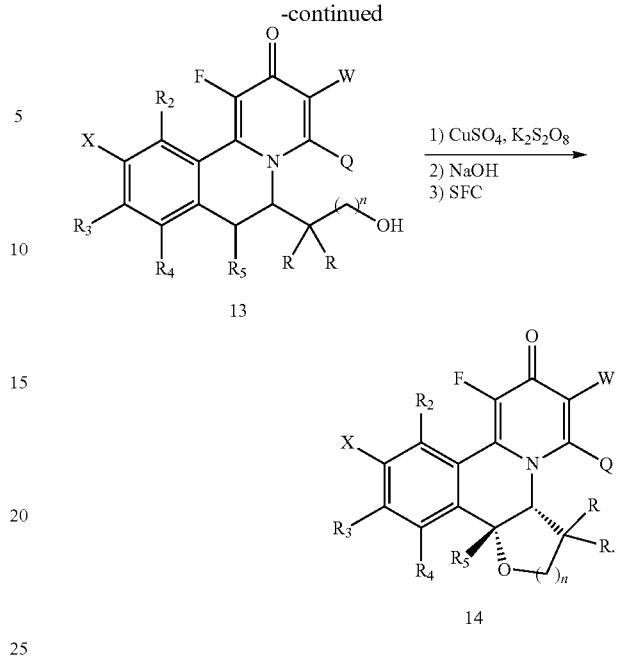

Illustrated in Scheme 2b, intermediate compounds such as 14 ($R_2$, $R_3$, $R_4$, $R_5$, $R_6$, $R_7$, $R_8$, Q, R, and W as defined previously; X defined as —Cl, —Br, —I, or —OTf; n=1, 2 or 3) can be produced similarly as described in U.S. Pat. No. 9,458,153; WO 2017/140821; WO 2017/017042; or CN 106810548A. More specifically, compounds such as intermediate 4 ($R_2$, $R_3$, $R_4$, and $R_5$ as defined previously; X defined as —Cl, —Br, —I, or —OTf) can be reacted with p-tosylhydrazide to form intermediate 5. This can be reacted with intermediate 6 (R as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 2b) mediated by an electrophilic reagent including, but not limited to: $POCl_3$, $FeCl_3$, or $SOCl_2$ to produce intermediate 10. This can be reacted in a cyclocondensation reaction with intermediate 11 (R, Q, and W as defined previously) to provide intermediate 12. This can undergo a deprotection reaction (denoted as [Deprotection] in Scheme 2b) mediated by an oxidant, a base, an acid, or a metal to produce intermediate 13. This can be reacted in a cyclization/hydrolysis sequence followed by a chiral purification to produce 14.

Scheme 3a

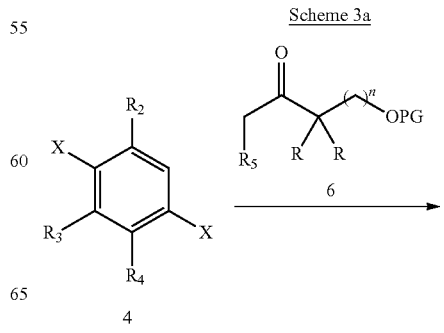

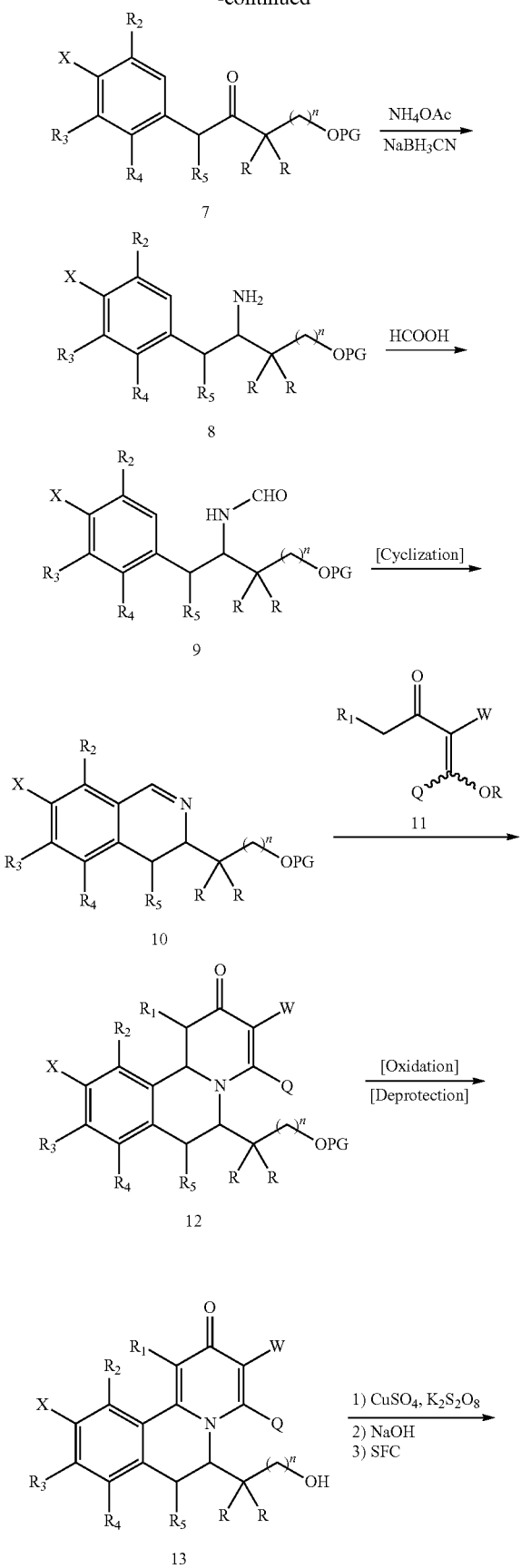

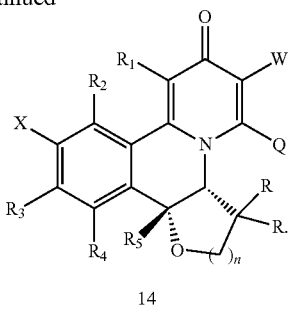

14

Illustrated in Scheme 3a, intermediate compounds such as 14 ($R_1$, $R_2$, $R_3$, $R_4$, $R_5$, $R_6$, $R_7$, $R_8$, Q, R, and W as defined previously; X defined as —Cl, —Br, —I, or —Otf; n=1, 2 or 3) can be produced similarly as described in U.S. Pat. No. 9,458,153; WO 2017/140821; WO 2017/017042; or CN 106810548A. More specifically, compounds such as intermediate 4 ($R_2$, $R_3$, and $R_4$ as defined previously; X defined as —Cl, —Br, —I, or —OTf) can be reacted in an enolate coupling reaction with intermediate 6 ($R_5$ and R as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 3a) mediated by an electrophilic reagent including, but not limited to: $POCl_3$, $FeCl_3$, or $SOCl_2$ to produce intermediate 10. This can be reacted in a cyclocondensation reaction with intermediate 11 ($R_1$, R, Q, and W as defined previously) to provide intermediate 12. This can undergo an oxidation reaction (denoted as [Oxidation] in Scheme 3a) mediated by an oxidant including, but not limited to: 12, DDQ, or p-chloranil followed by a deprotection reaction (denoted as [Deprotection] in Scheme 3a) mediated by an oxidant, a base, an acid, or a metal to produce intermediate 13. This can be reacted in a cyclization/hydrolysis sequence followed by a chiral purification to produce 14.

Scheme 3b

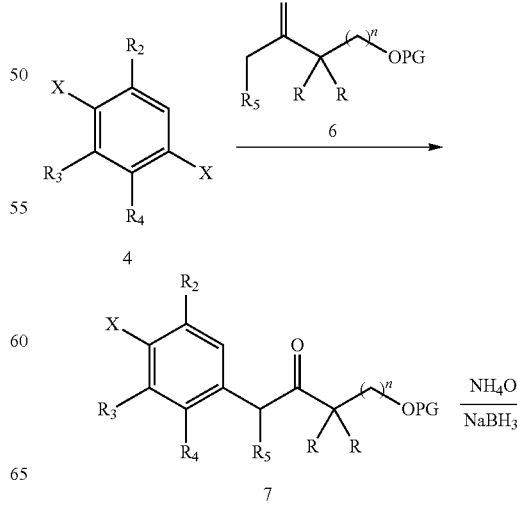

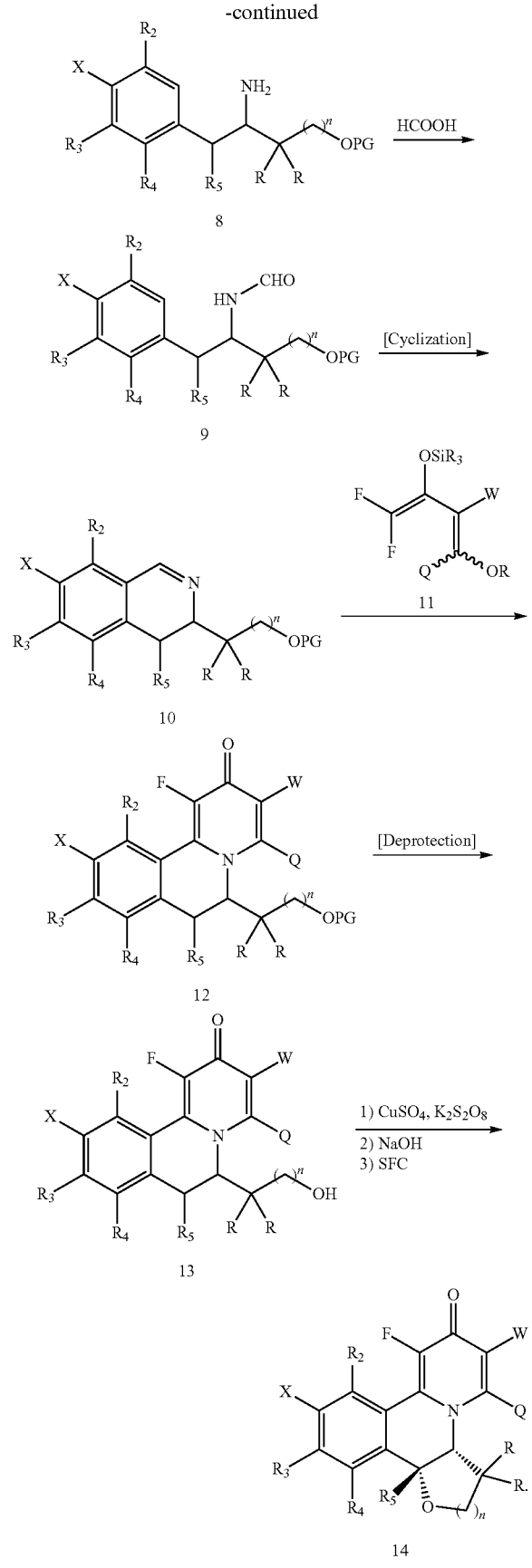

Illustrated in Scheme 3b, intermediate compounds such as 14 ($R_1$, $R_2$, $R_3$, $R_4$, $R_5$, $R_6$, $R_7$, $R_8$, Q, R, and W as defined previously; X defined as —Cl, —Br, —I, or —OTf; n=1, 2 or 3) can be produced similarly as described in U.S. Pat. No. 9,458,153; WO 2017/140821; WO 2017/017042; or CN 106810548A. More specifically, compounds such as intermediate 4 ($R_2$, $R_3$, and $R_4$ as defined previously; X defined as —Cl, —Br, —I, or —OTf) can be reacted in an enolate coupling reaction with intermediate 6 ($R_5$ and R as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 3b) mediated by an electrophilic reagent including, but not limited to: $POCl_3$, $FeCl_3$, or $SOCl_2$ to produce intermediate 10. This can be reacted in a cyclocondensation reaction with intermediate 11 (R, Q, and W as defined previously) to provide intermediate 12. This can undergo a deprotection reaction (denoted as [Deprotection] in Scheme 3b) mediated by an oxidant, a base, an acid, or a metal to produce intermediate 13. This can be reacted in a cyclization/hydrolysis sequence followed by a chiral purification to produce 14.

Scheme 4a

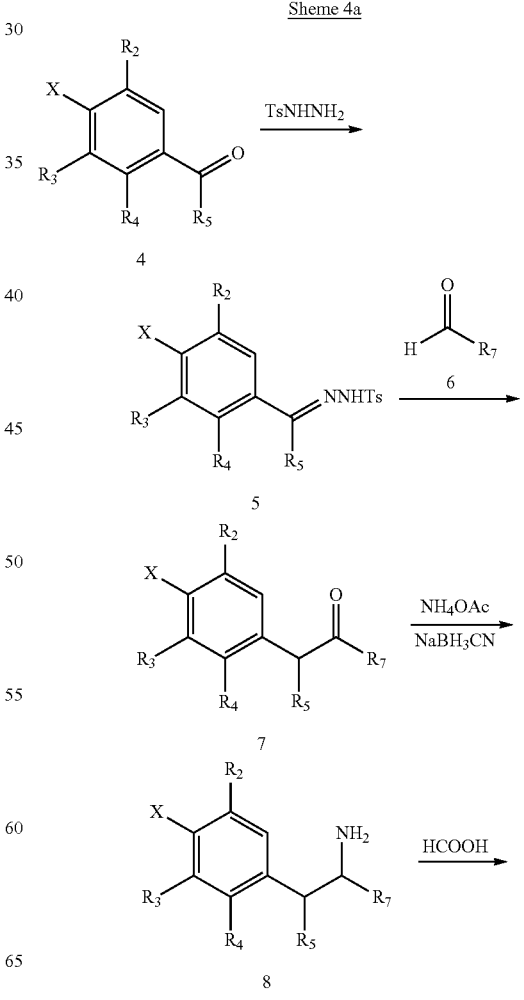

-continued

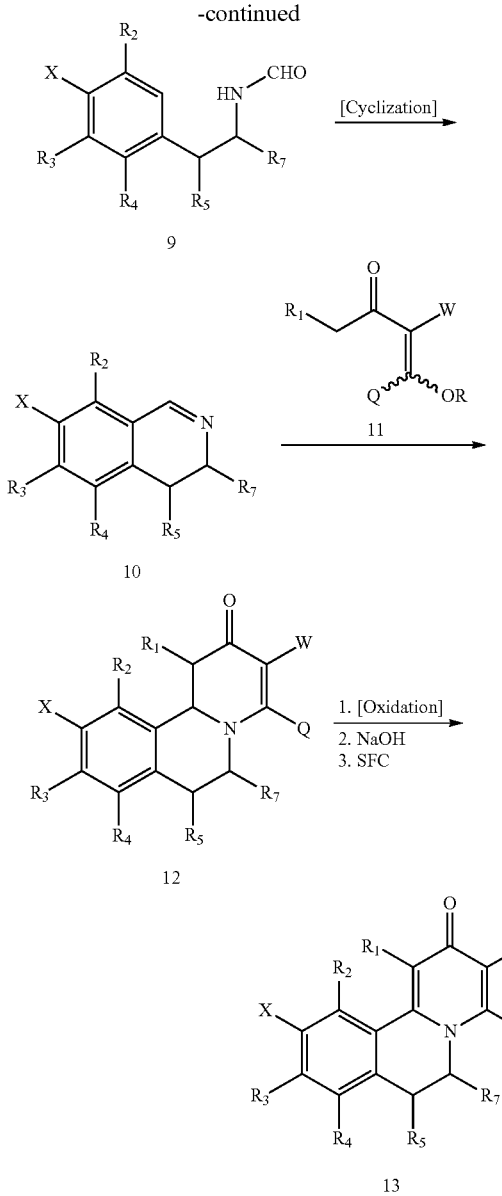

provide intermediate 12. This can undergo an oxidation reaction (denoted as [Oxidation] in Scheme 2a) mediated by an oxidant including, but not limited to: 12, DDQ, or p-chloranil, followed by a hydrolysis and chiral purification to produce 13.

Scheme 4b

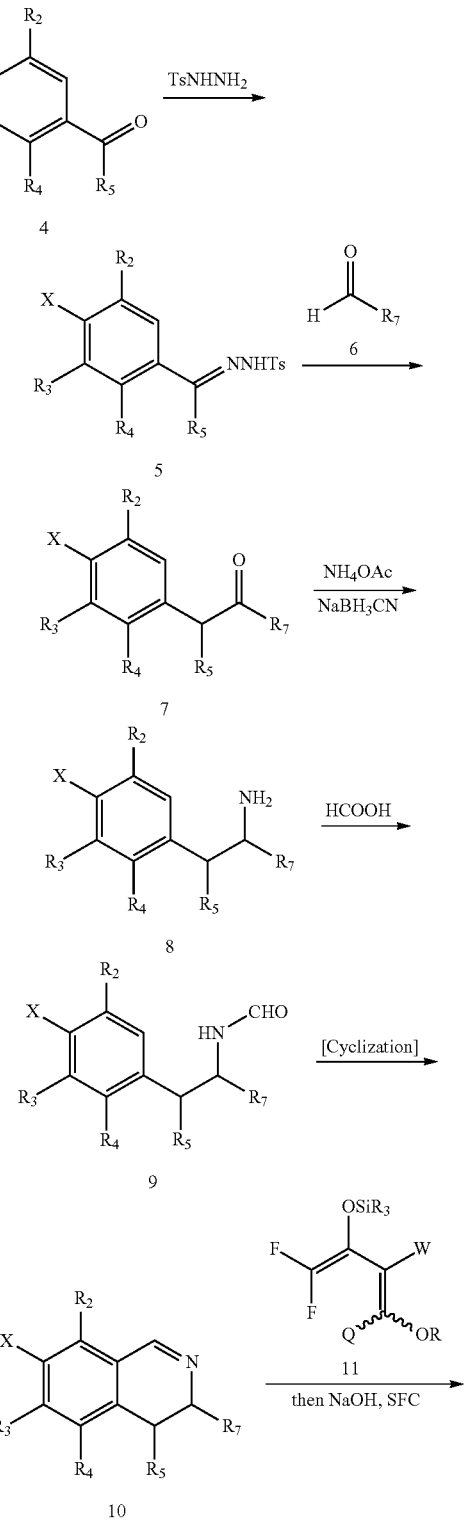

Illustrated in Scheme 4a, intermediate compounds such as 13 ($R_1$, $R_2$, $R_3$, $R_4$, $R_5$, $R_7$, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 ($R_2$, $R_3$, $R_4$, and $R_5$ as defined previously; X defined as —Cl, —Br, —I, or —OTf) can be reacted with p-tosylhydrazide to form intermediate 5. This can be reacted with intermediate 6 ($R_7$ as defined previously for formula I), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 4a) mediated by an electrophilic reagent including, but not limited to: $POCl_3$, $FeCl_3$, or $SOCl_2$ to produce intermediate 10. This can be reacted in a cyclocondensation reaction with intermediate 11 ($R_1$, R, Q, and W as defined previously) to

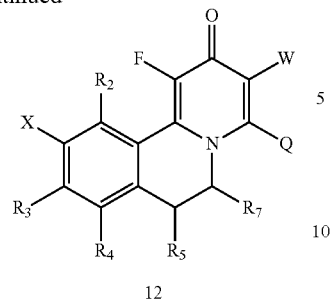

12

Illustrated in Scheme 4b, intermediate compounds such as 12 (R$_2$, R$_3$, R$_4$, R$_5$, R$_7$, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 (R$_2$, R$_3$, R$_4$, and R$_5$ as defined previously; X defined as —Cl, —Br, —I, or —OTf) can be reacted with p-tosylhydrazide to form intermediate 5. This can be reacted with intermediate 6 (R$_7$ as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 4b) mediated by an electrophilic reagent including, but not limited to: POCl$_3$, FeCl$_3$, or SOCl$_2$ to produce intermediate 10. This can be reacted in a cyclocondensation reaction with intermediate 11 (R, Q, and W as defined previously), followed by a hydrolysis and chiral purification to provide 12.

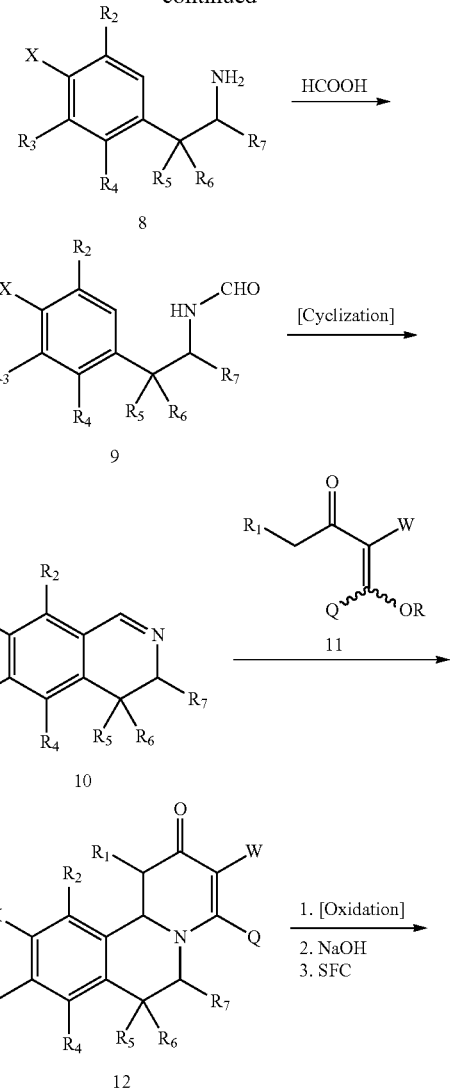

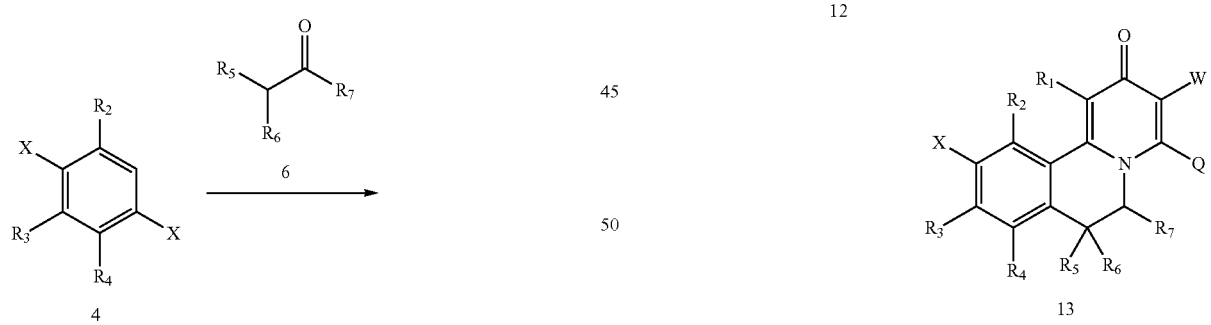

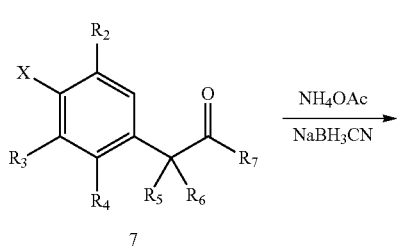

Illustrated in Scheme 5a, intermediate compounds such as 13 (R$_1$, R$_2$, R$_3$, R$_4$, R$_5$, R$_6$, R$_7$, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 (R$_2$, R$_3$, and R$_4$ as defined previously; X defined as —Cl, —Br, —I, or —OTf) can be reacted in an enolate coupling reaction with intermediate 6 (R$_5$, R$_6$, and R$_7$ as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 5a) mediated by an electrophilic reagent including, but not limited to: POCl₃, FeCl₃, or SOCl₂ to produce intermediate 10. This can be reacted in a cyclocondensation reaction with intermediate 11 (R₁, R, Q, and W as defined previously) to provide intermediate 12. This can undergo an oxidation reaction (denoted as [Oxidation] in Scheme 5a) mediated by an oxidant including, but not limited to: I₂, DDQ, or p-chloranil, followed by a hydrolysis and chiral purification to produce 13.

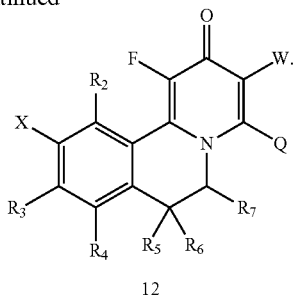

Illustrated in Scheme 5b, intermediate compounds such as 12 (R₂, R₃, R₄, R₅, R₆, R₇, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 (R₂, R₃, and R₄ are as defined previously; X defined as —Cl, —Br, —I, or —OTf) can be reacted in an enolate coupling reaction with intermediate 6 (R₅, R₆, and R₇ as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 5b) mediated by an electrophilic reagent including, but not limited to: POCl₃, FeCl₃, or SOCl₂ to produce intermediate 10. This can be reacted in a cyclocondensation reaction with intermediate 11 (R, Q, and W as defined previously), followed by a hydrolysis and chiral purification to provide 12.

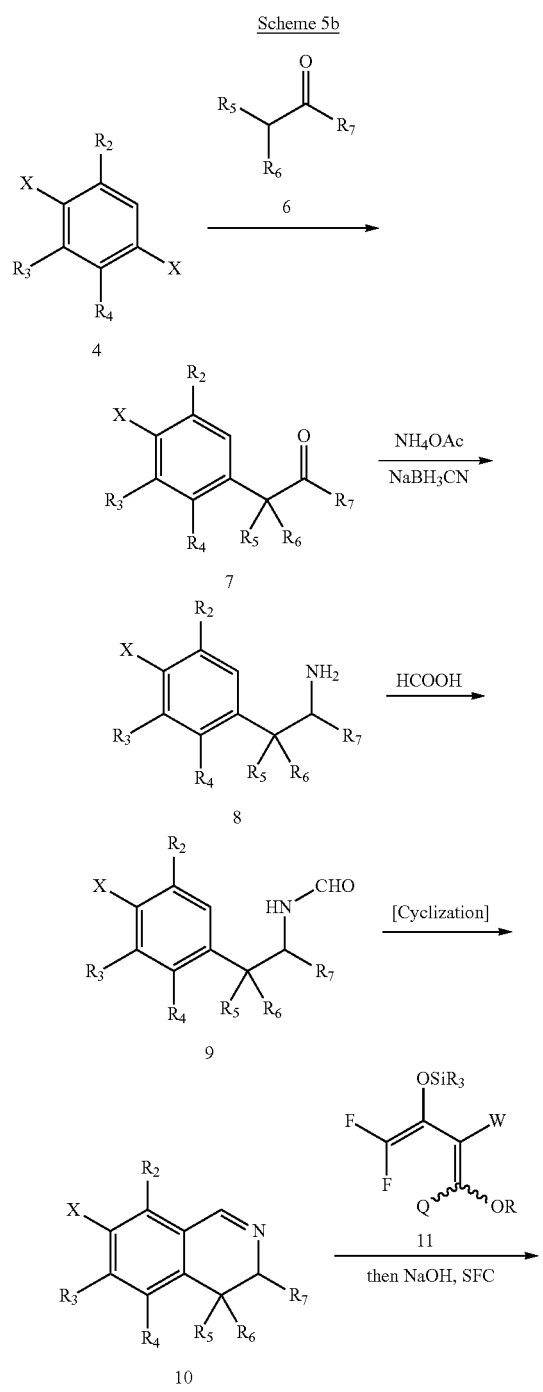

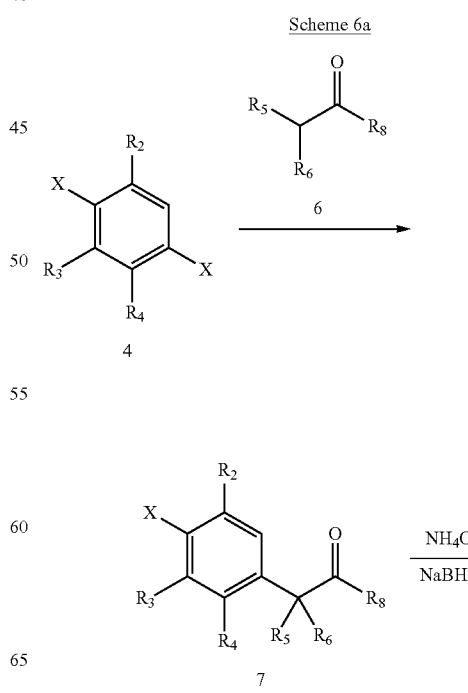

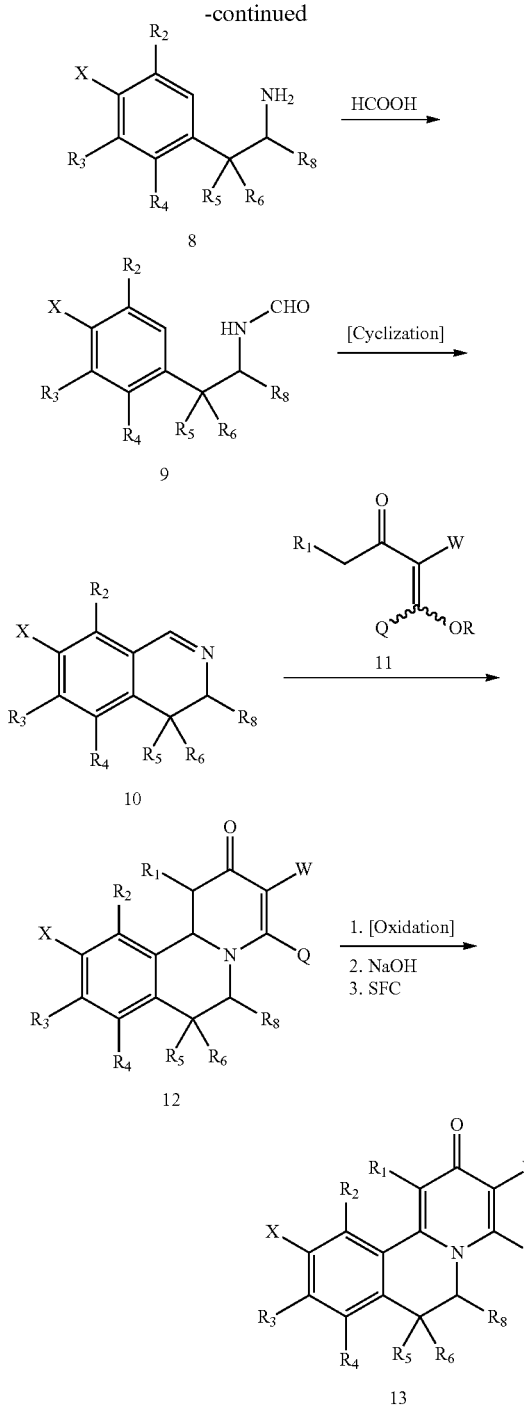

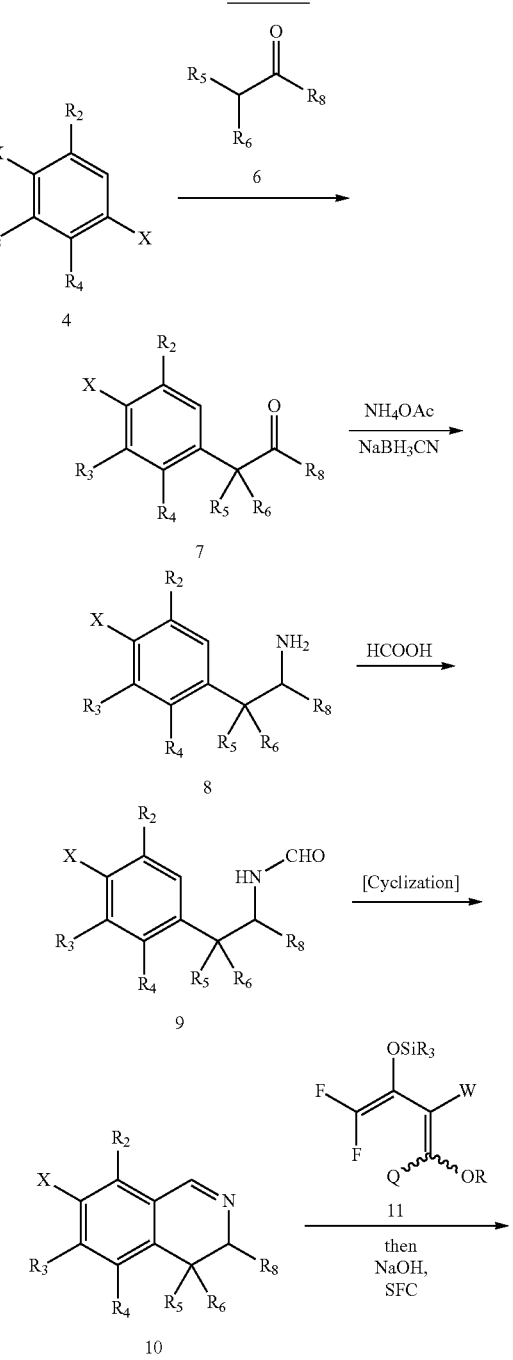

reaction to form intermediate 8. This can be reacted in a formylation reaction to provide 9. Intermediate 9 can undergo an intramolecular cyclization reaction (denoted as [Cyclization] in Scheme 6a) mediated by an electrophilic reagent including, but not limited to: POCl$_3$, FeCl$_3$, or SOCl$_2$ to produce intermediate 10. This can be reacted in a cyclocondensation reaction with intermediate 11 ($R_1$, R, Q, and W as defined previously) to provide intermediate 12. This can undergo an oxidation reaction (denoted as [Oxidation] in Scheme 6a) mediated by an oxidant including, but not limited to: 12, DDQ, or p-chloranil, followed by a hydrolysis and chiral purification to produce 13.

Scheme 6b

Illustrated in Scheme 6a, intermediate compounds such as 13 ($R_1$, $R_2$, $R_3$, $R_4$, $R_5$, $R_6$, $R_8$, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 ($R_2$, $R_3$, and $R_4$ as defined previously; X defined as —Cl, —Br, —I, or —OTf) can be reacted in an enolate coupling reaction with intermediate 6 ($R_5$, $R_6$, and $R_8$ as defined previously), whereby intermediate 6 is commercially available or can be prepared by those familiar with the skill of the arts, to form intermediate 7. This can be reacted in a reductive amination 95
-continued

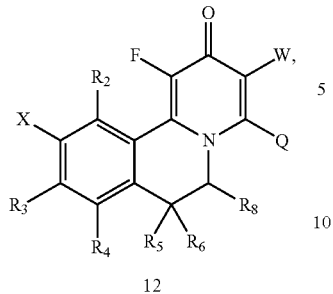

12

Illustrated in Scheme 6b, intermediate compounds such as 12 ($R_2$, $R_3$, $R_4$, $R_5$, $R_6$, $R_8$, Q, and W as defined previously; X defined as —Cl, —Br, —I, or —OTf) can be produced similarly as described in U.S. Pat. No. 9,458,153; WO 2017/140821; WO 2017/017042; or CN 106810548A. More specifically, compounds such as intermediate 4 ($R_2$, $R_3$, and $R_4$ as defined previously; X defined as —Cl, —Br, —I, or —OTf) can be reacted in an enolate coupling reaction with intermediate 6 ($R_5$, $R_6$, and $R_8$ as defined previously), whereby intermediate 6 is commercially available or can be prepared by those familiar with the skill of the arts, to form intermediate 7. This can be reacted in a reductive amination reaction to form intermediate 8. This can be reacted in a formylation reaction to provide 9. Intermediate 9 can undergo an intramolecular cyclization reaction (denoted as [Cyclization] in Scheme 6b) mediated by an electrophilic reagent including, but not limited to: $POCl_3$, $FeCl_3$, or $SOCl_2$ to produce intermediate 10. This can be reacted in a cyclocondensation reaction with intermediate 11 (R, Q, and W as defined previously), followed by a hydrolysis and chiral purification to provide 12.

96
-continued

14

Illustrated in Scheme 7a, intermediate compounds such as 12 can be produced as described in U.S. Pat. No. 9,458,153; WO 2017/140821; WO 2017/017042; CN 106810548A; or Schemes 2a, 2b, 3a, 3b, 4a, 4b, 5a, 5b, 6a, or 6b. Compounds such as intermediate 12 ($R_1$, $R_2$, $R_3$, $R_4$, $R_5$, $R_6$, $R_7$, $R_8$, R, and Q as defined previously; X defined as —Cl, —Br, —I, or —OTf) can be reacted directly in a coupling reaction with compounds such as A, as defined previously, whereby A is commercially available or can be prepared by those familiar with the skill of the arts. The coupling reaction can be mediated by a metal-based reagent (denoted as [Metal] in Scheme 7a) including, but not limited to: $Pd(OAc)_2$, $PdCl_2$(dppf), $Pd(Ph_3P)_4$, $Pd_2(dba)_3$, PdRuPhos G2, Pd$^t$BuXPhos G3, CuI, $Cu_2O$, or CuBr. The stated coupling reaction can be mediated by a base (denoted as [Base] in Scheme 7a) including, but not limited to: $Cs_2CO_3$, $K_2CO_3$, $Na_2CO_3$, CsF, KO$^t$Bu, NaO$^t$Bu, KOAc, $K_3PO_4$, $Et_3N$, or DBU. The stated coupling reaction can performed in a solvent or mixtures of solvents (denoted as [Solvent] in Scheme 7a) including, but not limited to: THF, toluene, benzene, DMF, DMA, 1,4-dioxane, or water. The stated coupling reaction can be performed at a temperature range between 0° C. and 180° C. where appropriate. Intermediate compound 13 can be reacted in a hydrolysis reaction followed by chiral purification to provide 14.

Scheme 7a

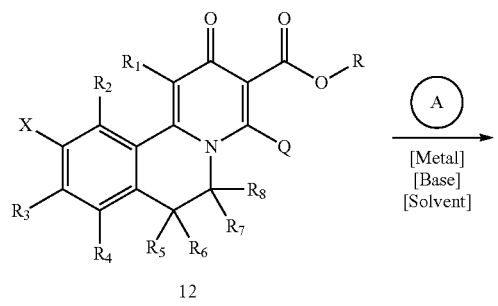

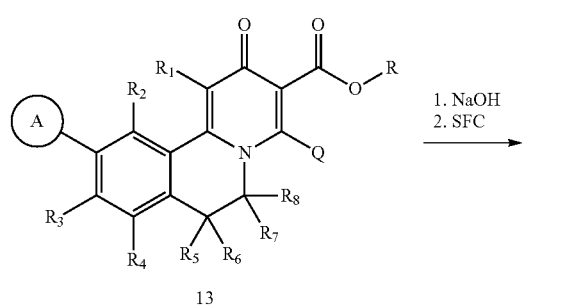

Scheme 7b

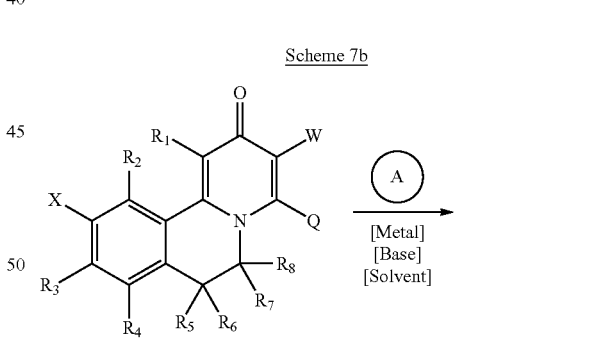

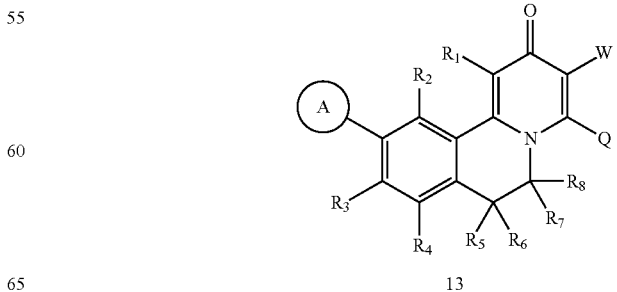

Illustrated in Scheme 7b, intermediate compounds such as 12 can be produced as described in U.S. Pat. No. 9,458,153; WO 2017/140821; WO 2017/017042; CN 106810548A; or Schemes 2a, 2b, 3a, 3b, 4a, 4b, 5a, 5b, 6a, or 6b. Compounds such as intermediate 12 ($R_1$, $R_2$, $R_3$, $R_4$, $R_5$, $R_6$, $R_7$, $R_8$, Q, and W as defined previously; X defined as —Cl, —Br, —I, or —OTf) can be reacted directly in a coupling reaction with compounds such as A, as defined previously, whereby A is commercially available or can be prepared by those familiar with the skill of the arts. The coupling reaction can be mediated by a metal-based reagent (denoted as [Metal] in Scheme 7b) including, but not limited to: $Pd(OAc)_2$, $PdCl_2$ (dppf), $Pd(Ph_3P)_4$, $Pd_2(dba)_3$, PdRuPhos G2, Pd$^t$BuXPhos G3, CuI, $Cu_2O$, or CuBr. The stated coupling reaction can be mediated by a base (denoted as [Base] in Scheme 7b) including, but not limited to: $Cs_2CO_3$, $K_2CO_3$, $Na_2CO_3$, CsF, KO$^t$Bu, NaO$^t$Bu, KOAc, $K_3PO_4$, $Et_3N$, or DBU. The stated coupling reaction can performed in a solvent or mixtures of solvents (denoted as [Solvent] in Scheme 7b) including, but not limited to: THF, toluene, benzene, DMF, DMA, 1,4-dioxane, or water. The stated coupling reaction can be performed at a temperature range between 0° C. and 180° C. where appropriate.

Scheme 8a

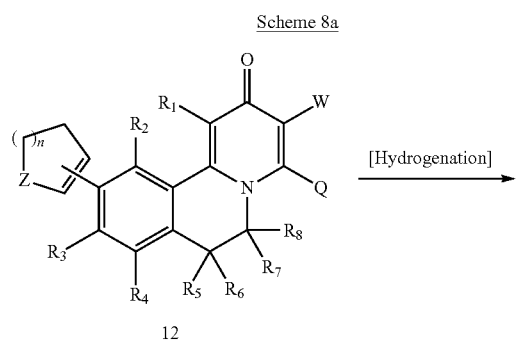

Illustrated in Scheme 8a, intermediate compounds such as 12 can be produced as described in Schemes 1, 7a, or 7b. Compounds such as intermediate 12 (Z is O, S, $CR_2$, or NR; n=0, 1, 2 or 3; R, $R_1$, $R_2$, $R_3$, $R_4$, $R_5$, $R_6$, $R_7$, $R_8$, Q, and W as defined previously.) can be reacted in a hydrogenation reaction (denoted as [Hydrogenation] in Scheme 8a) mediated by a metal-based reagent including, but not limited to: Pd/C, $PdCl_2$, or $PtO_2$ to provide 13.

Scheme 8b

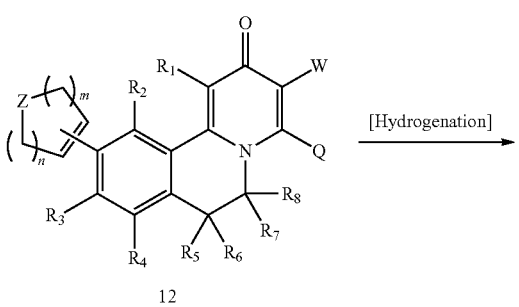

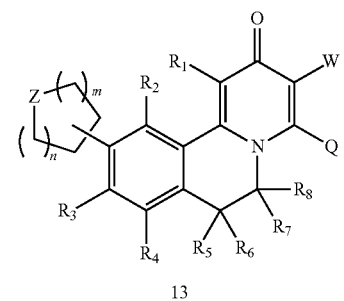

Illustrated in Scheme 8b, intermediate compounds such as 12 can be produced as described in Schemes 1, 7a, or 7b. Compounds such as intermediate 12 (Z is O, S, $CR_2$, or NR; m=0, 1, 2 or 3; n=0, 1, 2 or 3; R, $R_1$, $R_2$, $R_3$, $R_4$, $R_5$, $R_6$, $R_7$, $R_8$, Q, and W as defined previously.) can be reacted in a hydrogenation reaction (denoted as [Hydrogenation] in Scheme 8b) mediated by a metal-based reagent including, but not limited to: Pd/C, $PdCl_2$, or $PtO_2$ to provide 13.

Scheme 9a

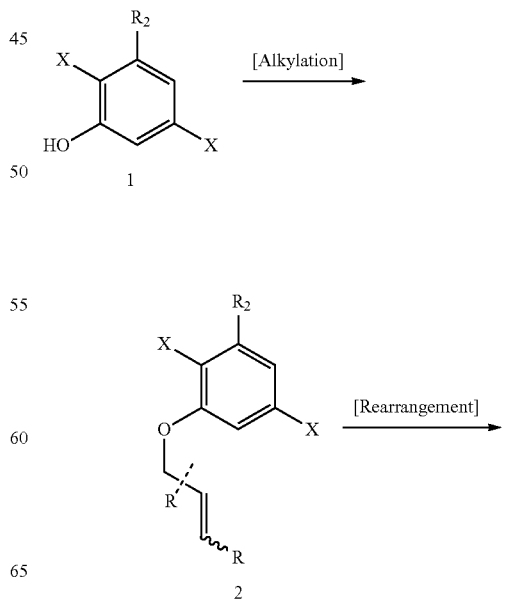

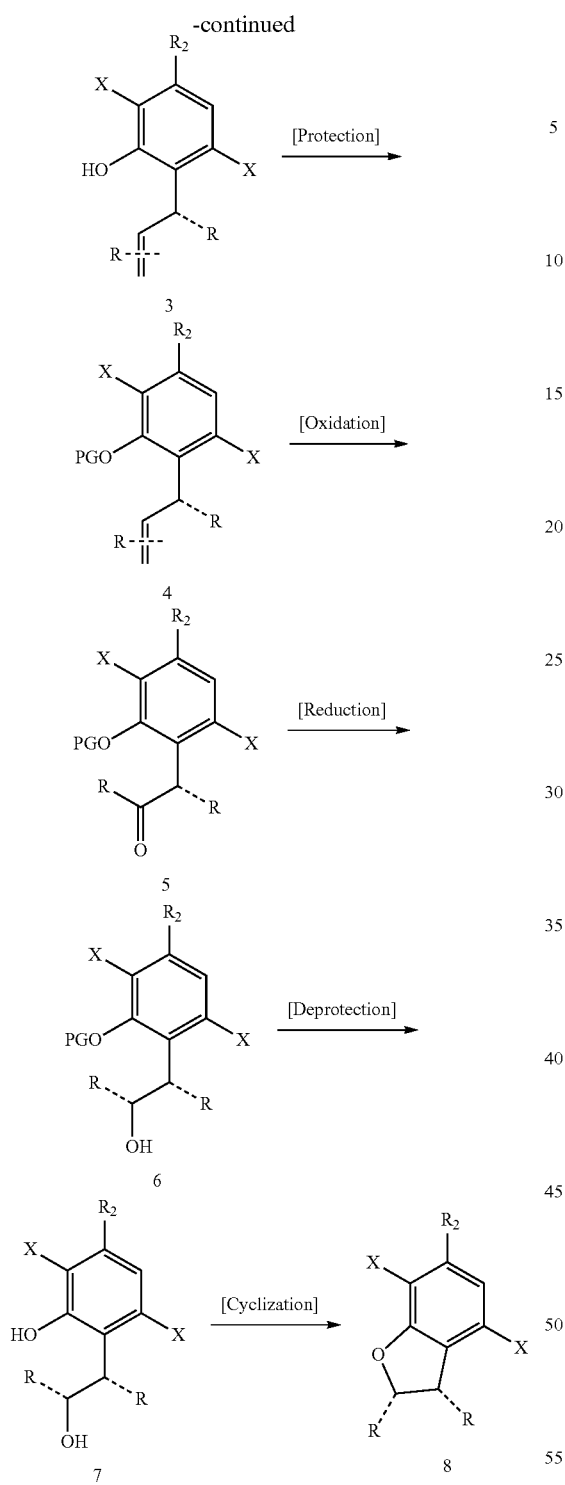

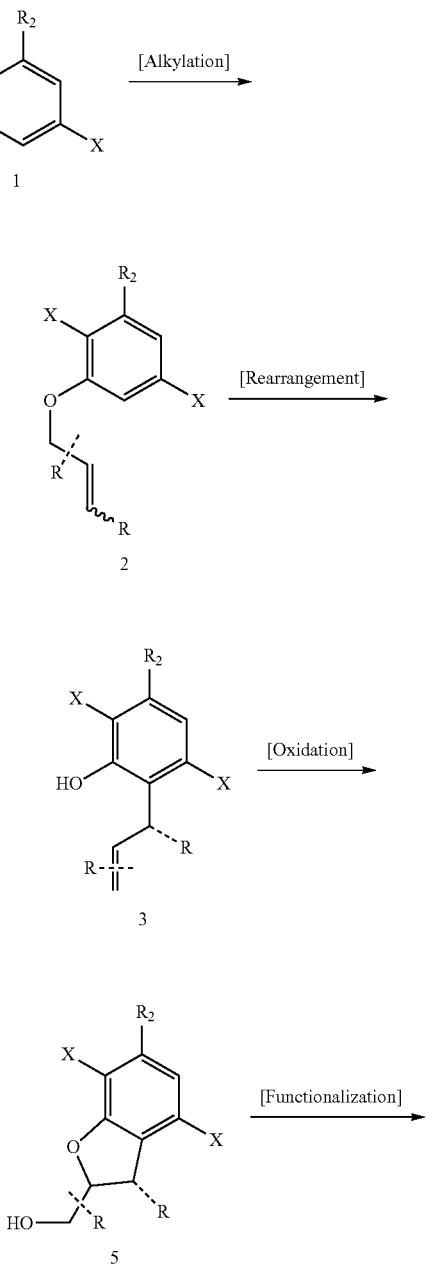

a rearrangement reaction (denoted as [Rearrangement] in Scheme 9a) to form intermediate 3. The phenol portion of 3 can be protected with an appropriate protecting group (denoted as [Protection] in Scheme 9a) including, but not limited to: TBS, TES, Ac, THP, or Ts to provide intermediate 4. Intermediate 4 can undergo an oxidation reaction (denoted as [Oxidation] in Scheme 9a) to produce intermediate 5. This can be reacted in a reduction reaction (denoted as [Reduction] in Scheme 9a) mediated by reducing agents including, but not limited to: $NaBH_4$, $LiBH_4$, and $LiAlH_4$ to produce intermediate 6. This can undergo a deprotection reaction (denoted as [Deprotection] in Scheme 9a) to produce 7, which can be reacted in a cyclization reaction (denoted as [Cyclization] in Scheme 9a) to produce 8.

Illustrated in Scheme 9a, intermediate compounds such as 8 ($R_2$ and R as defined previously; X defined as —Cl, —Br, —I, or —OTf) can be produced similarly as described in WO 2017/216686; or WO 2017/216685. More specifically, compounds such as intermediate intermediate 1 ($R_2$ as defined previously; X defined as —Cl, —Br, —I, or —OTf) can be reacted in an alkylation reaction (denoted as [Alkylation] in Scheme 9a) with an electrophilic compound including, but not limited to: allyl bromide or 3-methyl-2-bromopropene to form intermediate 2. This can be reacted in 101
-continued

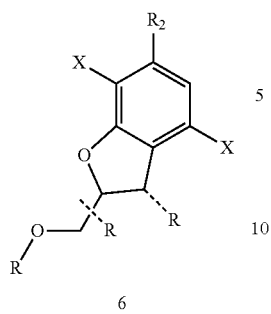

6

Illustrated in Scheme 9b, intermediate compounds such as 6 (R₂ and R as defined previously; X defined as —Cl, —Br, —I, or —OTf) can be produced similarly as described in WO 2017/216686; or WO 2017/216685. More specifically, compounds such as intermediate intermediate 1 (R₂ as defined previously; X defined as —Cl, —Br, —I, or —OTf) can be reacted in an alkylation reaction (denoted as [Alkylation] in Scheme 9b) with an electrophilic compound including, but not limited to: allyl bromide or 3-methyl-2-bromopropene to form intermediate 2. This can be reacted in a rearrangement reaction (denoted as [Rearrangement] in Scheme 9b) to form intermediate 3. This can undergo an oxidation reaction (denoted as [Oxidation] in Scheme 9b) to produce intermediate 5. This can be reacted in a functionalization reaction (denoted as [Functionalization] in Scheme 9b) mediated by a base including, but not limited to: NaH, KO$^t$Bu, Et₃N, or K₂CO₃ to produce 6.

Scheme 9c

5

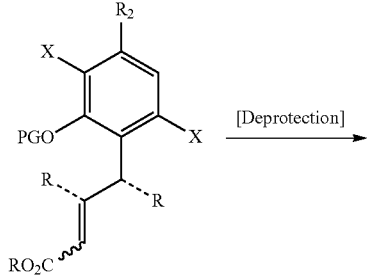

6

102
-continued

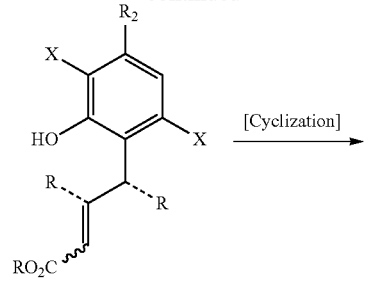

7

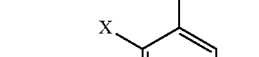

8

9

10

Illustrated in Scheme 9c, intermediate compounds such as 10 (R₂ and R as defined previously; X defined as —Cl, —Br, —I, or —OTf) can be produced similarly as described in WO 2017/216686; or WO 2017/216685. More specifically, compounds such as intermediate intermediate 5 (Scheme 9a; R₂ as defined previously; X defined as —Cl, —Br, —I, or —OTf) can be reacted in a homologation reaction (denoted as [Homologation] in Scheme 9c) with an ylide including, but not limited to: methyl (triphenylphosphoranylidine) acetate or ethyl (triphenylphosphoranylidine) acetate to form intermediate 6. This can undergo a deprotection reaction (denoted as [Deprotection] in Scheme 9c) to produce 7, which can be reacted in a cyclization reaction (denoted as [Cyclization] in Scheme 9c) to produce 8. This can be reacted in a reduction reaction (denoted as [Reduction] in Scheme 9c) mediated by reducing agents including, but not limited to: NaBH₄, LiBH₄, and LiAlH₄ to produce intermediate 9. This can be reacted in a functionalization reaction (denoted as [Functionalization] in Scheme 9c) mediated by a base including, but not limited to: NaH, KO$^t$Bu, Et₃N, or K₂CO₃ to produce 10.

Scheme 10a

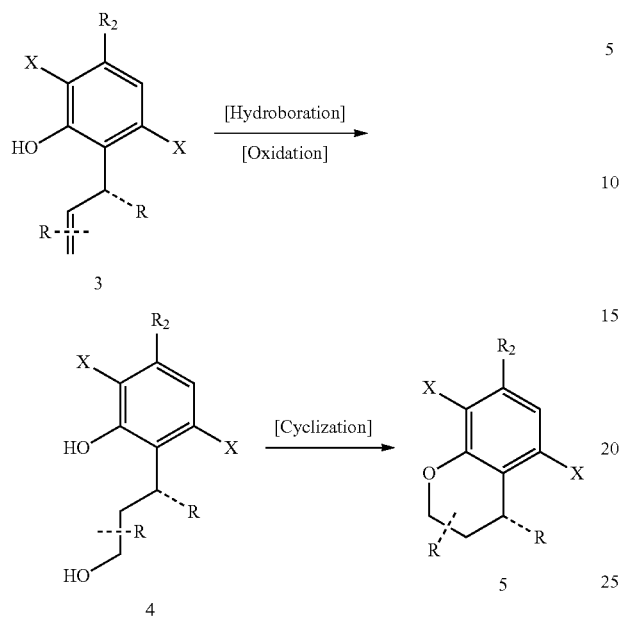

Illustrated in Scheme 10a, intermediate compounds such as 5 ($R_2$ and R as defined previously; X defined as —Cl, —Br, —I, or —OTf) can be produced similarly as described in WO 2017/216686; or WO 2017/216685. More specifically, compounds such as intermediate intermediate 3 (Scheme 9a; $R_2$ as defined previously; X defined as —Cl, —Br, —I, or —OTf) can be reacted in a hydroboration/oxidation sequence (denoted as [Hydroboration]/[Oxidation] in Scheme 10a) to form intermediate 4. This can undergo a cyclization reaction (denoted as [Cyclization] in Scheme 10a) to produce 5.

Scheme 10b

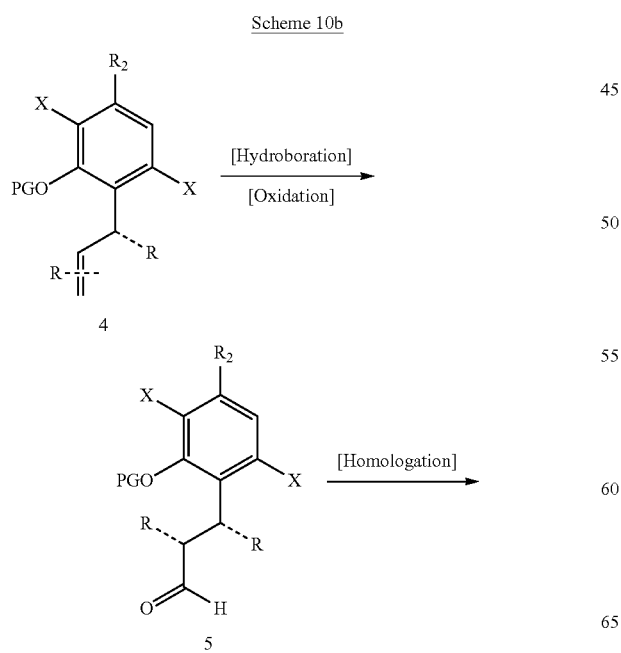

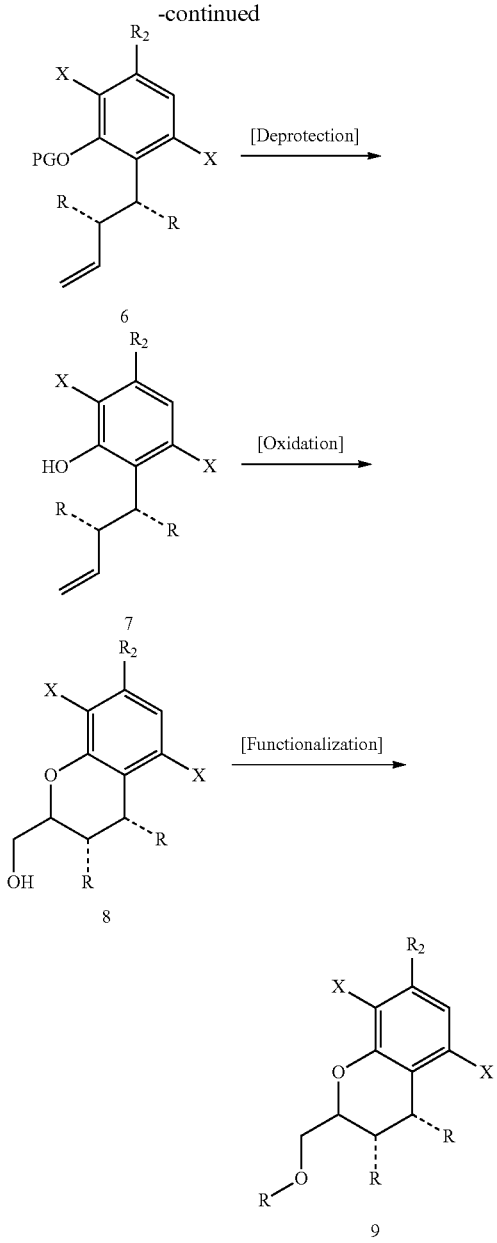

Illustrated in Scheme 10b, intermediate compounds such as 9 ($R_2$ and R as defined previously; X defined as —Cl, —Br, —I, or —Otf; PG is a hydroxyl protecting group) can be produced similarly as described in WO 2017/216686; or WO 2017/216685. More specifically, compounds such as intermediate 4 (Scheme 9a; $R_2$ as defined previously; X defined as —Cl, —Br, —I, or —OTf) can be reacted in a hydroboration/oxidation sequence (denoted as [Hydroboration]/[Oxidation] in Scheme 10b) to form intermediate 5. This can undergo a homologation reaction (denoted as [Homologation] in Scheme 10b) to produce 6, which can be deprotected (denoted as [Deprotection] in Scheme 10b) to produce 7. This can be reacted in an oxidation reaction (denoted as [Oxidation] in Scheme 10b) mediated by oxidizing agents including, but not limited to: mCPBA or $H_2O_2$ to produce intermediate 8. This can be reacted in a functionalization reaction (denoted as [Functionalization] in Scheme 10b) mediated by a base including, but not limited to: NaH, KO$^t$Bu, Et$_3$N, or $K_2CO_3$ to produce 9.

Scheme 10c

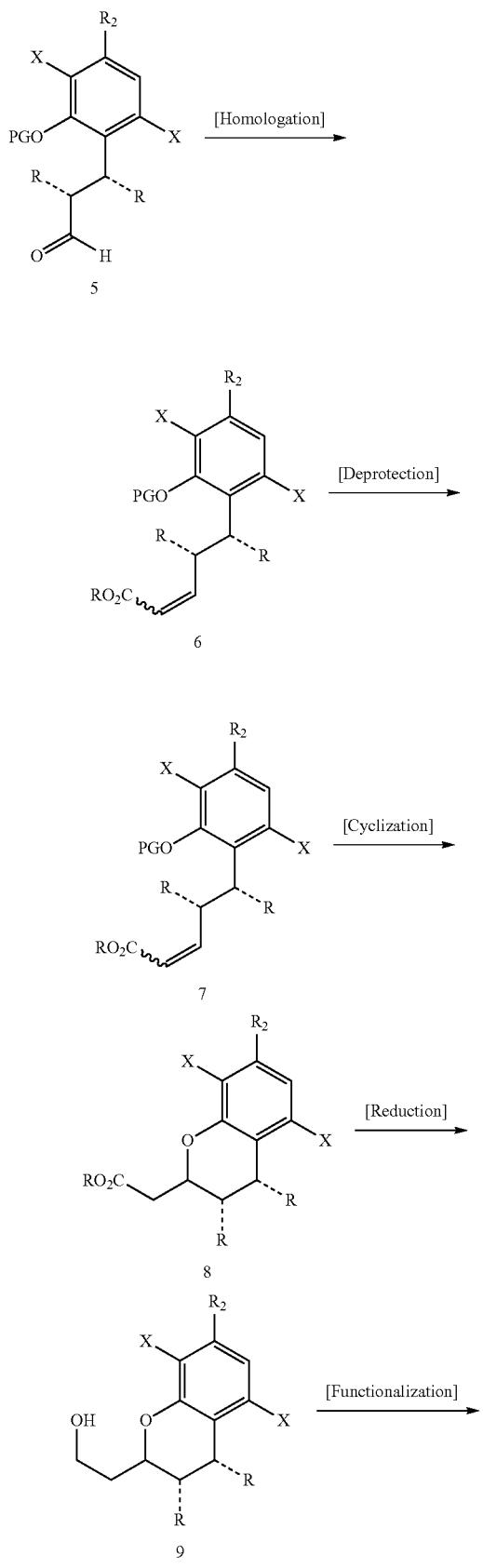

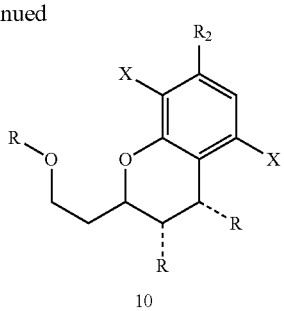

Illustrated in Scheme 10c, intermediate compounds such as 10 ($R_2$ and R as defined previously; X defined as —Cl, —Br, —I, or —OTf) can be produced similarly as described in WO 2017/216686; or WO 2017/216685. More specifically, compounds such as intermediate intermediate 5 (Scheme 10b; $R_2$ as defined previously; X defined as —Cl, —Br, —I, or —OTf) can be reacted in a homologation reaction (denoted as [Homologation] in Scheme 10c) with an ylide including, but not limited to: methyl (triphenylphosphoranylidine) acetate or ethyl (triphenylphosphoranylidine) acetate to form intermediate 6. This can undergo a deprotection reaction (denoted as [Deprotection] in Scheme 10c) to produce 7, which can be reacted in a cyclization reaction (denoted as [Cyclization] in Scheme 10c) to produce 8. This can be reacted in a reduction reaction (denoted as [Reduction] in Scheme 10c) mediated by reducing agents including, but not limited to: $NaBH_4$, $LiBH_4$, and $LiAlH_4$ to produce intermediate 9. This can be reacted in a functionalization reaction (denoted as [Functionalization] in Scheme 10c) mediated by a base including, but not limited to: NaH, KO$^t$Bu, $Et_3$N, or $K_2CO_3$ to produce 10.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. [M+H]$^+$ refers to mono-isotopic molecular weights.

NMR spectra were run on a Bruker 400 MHz spectrometer. Spectra were measured at 298K and referenced using the solvent peak. Chemical shifts for $^1$H NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Example 1: Synthesis of (S)-6-(tert-butyl)-9-(3-methoxypropoxy)-10-(5-methylfuran-2-yl)-2-oxo-6,7-dihydro-2H-pyrido[2,1-a]isoquinoline-3-carboxylic Acid

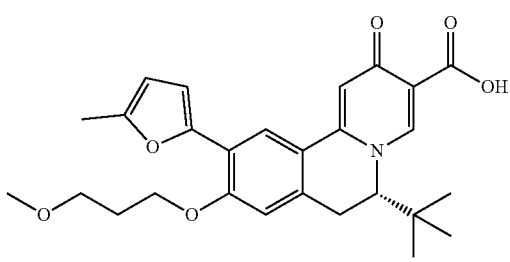 [SMILES: COCCCOc1cc2c(cc1-c1ccc(C)o1)-c1cc(=O)c(C(=O)O)cn1[C@H](C(C)(C)C)C2]

An oven-dried vial was charged with (S)-6-(tert-butyl)-10-chloro-9-(3-methoxypropoxy)-2-oxo-6,7-dihydro-2H-pyrido[2,1-a]isoquinoline-3-carboxylic acid (50 mg, 0.12 mmol), 4,4,5,5-tetramethyl-2-(5-methylfuran-2-yl)-1,3,2-dioxaborolane (124 mg, 0.6 mmol), Pd$^t$BuXPhos G3 (10 mg, 0.01 mmol), and Cs$_2$CO$_3$ (194 mg, 0.6 mmol). The vial was purged with nitrogen gas for 5 minutes, then DMF (1 mL) and water (0.2 mL) were added via syringe. The reaction mixture was heated under a nitrogen atmosphere for 80 minutes at 110° C. After cooling to room temperature, the reaction mixture was filtered and the product was purified by RPHPLC to provide the product as a white solid (39 mg, 70% yield). ESI MS m/z=466.1 [M+H]$^+$.

Example 2: (S)-6-(tert-butyl)-10-(furan-3-yl)-9-(3-methoxypropoxy)-2-oxo-6,7-dihydro-2H-pyrido[2,1-a]isoquinoline-3-carboxylic Acid

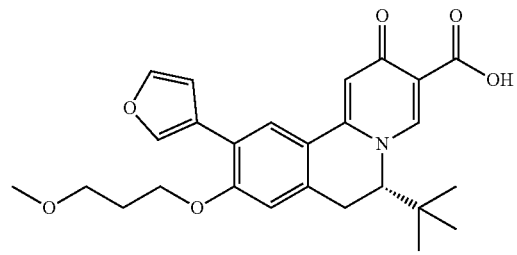

The title compound was prepared following similar procedure as Example 1. ESI MS m/z=452.1 [M+H]$^+$. $^1$H NMR (400 MHz, CDCl$_3$): δ 15.97 (br s, 1H), 8.47 (s, 1H), 8.05-8.04 (m, 1H), 7.84 (s, 1H), 7.52 (t, J=1.6 Hz, 1H), 7.16 (s, 1H), 6.84 (s, 1H), 6.81 (dd, J=1.8, 0.6 Hz, 1H), 4.32-4.21 (m, 2H), 4.05 (d, J=6.1 Hz, 1H), 3.64-3.58 (m, 2H), 3.48 (dd, J=16.8, 6.4 Hz, 1H), 3.38 (s, 3H), 3.25 (d, J=16.7 Hz, 1H), 2.23-2.17 (m, 2H). 0.84 (s, 9H).

Example 3: (S)-6-(tert-butyl)-9-(3-methoxypropoxy)-2-oxo-10-phenyl-6,7-dihydro-2H-pyrido[2,1-a]isoquinoline-3-carboxylic Acid

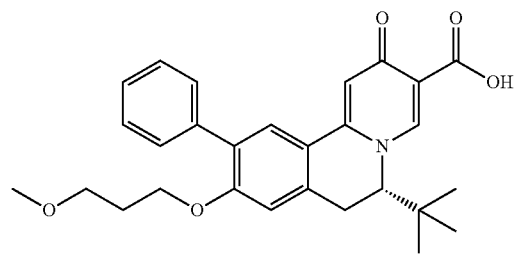 [SMILES: COCCCOc1cc2c(cc1-c1ccccc1)-c1cc(=O)c(C(=O)O)cn1[C@H](C(C)(C)C)C2]

The title compound was prepared following similar procedure as Example 1. ESI MS m/z=463.1 [M+H]$^+$. $^1$H NMR (400 MHz, CDCl$_3$): δ 16.03 (br s, 1H), 8.48 (s, 1H), 7.68 (s, 1H), 7.53-7.50 (m, 2H), 7.45-7.41 (m, 2H), 7.39-7.35 (m, 1H), 7.12 (s, 1H), 6.86 (s, 1H), 4.21-4.10 (m, 2H), 4.08 (d, J=6.2 Hz, 1H), 3.53-3.43 (m, 3H), 3.32 (s, 3H), 3.28 (d, J=16.8 Hz, 1H), 2.06-1.99 (m, 2H), 0.86 (s, 9H).

Example 4: (S)-6-(tert-butyl)-9-(3-methoxypropoxy)-10-(1-methyl-1H-pyrazol-4-yl)-2-oxo-6,7-dihydro-2H-pyrido[2,1-a]isoquinoline-3-carboxylic Acid

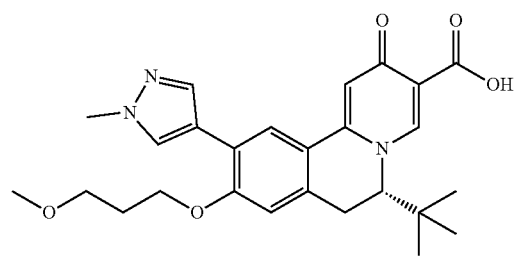

The title compound was prepared following similar procedure as Example 1. ESI MS m/z=466.1 [M+H]+.

Example 5: (S)-6-(tert-butyl)-9-(3-methoxypropoxy)-2-oxo-10-(thiophen-3-yl)-6,7-dihydro-2H-pyrido[2,1-a]isoquinoline-3-carboxylic Acid

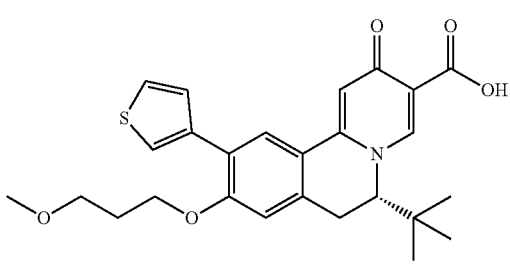

The title compound was prepared following similar procedure as Example 1. ESI MS m/z=468.1 [M+H]+. $^1$H NMR (400 MHz, CDCl$_3$): δ 15.98 (br s, 1H), 8.46 (s, 1H), 7.86 (s, 1H), 7.67-7.66 (m, 1H), 7.44-7.39 (m, 2H), 7.14 (s, 1H), 6.85 (s, 1H), 4.28-4.16 (m, 2H), 4.05 (d, J=6.1 Hz, 1H), 3.60-3.53 (m, 2H), 3.48 (dd, J=16.6, 6.7 Hz, 1H), 3.35 (s, 3H), 3.26 (d, J=16.6 Hz, 1H), 2.16-2.10 (m, 2H), 0.85 (s, 9H).

Example 6: (S)-6-(tert-butyl)-9-(3-methoxypropoxy)-10-(oxazol-5-yl)-2-oxo-6,7-dihydro-2H-pyrido[2,1-a]isoquinoline-3-carboxylic Acid

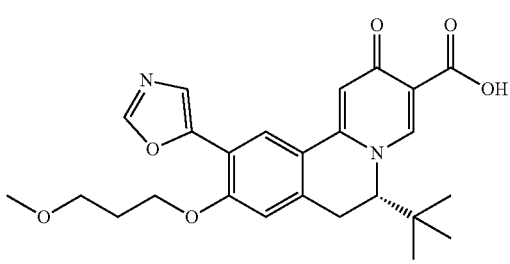

The title compound was prepared following similar procedure as Example 1. ESI MS m/z=453.1 [M+H]+. $^1$H NMR (400 MHz, CDCl$_3$): δ 15.91 (br s, 1H), 8.48 (s, 1H), 8.17 (s, 1H), 7.97 (s, 1H), 7.62 (s, 1H), 7.21 (s, 1H), 6.89 (s, 1H), 4.37-4.26 (m, 2H), 4.09 (d, J=6.3 Hz, 1H), 3.66-3.61 (m, 2H), 3.51 (dd, J=16.8, 6.7 Hz, 1H), 3.37 (s, 3H), 3.28 (d, J=16.8 Hz, 1H), 2.26-2.20 (m, 2H), 0.84 (s, 9H).

Example 7: (S)-6-(tert-butyl)-10-(furan-2-yl)-9-(3-methoxypropoxy)-2-oxo-6,7-dihydro-2H-pyrido[2,1-a]isoquinoline-3-carboxylic Acid

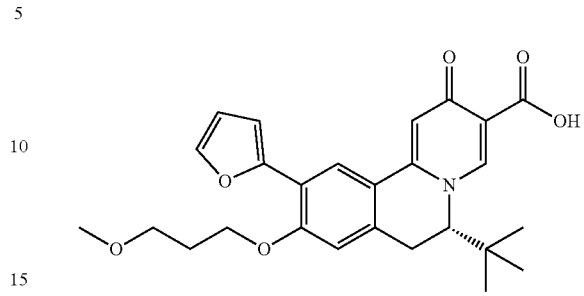

The title compound was prepared following similar procedure as Example 1. ESI MS m/z=452.1 [M+H]+. $^1$H NMR (400 MHz, CDCl$_3$): δ 16.07 (br s, 1H), 8.46 (s, 1H), 8.25 (s, 1H), 8.08 (d, J=7.9 Hz, 1H), 7.52-7.51 (m, 1H), 7.46-7.39 (m, 1H), 7.25-7.21 (m, 2H), 6.98 (d, J=3.1 Hz, 1H), 6.83 (s, 1H), 6.52 (dd, J=3.3, 1.7 Hz, 1H), 4.34-4.23 (m, 2H), 4.04 (d, J=6.4 Hz, 1H), 3.68-3.59 (m, 2H), 3.47 (dd, J=16.9, 6.7 Hz, 1H), 3.23 (d, J=16.3 Hz, 1H), 2.25-2.19 (m, 2H), 0.83 (s, 9H).

Example 8: (S)-6-(tert-butyl)-9-(3-methoxypropoxy)-2-oxo-10-(thiophen-2-yl)-6,7-dihydro-2H-pyrido[2,1-a]isoquinoline-3-carboxylic Acid

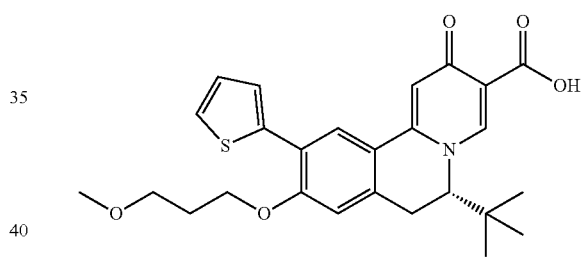

The title compound was prepared following similar procedure as Example 1. ESI MS m/z=468.1 [M+H]+. $^1$H NMR (400 MHz, CDCl$_3$): δ 15.98 (br s, 1H), 8.48 (s, 1H), 8.01 (s, 1H), 7.55 (dd, J=3.7, 1.0 Hz, 1H), 7.39 (dd, J=5.1, 1.0 Hz, 1H), 7.17 (s, 1H), 7.13 (dd, J=5.1, 3.6 Hz, 1H), 6.86 (s, 1H), 4.33-4.22 (m, 2H), 4.07 (d, J=6.3 Hz, 1H), 3.69-3.60 (m, 2H), 3.48 (dd, J=16.5, 6.4 Hz, 1H), 3.37 (s, 3H), 3.26 (d, J=16.6 Hz, 1H), 2.24-2.18 (m, 2H), 0.85 (s, 9H).

Example 9: (S)-10-(benzofuran-2-yl)-6-(tert-butyl)-9-(3-methoxypropoxy)-2-oxo-6,7-dihydro-2H-pyrido[2,1-a]isoquinoline-3-carboxylic Acid

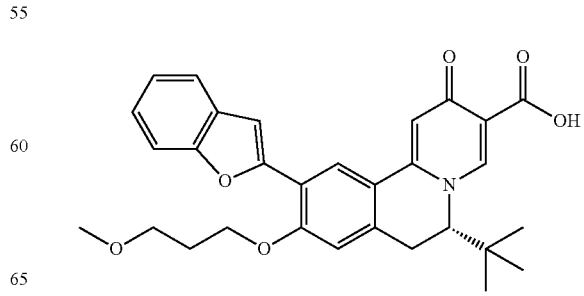

The title compound was prepared following similar procedure as Example 1. ESI MS m/z=502.1 [M+H]+. 1H NMR (400 MHz, CDCl3): δ 16.0 (br s, 1H), 8.49 (s, 1H), 8.48 (s, 1H), 7.62-7.56 (m, 2H), 7.37-7.33 (m, 3H), 7.28-7.23 (m, 1H), 6.90 (s, 1H), 4.41-4.30 (m, 2H), 4.08 (d, J=6.4 Hz, 1H), 3.72-3.64 (m, 2H), 3.51 (dd, J=16.8, 6.6 Hz, 1H), 3.40 (s, 3H), 3.28 (d, J=16.8 Hz, 1H), 2.32-2.36 (m, 2H), 0.86 (s, 9H).

Example 10: (S)-10-(benzofuran-3-yl)-6-(tert-butyl)-9-(3-methoxypropoxy)-2-oxo-6,7-dihydro-2H-pyrido[2,1-a]isoquinoline-3-carboxylic Acid

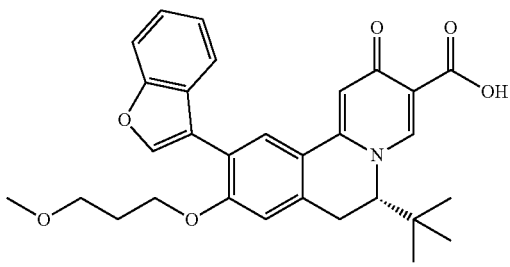 [SMILES: COCCCOc1cc2c(cc1-c1coc3ccccc13)-c1cc(=O)c(C(=O)O)cn1[C@H](C(C)(C)C)C2]

The title compound was prepared following similar procedure as Example 1. ESI MS m/z=502.1 [M+H]+. 1H NMR (400 MHz, CDCl3): δ 15.99 (br s, 1H), 8.50 (s, 1H), 8.04 (s, 1H), 8.02 (s, 1H), 7.73-7.71 (m, 1H), 7.59-7.57 (m, 1H), 7.40-7.32 (m, 2H), 7.15 (s, 1H), 6.92 (s, 1H), 4.30-4.17 (m, 2H), 4.10 (d, J=6.0 Hz, 1H), 3.56-3.45 (m, 3H), 3.32-3.28 (m, 4H), 2.12-2.06 (m, 2H), 0.87 (s, 9H).

Example 11: (S)-6-(tert-butyl)-9-(3-methoxypropoxy)-2-oxo-10-(1H-pyrrol-3-yl)-6,7-dihydro-2H-pyrido[2,1-a]isoquinoline-3-carboxylic Acid

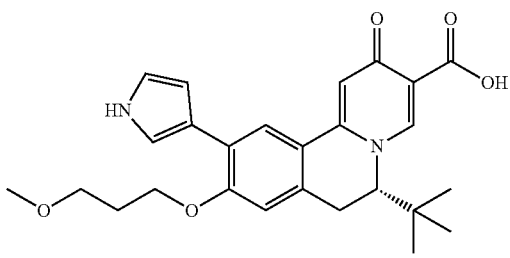

The title compound was prepared following similar procedure as Example 1. ESI MS m/z=451.1 [M+H]+. 1H NMR (400 MHz, CDCl3): δ 16.10 (br s, 1H), 8.45 (s, 1H), 8.39 (br s, 1H), 7.42-7.40 (m, 1H), 7.18 (s, 1H), 6.90-6.88 (m, 1H), 6.80 (s, 1H), 6.67-6.66 (m, 1H), 4.29-4.18 (m, 2H), 4.02 (d, J=6.3 Hz, 1H), 3.64-3.60 (m, 2H), 3.46 (dd, J=16.9, 6.6 Hz, 1H), 3.37 (s, 3H), 3.22 (d, J=16.9 Hz, 1H), 2.22-2.16 (m, 2H), 0.84 (s, 9H).

Example 12: (S)-6-(tert-butyl)-9-(3-methoxypropoxy)-2-oxo-10-(quinolin-3-yl)-6,7-dihydro-2H-pyrido[2,1-a]isoquinoline-3-carboxylic Acid

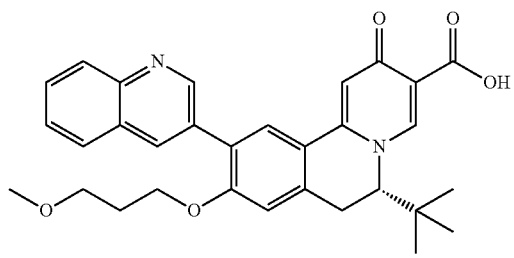 [SMILES: COCCCOc1cc2c(cc1-c1cnc3ccccc3c1)-c1cc(=O)c(C(=O)O)cn1[C@H](C(C)(C)C)C2]

The title compound was prepared following similar procedure as Example 1. ESI MS m/z=513.1 [M+H]+.

Example 13: (S)-6-(tert-butyl)-10-(2-fluorophenyl)-9-(3-methoxypropoxy)-2-oxo-6,7-dihydro-2H-pyrido[2,1-a]isoquinoline-3-carboxylic Acid

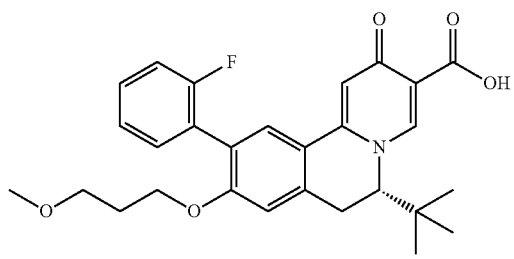 [SMILES: COCCCOc1cc2c(cc1-c1ccccc1F)-c1cc(=O)c(C(=O)O)cn1[C@H](C(C)(C)C)C2]

The title compound was prepared following similar procedure as Example 1. ESI MS m/z=480.1 [M+H]+.

Example 14: (S)-6-(tert-butyl)-10-(3-fluorophenyl)-9-(3-methoxypropoxy)-2-oxo-6,7-dihydro-2H-pyrido[2,1-a]isoquinoline-3-carboxylic Acid

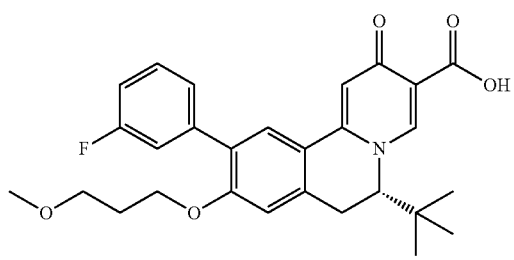 [SMILES: COCCCOc1cc2c(cc1-c1cccc(F)c1)-c1cc(=O)c(C(=O)O)cn1[C@H](C(C)(C)C)C2]

The title compound was prepared following similar procedure as Example 1. ESI MS m/z=480.1 [M+H]+.

Example 15: (S)-6-(tert-butyl)-10-(4-fluorophenyl)-9-(3-methoxypropoxy)-2-oxo-6,7-dihydro-2H-pyrido[2,1-a]isoquinoline-3-carboxylic Acid

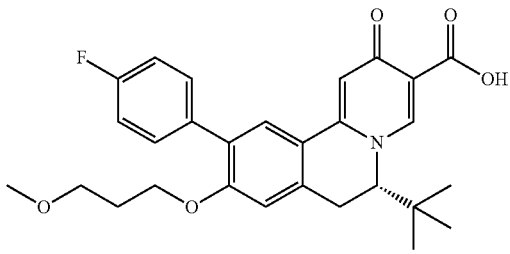

The title compound was prepared following similar procedure as Example 1. ESI MS m/z=480.1 [M+H]$^+$.

Example 16: (S)-6-(tert-butyl)-10-(3-methoxyphenyl)-9-(3-methoxypropoxy)-2-oxo-6,7-dihydro-2H-pyrido[2,1-a]isoquinoline-3-carboxylic Acid

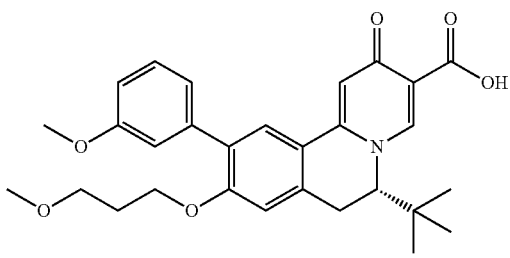 [SMILES: COCCCOc1cc2c(cc1-c1cccc(OC)c1)-c1cc(=O)c(C(=O)O)cn1[C@H](C(C)(C)C)C2]

The title compound was prepared following similar procedure as Example 1. ESI MS m/z=492.1 [M+H]$^+$.

Example 17: (S)-6-(tert-butyl)-10-(4-methoxyphenyl)-9-(3-methoxypropoxy)-2-oxo-6,7-dihydro-2H-pyrido[2,1-a]isoquinoline-3-carboxylic Acid

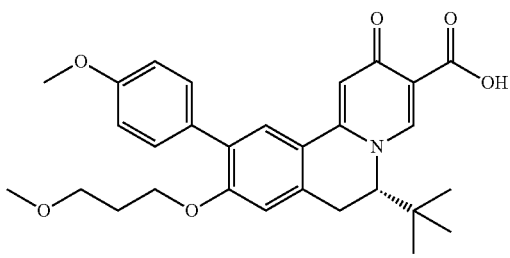 [SMILES: COCCCOc1cc2c(cc1-c1ccc(OC)cc1)-c1cc(=O)c(C(=O)O)cn1[C@H](C(C)(C)C)C2]

The title compound was prepared following similar procedure as Example 1. ESI MS m/z=492.1 [M+H]$^+$.

Example 18: (S)-6-(tert-butyl)-9-(3-methoxypropoxy)-10-(1-methyl-1H-pyrazol-5-yl)-2-oxo-6,7-dihydro-2H-pyrido[2,1-a]isoquinoline-3-carboxylic Acid

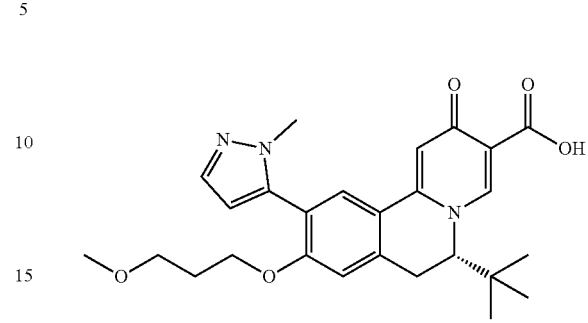

The title compound was prepared following similar procedure as Example 1. ESI MS m/z=466.1 [M+H]$^+$.

Example 19: (S)-6-(tert-butyl)-10-(1H-indol-2-yl)-9-(3-methoxypropoxy)-2-oxo-6,7-dihydro-2H-pyrido[2,1-a]isoquinoline-3-carboxylic Acid

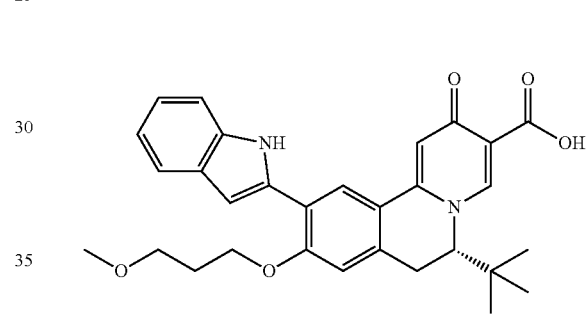

The title compound was prepared following similar procedure as Example 1. ESI MS m/z=501.1 [M+H]$^+$. $^1$H NMR (400 MHz, CDCl$_3$): δ 15.97 (br s, 1H), 10.6 (br s, 1H), 8.48 (s, 1H), 8.22 (s, 1H), 7.68 (d, J=8.0 Hz, 1H), 7.41 (d, J=8.0 Hz, 1H), 7.23-7.18 (m, 2H), 7.14-7.10 (m, 1H), 6.97 (d, J=1.7 Hz, 1H), 6.85 (s, 1H), 4.40-4.28 (m, 2H), 4.06 (d, J=6.2 Hz, 1H), 3.76 (t, J=5.5 Hz, 2H), 3.52 (s, 3H), 3.53-3.46 (m, 1H), 3.27 (d, J=16.6 Hz, 1H), 2.30-2.50 (m, 2H), 0.86 (s, 9H).

Example 20: (S)-6-(tert-butyl)-10-(2,4-dimethylthiazol-5-yl)-9-(3-methoxypropoxy)-2-oxo-6,7-dihydro-2H-pyrido[2,1-a]isoquinoline-3-carboxylic Acid

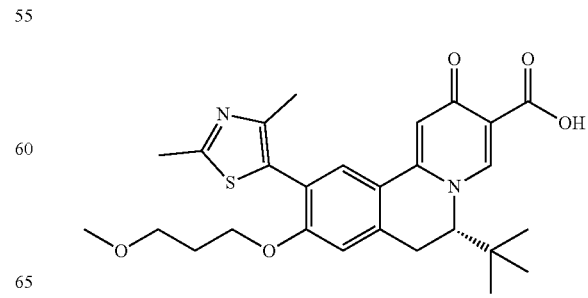

The title compound was prepared following similar procedure as Example 1. ESI MS m/z=497.1 [M+H].

Example 21: (S)-6-(tert-butyl)-9-(3-methoxy-propoxy)-10-(2-methylbenzofuran-3-yl)-2-oxo-6,7-dihydro-2H-pyrido[2,1-a]isoquinoline-3-carboxylic Acid

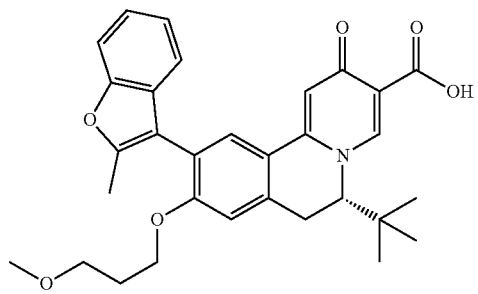 [SMILES: COCCCOc1cc2c(cc1-c1c(C)oc3ccccc13)-c1cc(=O)c(C(=O)O)cn1[C@H](C(C)(C)C)C2]

The title compound was prepared following similar procedure as Example 1. ESI MS m/z=516.1 [M+H]$^+$.

Example 22: (S)-6-(tert-butyl)-10-(2,4-difluorophenyl)-9-(3-methoxypropoxy)-2-oxo-6,7-dihydro-2H-pyrido[2,1-a]isoquinoline-3-carboxylic Acid

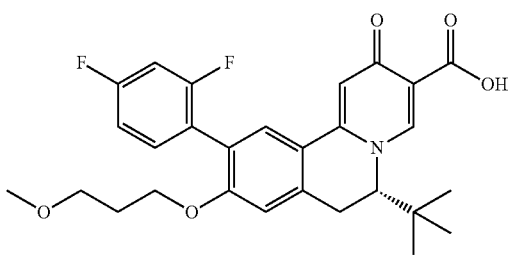

The title compound was prepared following similar procedure as Example 1. ESI MS m/z=498.1 [M+H]$^+$.

Example 23: (S)-6-(tert-butyl)-10-(2,3-difluorophenyl)-9-(3-methoxypropoxy)-2-oxo-6,7-dihydro-2H-pyrido[2,1-a]isoquinoline-3-carboxylic Acid

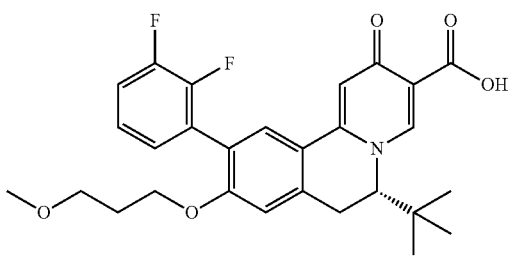 [SMILES: COCCCOc1cc2c(cc1-c1cccc(F)c1F)-c1cc(=O)c(C(=O)O)cn1[C@H](C(C)(C)C)C2]

The title compound was prepared following similar procedure as Example 1. ESI MS m/z=497.1 [M+H]$^+$.

Example 24: (S)-6-(tert-butyl)-9-(3-methoxy-propoxy)-10-(4-methyl-3,4-dihydro-2H-benzo[b][1,4]oxazin-7-yl)-2-oxo-6,7-dihydro-2H-pyrido[2,1-a]isoquinoline-3-carboxylic Acid

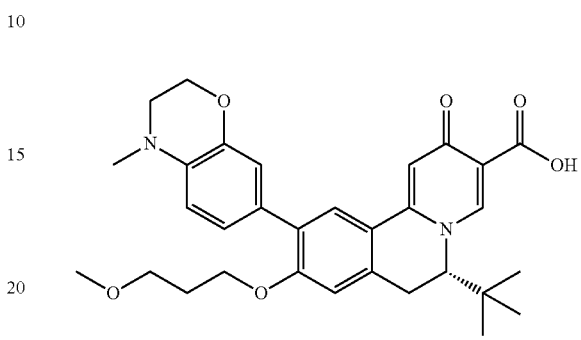

The title compound was prepared following similar procedure as Example 1. ESI MS m/z=533.1 [M+H]$^+$.

Example 25: (S)-10-(benzo[d]oxazol-2-yl)-6-(tert-butyl)-9-(3-methoxypropoxy)-2-oxo-6,7-dihydro-2H-pyrido[2,1-a]isoquinoline-3-carboxylic Acid

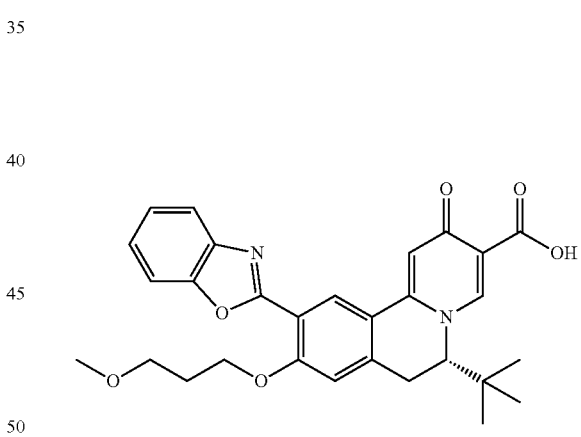

An oven-dried vial was charged with (S)-6-(tert-butyl)-10-chloro-9-(3-methoxypropoxy)-2-oxo-6,7-dihydro-2H-pyrido[2,1-a]isoquinoline-3-carboxylic acid (50 mg, 0.12 mmol), benzo[d]oxazole (71 mg, 0.6 mmol), PdRuPhos G2 (18 mg, 0.02 mmol), pivalic acid (7 mg, 0.07 mmol), and K$_2$CO$_3$ (165 mg, 1.2 mmol). The vial was purged with nitrogen gas for 5 minutes, then toluene (1.2 mL) was added via syringe. The reaction mixture was heated under a nitrogen atmosphere for 3 hours at 110° C. After cooling to room temperature, the reaction mixture was filtered and concentrated. The crude product was dissolved in DMSO (2 mL) and purified by RPHPLC to provide the product as a white solid (11 mg, 18% yield). ESI MS m/z=503.1 [M+H]$^+$.

Example 26: (S)-6-(tert-butyl)-9-(3-methoxypropoxy)-2-oxo-10-(4-(trifluoromethyl)oxazol-2-yl)-6,7-dihydro-2H-pyrido[2,1-a]isoquinoline-3-carboxylic Acid

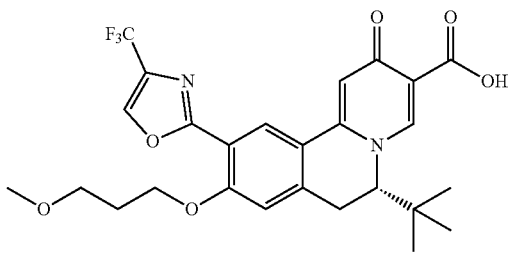 [SMILES: COCCCOc1cc2c(cc1-c1nc(C(F)(F)F)co1)-c1cc(=O)c(C(=O)O)cn1[C@H](C(C)(C)C)C2]

The title compound was prepared following similar procedure as Example 25. ESI MS m/z=521.1 [M+H]$^+$.

Example 27: (S)-6-(tert-butyl)-9-(3-methoxypropoxy)-2-oxo-10-(4-(trifluoromethyl)oxazol-5-yl)-6,7-dihydro-2H-pyrido[2,1-a]isoquinoline-3-carboxylic Acid

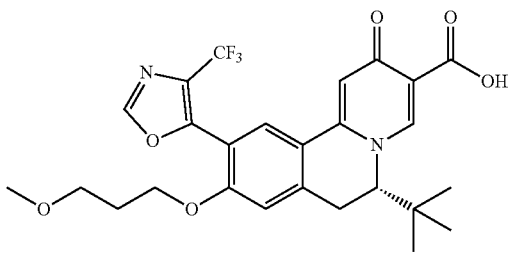 [SMILES: COCCCOc1cc2c(cc1-c1ocnc1C(F)(F)F)-c1cc(=O)c(C(=O)O)cn1[C@H](C(C)(C)C)C2]

The title compound was prepared following similar procedure as Example 25. ESI MS m/z=521.1 [M+H]$^+$.

Example 28: (S)-6-(tert-butyl)-9-(3-methoxypropoxy)-2-oxo-10-(1H-pyrazol-1-yl)-6,7-dihydro-2H-pyrido[2,1-a]isoquinoline-3-carboxylic Acid

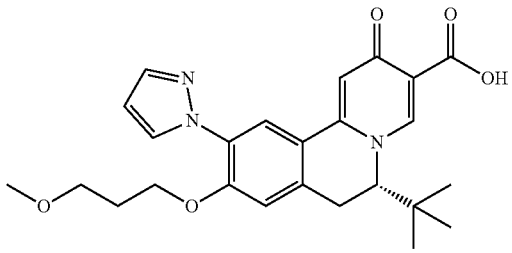 [SMILES: COCCCOc1cc2c(cc1-n1cccn1)-c1cc(=O)c(C(=O)O)cn1[C@H](C(C)(C)C)C2]

Step 1: An oven-dried vial was charged with (S)-6-(tert-butyl)-10-chloro-9-(3-methoxypropoxy)-2-oxo-6,7-dihydro-2H-pyrido[2,1-a]isoquinoline-3-carboxylic acid (50 mg, 0.12 mmol), pyrazole (81 mg, 1.2 mmol), Pd$^t$BuXPhos G3 (9 mg, 0.01 mmol), and NaO$^t$Bu (114 mg, 1.2 mmol). The vial was purged with nitrogen gas for 5 minutes, then toluene (1.2 mL) was added via syringe. The reaction mixture was heated under a nitrogen atmosphere for 4 hours at 110° C. After cooling to room temperature, the reaction mixture was filtered and concentrated. The crude product was dissolved in DMSO (2 mL) and purified by RPHPLC to provide the product as a white solid (2 mg, 3% yield). ESI MS m/z=452.1 [M+H]$^+$.

Example 29: (S)-6-(tert-butyl)-10-(3,4-dihydro-2H-pyran-6-yl)-9-(3-methoxypropoxy)-2-oxo-6,7-dihydro-2H-pyrido[2,1-a]isoquinoline-3-carboxylic Acid

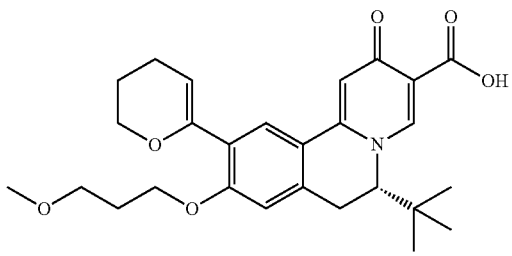 [SMILES: COCCCOc1cc2c(cc1C1=CCCCO1)-c1cc(=O)c(C(=O)O)cn1[C@H](C(C)(C)C)C2]

Step 1: An oven-dried vial was charged with (S)-6-(tert-butyl)-10-chloro-9-(3-methoxypropoxy)-2-oxo-6,7-dihydro-2H-pyrido[2,1-a]isoquinoline-3-carboxylic acid (150 mg, 0.36 mmol), 2-(3,4-dihydro-2H-pyran-6-yl)-4,4,5,5-tetramethyl-1,3,2-dioxaborolane (375 mg, 1.8 mmol), Pd$^t$BuXPhos G3 (28 mg, 0.04 mmol), and Cs$_2$CO$_3$ (582 mg, 1.8 mmol). The vial was purged with nitrogen gas for 5 minutes, then DMF (3 mL) and water (0.6 mL) were added via syringe. The reaction mixture was heated under a nitrogen atmosphere for 80 minutes at 110° C. After cooling to room temperature, the reaction mixture was filtered and concentrated. The crude product was dissolved in DMSO (2 mL) and purified by RPHPLC to provide the product as a white solid (18 mg, 11% yield). ESI MS m/z=468.1 [M+H]$^+$.

Example 30: (S)-5-(tert-butyl)-12-(3,3-difluoroazetidin-1-yl)-9-oxo-2,3,4,9-tetrahydro-5H-furo[3,2-f]pyrido[2,1-a]isoquinoline-8-carboxylic Acid

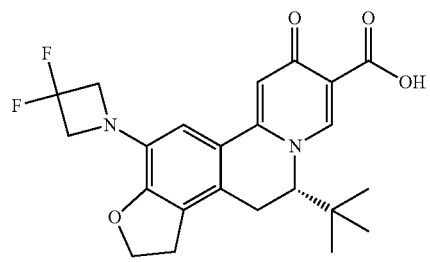 [SMILES: CC(C)(C)[C@@H]1Cc2c(cc(N3CC(F)(F)C3)c3c2CCO3)-c2cc(=O)c(C(=O)O)cn21]

Step 1: Into a round-bottom flask purged and maintained with an inert atmosphere of nitrogen, was placed 2-bromo-5-iodophenol (127 mg, 0.424 mmol) and acetone (5 mL). This was followed by the addition of 3-bromoprop-1-ene (77 mg, 0.637 mmol) dropwise with stirring at 25° C. To this was added K$_2$CO$_3$ (117 mg, 0.849 mmol) at 10° C. The resulting solution was stirred for 1.5 h at 60° C. The reaction mixture was cooled to room temperature and washed with MTBE (5 mL). The solids were filtered out. The filtrate was concentrated under vacuum. This resulted in 140 mg (crude) of 1-bromo-4-iodo-2-(prop-2-en-1-yloxy)benzene as a yellow oil, which was taken onto the next step without further purification.

Step 2: Into an oven dried vial was placed 1-bromo-4-iodo-2-(prop-2-en-1-yloxy)benzene (140 mg, crude). The material was stirred for 5 h at 160° C. The resulting product was diluted with 5 mL of EA. The resulting mixture was concentrated under vacuum. This resulted in 130 mg (crude) of 6-bromo-3-iodo-2-(prop-2-en-1-yl)phenol as a brown oil, which was taken onto the next step without further purification.

Step 3: Into a round-bottom flask purged and maintained with an inert atmosphere of nitrogen, was placed $K_2OsO_4 \cdot 2H_2O$ (2.83 mg, 7.670 μmol) in $H_2O$ (1 mL), 6-bromo-3-iodo-2-(prop-2-en-1-yl)phenol (130 mg, crude) in THF (1 mL). The resulting solution was stirred for 0.5 h. This was followed by the addition of $NaIO_4$ (205 mg, 0.958 mmol) in $H_2O$ (1 mL) dropwise with stirring at 10° C. The resulting solution was stirred for 16 h at rt. The resulting mixture was washed with 3 mL of $H_2O$. The resulting solution was extracted with 3×5 mL of ethyl acetate, dried over anhydrous sodium sulfate, filtered and concentrated. This resulted in 134 mg (crude) of 2-(3-bromo-2-hydroxy-6-iodophenyl)acetaldehyde as a dark orange solid, which was taken onto the next step without further purification.

Step 4: Into a round-bottom flask purged and maintained with an inert atmosphere of nitrogen, was placed 2-(3-bromo-2-hydroxy-6-iodophenyl)acetaldehyde (134 mg, crude) and MeOH (2 mL). This was followed by the addition of $NaBH_4$ (29 mg) at 0° C. The resulting solution was stirred for 3 h at 10° C. The reaction was then quenched by the addition of sat. Aq. $NH_4Cl$ (5 mL). The resulting solution was extracted with 2×5 mL of ethyl acetate and the organic layers combined. The resulting mixture was washed with 10 mL of brine. The mixture was dried over anhydrous sodium sulfate and concentrated under vacuum. The residue was applied onto a silica gel column and eluted with ethyl acetate/petroleum ether (5:100) to provide the product, 6-bromo-2-(2-hydroxyethyl)-3-iodophenol as a yellow solid (90 mg, 67% yield).

Step 5: Into a round-bottom flask purged and maintained with an inert atmosphere of nitrogen, was placed 6-bromo-2-(2-hydroxyethyl)-3-iodophenol (90 mg), THF (2 mL), and $PPh_3$ (103 mg). This was followed by the addition of DEAD (80 mg) dropwise with stirring at 10° C. The resulting solution was stirred for 120 min at room temperature. The reaction was then quenched by the addition of 2 mL of water. The resulting solution was extracted with 2×10 mL of ethyl acetate and the organic layers combined. The resulting mixture was washed with 5 mL of brine. The mixture was dried over anhydrous sodium sulfate and concentrated under vacuum. The residue was applied onto a silica gel column and eluted with ethyl acetate/petroleum ether (1:50) to provide the product, 7-bromo-4-iodo-2,3-dihydro-1-benzofuran as a yellow oil (50 mg, 59% yield).

Step 6: Into a round-bottom flask purged and maintained with an inert atmosphere of nitrogen, was placed 7-bromo-4-iodo-2,3-dihydro-1-benzofuran (52 mg, 0.160 mmol), THF (1 mL), 3,3-dimethylbutan-2-one (35 mg, 0.352 mmol), $Pd_2(dba)_3$ (4.4 mg, xantphos (5.5 mg), and t-BuONa (38.5 mg, 0.400 mmol). The resulting solution was stirred for 3 h at 50° C. The reaction was then quenched by the addition of 3 mL of water. The resulting solution was extracted with 2×2 mL of ethyl acetate and the organic layers combined. The resulting mixture was washed with 5 mL of brine. The mixture was dried over anhydrous sodium sulfate and concentrated under vacuum. The residue was applied onto a silica gel column and eluted with ethyl acetate/petroleum ether (0:1-1:50) to provide the product, 1-(7-bromo-2,3-dihydro-1-benzofuran-4-yl)-3,3-dimethylbutan-2-one as yellow oil (25 mg, 53% yield).

Step 7: Into a round-bottom flask purged and maintained with an inert atmosphere of nitrogen, was placed 1-(7-bromo-2,3-dihydro-1-benzofuran-4-yl)-3,3-dimethylbutan-2-one (40 mg, 0.134 mmol), MeOH (1 mL), $CH_3COONH_4$ (103 mg, 0.134 mmol), and $NaBH_3CN$ (17 mg, 0.270 mmol). The resulting solution was stirred for 16 h at 60° C. The reaction was then quenched by the addition of 5 mL of water. The resulting solution was extracted with 2×5 mL of ethyl acetate and the organic layers combined. The resulting mixture was washed with 1×5 mL of brine. The mixture was dried over anhydrous sodium sulfate, filtered, and concentrated under vacuum. This resulted in 40 mg (crude) of 1-(7-bromo-2,3-dihydro-1-benzofuran-4-yl)-3,3-dimethylbutan-2-amine as a yellow solid, which was taken onto the next step without further purification.

Step 8: Into a round-bottom flask purged and maintained with an inert atmosphere of nitrogen, was placed 1-(7-bromo-2,3-dihydro-1-benzofuran-4-yl)-3,3-dimethylbutan-2-amine (43 mg, 0.144 mmol), methyl formate (1 mL), formic acid (8 mg, 0.173 mmol). The resulting solution was stirred for 16 h at 60° C. The resulting mixture was concentrated under vacuum. This resulted in 43 mg (crude) of N-[1-(7-bromo-2,3-dihydro-1-benzofuran-4-yl)-3,3-dimethylbutan-2-yl]formamide as a yellow solid, which was taken onto the next step without further purification.

Step 9: Into a round-bottom flask purged and maintained with an inert atmosphere of nitrogen, was placed N-[1-(7-bromo-2,3-dihydro-1-benzofuran-4-yl)-3,3-dimethylbutan-2-yl]formamide (47 mg, 0.144 mmol), ACN (1 mL), and $POCl_3$ (26 mg, 0.174 mmol). The resulting solution was stirred for 2 h at 70° C. The resulting mixture was concentrated under vacuum. The resulting solution was diluted with 2 mL of EA. The resulting mixture was washed with 1×3 mL of sat. Aq. $NaHCO_3$. The mixture was dried over anhydrous sodium sulfate and concentrated under vacuum. This resulted in 45 mg (crude) of 4-bromo-8-(tert-butyl)-1,2,8,9-hexahydrofuro[3,2-f]isoquinoline as a yellow solid, which was taken to the next step without further purification.

Step 10: Into a round-bottom flask purged and maintained with an inert atmosphere of nitrogen, was placed 4-bromo-8-(tert-butyl)-1,2,8,9-hexahydrofuro[3,2-f]isoquinoline (47 mg, crude), ethyl (2E)-2-(ethoxymethylidene)-3-oxobutanoate (85 mg, 3.00 equiv), EtOH (2 mL). The resulting solution was stirred for 20 h at 60° C. The resulting mixture was concentrated under vacuum. The resulting mixture was washed with 1×2 mL of EtOAc. The solids were collected by filtration to provide the product, ethyl 12-bromo-5-(tert-butyl)-9-oxo-2,3,4,9,10,10a-hexahydro-5H-furo[3,2-f]pyrido[2,1-a]isoquinoline-8-carboxylate as a white solid (20 mg, 29% yield).

Step 11: Into a vial purged and maintained with an inert atmosphere of nitrogen, was placed ethyl 12-bromo-5-(tert-butyl)-9-oxo-2,3,4,9,10,10a-hexahydro-5H-furo[3,2-f]pyrido[2,1-a]isoquinoline-8-carboxylate (20 mg), DCE (2 mL), and tetrachlorocyclohexa-2,5-diene-1,4-dione (14 mg). The resulting solution was stirred for 15 h at 80° C. The resulting mixture was concentrated under vacuum. The residue was purified by SFC (Column: CHIRAL ART Cellulose-SB, mobile phase: 50% $CO_2$/(2 mM ammonia in EtOH) to provide the product, ethyl (S)-12-bromo-5-(tert-butyl)-9-oxo-2,3,4,9-tetrahydro-5H-furo[3,2-f]pyrido[2,1-a]isoquinoline-8-carboxylate as a off-white solid (5 mg, 25% yield).

Step 12: Into a vial was placed ethyl (S)-12-bromo-5-(tert-butyl)-9-oxo-2,3,4,9-tetrahydro-5H-furo[3,2-f]pyrido

[2,1-a]isoquinoline-8-carboxylate (5 mg), EtOH (1 mL), and 1 M Aq. NaOH (0.5 mL). The resulting solution was stirred for 120 min at room temperature. Most of the EtOH was removed under vacuum. The resulting solution was diluted with 1 mL of water.

The pH value of the solution was adjusted to 3 with 1 M aq. HCl. The solids were collected by filtration to provide the product, (S)-12-bromo-5-(tert-butyl)-9-oxo-2,3,4,9-tetrahydro-5H-furo[3,2-f]pyrido[2,1-a]isoquinoline-8-carboxylic acid as a off-white solid (3 mg, 78% yield). ESI MS m/z=418.1 [M+H]+. 1H NMR (400 MHz, DMSO-d6): δ 8.72 (s, 1H), 8.11 (s, 1H), 7.37 (s, 1H), 4.80 (m, 2H), 4.64 (d, J=6.5 Hz, 1H), 3.47 (dd, J=16.2, 8.5 Hz, 1H), 3.11 (d, J=17.1 Hz, 1H), 0.78-0.72 (m, 8H).

Step 13: An oven-dried vial was charged with (S)-12-bromo-5-(tert-butyl)-9-oxo-2,3,4,9-tetrahydro-5H-furo[3,2-f]pyrido[2,1-a]isoquinoline-8-carboxylic acid (50 mg, 0.12 mmol), 3,3-difluoroazetidine hydrochloride (47 mg, 0.359 mmol), Pd<sup>t</sup>BuPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 4 h at 110° C. After cooling to room temperature, the reaction mixture was filtered and concentrated. The crude product was dissolved in DMSO (2 mL) and purified by RPHPLC to provide the product as a white solid (5 mg, 10% yield). ESI MS m/z=431.1 [M+H]+.

Example 31: (S)-6-(tert-butyl)-10-(2,3-dihydrobenzo[b][1,4]dioxin-6-yl)-9-(3-methoxypropoxy)-2-oxo-6,7-dihydro-2H-pyrido[2,1-a]isoquinoline-3-carboxylic Acid

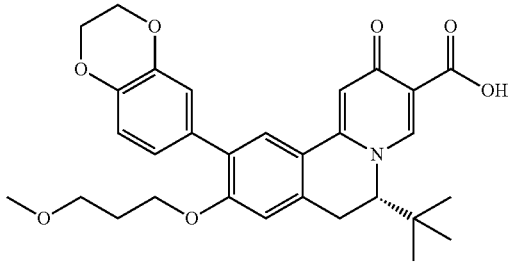

The title compound was prepared following similar procedure as Example 1. ESI MS m/z=497.1 [M+H]+.

Example 32: (S)-6-(tert-butyl)-10-(1,3-dimethyl-1H-pyrazol-4-yl)-9-(3-methoxypropoxy)-2-oxo-6,7-dihydro-2H-pyrido[2,1-a]isoquinoline-3-carboxylic Acid

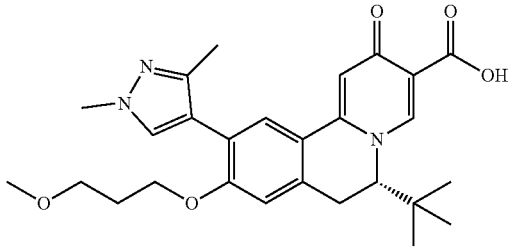

The title compound was prepared following similar procedure as Example 1. ESI MS m/z=480.1 [M+H]+.

Example 33: (S)-6-(tert-butyl)-9-(3-methoxypropoxy)-2-oxo-10-(1,3,5-trimethyl-1H-pyrazol-4-yl)-6,7-dihydro-2H-pyrido[2,1-a]isoquinoline-3-carboxylic Acid

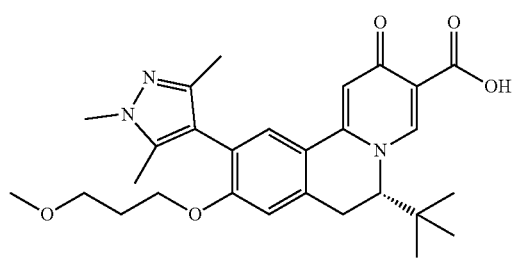

The title compound was prepared following similar procedure as Example 1. ESI MS m/z=494.1 [M+H]+.

Example 34: (S)-6-(tert-butyl)-10-(1-ethyl-1H-pyrazol-4-yl)-9-(3-methoxypropoxy)-2-oxo-6,7-dihydro-2H-pyrido[2,1-a]isoquinoline-3-carboxylic Acid

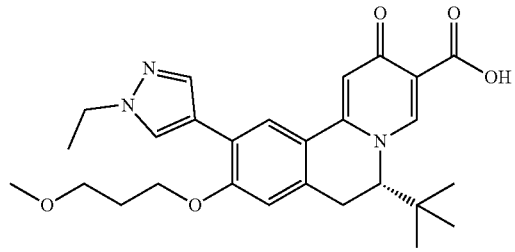 [SMILES: CCn1cc(-c2cc3c(cc2OCCCOC)C[C@@H](C(C)(C)C)n2cc(C(=O)O)c(=O)cc2-3)cn1]

The title compound was prepared following similar procedure as Example 1. ESI MS m/z=480.1 [M+H]+.

Example 35: (S)-6-(tert-butyl)-9-(3-methoxypropoxy)-10-(1-methyl-1H-tetrazol-5-yl)-2-oxo-6,7-dihydro-2H-pyrido[2,1-a]isoquinoline-3-carboxylic Acid

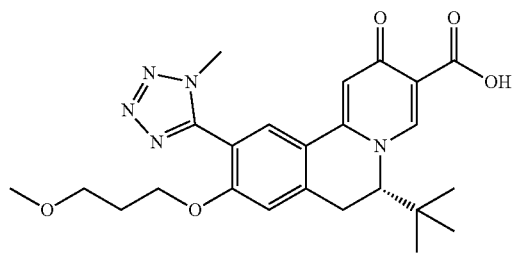

The title compound was prepared following similar procedure as Example 25. ESI MS m/z=468.1 [M+H]+.

Example 36: (S)-6-(tert-butyl)-9-(3-methoxypropoxy)-10-(1,3,4-oxadiazol-2-yl)-2-oxo-6,7-dihydro-2H-pyrido[2,1-a]isoquinoline-3-carboxylic Acid

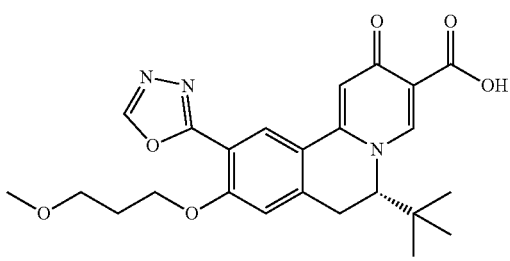

The title compound was prepared following similar procedure as Example 25. ESI MS m/z=454.1 [M+H]+.

Example 37: (S)-6-(tert-butyl)-9-(3-methoxypropoxy)-2-oxo-10-(4-(trifluoromethoxy)phenyl)-6,7-dihydro-2H-pyrido[2,1-a]isoquinoline-3-carboxylic Acid

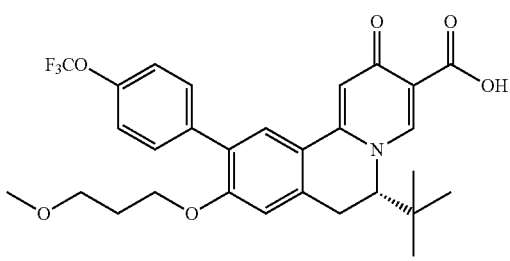 [SMILES: COCCCOc1cc2c(cc1-c1ccc(OC(F)(F)F)cc1)-c1cc(=O)c(C(=O)O)cn1[C@H](C(C)(C)C)C2]

The title compound was prepared following similar procedure as Example 1. ESI MS m/z=546.1 [M+H]+.

Example 38: (S)-6-(tert-butyl)-10-(4-isopropoxyphenyl)-9-(3-methoxypropoxy)-2-oxo-6,7-dihydro-2H-pyrido[2,1-a]isoquinoline-3-carboxylic Acid

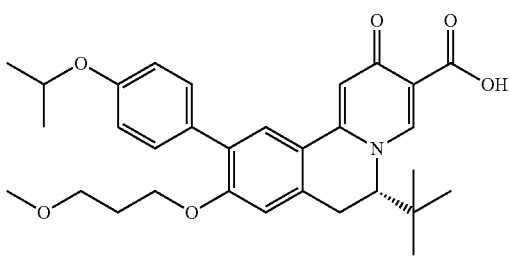 [SMILES: COCCCOc1cc2c(cc1-c1ccc(OC(C)C)cc1)-c1cc(=O)c(C(=O)O)cn1[C@H](C(C)(C)C)C2]

The title compound was prepared following similar procedure as Example 1. ESI MS m/z=520.1 [M+H]+.

Example 39: (S)-6-(tert-butyl)-10-(chroman-7-yl)-9-(3-methoxypropoxy)-2-oxo-6,7-dihydro-2H-pyrido[2,1-a]isoquinoline-3-carboxylic Acid

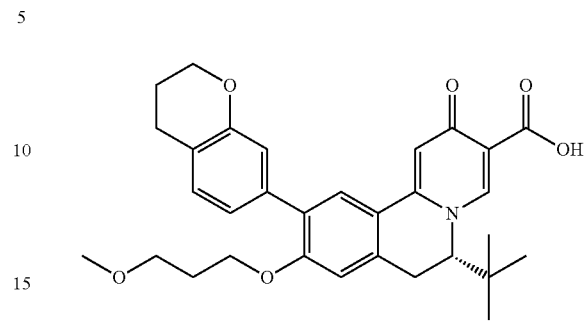

The title compound was prepared following similar procedure as Example 1. ESI MS m/z=518.1 [M+H]+.

Example 40: (S)-6-(tert-butyl)-10-(4-cyclopropoxyphenyl)-9-(3-methoxypropoxy)-2-oxo-6,7-dihydro-2H-pyrido[2,1-a]isoquinoline-3-carboxylic Acid

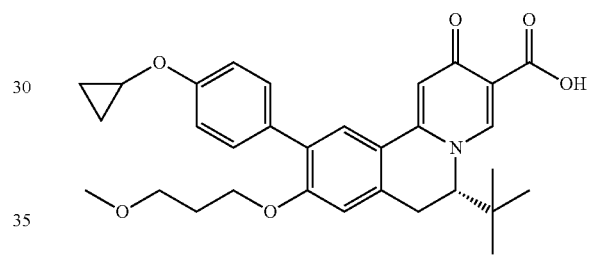

The title compound was prepared following similar procedure as Example 1. ESI MS m/z=518.1 [M+H]+.

Example 41: (6S)-6-(tert-butyl)-9-(3-methoxypropoxy)-2-oxo-10-(tetrahydro-2H-pyran-2-yl)-6,7-dihydro-2H-pyrido[2,1-a]isoquinoline-3-carboxylic Acid

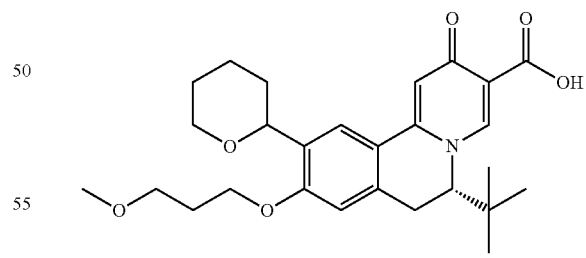

Step 1: A vial was charged with (S)-6-(tert-butyl)-10-(3,4-dihydro-2H-pyran-6-yl)-9-(3-methoxypropoxy)-2-oxo-6,7-dihydro-2H-pyrido[2,1-a]isoquinoline-3-carboxylic acid (50 mg, 0.1 mmol), 10% Pd/C (10 mg), and MeOH (5 mL). The vial was placed under an atmosphere of hydrogen and stirred at room temperature. After 5 h, the mixture was filtered and concentrated. The residue was purified by RPHPLC to provide (6S)-6-(tert-butyl)-9-(3-methoxypropoxy)-2-oxo-10-(tetrahydro-2H-pyran-2-yl)-6,7-dihydro-2H-pyrido[2,1-a]isoquinoline-3-carboxylic acid (10 mg, 20% yield). ESI MS m/z=470.1 [M+H]⁺.

Example 42: (S)-6-(tert-butyl)-10-(3,4-dihydro-2H-pyran-5-yl)-9-(3-methoxypropoxy)-2-oxo-6,7-dihydro-2H-pyrido[2,1-a]isoquinoline-3-carboxylic Acid

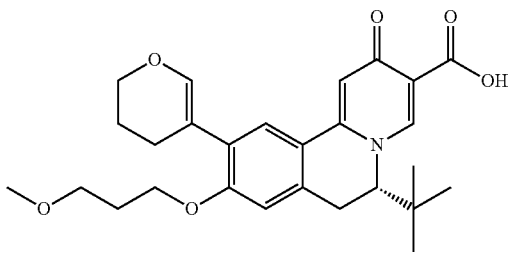

The title compound was prepared following similar procedure as Example 1. ESI MS m/z=468.1 [M+H]⁺.

Example 43: (S)-6-(tert-butyl)-10-(5-ethyl-1,3,4-oxadiazol-2-yl)-9-(3-methoxypropoxy)-2-oxo-6,7-dihydro-2H-pyrido[2,1-a]isoquinoline-3-carboxylic Acid

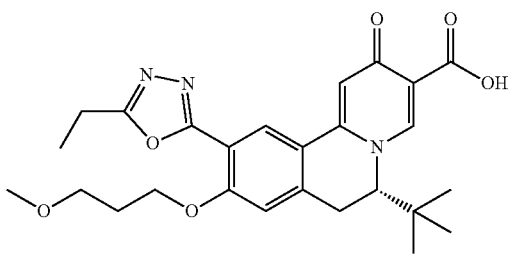 [SMILES: CCc1nnc(-c2cc3c(cc2OCCCOC)C[C@@H](C(C)(C)C)n2cc(C(=O)O)c(=O)cc2-3)o1]

The title compound was prepared following similar procedure as Example 25. ESI MS m/z=482.1 [M+H]⁺.

Example 44: (S)-6-(tert-butyl)-9-(3-methoxypropoxy)-10-(2-methoxypyrimidin-5-yl)-2-oxo-6,7-dihydro-2H-pyrido[2,1-a]isoquinoline-3-carboxylic Acid

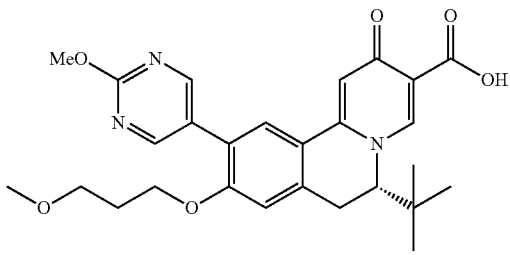

The title compound was prepared following similar procedure as Example 1. ESI MS m/z=494.1 [M+H]⁺.

Example 45: (S)-6-(tert-butyl)-10-(3,6-dimethoxypyridazin-4-yl)-9-(3-methoxypropoxy)-2-oxo-6,7-dihydro-2H-pyrido[2,1-a]isoquinoline-3-carboxylic Acid

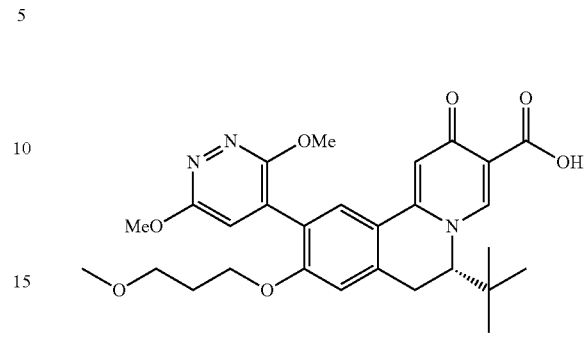

The title compound was prepared following similar procedure as Example 1. ESI MS m/z=524.1 [M+H]⁺.

Example 46: (S)-6-(tert-butyl)-10-(4,5-dihydrofuran-3-yl)-9-(3-methoxypropoxy)-2-oxo-6,7-dihydro-2H-pyrido[2,1-a]isoquinoline-3-carboxylic Acid

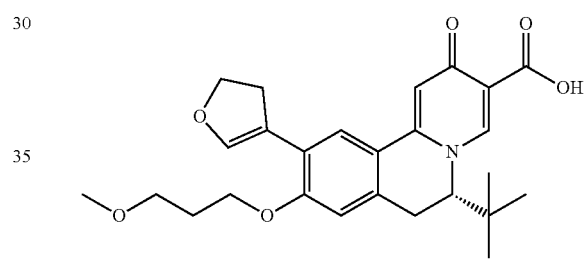

The title compound was prepared following similar procedure as Example 1. ESI MS m/z=454.1 [M+H]⁺.

Example 47: (S)-10-(benzo[d]isoxazol-5-yl)-6-(tert-butyl)-9-(3-methoxypropoxy)-2-oxo-6,7-dihydro-2H-pyrido[2,1-a]isoquinoline-3-carboxylic Acid

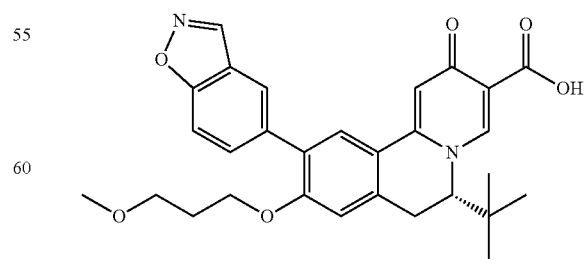

The title compound was prepared following similar procedure as Example 1. ESI MS m/z=503.1 [M+H]⁺.

Example 48: (S)-6-(tert-butyl)-9-(3-methoxypropoxy)-10-(1-methyl-1H-1,2,3-triazol-5-yl)-2-oxo-6,7-dihydro-2H-pyrido[2,1-a]isoquinoline-3-carboxylic Acid

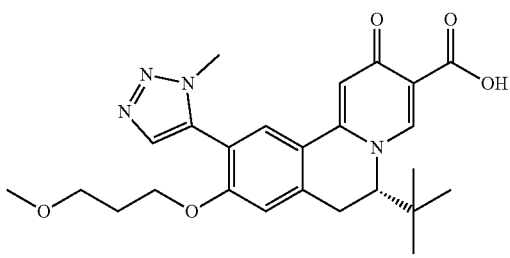 [SMILES: COCCCOc1cc2c(cc1-c1cnnn1C)-c1cc(=O)c(C(=O)O)cn1[C@H](C(C)(C)C)C2]

The title compound was prepared following similar procedure as Example 25. ESI MS m/z=467.1 [M+H].

Example 49: (S)-6-(tert-butyl)-9-(3-methoxypropoxy)-10-(5-methyl-1,3,4-oxadiazol-2-yl)-2-oxo-6,7-dihydro-2H-pyrido[2,1-a]isoquinoline-3-carboxylic Acid

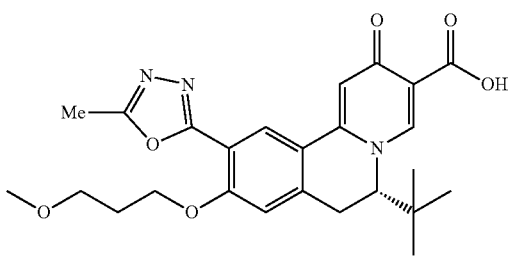 [SMILES: COCCCOc1cc2c(cc1-c1nnc(C)o1)-c1cc(=O)c(C(=O)O)cn1[C@H](C(C)(C)C)C2]

The title compound was prepared following similar procedure as Example 25. ESI MS m/z=468.1 [M+H]$^+$.

Example 50: (R)-6-(tert-butyl)-9-(3-methoxypropoxy)-2-oxo-10-(pyrrolidin-1-yl)-6,7-dihydro-2H-pyrido[2,1-a]isoquinoline-3-carboxylic Acid

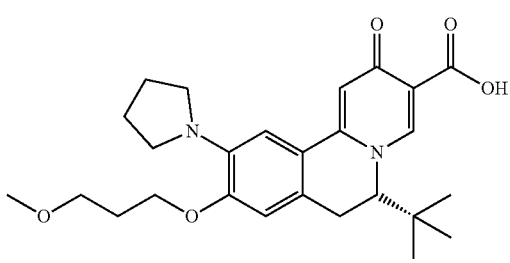

The title compound was prepared following similar procedure as Example 28. ESI MS m/z=455.1 [M+H]$^+$.

Example 51: (R)-6-(tert-butyl)-9-(3-methoxypropoxy)-2-oxo-10-(1H-pyrazol-1-yl)-6,7-dihydro-2H-pyrido[2,1-a]isoquinoline-3-carboxylic Acid

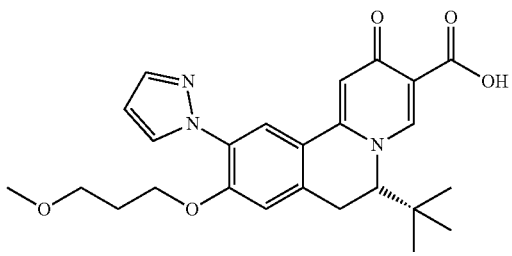

The title compound was prepared following similar procedure as Example 28. ESI MS m/z=452.1 [M+H]$^+$.

Example 52: (S)-6-(tert-butyl)-10-(1H-indol-1-yl)-9-(3-methoxypropoxy)-2-oxo-6,7-dihydro-2H-pyrido[2,1-a]isoquinoline-3-carboxylic Acid

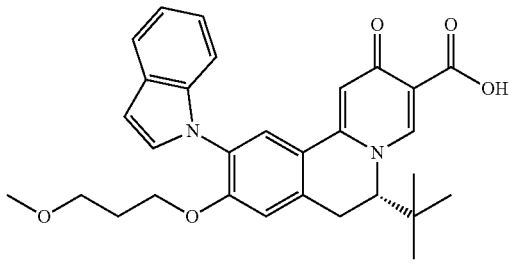 [SMILES: COCCCOc1cc2c(cc1-n1ccc3ccccc31)-c1cc(=O)c(C(=O)O)cn1[C@H](C(C)(C)C)C2]

The title compound was prepared following similar procedure as Example 28. ESI MS m/z=501.1 [M+H]$^+$.

Example 53: (S)-6-(tert-butyl)-9-(3-methoxypropoxy)-2-oxo-10-(5-(trifluoromethyl)-1,3,4-oxadiazol-2-yl)-6,7-dihydro-2H-pyrido[2,1-a]isoquinoline-3-carboxylic Acid

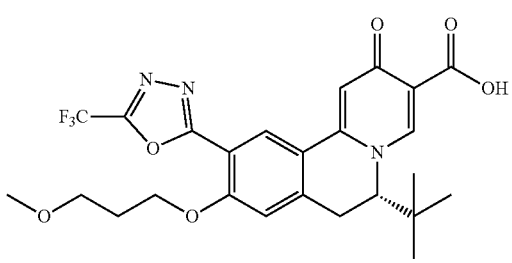 [SMILES: COCCCOc1cc2c(cc1-c1nnc(C(F)(F)F)o1)-c1cc(=O)c(C(=O)O)cn1[C@H](C(C)(C)C)C2]

The title compound was prepared following similar procedure as Example 25. ESI MS m/z=521.1 [M+H]$^+$.

Example 54: (S)-6-(tert-butyl)-10-(3,3-difluoropyrrolidin-1-yl)-9-(3-methoxypropoxy)-2-oxo-6,7-dihydro-2H-pyrido[2,1-a]isoquinoline-3-carboxylic Acid

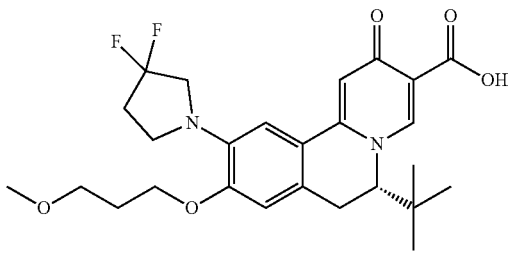 [SMILES: COCCCOc1cc2c(cc1N1CCC(F)(F)C1)-c1cc(=O)c(C(=O)O)cn1[C@H](C(C)(C)C)C2]

The title compound was prepared following similar procedure as Example 28. ESI MS m/z=491.1 [M+H]+.

Example 55: (S)-10-(azetidin-1-yl)-6-(tert-butyl)-9-(3-methoxypropoxy)-2-oxo-6,7-dihydro-2H-pyrido[2,1-a]isoquinoline-3-carboxylic Acid

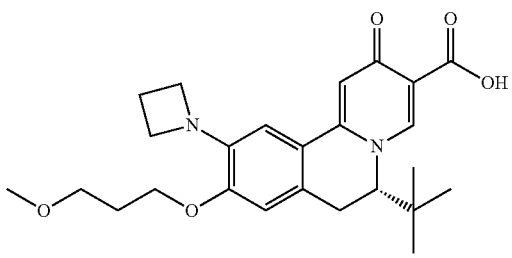 [SMILES: COCCCOc1cc2c(cc1N1CCC1)-c1cc(=O)c(C(=O)O)cn1[C@H](C(C)(C)C)C2]

The title compound was prepared following similar procedure as Example 28. ESI MS m/z=441.1 [M+H]+.

Example 56: (S)-6-(tert-butyl)-10-(4-(difluoromethoxy)phenyl)-9-(3-methoxypropoxy)-2-oxo-6,7-dihydro-2H-pyrido[2,1-a]isoquinoline-3-carboxylic Acid

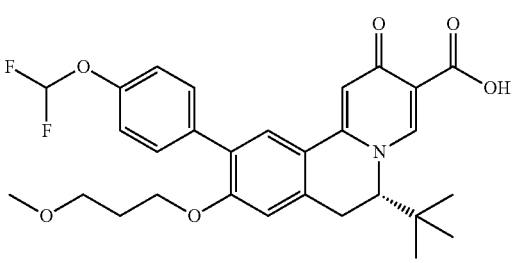 [SMILES: COCCCOc1cc2c(cc1-c1ccc(OC(F)F)cc1)-c1cc(=O)c(C(=O)O)cn1[C@H](C(C)(C)C)C2]

The title compound was prepared following similar procedure as Example 1. ESI MS m/z=528.1 [M+H]+.

Example 57: (S)-6-(tert-butyl)-9-(3-methoxypropoxy)-2-oxo-10-(3-(trifluoromethoxy)phenyl)-6,7-dihydro-2H-pyrido[2,1-a]isoquinoline-3-carboxylic Acid

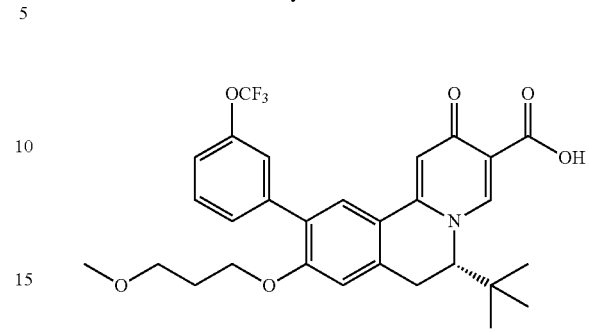

The title compound was prepared following similar procedure as Example 1. ESI MS m/z=546.1 [M+H]+.

Example 58: (S)-6-(tert-butyl)-9-(3-methoxypropoxy)-2-oxo-10-(2-(trifluoromethoxy)phenyl)-6,7-dihydro-2H-pyrido[2,1-a]isoquinoline-3-carboxylic Acid

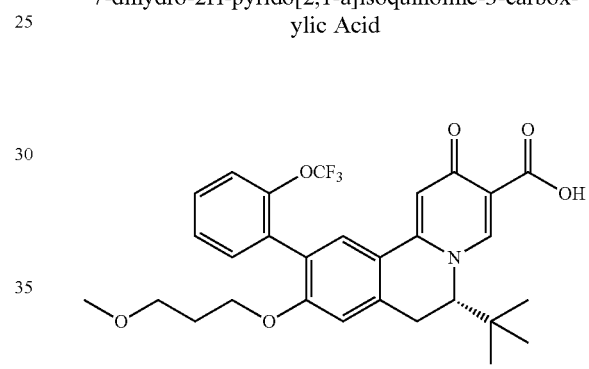

The title compound was prepared following similar procedure as Example 1. ESI MS m/z=546.1 [M+H]+.

Example 59: (3aS,12bR)-10-(4-fluorophenyl)-1-(3-methoxypropoxy)-3,3-dimethyl-7-oxo-1,2,3,3a,7,12b-hexahydrocyclopenta[c]pyrido[2,1-a]isoquinoline-6-carboxylic Acid

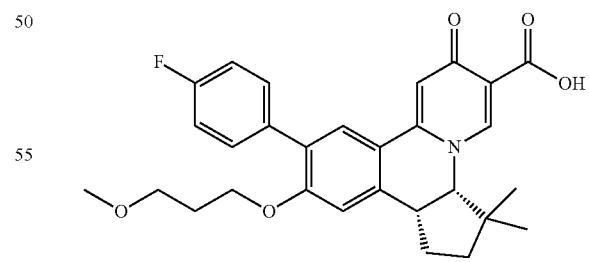

An oven-dried vial was charged (3aS,12bR)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (50 mg, 0.12 mmol), (4-fluorophenyl)boronic acid (84 mg, 0.6 mmol), Pd$^t$BuXPhos G3 (10 mg, 0.01 mmol), and Cs$_2$CO$_3$ (194 mg, 0.6 mmol). The vial was purged with nitrogen gas for 5 minutes, then DMF (1 mL)

and water (0.2 mL) were added via syringe. The reaction mixture was heated under a nitrogen atmosphere for 80 minutes at 110° C. After cooling to room temperature, the reaction mixture was filtered and the product was purified by RPHPLC to provide the product as a white solid (17 mg, 35% yield). ESI MS m/z=492.1 [M+H]⁺.

Example 60: (3aS,12bR)-10-(furan-3-yl)-11-(3-methoxypropoxy)-3,3-dimethyl-7-oxo-1,2,3,3a,7,12b-hexahydrocyclopenta[c]pyrido[2,1-a]isoquinoline-6-carboxylic Acid

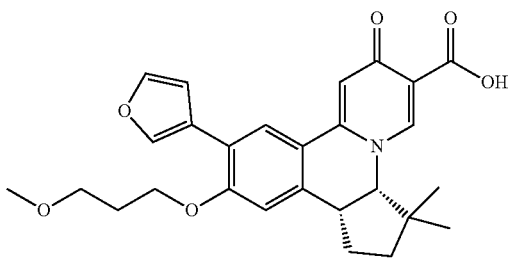 [SMILES: COCCCOc1cc2c(cc1-c1ccoc1)-c1cc(=O)c(C(=O)O)cn1[C@H]1[C@@H]2CCC1(C)C]

The title compound was prepared following similar procedure as Example 59. ESI MS m/z=464.1 [M+H]⁺.

Example 61: (3aS,12bR)-10-(4-fluorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

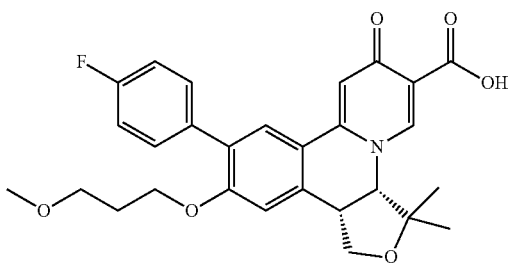 [SMILES: COCCCOc1cc2c(cc1-c1ccc(F)cc1)-c1cc(=O)c(C(=O)O)cn1[C@H]1[C@@H]2COC1(C)C]

Step 1: Into a round-bottom flask purged and maintained with an inert atmosphere of nitrogen was placed 2-bromo-5-iodophenol (900 g, 3 mol), potassium carbonate (832 g, 6 mol), and DMF (10 L). Then, 1-bromo-3-methoxypropane (553 g, 3.6 mol) was added. The mixture was stirred at 50° C. for 4 h. Then, the solids were filtered off and the filtrate was diluted with ethyl acetate (5 L) and washed with water (5 L). The organic layer was concentrated and the residue was purified on silica gel with ethyl acetate:petroleum ether (4:1) to provide the product, 1-bromo-4-iodo-2-(3-methoxypropoxy)benzene as a light yellow oil (1.6 kg, 66% yield).

Step 2: Into a round-bottom flask purged and maintained with an inert atmosphere of nitrogen was placed 3-hydroxy-3-methylbutan-2-one (344 g, 3369 mmol), 1-bromo-4-iodo-2-(3-methoxypropoxy)benzene (500 g, 1347 mmol), t-BuONa (388 g, 4042 mmol), THF (5 L), Pd₂(dba)₃ (61 g, 67 mmol), XantPhos (77 g, 134 mmol). The resulting solution was stirred for 2 h at 70° C. in an oil bath. The reaction was then quenched by the addition of 5 L of water. The pH of the solution was adjusted to 2 with aq. HCl. The resulting solution was extracted with 2×5 L of ethyl acetate. The residue was purified on silica gel with ethyl acetate/petroleum ether (25%) to provide the product, 1-[4-bromo-3-(3-methoxypropoxy)phenyl]-3-hydroxy-3-methylbutan-2-one as brown oil (250 g, 48% yield).

Step 3: Into a flask purged and maintained with an inert atmosphere of nitrogen was placed 1-[4-bromo-3-(3-methoxypropoxy)phenyl]-3-hydroxy-3-methylbutan-2-one (250 g, 724 mmol), [(tert-butoxy)(dimethylamino)methyl]dimethylamine (378 g, 2172 mmol), and toluene (2 L). The resulting solution was stirred for 2 h at 100° C. in an oil bath. The resulting mixture was concentrated. The residue was purified on silica gel with ethyl acetate/petroleum ether (40%) to provide the product, 4-[4-bromo-3-(3-methoxypropoxy)phenyl]-2,2-dimethyl-2,3-dihydrofuran-3-one as a dark brown solid (200 g, 70% yield).

Step 4: Into a round-bottom flask purged and maintained with an inert atmosphere of nitrogen was placed 4-[4-bromo-3-(3-methoxypropoxy)phenyl]-2,2-dimethyl-2,3-dihydrofuran-3-one (200 g, 563 mmol), NaBH₄ (42 g, 1126 mmol), MeOH (2 L), CH₃COONH₄ (520 g, 6756 mmol). The resulting solution was stirred for 16 h at 80° C. in an oil bath. The reaction was then quenched by the addition of 3 L of ice/salt. The resulting solution was extracted with 3×2 L of dichloromethane and the organic layers combined. The residue was purified on silica gel with dichloromethane/ethyl acetate (1:1) to provide the product, 4-[4-bromo-3-(3-methoxypropoxy)phenyl]-2,2-dimethyloxolan-3-ol as a brown solid (180 g, 80% yield).

Step 5: Into a round-bottom flask purged and maintained with an inert atmosphere of nitrogen was placed 4-[4-bromo-3-(3-methoxypropoxy)phenyl]-2,2-dimethyloxolan-3-ol (180 g, 501 mmol), Dess-martin periodinane (425 g, 1002 mmol), and DCM (1800 mL). The resulting solution was stirred for 2 h at room temperature. The reaction was then quenched by the addition of 2000 mL of sat. Na₂S₂O₃ (aq.). The resulting solution was extracted with 2×1 L of dichloromethane and concentrated to provide the product, 4-[4-bromo-3-(3-methoxypropoxy)phenyl]-2,2-dimethyloxolan-3-one as a dark brown solid (180 g, 80% yield), which was used in the next step without further purification.

Step 6: Into a round-bottom flask purged and maintained with an inert atmosphere of nitrogen, was placed 4-[4-bromo-3-(3-methoxypropoxy)phenyl]-2,2-dimethyloxolan-3-one (180 g, 503 mmol), CH₃COONH₄ (466 g, 6046 mmol), MeOH (1.8 L), NaBH₃CN (126 g, 2015 mmol). The resulting solution was stirred for 48 h at 80° C. in an oil bath. The reaction was then quenched by the addition of 1000 mL of water/ice. The resulting solution was extracted with 2×1 L of dichloromethane. The residue was purified on silica gel with dichloromethane/ethyl acetate (50%) to provide the product, 4-[4-bromo-3-(3-methoxypropoxy)phenyl]-2,2-dimethyloxolan-3-amine as a brown solid (100 g, 50% yield).

Step 7: Into a round-bottom flask purged and maintained with an inert atmosphere of nitrogen was placed 4-[4-bromo-3-(3-methoxypropoxy)phenyl]-2,2-dimethyloxolan-3-amine (100 g, 279 mmol), HCOOH (51 g, 1116 mmol), and 1,4-dioxane (1 L). The resulting solution was stirred for 2 h at 80° C. in an oil bath. The resulting mixture was concentrated to provide the product, N-[4-[4-bromo-3-(3-methoxypropoxy)phenyl]-2,2-dimethyloxolan-3-yl]formamide as brown oil (100 g, 74% yield), which was used without further purification.

Step 8: Into a round-bottom flask purged and maintained with an inert atmosphere of nitrogen was placed N-[4-[4-bromo-3-(3-methoxypropoxy)phenyl]-2,2-dimethyloxolan-3-yl]formamide (100 g, 258 mmol), POCl₃ (79 g, 517 mmol), and MeCN (1 L). The resulting solution was stirred for 2 h at 70° C. in an oil bath. The reaction was then quenched by the addition of 1 L of ice/salt. The pH value of the solution was adjusted to 11 with conc. NH₄OH. The residue was purified on silica gel with DCM:ethyl acetate (1:1) to provide the product, 7-bromo-8-(3-methoxypropoxy)-3,3-dimethyl-1H,3H,3aH,9bH-furo[3,4-c]isoquinoline as brown oil (40 g, 38% yield).

Step 9: Into a round-bottom flask purged and maintained with an inert atmosphere of nitrogen was placed 7-bromo-8-(3-methoxypropoxy)-3,3-dimethyl-1H,3H,3aH,9bH-furo[3,4-c]isoquinoline (40 g, 108 mmol), ethyl (2E)-2-(ethoxymethylidene)-3-oxobutanoate (60 g, 325 mmol), and EtOH (400 mL). The resulting solution was stirred for 48 h at 80° C. in an oil bath. The resulting mixture was concentrated. The residue was purified on silica gel with dichloromethane/ethyl acetate (50%) to provide the product, ethyl 10-bromo-9-(3-methoxypropoxy)-3,3-dimethyl-15-oxo-4-oxa-1-azatetracyclo[11.4.0.0[2,6]0.0[7,12]]heptadeca-7,9,11,16-tetraene-16-carboxylate as a brown solid (20 g, 33% yield).

Step 10: Into a round-bottom flask purged and maintained with an inert atmosphere of nitrogen was placed ethyl 10-bromo-9-(3-methoxypropoxy)-3,3-dimethyl-15-oxo-4-oxa-1-azatetracyclo[11.4.0.0[2,6]0.0[7,12]]heptadeca-7,9,11,16-tetraene-16-carboxylate (10 g, 20 mmol), DDQ (8.93 g, 39 mmol), and DCM (100 mL). The resulting solution was stirred for 2 h at room temperature. The reaction mixture was quenched with 100 ml of water. The pH of the solution was adjusted to 8 with aq. NaHCO₃(sat.). The mixture was extracted with 2×200 ml of DCM and concentrated under vacuum. The residue was purified on C18 silica gel with water/MeCN (50%) to provide the product, ethyl 10-bromo-9-(3-methoxypropoxy)-3,3-dimethyl-15-oxo-4-oxa-1-azatetracyclo[11.4.0.0[2,6]0.0[7,12]]heptadeca-7,9,11,13,16-pentaene-16-carboxylate as a yellow solid (7.5 g, 74% yield). The resulting mixture of enantiomers was purified by SFC (Column: CHIRALPAK IA-3, mobile phase: 50% CO₂/(1:1 hexane (0.1% diethylamine):ethanol)) to provide the product, ethyl (3aS,12bR)-10-bromo-11-(3-methoxypropoxy)-3,3-dimethyl-7-oxo-3,3a,7,12b-tetrahydro-1H-furo[3,4-c]pyrido[2,1-a]isoquinoline-6-carboxylate as a yellow solid (2.4 g, 32% yield). ¹H NMR (400 MHz, CDCl₃): δ 8.17 (s, 1H), 7.99 (s, 1H), 7.04 (s, 1H), 6.79 (s, 1H), 4.55-4.40 (m, 4H), 4.33 (dd, J=9.6, 2.2 Hz, 1H), 4.28-4.17 (m, 2H), 3.95 (t, J=7.5 Hz, 1H), 3.64 (t, J=5.9 Hz, 2H), 3.39 (s, 3H), 2.16 (p, J=6.1 Hz, 2H), 1.43 (t, J=7.1 Hz, 3H), 0.80 (s, 3H).

Step 11: Into a flask was placed ethyl (3aS,12bR)-10-bromo-11-(3-methoxypropoxy)-3,3-dimethyl-7-oxo-3,3a,7,12b-tetrahydro-1H-furo[3,4-c]pyrido[2,1-a]isoquinoline-6-carboxylate (2.4 g, 4.8 mmol), EtOH (50 mL), and 1 M Aq. NaOH (50 mL). The resulting solution was stirred for 5 h at room temperature. Most of the EtOH was removed under vacuum. The resulting solution was diluted with 50 mL of water. The pH value of the solution was adjusted to 3 with 1 M aq. HCl. The solids were collected by filtration to provide the product (3aS,12bR)-10-bromo-11-(3-methoxypropoxy)-3,3-dimethyl-7-oxo-3,3a,7,12b-tetrahydro-1H-furo[3,4-c]pyrido[2,1-a]isoquinoline-6-carboxylic acid as a yellow solid (2 g, 90% yield). ESI MS m/z=478.1 [M+H]⁺.

Step 13: An oven-dried vial was charged with (3aS,12bR)-10-bromo-11-(3-methoxypropoxy)-3,3-dimethyl-7-oxo-3,3a,7,12b-tetrahydro-1H-furo[3,4-c]pyrido[2,1-a]isoquinoline-6-carboxylic acid (50 mg, 0.1 mmol), 4-fluorophenyl boronic acid (70 mg, 0.5 mmol), Pd'BuXPhos G3 (8 mg, 0.01 mmol), and Cs₂CO₃ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (3aS,12bR)-10-(4-fluorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic acid (10 mg, 20% yield). ESI MS m/z=494.1 [M+H]⁺.

Example 62: (S)-5-(tert-butyl)-12-(4-fluorophenyl)-9-oxo-2,3,4,9-tetrahydro-5H-furo[3,2-f]pyrido[2,1-a]isoquinoline-8-carboxylic Acid

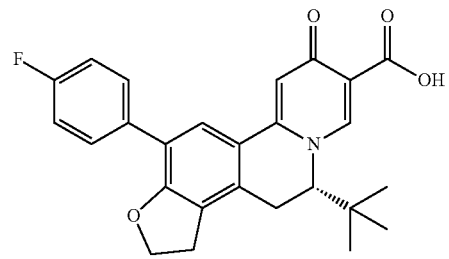

Step 1: An oven-dried vial was charged with (S)-12-bromo-5-(tert-butyl)-9-oxo-2,3,4,9-tetrahydro-5H-furo[3,2-f]pyrido[2,1-a]isoquinoline-8-carboxylic acid (41 mg, 0.1 mmol), 4-fluorophenyl boronic acid (70 mg, 0.5 mmol), Pd'BuXPhos G3 (8 mg, 0.01 mmol), and Cs₂CO₃ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (3 aS,12bR)-10-(4-fluorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic acid (12 mg, 28% yield). ESI MS m/z=434.1 [M+H]⁺.

Example 63: (3aS,12bR)-11-(3-methoxypropoxy)-3,3-dimethyl-10-(oxazol-5-yl)-7-oxo-1,2,3,3a,7,12b-hexahydrocyclopenta[c]pyrido[2,1-a]isoquinoline-6-carboxylic Acid

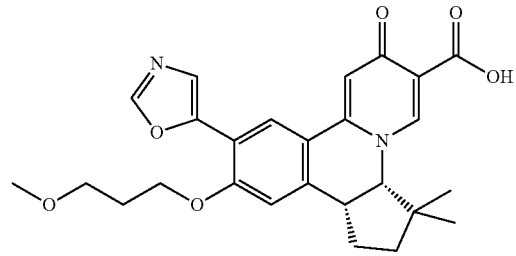 [SMILES: COCCCOc1cc2c(cc1-c1cnco1)-c1cc(=O)c(C(=O)O)cn1[C@H]1[C@@H]2CCC1(C)C]

The title compound was prepared following similar procedure as Example 59. ESI MS m/z=465.1 [M+H]⁺.

Example 64: (S)-5-(tert-butyl)-12-(furan-3-yl)-9-oxo-2,3,4,9-tetrahydro-5H-furo[3,2-f]pyrido[2,1-a]isoquinoline-8-carboxylic Acid

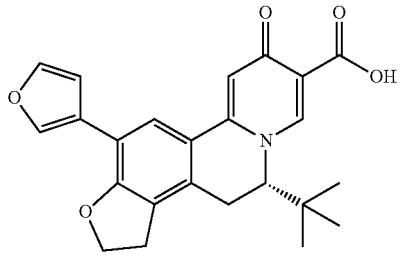 [SMILES: CC(C)(C)[C@@H]1Cc2c(cc(-c3ccoc3)c3c2CCO3)-c2cc(=O)c(C(=O)O)cn21]

The title compound was prepared following similar procedure as Example 62. ESI MS m/z=406.1 [M+H]⁺.

Example 65: (S)-5-(tert-butyl)-12-(3-fluorophenyl)-9-oxo-2,3,4,9-tetrahydro-5H-furo[3,2-f]pyrido[2,1-a]isoquinoline-8-carboxylic Acid

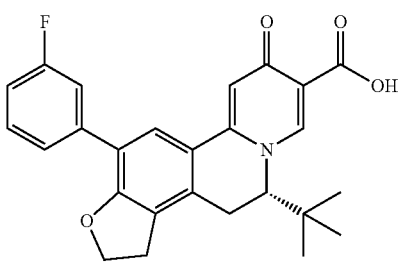 [SMILES: CC(C)(C)[C@@H]1Cc2c(cc(-c3cccc(F)c3)c3c2CCO3)-c2cc(=O)c(C(=O)O)cn21]

The title compound was prepared following similar procedure as Example 62. ESI MS m/z=434.1 [M+H]⁺.

Example 66: (S)-5-(tert-butyl)-12-(2-fluorophenyl)-9-oxo-2,3,4,9-tetrahydro-5H-furo[3,2-f]pyrido[2,1-a]isoquinoline-8-carboxylic Acid

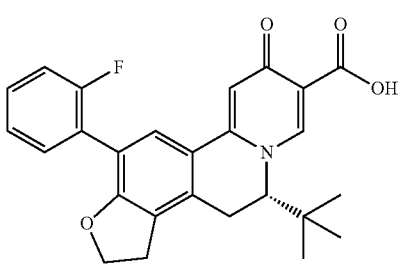 [SMILES: CC(C)(C)[C@@H]1Cc2c(cc(-c3ccccc3F)c3c2CCO3)-c2cc(=O)c(C(=O)O)cn21]

The title compound was prepared following similar procedure as Example 62. ESI MS m/z=434.1 [M+H]⁺.

Example 67: (S)-5-(tert-butyl)-9-oxo-12-phenyl-2,3,4,9-tetrahydro-5H-furo[3,2-f]pyrido[2,1-a]isoquinoline-8-carboxylic Acid

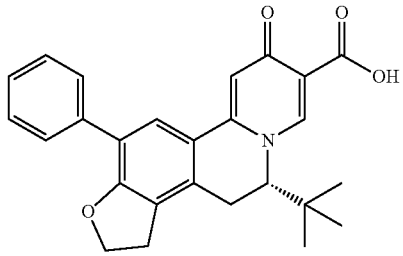 [SMILES: CC(C)(C)[C@@H]1Cc2c(cc(-c3ccccc3)c3c2CCO3)-c2cc(=O)c(C(=O)O)cn21]

The title compound was prepared following similar procedure as Example 62. ESI MS m/z=416.1 [M+H]⁺.

Example 68: (S)-5-(tert-butyl)-12-(1-methyl-1H-pyrazol-5-yl)-9-oxo-2,3,4,9-tetrahydro-5H-furo[3,2-f]pyrido[2,1-a]isoquinoline-8-carboxylic Acid

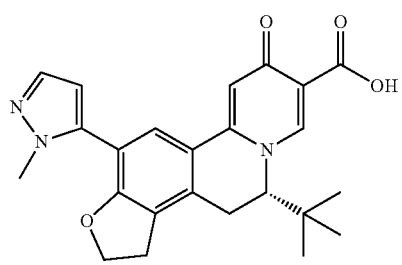 [SMILES: Cn1nccc1-c1cc2c(c3c1OCC3)C[C@@H](C(C)(C)C)n1cc(C(=O)O)c(=O)cc1-2]

The title compound was prepared following similar procedure as Example 62. ESI MS m/z=420.1 [M+H]⁺.

Example 69: (S)-5-(tert-butyl)-12-(1-methyl-1H-pyrazol-4-yl)-9-oxo-2,3,4,9-tetrahydro-5H-furo[3,2-f]pyrido[2,1-a]isoquinoline-8-carboxylic Acid

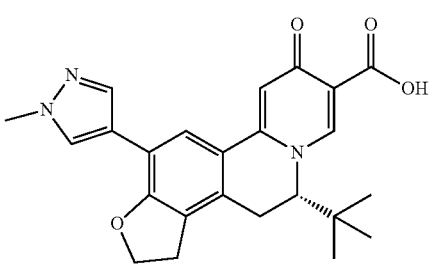 [SMILES: Cn1cc(-c2cc3c(c4c2OCC4)C[C@@H](C(C)(C)C)n2cc(C(=O)O)c(=O)cc2-3)cn1]

The title compound was prepared following similar procedure as Example 62. ESI MS m/z=420.1 [M+H]⁺.

Example 70: (S)-5-(tert-butyl)-12-(1-methyl-1H-pyrazol-3-yl)-9-oxo-2,3,4,9-tetrahydro-5H-furo[3,2-f]pyrido[2,1-a]isoquinoline-8-carboxylic Acid

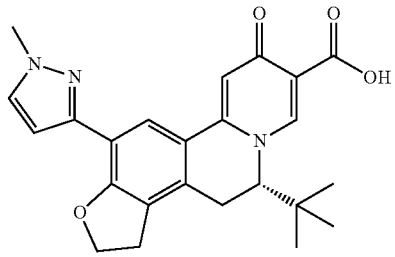 [SMILES: Cn1ccc(-c2cc3c(c4c2OCC4)C[C@@H](C(C)(C)C)n2cc(C(=O)O)c(=O)cc2-3)n1]

The title compound was prepared following similar procedure as Example 62. ESI MS m/z=420.1 [M+H]+.

Example 71: (S)-5-(tert-butyl)-9-oxo-12-(thiophen-3-yl)-2,3,4,9-tetrahydro-5H-furo[3,2-f]pyrido[2,1-a]isoquinoline-8-carboxylic Acid

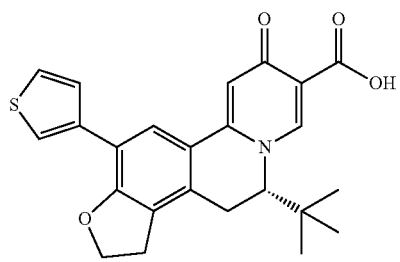 [SMILES: CC(C)(C)[C@@H]1Cc2c(cc(-c3ccsc3)c3c2CCO3)-c2cc(=O)c(C(=O)O)cn21]

The title compound was prepared following similar procedure as Example 62. ESI MS m/z=422.1 [M+H]+.

Example 72: (S)-5-(tert-butyl)-12-(furan-2-yl)-9-oxo-2,3,4,9-tetrahydro-5H-furo[3,2-f]pyrido[2,1-a]isoquinoline-8-carboxylic Acid

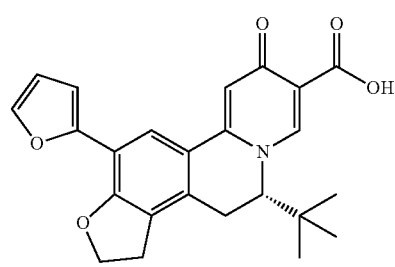

The title compound was prepared following similar procedure as Example 62. ESI MS m/z=406.1 [M+H]+.

Example 73: (S)-5-(tert-butyl)-12-(isothiazol-4-yl)-9-oxo-2,3,4,9-tetrahydro-5H-furo[3,2-f]pyrido[2,1-a]isoquinoline-8-carboxylic Acid

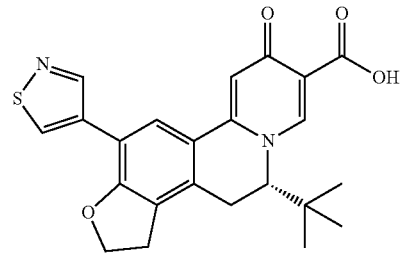 [SMILES: CC(C)(C)[C@@H]1Cc2c(cc(-c3cnsc3)c3c2CCO3)-c2cc(=O)c(C(=O)O)cn21]

The title compound was prepared following similar procedure as Example 62. ESI MS m/z=423.1 [M+H]+.

Example 74: (S)-5-(tert-butyl)-9-oxo-12-(pyridin-4-yl)-2,3,4,9-tetrahydro-5H-furo[3,2-f]pyrido[2,1-a]isoquinoline-8-carboxylic Acid

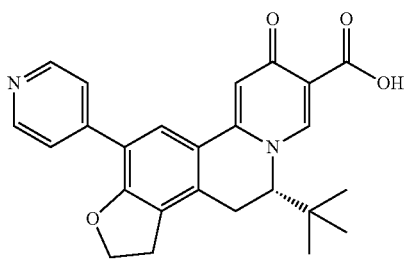 [SMILES: CC(C)(C)[C@@H]1Cc2c(cc(-c3ccncc3)c3c2CCO3)-c2cc(=O)c(C(=O)O)cn21]

The title compound was prepared following similar procedure as Example 62. ESI MS m/z=417.1 [M+H]+.

Example 75: (S)-5-(tert-butyl)-9-oxo-12-(pyridin-3-yl)-2,3,4,9-tetrahydro-5H-furo[3,2-f]pyrido[2,1-a]isoquinoline-8-carboxylic Acid

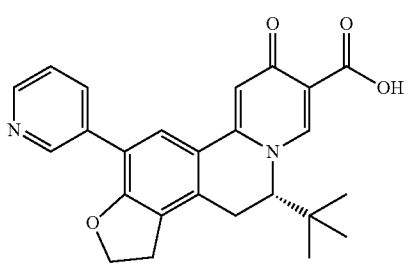 [SMILES: CC(C)(C)[C@@H]1Cc2c(cc(-c3cccnc3)c3c2CCO3)-c2cc(=O)c(C(=O)O)cn21]

The title compound was prepared following similar procedure as Example 62. ESI MS m/z=417.1 [M+H]+.

Example 76: (S)-5-(tert-butyl)-12-(2-chlorophenyl)-9-oxo-2,3,4,9-tetrahydro-5H-furo[3,2-f]pyrido[2,1-a]isoquinoline-8-carboxylic Acid

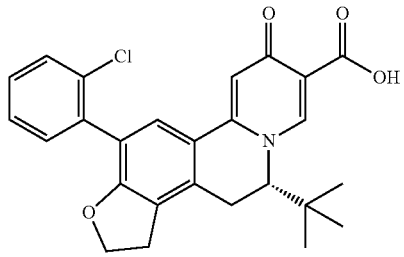 [SMILES: CC(C)(C)[C@@H]1Cc2c(cc(-c3ccccc3Cl)c3c2CCO3)-c2cc(=O)c(C(=O)O)cn21]

The title compound was prepared following similar procedure as Example 62. ESI MS m/z=450.1 [M+H]⁺.

Example 77: (S)-5-(tert-butyl)-12-(3,4-difluorophenyl)-9-oxo-2,3,4,9-tetrahydro-5H-furo[3,2-f]pyrido[2,1-a]isoquinoline-8-carboxylic Acid

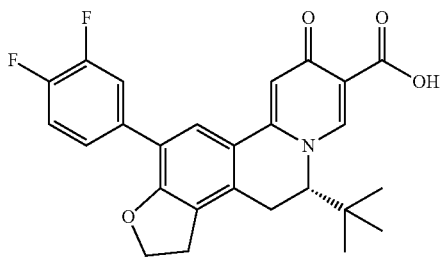 [SMILES: CC(C)(C)[C@@H]1Cc2c(cc(-c3ccc(F)c(F)c3)c3c2CCO3)-c2cc(=O)c(C(=O)O)cn21]

The title compound was prepared following similar procedure as Example 62. ESI MS m/z=452.1 [M+H]⁺.

Example 78: (S)-5-(tert-butyl)-12-(4-methoxyphenyl)-9-oxo-2,3,4,9-tetrahydro-5H-furo[3,2-f]pyrido[2,1-a]isoquinoline-8-carboxylic Acid

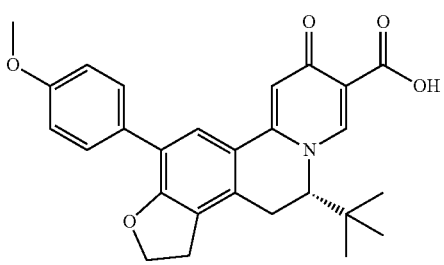

The title compound was prepared following similar procedure as Example 62. ESI MS m/z=446.1 [M+H]⁺.

Example 79: (S)-5-(tert-butyl)-12-(3-methoxyphenyl)-9-oxo-2,3,4,9-tetrahydro-5H-furo[3,2-f]pyrido[2,1-a]isoquinoline-8-carboxylic Acid

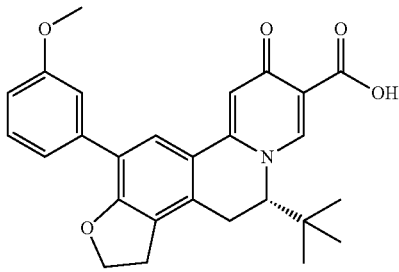 [SMILES: COc1cccc(-c2cc3c(c4c2OCC4)C[C@@H](C(C)(C)C)n2cc(C(=O)O)c(=O)cc2-3)c1]

The title compound was prepared following similar procedure as Example 62. ESI MS m/z=446.1 [M+H]⁺.

Example 80: (S)-5-(tert-butyl)-9-oxo-12-(4-(trifluoromethyl)phenyl)-2,3,4,9-tetrahydro-5H-furo[3,2-f]pyrido[2,1-a]isoquinoline-8-carboxylic Acid

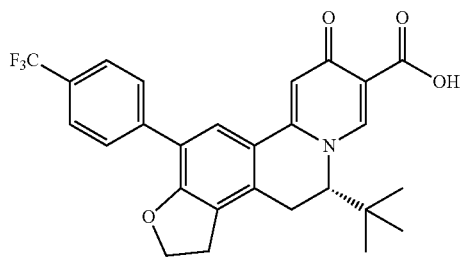 [SMILES: CC(C)(C)[C@@H]1Cc2c(cc(-c3ccc(C(F)(F)F)cc3)c3c2CCO3)-c2cc(=O)c(C(=O)O)cn21]

The title compound was prepared following similar procedure as Example 62. ESI MS m/z=484.1 [M+H]⁺.

Example 81: (S)-5-(tert-butyl)-9-oxo-12-(3-(trifluoromethyl)phenyl)-2,3,4,9-tetrahydro-5H-furo[3,2-f]pyrido[2,1-a]isoquinoline-8-carboxylic Acid

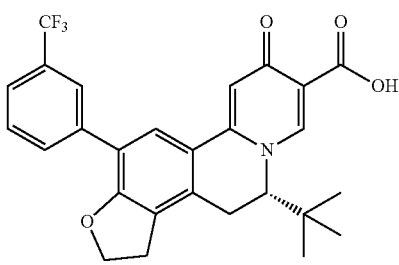

The title compound was prepared following similar procedure as Example 62. ESI MS m/z=484.1 [M+H]⁺.

Example 82: (S)-5-(tert-butyl)-9-oxo-12-(1H-pyrazol-5-yl)-2,3,4,9-tetrahydro-5H-furo[3,2-f]pyrido[2,1-a]isoquinoline-8-carboxylic Acid

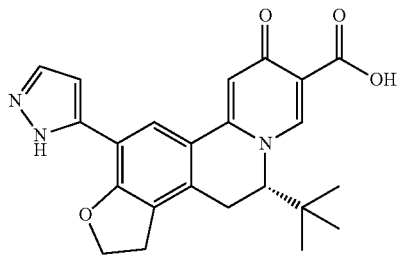 [SMILES: CC(C)(C)[C@@H]1Cc2c(cc(-c3ccn[nH]3)c3c2CCO3)-c2cc(=O)c(C(=O)O)cn21]

The title compound was prepared following similar procedure as Example 62. ESI MS m/z=406.1 [M+H]+.

Example 83: (S)-5-(tert-butyl)-12-(oxazol-5-yl)-9-oxo-2,3,4,9-tetrahydro-5H-furo[3,2-f]pyrido[2,1-a]isoquinoline-8-carboxylic Acid

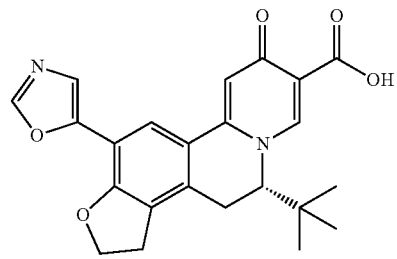 [SMILES: CC(C)(C)[C@@H]1Cc2c(cc(-c3cnco3)c3c2CCO3)-c2cc(=O)c(C(=O)O)cn21]

The title compound was prepared following similar procedure as Example 62. ESI MS m/z=407.1 [M+H]+.

Example 84: (S)-5-(tert-butyl)-12-(4-chlorophenyl)-9-oxo-2,3,4,9-tetrahydro-5H-furo[3,2-f]pyrido[2,1-a]isoquinoline-8-carboxylic Acid

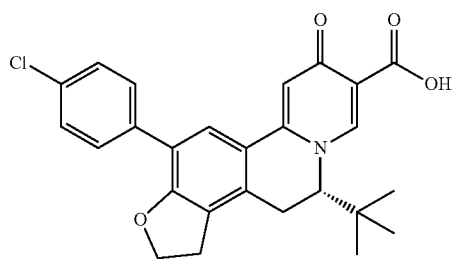 [SMILES: CC(C)(C)[C@@H]1Cc2c(cc(-c3ccc(Cl)cc3)c3c2CCO3)-c2cc(=O)c(C(=O)O)cn21]

The title compound was prepared following similar procedure as Example 62. ESI MS m/z=450.1 [M+H]+.

Example 85: (S)-5-(tert-butyl)-12-(3-chlorophenyl)-9-oxo-2,3,4,9-tetrahydro-5H-furo[3,2-f]pyrido[2,1-a]isoquinoline-8-carboxylic Acid

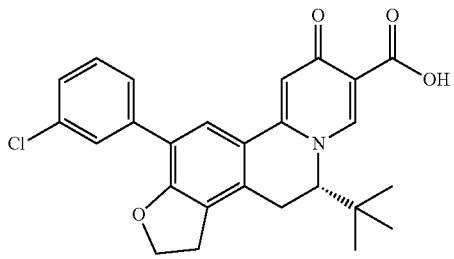 [SMILES: CC(C)(C)[C@@H]1Cc2c(cc(-c3cccc(Cl)c3)c3c2CCO3)-c2cc(=O)c(C(=O)O)cn21]

The title compound was prepared following similar procedure as Example 62. ESI MS m/z=450.1 [M+H]+.

Example 86: (S)-5-(tert-butyl)-9-oxo-12-(thiophen-2-yl)-2,3,4,9-tetrahydro-5H-furo[3,2-f]pyrido[2,1-a]isoquinoline-8-carboxylic Acid

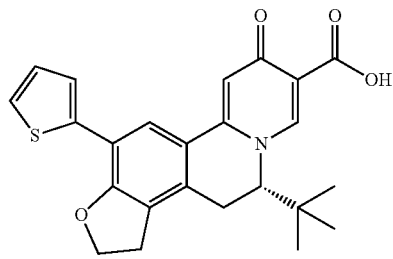

The title compound was prepared following similar procedure as Example 62. ESI MS m/z=422.1 [M+H]+.

Example 87: (S)-5-(tert-butyl)-9-oxo-12-(1H-pyrazol-4-yl)-2,3,4,9-tetrahydro-5H-furo[3,2-f]pyrido[2,1-a]isoquinoline-8-carboxylic Acid

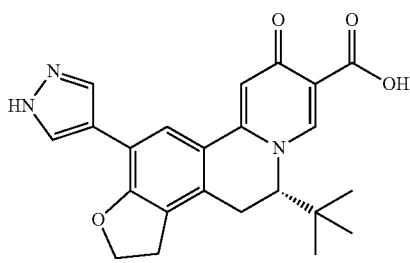 [SMILES: CC(C)(C)[C@@H]1Cc2c(cc(-c3cn[nH]c3)c3c2CCO3)-c2cc(=O)c(C(=O)O)cn21]

The title compound was prepared following similar procedure as Example 62. ESI MS m/z=406.1 [M+H]+.

Example 88: (S)-5-(tert-butyl)-9-oxo-12-(pyrrolidin-1-yl)-2,3,4,9-tetrahydro-5H-furo[3,2-f]pyrido[2,1-a]isoquinoline-8-carboxylic Acid

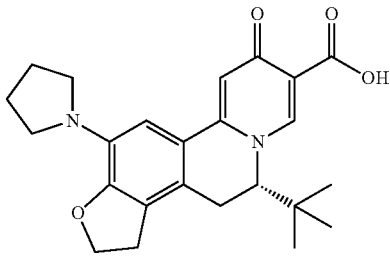 [SMILES: CC(C)(C)[C@@H]1Cc2c(cc(N3CCCC3)c3c2CCO3)-c2cc(=O)c(C(=O)O)cn21]

The title compound was prepared following similar procedure as Example 30. ESI MS m/z=409.1 [M+H]+.

Example 89: (S)-12-(4-fluorophenyl)-5-isopropyl-9-oxo-2,3,4,9-tetrahydro-5H-furo[3,2-f]pyrido[2,1-a]isoquinoline-8-carboxylic Acid

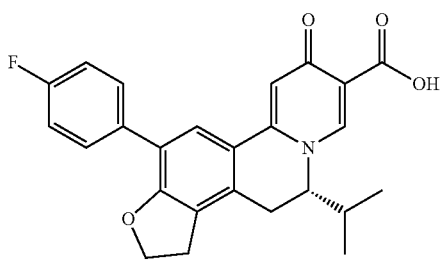 [SMILES: CC(C)[C@@H]1Cc2c(cc(-c3ccc(F)cc3)c3c2CCO3)-c2cc(=O)c(C(=O)O)cn21]

Step 1: Into a round-bottom flask purged and maintained with an inert atmosphere of nitrogen, was placed 7-bromo-4-iodo-2,3-dihydro-1-benzofuran (52 mg, 0.160 mmol), THF (1 mL), 3-methylbutan-2-one (30 mg, 0.352 mmol), Pd₂(dba)₃ (4.4 mg), xantphos (5.5 mg), and t-BuONa (38.5 mg, 0.400 mmol). The resulting solution was stirred for 3 h at 50° C. The reaction was then quenched by the addition of 3 mL of water. The resulting solution was extracted with 2×2 mL of ethyl acetate and the organic layers combined. The resulting mixture was washed with 5 mL of brine. The mixture was dried over anhydrous sodium sulfate and concentrated under vacuum. The residue was applied onto a silica gel column and eluted with ethyl acetate/petroleum ether (0:1-1:50) to provide the product, 1-(7-bromo-2,3-dihydrobenzofuran-4-yl)-3-methylbutan-2-one as yellow oil (38 mg, 85% yield).

Step 2: Into a round-bottom flask purged and maintained with an inert atmosphere of nitrogen, was placed 1-(7-bromo-2,3-dihydrobenzofuran-4-yl)-3-methylbutan-2-one (38 mg, 0.134 mmol), MeOH (1 mL), CH₃COONH₄ (103 mg, 0.134 mmol), and NaBH₃CN (17 mg, 0.270 mmol). The resulting solution was stirred for 16 h at 60° C. The reaction was then quenched by the addition of 5 mL of water. The resulting solution was extracted with 2×5 mL of ethyl acetate and the organic layers combined. The resulting mixture was washed with 1×5 mL of brine. The mixture was dried over anhydrous sodium sulfate, filtered, and concentrated under vacuum. This resulted in 40 mg (crude) of 1-(7-bromo-2,3-dihydrobenzofuran-4-yl)-3-methylbutan-2-amine as a yellow solid, which was taken onto the next step without further purification.

Step 3: Into a round-bottom flask purged and maintained with an inert atmosphere of nitrogen, was placed 1-(7-bromo-2,3-dihydrobenzofuran-4-yl)-3-methylbutan-2-amine (41 mg, 0.144 mmol), methyl formate (1 mL), formic acid (8 mg, 0.173 mmol). The resulting solution was stirred for 16 h at 60° C. The resulting mixture was concentrated under vacuum. This resulted in 43 mg (crude) of N-(1-(7-bromo-2,3-dihydrobenzofuran-4-yl)-3-methylbutan-2-yl)formamide as a yellow solid, which was taken onto the next step without further purification.

Step 4: Into a round-bottom flask purged and maintained with an inert atmosphere of nitrogen, was placed N-(1-(7-bromo-2,3-dihydrobenzofuran-4-yl)-3-methylbutan-2-yl)formamide (45 mg, 0.144 mmol), ACN (1 mL), and POCl₃ (26 mg, 0.174 mmol). The resulting solution was stirred for 2 h at 70° C. The resulting mixture was concentrated under vacuum. The resulting solution was diluted with 2 mL of EA. The resulting mixture was washed with 1×3 mL of sat. Aq. NaHCO₃. The mixture was dried over anhydrous sodium sulfate and concentrated under vacuum. This resulted in 45 mg (crude) of 4-bromo-8-isopropyl-1,2,8,9-tetrahydrofuro[3,2-f]isoquinoline as a yellow solid, which was taken to the next step without further purification.

Step 5: Into a round-bottom flask purged and maintained with an inert atmosphere of nitrogen, was placed 4-bromo-8-isopropyl-1,2,8,9-tetrahydrofuro[3,2-f]isoquinoline (47 mg, crude), ethyl (2E)-2-(ethoxymethylidene)-3-oxobutanoate (85 mg, 3.00 equiv), EtOH (2 mL). The resulting solution was stirred for 20 h at 60° C. The resulting mixture was concentrated under vacuum. The resulting mixture was washed with 1×2 mL of EtOAc. The solids were collected by filtration to provide the product, ethyl 12-bromo-5-isopropyl-9-oxo-2,3,4,9,10,10a-hexahydro-5H-furo[3,2-f]pyrido[2,1-a]isoquinoline-8-carboxylate as a white solid (40 mg, 58% yield).

Step 6: Into a vial purged and maintained with an inert atmosphere of nitrogen, was placed ethyl 12-bromo-5-isopropyl-9-oxo-2,3,4,9,10,10a-hexahydro-5H-furo[3,2-f]pyrido[2,1-a]isoquinoline-8-carboxylate (20 mg), DCE (2 mL), and tetrachlorocyclohexa-2,5-diene-1,4-dione (14 mg). The resulting solution was stirred for 15 h at 80° C. The resulting mixture was concentrated under vacuum. The residue was purified by SFC (Column: CHIRAL ART Cellulose-SB, mobile phase: 50% CO₂/(2 mM ammonia in EtOH) to provide the product, ethyl (S)-12-bromo-5-isopropyl-9-oxo-2,3,4,9-tetrahydro-5H-furo[3,2-f]pyrido[2,1-a]isoquinoline-8-carboxylate as a yellow solid (10 mg, 50% yield).

Step 7: Into a vial was placed ethyl (S)-12-bromo-5-isopropyl-9-oxo-2,3,4,9-tetrahydro-5H-furo[3,2-f]pyrido[2,1-a]isoquinoline-8-carboxylate (10 mg), EtOH (1 mL), and 1 M Aq. NaOH (1 mL). The resulting solution was stirred for 120 min at room temperature. Most of the EtOH was removed under vacuum. The resulting solution was diluted with 1 mL of water. The pH value of the solution was adjusted to 3 with 1 M aq. HCl. The solids were collected by filtration to provide the product, (S)-12-bromo-5-isopropyl-9-oxo-2,3,4,9-tetrahydro-5H-furo[3,2-f]pyrido[2,1-a]isoquinoline-8-carboxylic acid as a yellow solid (7 mg, 84% yield). ESI MS m/z=404.1 [M+H]+.

Step 8: An oven-dried vial was charged with (S)-12-bromo-5-isopropyl-9-oxo-2,3,4,9-tetrahydro-5H-furo[3,2-f]pyrido[2,1-a]isoquinoline-8-carboxylic acid (40 mg, 0.1 mmol), 4-fluorophenyl boronic acid (70 mg, 0.5 mmol), Pd^tBuXPhos G3 (8 mg, 0.01 mmol), and Cs₂CO₃ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (S)-12-(4-fluorophenyl)-5-isopropyl-9-oxo-2,3,4,9-tetrahydro-5H-furo[3,2-f]pyrido[2,1-a]isoquinoline-8-carboxylic acid (21 mg, 50% yield). ESI MS m/z=420.1 [M+H]+.

Example 90: (S)-12-(furan-3-yl)-5-isopropyl-9-oxo-2,3,4,9-tetrahydro-5H-furo[3,2-f]pyrido[2,1-a]isoquinoline-8-carboxylic Acid

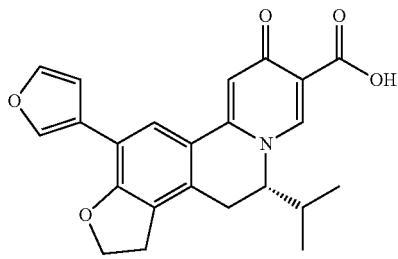 [SMILES: CC(C)[C@@H]1Cc2c(cc(-c3ccoc3)c3c2CCO3)-c2cc(=O)c(C(=O)O)cn21]

The title compound was prepared following similar procedure as Example 89. ESI MS m/z=392.1 [M+H]+.

Example 91: (S)-5-isopropyl-12-(oxazol-5-yl)-9-oxo-2,3,4,9-tetrahydro-5H-furo[3,2-f]pyrido[2,1-a]isoquinoline-8-carboxylic Acid

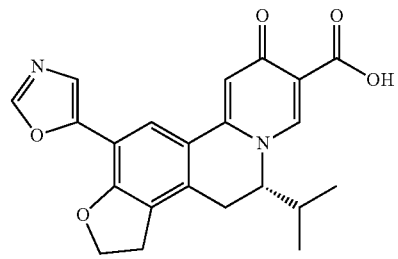 [SMILES: CC(C)[C@@H]1Cc2c(cc(-c3cnco3)c3c2CCO3)-c2cc(=O)c(C(=O)O)cn21]

The title compound was prepared following similar procedure as Example 89. ESI MS m/z=393.1 [M+H]+.

Example 92: (S)-5-isopropyl-12-(3-methoxyphenyl)-9-oxo-2,3,4,9-tetrahydro-5H-furo[3,2-f]pyrido[2,1-a]isoquinoline-8-carboxylic Acid

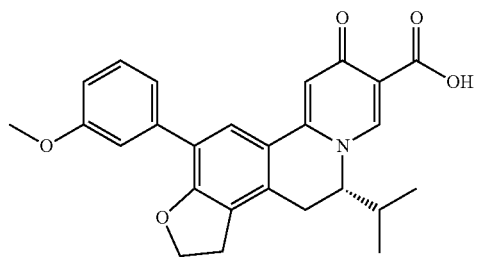 [SMILES: COc1cccc(-c2cc3c(c4c2OCC4)C[C@@H](C(C)C)n2cc(C(=O)O)c(=O)cc2-3)c1]

The title compound was prepared following similar procedure as Example 89. ESI MS m/z=432.1 [M+H]+.

Example 93: (S)-5-isopropyl-9-oxo-12-phenyl-2,3,4,9-tetrahydro-5H-furo[3,2-f]pyrido[2,1-a]isoquinoline-8-carboxylic Acid

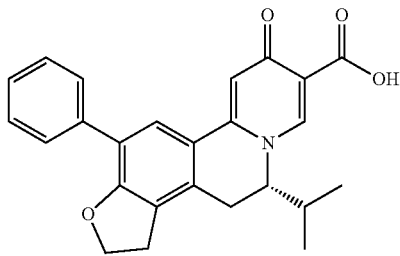 [SMILES: CC(C)[C@@H]1Cc2c(cc(-c3ccccc3)c3c2CCO3)-c2cc(=O)c(C(=O)O)cn21]

The title compound was prepared following similar procedure as Example 89. ESI MS m/z=402.1 [M+H]+.

Example 94: (S)-5-isopropyl-9-oxo-12-(4-(trifluoromethyl)phenyl)-2,3,4,9-tetrahydro-5H-furo[3,2-f]pyrido[2,1-a]isoquinoline-8-carboxylic Acid

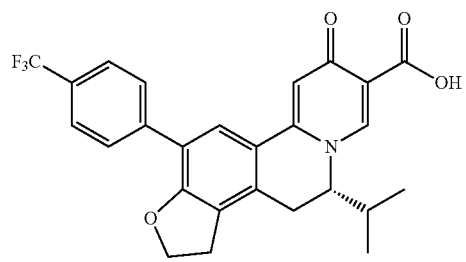 [SMILES: CC(C)[C@@H]1Cc2c(cc(-c3ccc(C(F)(F)F)cc3)c3c2CCO3)-c2cc(=O)c(C(=O)O)cn21]

The title compound was prepared following similar procedure as Example 89. ESI MS m/z=470.1 [M+H]+.

Example 95: (S)-5-isopropyl-9-oxo-12-(3-(trifluoromethyl)phenyl)-2,3,4,9-tetrahydro-5H-furo[3,2-f]pyrido[2,1-a]isoquinoline-8-carboxylic Acid

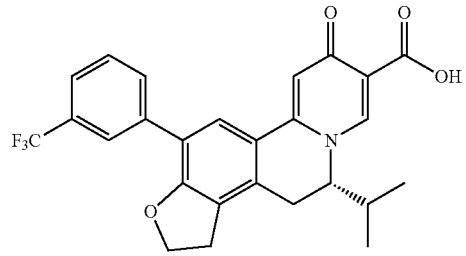 [SMILES: CC(C)[C@@H]1Cc2c(cc(-c3cccc(C(F)(F)F)c3)c3c2CCO3)-c2cc(=O)c(C(=O)O)cn21]

The title compound was prepared following similar procedure as Example 89. ESI MS m/z=469.1 [M+H]+.

Example 96: (S)-5-isopropyl-12-(1-methyl-1H-pyrazol-5-yl)-9-oxo-2,3,4,9-tetrahydro-5H-furo[3,2-f]pyrido[2,1-a]isoquinoline-8-carboxylic Acid

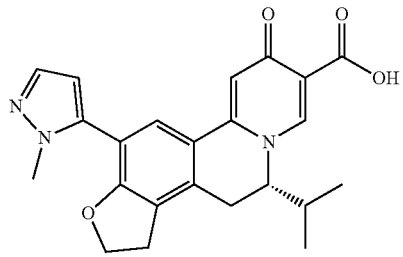 [SMILES: CC(C)[C@@H]1Cc2c(cc(-c3ccnn3C)c3c2CCO3)-c2cc(=O)c(C(=O)O)cn21]

The title compound was prepared following similar procedure as Example 89. ESI MS m/z=406.1 [M+H]⁺.

Example 97: (S)-5-isopropyl-12-(1-methyl-1H-pyrazol-4-yl)-9-oxo-2,3,4,9-tetrahydro-5H-furo[3,2-f]pyrido[2,1-a]isoquinoline-8-carboxylic Acid

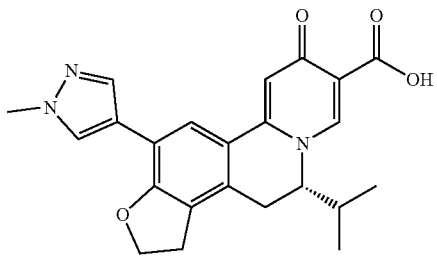 [SMILES: CC(C)[C@@H]1Cc2c(cc(-c3cnn(C)c3)c3c2CCO3)-c2cc(=O)c(C(=O)O)cn21]

The title compound was prepared following similar procedure as Example 89. ESI MS m/z=406.1 [M+H]⁺.

Example 98: (S)-5-isopropyl-12-(1-methyl-1H-pyrazol-3-yl)-9-oxo-2,3,4,9-tetrahydro-5H-furo[3,2-f]pyrido[2,1-a]isoquinoline-8-carboxylic Acid

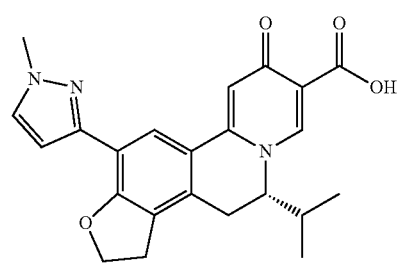 [SMILES: CC(C)[C@@H]1Cc2c(cc(-c3ccn(C)n3)c3c2CCO3)-c2cc(=O)c(C(=O)O)cn21]

The title compound was prepared following similar procedure as Example 89. ESI MS m/z=406.1 [M+H]⁺.

Example 99: (S)-5-isopropyl-9-oxo-12-(thiophen-2-yl)-2,3,4,9-tetrahydro-5H-furo[3,2-f]pyrido[2,1-a]isoquinoline-8-carboxylic Acid

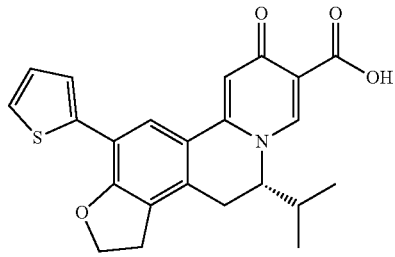

The title compound was prepared following similar procedure as Example 89. ESI MS m/z=408.1 [M+H]⁺.

Example 100: (S)-5-isopropyl-9-oxo-12-(thiophen-3-yl)-2,3,4,9-tetrahydro-5H-furo[3,2-f]pyrido[2,1-a]isoquinoline-8-carboxylic Acid

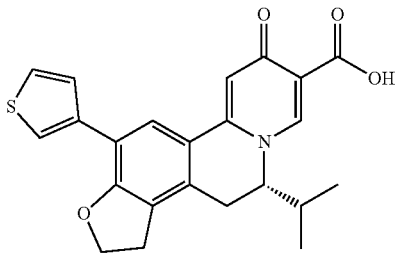 [SMILES: CC(C)[C@@H]1Cc2c(cc(-c3ccsc3)c3c2CCO3)-c2cc(=O)c(C(=O)O)cn21]

The title compound was prepared following similar procedure as Example 89. ESI MS m/z=408.1 [M+H]⁺.

Example 101: (S)-12-(furan-2-yl)-5-isopropyl-9-oxo-2,3,4,9-tetrahydro-5H-furo[3,2-f]pyrido[2,1-a]isoquinoline-8-carboxylic Acid

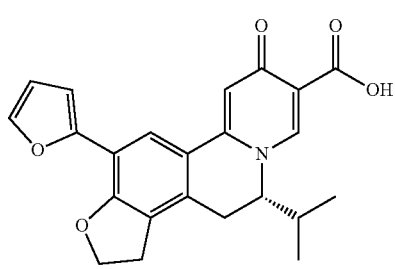

The title compound was prepared following similar procedure as Example 89. ESI MS m/z=392.1 [M+H]⁺.

Example 102: (S)-5-isopropyl-9-oxo-12-(1H-pyrazol-4-yl)-2,3,4,9-tetrahydro-5H-furo[3,2-f]pyrido[2,1-a]isoquinoline-8-carboxylic Acid

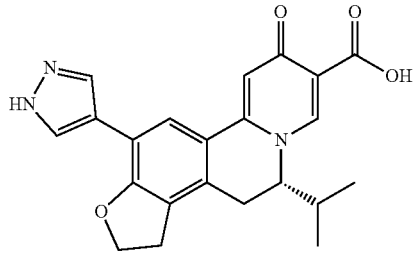 [SMILES: CC(C)[C@@H]1Cc2c(cc(-c3cn[nH]c3)c3c2CCO3)-c2cc(=O)c(C(=O)O)cn21]

The title compound was prepared following similar procedure as Example 89. ESI MS m/z=392.1 [M+H]+.

Example 103: (S)-5-isopropyl-12-(isothiazol-4-yl)-9-oxo-2,3,4,9-tetrahydro-5H-furo[3,2-f]pyrido[2,1-a]isoquinoline-8-carboxylic Acid

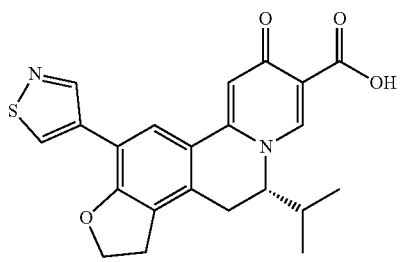 [SMILES: CC(C)[C@@H]1Cc2c(cc(-c3cnsc3)c3c2CCO3)-c2cc(=O)c(C(=O)O)cn21]

The title compound was prepared following similar procedure as Example 89. ESI MS m/z=409.1 [M+H]+.

Example 104: (S)-5-isopropyl-9-oxo-12-(pyridin-4-yl)-2,3,4,9-tetrahydro-5H-furo[3,2-f]pyrido[2,1-a]isoquinoline-8-carboxylic Acid

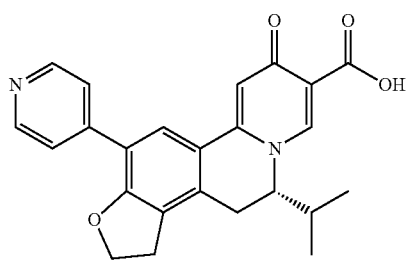 [SMILES: CC(C)[C@@H]1Cc2c(cc(-c3ccncc3)c3c2CCO3)-c2cc(=O)c(C(=O)O)cn21]

The title compound was prepared following similar procedure as Example 89. ESI MS m/z=403.1 [M+H]+.

Example 105: (S)-5-isopropyl-9-oxo-12-(pyridin-3-yl)-2,3,4,9-tetrahydro-5H-furo[3,2-f]pyrido[2,1-a]isoquinoline-8-carboxylic Acid

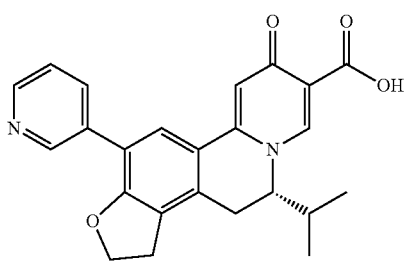 [SMILES: CC(C)[C@@H]1Cc2c(cc(-c3cccnc3)c3c2CCO3)-c2cc(=O)c(C(=O)O)cn21]

The title compound was prepared following similar procedure as Example 89. ESI MS m/z=403.1 [M+H]+.

Example 106: (S)-5-isopropyl-9-oxo-12-(1H-pyrazol-5-yl)-2,3,4,9-tetrahydro-5H-furo[3,2-f]pyrido[2,1-a]isoquinoline-8-carboxylic Acid

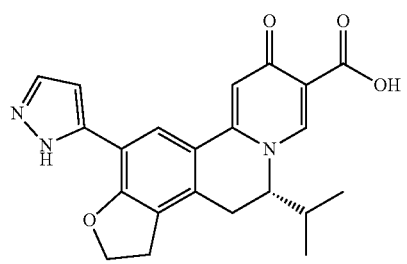 [SMILES: CC(C)[C@@H]1Cc2c(cc(-c3ccn[nH]3)c3c2CCO3)-c2cc(=O)c(C(=O)O)cn21]

The title compound was prepared following similar procedure as Example 89. ESI MS m/z=392.1 [M+H]+.

Example 107: (S)-12-(3-fluorophenyl)-5-isopropyl-9-oxo-2,3,4,9-tetrahydro-5H-furo[3,2-f]pyrido[2,1-a]isoquinoline-8-carboxylic Acid

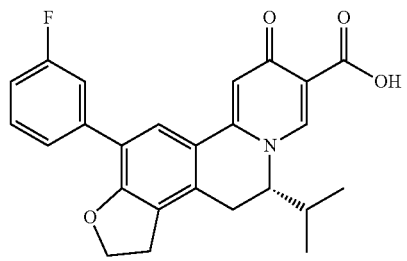

The title compound was prepared following similar procedure as Example 89. ESI MS m/z=420.1 [M+H]+.

Example 108: (S)-12-(2-fluorophenyl)-5-isopropyl-9-oxo-2,3,4,9-tetrahydro-5H-furo[3,2-f]pyrido[2,1-a]isoquinoline-8-carboxylic Acid

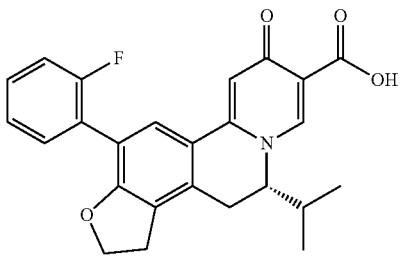

The title compound was prepared following similar procedure as Example 89. ESI MS m/z=420.1 [M+H]⁺.

Example 109: (S)-12-(4-chlorophenyl)-5-isopropyl-9-oxo-2,3,4,9-tetrahydro-5H-furo[3,2-f]pyrido[2,1-a]isoquinoline-8-carboxylic Acid

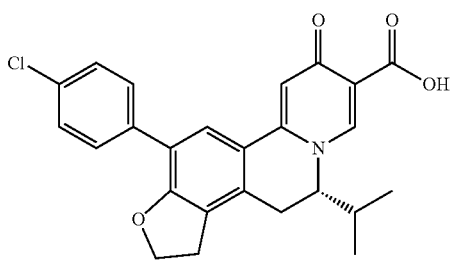 [SMILES: CC(C)[C@@H]1Cc2c(cc(-c3ccc(Cl)cc3)c3c2CCO3)-c2cc(=O)c(C(=O)O)cn21]

The title compound was prepared following similar procedure as Example 89. ESI MS m/z=436.1 [M+H]⁺.

Example 110: (S)-5-isopropyl-9-oxo-12-(pyrrolidin-1-yl)-2,3,4,9-tetrahydro-5H-furo[3,2-f]pyrido[2,1-a]isoquinoline-8-carboxylic Acid

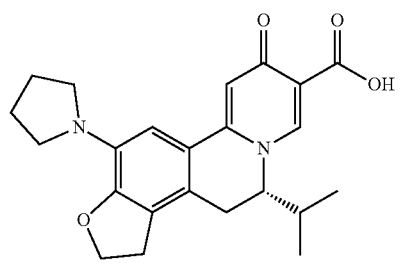 [SMILES: CC(C)[C@@H]1Cc2c(cc(N3CCCC3)c3c2CCO3)-c2cc(=O)c(C(=O)O)cn21]

Step 1: An oven-dried vial was charged with (S)-12-bromo-5-(isopropyl)-9-oxo-2,3,4,9-tetrahydro-5H-furo[3,2-f]pyrido[2,1-a]isoquinoline-8-carboxylic acid (50 mg, 0.12 mmol), pyrrolidine (25 mg, 0.359 mmol), Pd'BuXPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 8 h at 110° C. After cooling to room temperature, the reaction mixture was filtered and concentrated. The crude product was dissolved in DMSO (2 mL) and purified by RPHPLC to provide the product as a yellow solid (15 mg, 29% yield). ESI MS m/z=395.1 [M+H]⁺.

Example 111: (S)-12-(azetidin-1-yl)-5-(tert-butyl)-9-oxo-2,3,4,9-tetrahydro-5H-furo[3,2-f]pyrido[2,1-a]isoquinoline-8-carboxylic Acid

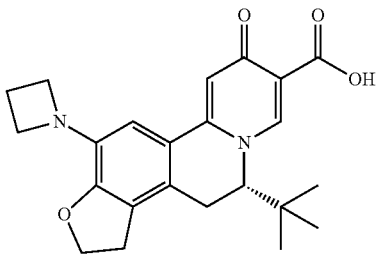 [SMILES: CC(C)(C)[C@@H]1Cc2c(cc(N3CCC3)c3c2CCO3)-c2cc(=O)c(C(=O)O)cn21]

The title compound was prepared following similar procedure as Example 30. ESI MS m/z=395.1 [M+H]⁺.

Example 112: (S)-12-(3-chlorophenyl)-5-isopropyl-9-oxo-2,3,4,9-tetrahydro-5H-furo[3,2-f]pyrido[2,1-a]isoquinoline-8-carboxylic Acid

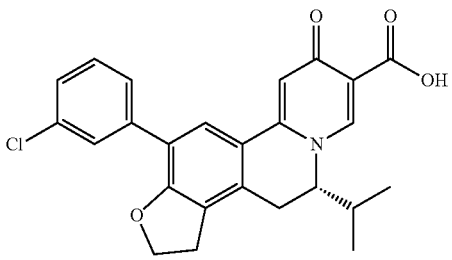 [SMILES: CC(C)[C@@H]1Cc2c(cc(-c3cccc(Cl)c3)c3c2CCO3)-c2cc(=O)c(C(=O)O)cn21]

The title compound was prepared following similar procedure as Example 89. ESI MS m/z=436.1 [M+H]⁺.

Example 113: (S)-5-isopropyl-9-oxo-12-(1H-pyrazol-1-yl)-2,3,4,9-tetrahydro-5H-furo[3,2-f]pyrido[2,1-a]isoquinoline-8-carboxylic Acid

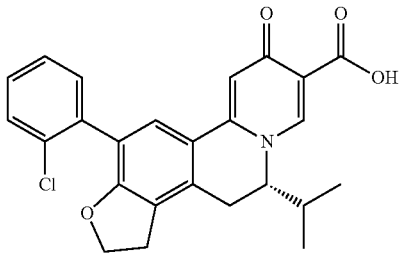

The title compound was prepared following similar procedure as Example 89. ESI MS m/z=436.1 [M+H]⁺.

Example 114: (S)-12-(3,4-difluorophenyl)-5-isopropyl-9-oxo-2,3,4,9-tetrahydro-5H-furo[3,2-f]pyrido[2,1-a]isoquinoline-8-carboxylic Acid

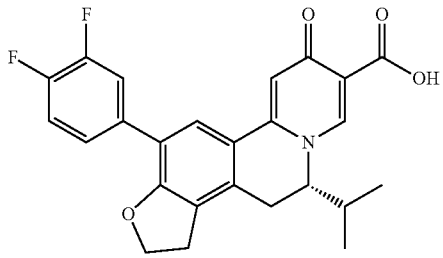 [SMILES: CC(C)[C@@H]1Cc2c(cc(-c3ccc(F)c(F)c3)c3c2CCO3)-c2cc(=O)c(C(=O)O)cn21]

The title compound was prepared following similar procedure as Example 89. ESI MS m/z=438.1 [M+H]+.

Example 115: (S)-5-isopropyl-12-(4-methoxyphenyl)-9-oxo-2,3,4,9-tetrahydro-5H-furo[3,2-f]pyrido[2,1-a]isoquinoline-8-carboxylic Acid

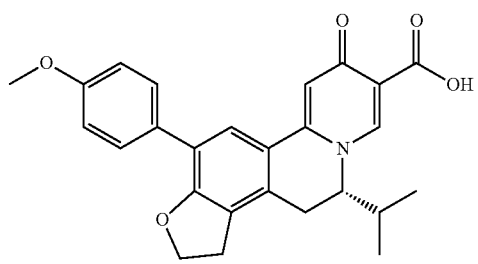 [SMILES: COc1ccc(-c2cc3c(c4c2OCC4)C[C@@H](C(C)C)n2cc(C(=O)O)c(=O)cc2-3)cc1]

The title compound was prepared following similar procedure as Example 89. ESI MS m/z=432.1 [M+H]+.

Example 116: (S)-5-(tert-butyl)-9-oxo-12-(3-(trifluoromethyl)phenyl)-2,3,4,9-tetrahydro-5H-furo[3,2-f]pyrido[2,1-a]isoquinoline-8-carboxylic Acid

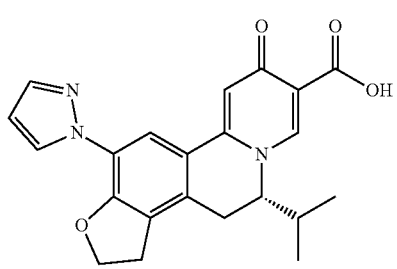 [SMILES: CC(C)[C@@H]1Cc2c(cc(-n3cccn3)c3c2CCO3)-c2cc(=O)c(C(=O)O)cn21]

The title compound was prepared following similar procedure as Example 110. ESI MS m/z=392.1 [M+H]+.

Example 117: (S)-12-(azetidin-1-yl)-5-isopropyl-9-oxo-2,3,4,9-tetrahydro-5H-furo[3,2-f]pyrido[2,1-a]isoquinoline-8-carboxylic Acid

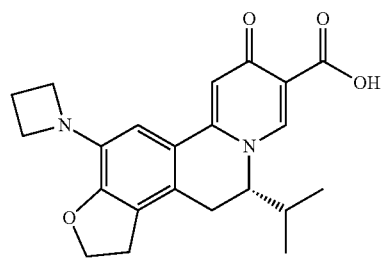 [SMILES: CC(C)[C@@H]1Cc2c(cc(N3CCC3)c3c2CCO3)-c2cc(=O)c(C(=O)O)cn21]

The title compound was prepared following similar procedure as Example 110. ESI MS m/z=380.1 [M+H]+.

Example 118: (S)-5-(tert-butyl)-12-morpholino-9-oxo-2,3,4,9-tetrahydro-5H-furo[3,2-f]pyrido[2,1-a]isoquinoline-8-carboxylic Acid

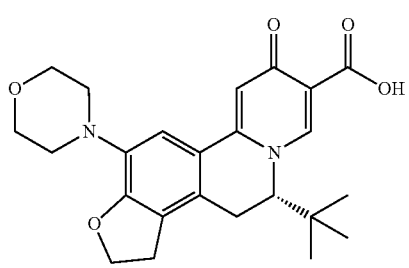 [SMILES: CC(C)(C)[C@@H]1Cc2c(cc(N3CCOCC3)c3c2CCO3)-c2cc(=O)c(C(=O)O)cn21]

The title compound was prepared following similar procedure as Example 30. ESI MS m/z=425.1 [M+H]+.

Example 119: (S)-5-(tert-butyl)-9-oxo-12-(2-oxa-6-azaspiro[3.3]heptan-6-yl)-2,3,4,9-tetrahydro-5H-furo[3,2-f]pyrido[2,1-a]isoquinoline-8-carboxylic Acid

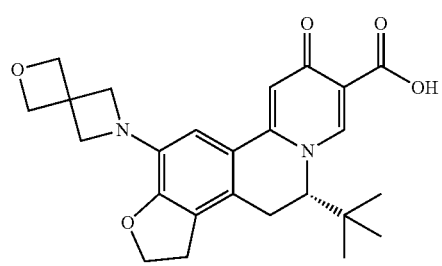 [SMILES: CC(C)(C)[C@@H]1Cc2c(cc(N3CC4(COC4)C3)c3c2CCO3)-c2cc(=O)c(C(=O)O)cn21]

The title compound was prepared following similar procedure as Example 30. ESI MS m/z=437.1 [M+H]+.

Example 120: (S)-5-(tert-butyl)-9-oxo-12-(1-oxa-6-azaspiro[3.3]heptan-6-yl)-2,3,4,9-tetrahydro-5H-furo[3,2-f]pyrido[2,1-a]isoquinoline-8-carboxylic Acid

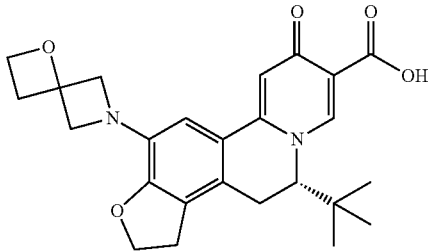 [SMILES: CC(C)(C)[C@@H]1Cc2c(cc(N3CC4(CCO4)C3)c3c2CCO3)-c2cc(=O)c(C(=O)O)cn21]

The title compound was prepared following similar procedure as Example 30. ESI MS m/z=437.1 [M+H]$^+$.

Example 121: (3aS,12bR)-11-(3-methoxypropoxy)-3,3-dimethyl-10-(oxazol-5-yl)-7-oxo-3,3a,7,12b-tetrahydro-1H-furo[3,4-c]pyrido[2,1-a]isoquinoline-6-carboxylic Acid

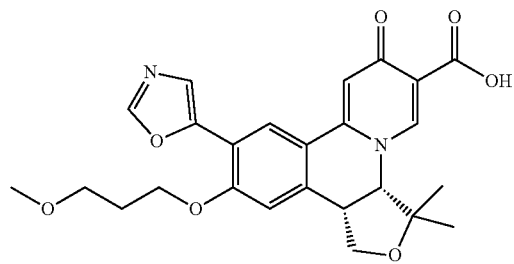

The title compound was prepared following similar procedure as Example 61. ESI MS m/z=467.1 [M+H]$^+$.

Example 122: (3aS,12bR)-11-(3-methoxypropoxy)-3,3-dimethyl-10-(1-methyl-1H-pyrazol-5-yl)-7-oxo-3,3a,7,12b-tetrahydro-1H-furo[3,4-c]pyrido[2,1-a]isoquinoline-6-carboxylic Acid

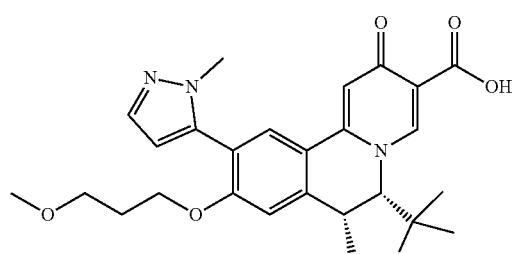

The title compound was prepared following similar procedure as Example 61. ESI MS m/z=480.1 [M+H]$^+$.

Example 123: (3aS,12bR)-11-(3-methoxypropoxy)-3,3-dimethyl-10-(1-methyl-1H-pyrazol-4-yl)-7-oxo-3,3a,7,12b-tetrahydro-1H-furo[3,4-c]pyrido[2,1-a]isoquinoline-6-carboxylic Acid

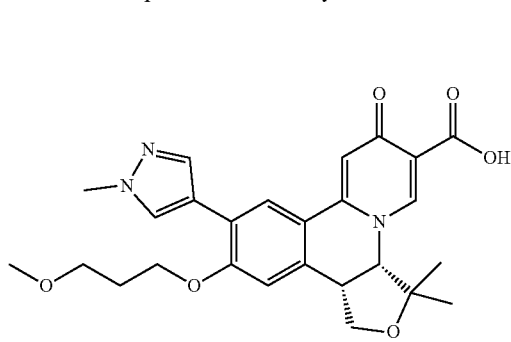

The title compound was prepared following similar procedure as Example 61. ESI MS m/z=480.1 [M+H]$^+$.

Example 124: (3aS,12bR)-11-(3-methoxypropoxy)-3,3-dimethyl-10-(1-methyl-1H-pyrazol-3-yl)-7-oxo-3,3a,7,12b-tetrahydro-1H-furo[3,4-c]pyrido[2,1-a]isoquinoline-6-carboxylic Acid

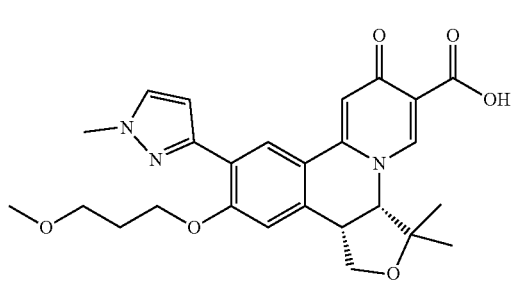 [SMILES: COCCCOc1cc2c(cc1-c1ccn(C)n1)-c1cc(=O)c(C(=O)O)cn1[C@H]1[C@@H]2COC1(C)C]

The title compound was prepared following similar procedure as Example 61. ESI MS m/z=480.1 [M+H]$^+$.

Example 125: (3aS,12bR)-10-(furan-2-yl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

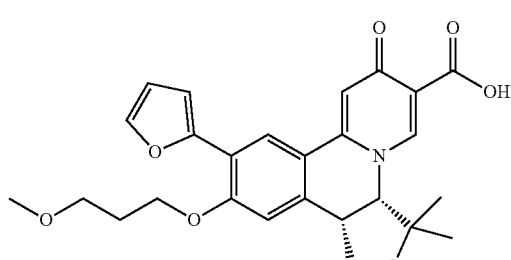

The title compound was prepared following similar procedure as Example 61. ESI MS m/z=465.1 [M+H]$^+$.

Example 126: (3aS,12bR)-10-(furan-3-yl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

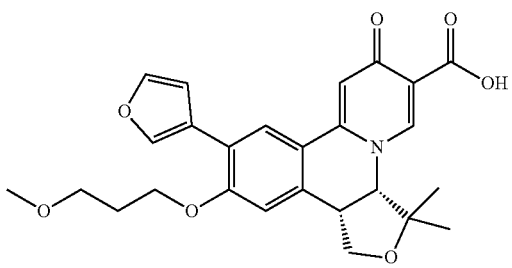 [SMILES: COCCCOc1cc2c(cc1-c1ccoc1)-c1cc(=O)c(C(=O)O)cn1[C@H]1[C@@H]2COC1(C)C]

The title compound was prepared following similar procedure as Example 61. ESI MS m/z=465.1 [M+H]$^+$.

Example 127: (3aS,12bR)-10-(isothiazol-4-yl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

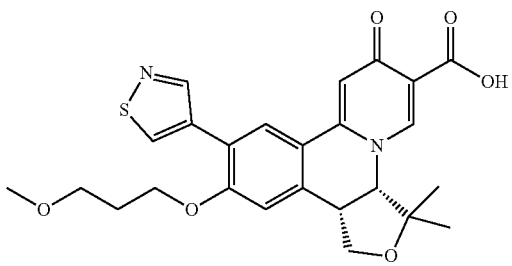

The title compound was prepared following similar procedure as Example 61. ESI MS m/z=483.1 [M+H]$^+$.

Example 128: (3aS,12bR)-11-(3-methoxypropoxy)-3,3-dimethyl-7-oxo-10-(pyridin-3-yl)-3,3a,7,12b-tetrahydro-1H-furo[3,4-c]pyrido[2,1-a]isoquinoline-6-carboxylic Acid

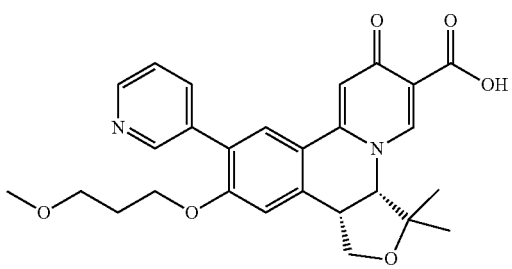 [SMILES: COCCCOc1cc2c(cc1-c1cccnc1)-c1cc(=O)c(C(=O)O)cn1[C@H]1[C@@H]2COC1(C)C]

The title compound was prepared following similar procedure as Example 61. ESI MS m/z=477.1 [M+H]$^+$.

Example 129: (5S)-5-(tert-butyl)-9-oxo-12-(tetrahydrofuran-2-yl)-2,3,4,9-tetrahydro-5H-furo[3,2-f]pyrido[2,1-a]isoquinoline-8-carboxylic Acid

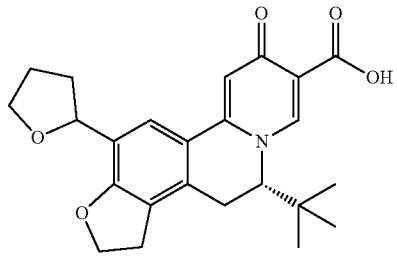 [SMILES: CC(C)(C)[C@@H]1Cc2c(cc(C3CCCO3)c3c2CCO3)-c2cc(=O)c(C(=O)O)cn21]

Step 1: An oven-dried vial was charged with (S)-12-bromo-5-(tert-butyl)-9-oxo-2,3,4,9-tetrahydro-5H-furo[3,2-f]pyrido[2,1-a]isoquinoline-8-carboxylic acid (150 mg, 0.36 mmol), 2-(3,4-dihydro-2H-pyran-6-yl)-4,4,5,5-tetramethyl-1,3,2-dioxaborolane (353 mg, 1.8 mmol), Pd$^t$BuXPhos G3 (28 mg, 0.04 mmol), and Cs$_2$CO$_3$ (582 mg, 1.8 mmol). The vial was purged with nitrogen gas for 5 minutes, then DMF (3 mL) and water (0.6 mL) were added via syringe. The reaction mixture was heated under a nitrogen atmosphere for 80 minutes at 110° C. After cooling to room temperature, the reaction mixture was filtered, concentrated, and used directly in the next step.

Step 2: A vial was charged with (S)-5-(tert-butyl)-12-(4,5-dihydrofuran-2-yl)-9-oxo-2,3,4,9-tetrahydro-5H-furo[3,2-f]pyrido[2,1-a]isoquinoline-8-carboxylic acid (50 mg, 0.1 mmol), 10% Pd/C (10 mg), and MeOH (5 mL). The vial was placed under an atmosphere of hydrogen and stirred at room temperature. After 15 h, the mixture was filtered and concentrated. The residue was purified by RPHPLC to provide (5S)-5-(tert-butyl)-9-oxo-12-(tetrahydrofuran-2-yl)-2,3,4,9-tetrahydro-5H-furo[3,2-f]pyrido[2,1-a]isoquinoline-8-carboxylic acid (15 mg, 30% yield). ESI MS m/z=410.1 [M+H]$^+$.

Example 130: (5S)-5-(tert-butyl)-9-oxo-12-(tetrahydrofuran-3-yl)-2,3,4,9-tetrahydro-5H-furo[3,2-f]pyrido[2,1-a]isoquinoline-8-carboxylic Acid

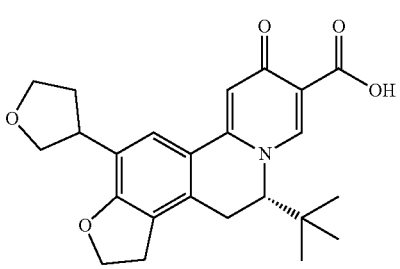 [SMILES: CC(C)(C)[C@@H]1Cc2c(cc(C3CCOC3)c3c2CCO3)-c2cc(=O)c(C(=O)O)cn21]

The title compound was prepared following similar procedure as Example 129. ESI MS m/z=410.1 [M+H]$^+$.

Example 131: (S)-5-(tert-butyl)-12-(oxetan-3-yl)-9-oxo-2,3,4,9-tetrahydro-5H-furo[3,2-f]pyrido[2,1-a]isoquinoline-8-carboxylic Acid

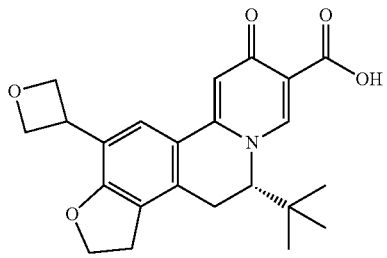 [SMILES: CC(C)(C)[C@@H]1Cc2c(cc(C3COC3)c3c2CCO3)-c2cc(=O)c(C(=O)O)cn21]

The title compound was prepared following similar procedure as Example 62. ESI MS m/z=395.1 [M+H]+.

Example 132: (2S,5S)-5-(tert-butyl)-12-(furan-3-yl)-2-methyl-9-oxo-2,3,4,9-tetrahydro-5H-furo[3,2-f]pyrido[2,1-a]isoquinoline-8-carboxylic Acid

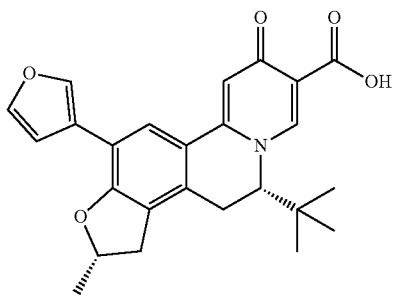 [SMILES: C[C@H]1Cc2c3c(cc(-c4ccoc4)c2O1)-c1cc(=O)c(C(=O)O)cn1[C@H](C(C)(C)C)C3]

Step 1: Into a round-bottom flask purged and maintained with an inert atmosphere of nitrogen, was placed 2-chloro-5-iodophenol (20 g, 78.7 mmol) and acetone (500 mL). This was followed by the addition of 3-bromoprop-1-ene (14.2 g, 118 mmol) dropwise with stirring at 25° C. To this was added $K_2CO_3$ (21.7 g, 157 mmol). The resulting solution was stirred for 3 h at 60° C. The solids were filtered out. The filtrate was concentrated under vacuum. This resulted in 24 g (crude) of 2-(allyloxy)-1-chloro-4-iodobenzene as a yellow oil, which was taken onto the next step without further purification.

Step 2: Into an oven dried flask was placed 2-(allyloxy)-1-chloro-4-iodobenzene (5 g, crude). The material was stirred for 18 h at 160° C. The oil was purified on silica gel with 50% ethyl acetate:hexanes to provide the product, 2-allyl-6-chloro-3-iodophenol (4 g, 80% yield over two steps).

Step 3: Into a round-bottom flask purged and maintained with an inert atmosphere of nitrogen, was placed 2-allyl-6-chloro-3-iodophenol (2 g, 6.8 mmol), p-TSA (4.6 g, 27.2 mmol), and toluene (40 mL). The mixture was stirred at 110° C. overnight, then concentrated. The residue was purified on silica gel with 50% ethyl acetate:hexanes to provide the product, 7-chloro-4-iodo-2-methyl-2,3-dihydrobenzofuran (1.8 g, 89% yield).

Step 4: Into a round-bottom flask purged and maintained with an inert atmosphere of nitrogen, was placed 7-chloro-4-iodo-2-methyl-2,3-dihydrobenzofuran (1.7 g, 5.8 mmol), THF (40 mL), 3,3-dimethylbutan-2-one (1.7 g, 17.4 mmol), $Pd_2(dba)_3$ (150 mg, 0.17 mmol), Xantphos (200 mg, 0.34 mmol), and t-BuONa (1.6 g, 17.4 mmol). The resulting solution was stirred for 3 h at 60° C. The reaction was then quenched by the addition of 3 mL of sat. $NH_4Cl$. The resulting solution was extracted with 2×50 mL of ethyl acetate and the organic layers combined. The mixture was dried over anhydrous sodium sulfate and concentrated under vacuum. The residue was applied onto a silica gel column and eluted with ethyl acetate:petroleum ether (0:1-1:50) to provide the product, 1-(7-chloro-2-methyl-2,3-dihydrobenzofuran-4-yl)-3,3-dimethylbutan-2-one as yellow oil (1.3 g, 80% yield).

Step 5: Into a round-bottom flask purged and maintained with an inert atmosphere of nitrogen, was placed 1-(7-chloro-2-methyl-2,3-dihydrobenzofuran-4-yl)-3,3-dimethylbutan-2-one (1.3 g, 4.9 mmol), MeOH (40 mL), $CH_3COONH_4$ (3.8 g, 49 mmol), and $NaBH_3CN$ (1.2 g, 19.6 mmol). The resulting solution was stirred for 24 h at 60° C. The reaction was concentrated then washed with 1N aq. NaOH (50 mL). The resulting solution was extracted with 2×50 mL of ethyl acetate and the organic layers combined. The resulting mixture was washed with 1×50 mL of brine. The mixture was dried over anhydrous sodium sulfate, filtered, and concentrated under vacuum. This resulted in 1.1 g (crude) of 1-(7-chloro-2-methyl-2,3-dihydrobenzofuran-4-yl)-3,3-dimethylbutan-2-amine as a yellow solid, which was taken onto the next step without further purification.

Step 6: Into a round-bottom flask purged and maintained with an inert atmosphere of nitrogen, was placed 1-(7-chloro-2-methyl-2,3-dihydrobenzofuran-4-yl)-3,3-dimethylbutan-2-amine (1.1 g, 4.1 mmol), formic acid (754 mg, 16.4 mmol), and dioxane (30 mL). The resulting solution was stirred for 3 h at 110° C. The resulting mixture was concentrated under vacuum. This resulted in 1.1 g (crude) of N-(1-(7-chloro-2-methyl-2,3-dihydrobenzofuran-4-yl)-3,3-dimethylbutan-2-yl)formamide as a yellow solid, which was taken onto the next step without further purification.

Step 7: Into a round-bottom flask purged and maintained with an inert atmosphere of nitrogen, was placed N-(1-(7-chloro-2-methyl-2,3-dihydrobenzofuran-4-yl)-3,3-dimethylbutan-2-yl)formamide (1.1 g, 3.7 mmol), ACN (20 mL), and $POCl_3$ (790 mg, 5.2 mmol). The resulting solution was stirred for 2 h at 70° C. The resulting mixture was concentrated under vacuum. The resulting solution was diluted with 50 mL of EA. The resulting mixture was washed with 1×50 mL of sat. Aq. $NaHCO_3$. The mixture was dried over anhydrous sodium sulfate and concentrated under vacuum. This resulted in 900 mg (crude) of 8-(tert-butyl)-4-chloro-2-methyl-1,2,8,9-tetrahydrofuro[3,2-f]isoquinoline as a yellow solid, which was taken to the next step without further purification.

Step 8: Into a round-bottom flask purged and maintained with an inert atmosphere of nitrogen, was placed 8-(tert-butyl)-4-chloro-2-methyl-1,2,8,9-tetrahydrofuro[3,2-f]isoquinoline (900 mg, crude), ethyl (2E)-2-(ethoxymethylidene)-3-oxobutanoate (1.8 g, 9.6 mmol), EtOH (30 mL), and water (10 mL). The resulting solution was stirred for 20 h at 100° C. The resulting mixture was concentrated under vacuum. The resulting mixture was washed with 1×2 mL of EtOAc. The residue was purified on silica gel with ethyl acetate to provide the product, The solids were collected by filtration to provide the product, ethyl 5-(tert-butyl)-12-chloro-2-methyl-9-oxo-2,3,4,9,10,10a-hexahydro-5H-furo[3,2-f]pyrido[2,1-a]isoquinoline-8-carboxylate (1 g, 58% yield over four steps).

Step 9: Into a vial purged and maintained with an inert atmosphere of nitrogen, was placed ethyl 5-(tert-butyl)-12-chloro-2-methyl-9-oxo-2,3,4,9,10,10a-hexahydro-5H-furo[3,2-f]pyrido[2,1-a]isoquinoline-8-carboxylate (1.0 g, 2.4 mmol), DME (20 mL), and tetrachlorocyclohexa-2,5-diene-1,4-dione (1.1 g, 4.8 mmol). The resulting solution was stirred for 1 h at 70° C. The resulting mixture was concentrated under vacuum. The residue was purified by SFC (Column: CHIRAL ART Cellulose-SB, mobile phase: 50% CO₂/(2 mM ammonia in EtOH) to provide the product, ethyl (2S,5S)-5-(tert-butyl)-12-chloro-2-methyl-9-oxo-2,3,4,9-tetrahydro-5H-furo[3,2-f]pyrido[2,1-a]isoquinoline-8-carboxylate (250 mg, 23% yield).

Step 10: Into a vial was placed ethyl (2S,5S)-5-(tert-butyl)-12-chloro-2-methyl-9-oxo-2,3,4,9-tetrahydro-5H-furo[3,2-f]pyrido[2,1-a]isoquinoline-8-carboxylate (250 mg, 0.6 mmol), EtOH (10 mL), and 1 M Aq. NaOH (10 mL). The resulting solution was stirred for 5 h at room temperature. Most of the EtOH was removed under vacuum. The resulting solution was diluted with 10 mL of water. The pH value of the solution was adjusted to 3 with 1 M aq. HCl. The solids were collected by filtration to provide the product, (2S,5S)-5-(tert-butyl)-12-chloro-2-methyl-9-oxo-2,3,4,9-tetrahydro-5H-furo[3,2-f]pyrido[2,1-a]isoquinoline-8-carboxylic acid as a off-white solid (220 mg, 95% yield). ESI MS m/z=389.1 [M+H]⁺.

Step 11: An oven-dried vial was charged with (2S,5S)-5-(tert-butyl)-12-chloro-2-methyl-9-oxo-2,3,4,9-tetrahydro-5H-furo[3,2-f]pyrido[2,1-a]isoquinoline-8-carboxylic acid (38 mg, 0.1 mmol), 3-furylboronic acid (56 mg, 0.5 mmol), Pd$^t$BuXPhos G3 (8 mg, 0.01 mmol), and Cs₂CO₃ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (2S,5S)-5-(tert-butyl)-12-(furan-3-yl)-2-methyl-9-oxo-2,3,4,9-tetrahydro-5H-furo[3,2-f]pyrido[2,1-a]isoquinoline-8-carboxylic acid (19 mg, 45% yield). ESI MS m/z=420.1 [M+H]⁺.

Example 133: (S)-5-(tert-butyl)-9-oxo-12-(2-oxa-6-azaspiro[3.3]heptan-6-yl)-2,3,4,9-tetrahydro-5H-furo[3,2-f]pyrido[2,1-a]isoquinoline-8-carboxylic Acid

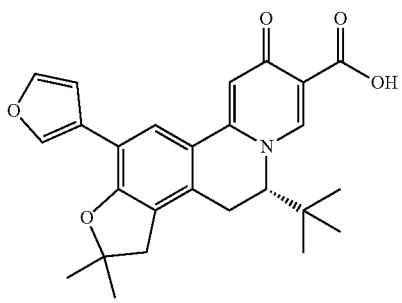 [SMILES: CC1(C)Cc2c3c(cc(-c4ccoc4)c2O1)-c1cc(=O)c(C(=O)O)cn1[C@H](C(C)(C)C)C3]

Step 1: Into a round-bottom flask purged and maintained with an inert atmosphere of nitrogen, was placed 2-chloro-5-iodophenol (20 g, 78.7 mmol) and acetone (500 mL). This was followed by the addition of 3-bromo-2-methylprop-1-ene (15.8 g, 118 mmol) dropwise with stirring at 25° C. To this was added K₂CO₃ (21.7 g, 157 mmol). The resulting solution was stirred for 3 h at 60° C. The solids were filtered out. The filtrate was concentrated under vacuum. This resulted in 24 g (crude) of 1-chloro-4-iodo-2-((2-methylallyl)oxy)benzene as a yellow oil, which was taken onto the next step without further purification.

Step 2: Into an oven dried flask was placed 1-chloro-4-iodo-2-((2-methylallyl)oxy)benzene (4 g, crude). The material was stirred for 18 h at 160° C. The oil was purified on silica gel with 50% ethyl acetate:hexanes to provide the product, 6-chloro-3-iodo-2-(2-methylallyl)phenol (3.5 g, 80% yield over two steps).

Step 3: Into a round-bottom flask purged and maintained with an inert atmosphere of nitrogen, was placed 6-chloro-3-iodo-2-(2-methylallyl)phenol (2 g, 6.5 mmol), p-TSA (4.5 g, 26 mmol), and toluene (40 mL). The mixture was stirred at 110° C. overnight, then concentrated. The residue was purified on silica gel with 50% ethyl acetate:hexanes to provide the product, 7-chloro-4-iodo-2,2-dimethyl-2,3-dihydrobenzofuran (1.8 g, 90% yield).

Step 4: Into a round-bottom flask purged and maintained with an inert atmosphere of nitrogen, was placed 7-chloro-4-iodo-2,2-dimethyl-2,3-dihydrobenzofuran (1.7 g, 5.5 mmol), THF (40 mL), 3,3-dimethylbutan-2-one (1.6 g, 16.5 mmol), Pd₂(dba)₃ (160 mg, 0.17 mmol), Xantphos (200 mg, 0.34 mmol), and t-BuONa (1.6 g, 16.5 mmol). The resulting solution was stirred for 3 h at 60° C. The reaction was then quenched by the addition of 3 mL of sat. NH₄Cl. The resulting solution was extracted with 2×50 mL of ethyl acetate and the organic layers combined. The mixture was dried over anhydrous sodium sulfate and concentrated under vacuum. The residue was applied onto a silica gel column and eluted with ethyl acetate:petroleum ether (0:1-1:50) to provide the product, 1-(7-chloro-2,2-dimethyl-2,3-dihydrobenzofuran-4-yl)-3,3-dimethylbutan-2-one as yellow oil (1.2 g, 80% yield).

Step 5: Into a round-bottom flask purged and maintained with an inert atmosphere of nitrogen, was placed 1-(7-chloro-2,2-dimethyl-2,3-dihydrobenzofuran-4-yl)-3,3-dimethylbutan-2-one (1.2 g, 4.3 mmol), MeOH (40 mL), CH₃COONH₄ (3.8 g, 43 mmol), and NaBH₃CN (1.1 g, 17.2 mmol). The resulting solution was stirred for 24 h at 60° C. The reaction was concentrated then washed with 1N aq. NaOH (50 mL). The resulting solution was extracted with 2×50 mL of ethyl acetate and the organic layers combined. The resulting mixture was washed with 1×50 mL of brine. The mixture was dried over anhydrous sodium sulfate, filtered, and concentrated under vacuum. This resulted in 1.2 g (crude) of 1-(7-chloro-2,2-dimethyl-2,3-dihydrobenzofuran-4-yl)-3,3-dimethylbutan-2-amine as a yellow solid, which was taken onto the next step without further purification.

Step 6: Into a round-bottom flask purged and maintained with an inert atmosphere of nitrogen, was placed 1-(7-chloro-2,2-dimethyl-2,3-dihydrobenzofuran-4-yl)-3,3-dimethylbutan-2-amine (1.2 g, 4.2 mmol), formic acid (772 mg, 16.8 mmol), and dioxane (30 mL). The resulting solution was stirred for 3 h at 110° C. The resulting mixture was concentrated under vacuum. This resulted in 1.2 g (crude) of N-(1-(7-chloro-2,2-dimethyl-2,3-dihydrobenzofuran-4-yl)-3,3-dimethylbutan-2-yl)formamide as a yellow solid, which was taken onto the next step without further purification.

Step 7: Into a round-bottom flask purged and maintained with an inert atmosphere of nitrogen, was placed N-(1-(7-chloro-2,2-dimethyl-2,3-dihydrobenzofuran-4-yl)-3,3-dimethylbutan-2-yl)formamide (1.2 g, 3.8 mmol), ACN (20 mL), and POCl₃ (790 mg, 5.2 mmol). The resulting solution was stirred for 2 h at 70° C. The resulting mixture was concentrated under vacuum. The resulting solution was diluted with 50 mL of EA. The resulting mixture was washed with 1×50 mL of sat. Aq. NaHCO₃. The mixture was dried over anhydrous sodium sulfate and concentrated under vacuum. This resulted in 730 mg (crude) of 8-(tert-butyl)-4-chloro-2,2-dimethyl-1,2,8,9-tetrahydrofuro[3,2-f]isoquinoline as a yellow solid, which was taken to the next step without further purification.

Step 8: Into a round-bottom flask purged and maintained with an inert atmosphere of nitrogen, was placed 8-(tert-butyl)-4-chloro-2,2-dimethyl-1,2,8,9-tetrahydrofuro[3,2-f]isoquinoline (700 mg, crude), ethyl (2E)-2-(ethoxymethylidene)-3-oxobutanoate (1.3 g, 7.2 mmol), EtOH (30 mL), and water (10 mL). The resulting solution was stirred for 20 h at 100° C. The resulting mixture was concentrated under vacuum. The resulting mixture was washed with 1×2 mL of EtOAc. The residue was purified on silica gel with ethyl acetate to provide the product, The solids were collected by filtration to provide the product, ethyl 5-(tert-butyl)-12-chloro-2,2-dimethyl-9-oxo-2,3,4,9,10,10a-hexahydro-5H-furo[3,2-f]pyrido[2,1-a]isoquinoline-8-carboxylate (0.5 g, 28% yield over four steps).

Step 9: Into a vial purged and maintained with an inert atmosphere of nitrogen, was placed ethyl 5-(tert-butyl)-12-chloro-2,2-dimethyl-9-oxo-2,3,4,9,10,10a-hexahydro-5H-furo[3,2-f]pyrido[2,1-a]isoquinoline-8-carboxylate (0.5 g, 1.2 mmol), DME (20 mL), and tetrachlorocyclohexa-2,5-diene-1,4-dione (0.6 g, 2.4 mmol). The resulting solution was stirred for 1 h at 70° C. The resulting mixture was concentrated under vacuum. The residue was purified by SFC (Column: CHIRAL ART Cellulose-SB, mobile phase: 50% CO₂/(2 mM ammonia in EtOH) to provide the product, ethyl (S)-5-(tert-butyl)-12-chloro-2,2-dimethyl-9-oxo-2,3,4,9-tetrahydro-5H-furo[3,2-f]pyrido[2,1-a]isoquinoline-8-carboxylate (120 mg, 23% yield).

Step 10: Into a vial was placed ethyl (S)-5-(tert-butyl)-12-chloro-2,2-dimethyl-9-oxo-2,3,4,9-tetrahydro-5H-furo[3,2-f]pyrido[2,1-a]isoquinoline-8-carboxylate (120 mg, 0.28 mmol), EtOH (10 mL), and 1 M Aq. NaOH (10 mL). The resulting solution was stirred for 5 h at room temperature. Most of the EtOH was removed under vacuum. The resulting solution was diluted with 10 mL of water. The pH value of the solution was adjusted to 3 with 1 M aq. HCl. The solids were collected by filtration to provide the product, (S)-5-(tert-butyl)-12-chloro-2,2-dimethyl-9-oxo-2,3,4,9-tetrahydro-5H-furo[3,2-f]pyrido[2,1-a]isoquinoline-8-carboxylic acid as a off-white solid (101 mg, 90% yield). ESI MS m/z=402.1 [M+H]⁺.

Step 11: An oven-dried vial was charged with (S)-5-(tert-butyl)-12-chloro-2,2-dimethyl-9-oxo-2,3,4,9-tetrahydro-5H-furo[3,2-f]pyrido[2,1-a]isoquinoline-8-carboxylic acid (40 mg, 0.1 mmol), 3-furylboronic acid (56 mg, 0.5 mmol), Pd'BuXPhos G3 (8 mg, 0.01 mmol), and Cs₂CO₃ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (S)-5-(tert-butyl)-12-(furan-3-yl)-2,2-dimethyl-9-oxo-2,3,4,9-tetrahydro-5H-furo[3,2-f]pyrido[2,1-a]isoquinoline-8-carboxylic acid (10 mg, 23% yield). ESI MS m/z=434.1 [M+H]⁺.

Example 134: (S)-6-(tert-butyl)-10-(4-fluorophenyl)-9-(4-methoxybutyl)-2-oxo-6,7-dihydro-2H-pyrido[2,1-a]isoquinoline-3-carboxylic Acid

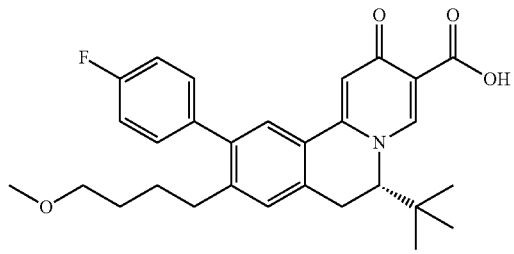 [SMILES: COCCCCc1cc2c(cc1-c1ccc(F)cc1)-c1cc(=O)c(C(=O)O)cn1[C@H](C(C)(C)C)C2]

Step 1: Into a 500-mL 3-necked round-bottom flask purged and maintained with an inert atmosphere of nitrogen, was placed 1-bromo-3-methoxypropane (60 g, 393.0 mmol), triphenylphosphine (102.8 g, 393.1 mmol) and toluene (300 mL). The resulting solution was stirred for 16 h at 150° C. in an oil bath. The solids were collected by filtration. This resulted in (3-methoxypropyl)triphenylphosphonium bromide (120 g, 91% yield) as a white solid.

Step 2: Into a 500-mL 3-necked round-bottom flask purged and maintained with an inert atmosphere of nitrogen, was placed a solution of (3-methoxypropyl)triphenylphosphonium bromide (49.3 g, 118.5 mmol) in THF (200 mL). Then, NaHMDS (118.4 mL, 118.5 mmol, 1 M in THF) was added at 0° C. and stirred for 30 mins. Then 5-bromo-2-chlorobenzaldehyde (20 g, 91.1 mmol) was added. The resulting solution was stirred for 1 h at 0° C. in a water/ice bath, then most of the THF was removed. The residue was purified by silica gel column chromatography to afford (E)-4-bromo-1-chloro-2-(4-methoxybut-1-en-1-yl)benzene (17 g, 67% yield).

Step 3: Into a 500-mL sealed tube was placed (E)-4-bromo-1-chloro-2-(4-methoxybut-1-en-1-yl)benzene (17 g, 61.7 mmol) and THF (170 mL). Rh/C (1.7 g, 16.5 mmol) was added in portionwise. The mixture was purged with 5 atmospheric pressure of hydrogen. The resulting solution was stirred for 6 h at room temperature. The mixture was filtered and the solid was rinsed repeatedly with THF. The combined filtrates were concentrated. The resulting crude 4-bromo-1-chloro-2-(4-methoxybutyl)benzene (14 g, 82% yield) was used in next step without further purification.

Step 4: Into a 500-mL 3-necked round-bottom flask purged and maintained with an inert atmosphere of nitrogen, was placed 4-bromo-1-chloro-2-(4-methoxybutyl)benzene (14 g, 50.4 mmol), 3,3-dimethylbutan-2-one (15.2 g, 151.3 mmol), Pd₂(dba)₃ (2.3 g, 2.5 mmol), Xantphos (2.9 g, 5.1 mmol), t-BuONa (14.5 g, 151.3 mmol) and THF (140 mL). The resulting solution was stirred for 5 h at 50° C. in an oil bath. The reaction was then quenched by the addition of aq. NH₄Cl and extracted with ethyl acetate. The combined organic layers were dried, filtered and concentrated. The residue was purified by silica gel column chromatography to result in 1-(4-chloro-3-(4-methoxybutyl)phenyl)-3,3-dimethylbutan-2-one (8 g, 53% yield) as a light yellow oil.

Step 5: Into a 250-mL 3-necked round-bottom flask purged and maintained with an inert atmosphere of nitrogen, was placed 1-(4-chloro-3-(4-methoxybutyl)phenyl)-3,3-dimethylbutan-2-one (8 g, 26.9 mmol), NH₄OAc (31.2 g, 404.2 mmol), NaBH₃CN (3.4 g, 53.9 mmol) and methanol (80 mL). The resulting solution was stirred for 5 h at 70° C. in an oil bath. The mixture was concentrated, washed with 1N NaOH solution and extracted with EA. The combined organic layers were dried, filtered and concentrated to afford crude 1-(4-chloro-3-(4-methoxybutyl)phenyl)-3,3-dimethylbutan-2-one (8 g) which was used in next step without further purification.

Step 6: To a stirred solution of 1-(4-chloro-3-(4-methoxybutyl)phenyl)-3,3-dimethylbutan-2-one (8.0 g, 26.8 mmol) and pyridine (4.2 g, 53.7 mmol) in DCM (160 mL) was added TFAA (6.8 g, 32.2 mmol) dropwise at −10° C. The mixture was warmed to room temperature and stirred overnight. Then, the mixture was concentrated. The resulting residue was purified by C18-silica gel chromatography with 70% MeCN/water to afford N-(1-(4-chloro-3-(4-methoxybutyl)phenyl)-3,3-dimethylbutan-2-yl)-2,2,2-trifluoroacetamide (7 g, 66% yield for 2 steps) as a brown yellow solid.

Step 7: Into a solution of N-(1-(4-chloro-3-(4-methoxybutyl)phenyl)-3,3-dimethylbutan-2-yl)-2,2,2-trifluoroacetamide (6.7 g, 17.1 mmol) and $Py_2IBF_4$ (6.9 g, 18.7 mmol) in DCM (140 mL) was added $CF_3SO_3H$ (5.6 g, 37.5 mmol) dropwise at 0° C. The mixture was warmed to room temperature and stirred for overnight. Then, the mixture was concentrated and re-dissolved in EA. The organic layer was washed sequentially with aq. $NaHSO_3$ solution, aq. $NaHCO_3$ solution and brine. The solvent was evaporated and the resulting residue was purified by C18-silica gel chromatography with 70% MeCN/water to afford N-(1-(4-chloro-2-iodo-5-(4-methoxybutyl)phenyl)-3,3-dimethylbutan-2-yl)-2,2,2-trifluoroacetamide (6.8 g, 77% yield) as a light yellow solid.

Step 8: A solution of N-(1-(4-chloro-2-iodo-5-(4-methoxybutyl)phenyl)-3,3-dimethylbutan-2-yl)-2,2,2-trifluoroacetamide (6.8 g, 13.2 mmol), KOH (5.9 g, 105.5 mmol), i-PrOH (120 mL) and $H_2O$ (18 mL) was stirred for 24 h at 60° C. Then, the mixture was concentrated and extracted with DCM. The combined organic layers were dried, filtered and concentrated. The resulting residue was purified by C18-silica gel chromatography with 40% MeCN/water to afford 1-(4-chloro-2-iodo-5-(4-methoxybutyl)phenyl)-3,3-dimethylbutan-2-amine (3.4 g, 61% yield) as a white solid.

Step 9: A solution of 1-(4-chloro-2-iodo-5-(4-methoxybutyl)phenyl)-3,3-dimethylbutan-2-amine (4.1 g, 9.6 mmol) and ethyl 4-oxopyran-3-carboxylate (3.1 g, 18.2 mmol) in EtOH (200 mL) was stirred for 24 h at 100° C. After completion of the reaction indicated by LCMS, the mixture was purified by C18-silica gel chromatography with 70% MeCN/water to afford ethyl 1-(1-(4-chloro-2-iodo-5-(4-methoxybutyl)phenyl)-3,3-dimethylbutan-2-yl)-4-oxo-1,4-dihydropyridine-3-carboxylate (0.8 g, 14% yield).

Step 10: Into a 20 mL vial was added ethyl 1-(1-(4-chloro-2-iodo-5-(4-methoxybutyl)phenyl)-3,3-dimethylbutan-2-yl)-4-oxo-1,4-dihydropyridine-3-carboxylate (0.9 g, 1.6 mmol), Pd-SPhos-G3 (0.27 g, 0.3 mmol), KOAc (0.46 g, 4.7 mmol) and DMF (20 mL). The mixture was stirred for 1 h at 100° C. under nitrogen atmosphere, then diluted with water (20 mL). Then, the mixture was extracted with EA and concentrated. The residue was purified by SFC (Column: CHIRAL ART Cellulose-SB, mobile phase: 50% $CO_2$/(2 mM ammonia in EtOH) to provide the product, ethyl (S)-6-(tert-butyl)-10-chloro-9-(4-methoxybutyl)-2-oxo-6,7-dihydro-2H-pyrido[2,1-a]isoquinoline-3-carboxylate (150 mg, 21% yield).

Step 11: Into a vial was placed ethyl (S)-6-(tert-butyl)-10-chloro-9-(4-methoxybutyl)-2-oxo-6,7-dihydro-2H-pyrido[2,1-a]isoquinoline-3-carboxylate (150 mg, 0.34 mmol), EtOH (5 mL), and 1 M Aq. NaOH (5 mL). The resulting solution was stirred for 5 h at room temperature. Most of the EtOH was removed under vacuum. The resulting solution was diluted with 10 mL of water. The pH value of the solution was adjusted to 3 with 1 M aq. HCl. The solids were collected by filtration to provide the product, (S)-6-(tert-butyl)-10-chloro-9-(4-methoxybutyl)-2-oxo-6,7-dihydro-2H-pyrido[2,1-a]isoquinoline-3-carboxylic acid as a off-white solid (138 mg, 98% yield). ESI MS m/z=418.1 $[M+H]^+$.

Step 12: An oven-dried vial was charged with (S)-6-(tert-butyl)-10-chloro-9-(4-methoxybutyl)-2-oxo-6,7-dihydro-2H-pyrido[2,1-a]isoquinoline-3-carboxylic acid (41 mg, 0.1 mmol), (4-fluorophenyl)boronic acid (70 mg, 0.5 mmol), Pd$^t$BuXPhos G3 (8 mg, 0.01 mmol), and $Cs_2CO_3$ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (S)-6-(tert-butyl)-10-(4-fluorophenyl)-9-(4-methoxybutyl)-2-oxo-6,7-dihydro-2H-pyrido[2,1-a]isoquinoline-3-carboxylic acid (40 mg, 83% yield). ESI MS m/z=478.1 $[M+H]^+$.

Example 135: (3aS,12bR)-11-(3-methoxypropoxy)-3,3-dimethyl-7-oxo-10-(1H-pyrazol-4-yl)-3,3a,7,12b-tetrahydro-1H-furo[3,4-c]pyrido[2,1-a]isoquinoline-6-carboxylic Acid

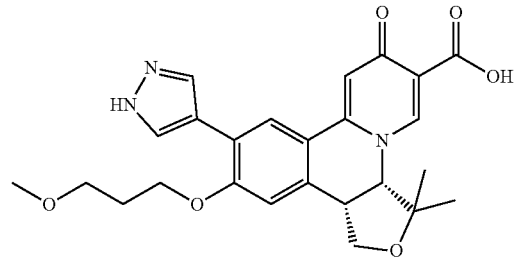 [SMILES: COCCCOc1cc2c(cc1-c1cn[nH]c1)-c1cc(=O)c(C(=O)O)cn1[C@H]1[C@@H]2COC1(C)C]

The title compound was prepared following similar procedure as Example 61. ESI MS m/z=466.1 $[M+H]^+$.

Example 136: (3aS,12bR)-10-(2-fluorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

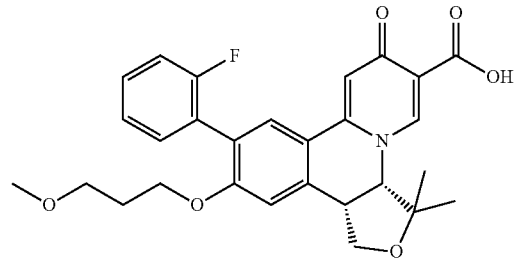

The title compound was prepared following similar procedure as Example 61. ESI MS m/z=494.1 $[M+H]^+$.

Example 137: (3aS,12bR)-10-(4-chlorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

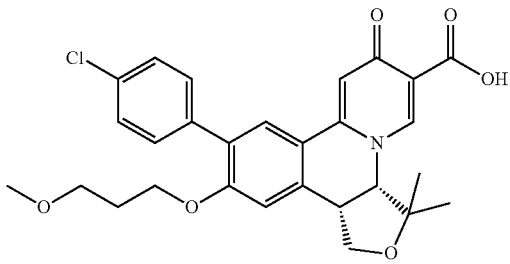 [SMILES: COCCCOc1cc2c(cc1-c1ccc(Cl)cc1)-c1cc(=O)c(C(=O)O)cn1[C@H]1[C@@H]2COC1(C)C]

The title compound was prepared following similar procedure as Example 61. ESI MS m/z=510.1 [M+H]$^+$.

Example 138: (3aS,12bR)-10-(3-chlorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

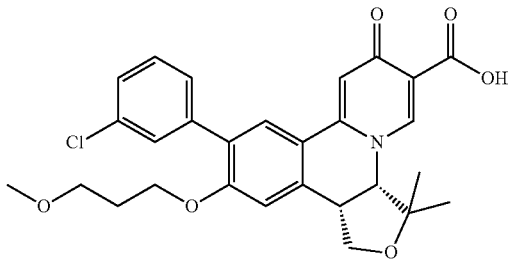 [SMILES: COCCCOc1cc2c(cc1-c1cccc(Cl)c1)-c1cc(=O)c(C(=O)O)cn1[C@H]1[C@@H]2COC1(C)C]

The title compound was prepared following similar procedure as Example 61. ESI MS m/z=510.1 [M+H]$^+$.

Example 139: (3aS,12bR)-10-(2-chlorophenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

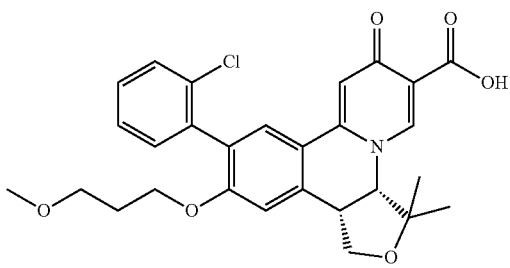

The title compound was prepared following similar procedure as Example 61. ESI MS m/z=510.1 [M+H]$^+$.

Example 140: (3aS,12bR)-10-(3-methoxyphenyl)-11-(3-methoxypropoxy)-3,3-dimethyl-7-oxo-3,3a,7,12b-tetrahydro-1H-furo[3,4-c]pyrido[2,1-a]isoquinoline-6-carboxylic Acid

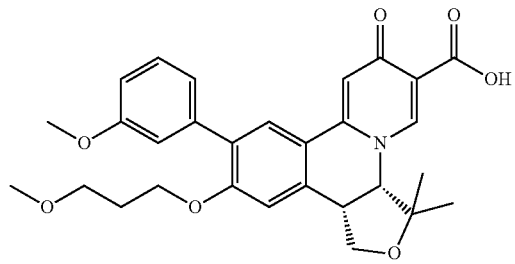 [SMILES: COCCCOc1cc2c(cc1-c1cccc(OC)c1)-c1cc(=O)c(C(=O)O)cn1[C@H]1[C@@H]2COC1(C)C]

The title compound was prepared following similar procedure as Example 61. ESI MS m/z=506.1 [M+H]$^+$.

Example 141: (3aS,12bR)-1-(3-methoxypropoxy)-3,3-dimethyl-7-oxo-10-phenyl-3,3a,7,12b-tetrahydro-1H-furo[3,4-c]pyrido[2,1-a]isoquinoline-6-carboxylic Acid

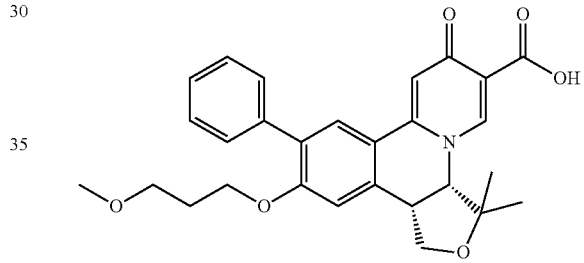

The title compound was prepared following similar procedure as Example 61. ESI MS m/z=476.1 [M+H]$^+$.

Example 142: (3aS,12bR)-11-(3-methoxypropoxy)-3,3-dimethyl-7-oxo-10-(thiophen-2-yl)-3,3a,7,12b-tetrahydro-1H-furo[3,4-c]pyrido[2,1-a]isoquinoline-6-carboxylic Acid

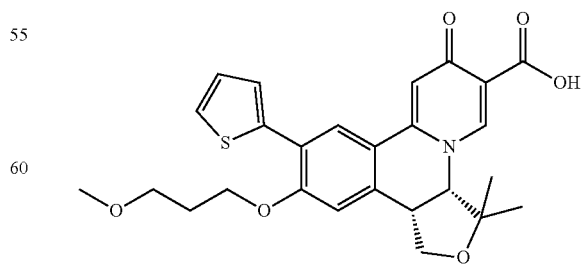

The title compound was prepared following similar procedure as Example 61. ESI MS m/z=482.1 [M+H]$^+$.

Example 143: (3aS,12bR)-11-(3-methoxypropoxy)-3,3-dimethyl-7-oxo-10-(thiophen-3-yl)-3,3a,7,12b-tetrahydro-1H-furo[3,4-c]pyrido[2,1-a]isoquinoline-6-carboxylic Acid

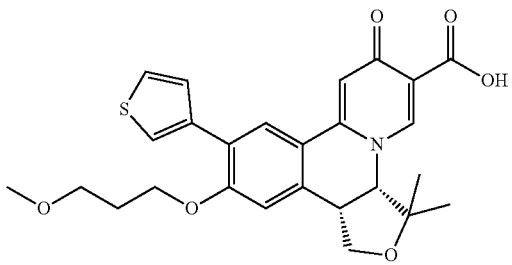 [SMILES: COCCCOc1cc2c(cc1-c1ccsc1)-c1cc(=O)c(C(=O)O)cn1[C@H]1[C@@H]2COC1(C)C]

The title compound was prepared following similar procedure as Example 61. ESI MS m/z=482.1 [M+H]$^+$.

Example 144: (S)-5-(tert-butyl)-2,2-dimethyl-12-(1-methyl-1H-pyrazol-3-yl)-9-oxo-2,3,4,9-tetrahydro-5H-furo[3,2-f]pyrido[2,1-a]isoquinoline-8-carboxylic Acid

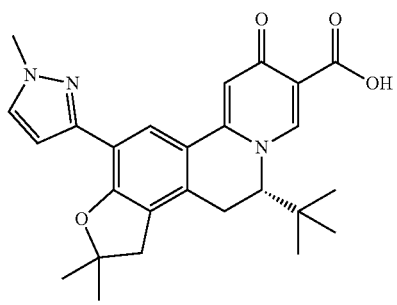 [SMILES: Cn1ccc(-c2cc3c(c4c2OC(C)(C)C4)C[C@@H](C(C)(C)C)n2cc(C(=O)O)c(=O)cc2-3)n1]

The title compound was prepared following similar procedure as Example 133. ESI MS m/z=448.1 [M+H]$^+$.

Example 145: (S)-5-(tert-butyl)-12-(isothiazol-4-yl)-2,2-dimethyl-9-oxo-2,3,4,9-tetrahydro-5H-furo[3,2-f]pyrido[2,1-a]isoquinoline-8-carboxylic Acid

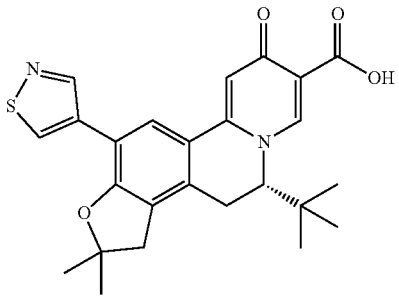

The title compound was prepared following similar procedure as Example 133. ESI MS m/z=451.1 [M+H]$^+$.

Example 146: (S)-5-(tert-butyl)-2,2-dimethyl-9-oxo-12-(1H-pyrazol-5-yl)-2,3,4,9-tetrahydro-5H-furo[3,2-f]pyrido[2,1-a]isoquinoline-8-carboxylic Acid

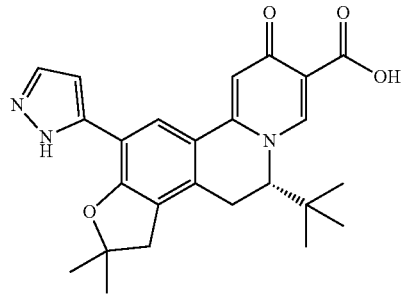 [SMILES: CC1(C)Cc2c3c(cc(-c4ccn[nH]4)c2O1)-c1cc(=O)c(C(=O)O)cn1[C@H](C(C)(C)C)C3]

The title compound was prepared following similar procedure as Example 133. ESI MS m/z=434.1 [M+H]$^+$.

Example 147: (S)-5-(tert-butyl)-2,2-dimethyl-9-oxo-12-(1H-pyrazol-4-yl)-2,3,4,9-tetrahydro-5H-furo[3,2-f]pyrido[2,1-a]isoquinoline-8-carboxylic Acid

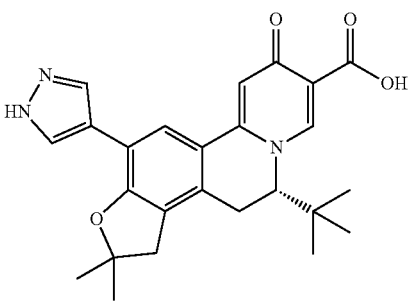 [SMILES: CC1(C)Cc2c3c(cc(-c4cn[nH]c4)c2O1)-c1cc(=O)c(C(=O)O)cn1[C@H](C(C)(C)C)C3]

The title compound was prepared following similar procedure as Example 133. ESI MS m/z=434.1 [M+H]$^+$.

Example 148: (S)-5-(tert-butyl)-12-(furan-2-yl)-2,2-dimethyl-9-oxo-2,3,4,9-tetrahydro-5H-furo[3,2-f]pyrido[2,1-a]isoquinoline-8-carboxylic Acid

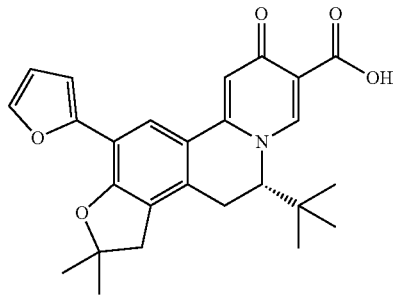

The title compound was prepared following similar procedure as Example 133. ESI MS m/z=434.1 [M+H]$^+$.

Example 149: (S)-5-(tert-butyl)-2,2-dimethyl-9-oxo-12-(thiophen-3-yl)-2,3,4,9-tetrahydro-5H-furo[3,2-f]pyrido[2,1-a]isoquinoline-8-carboxylic Acid

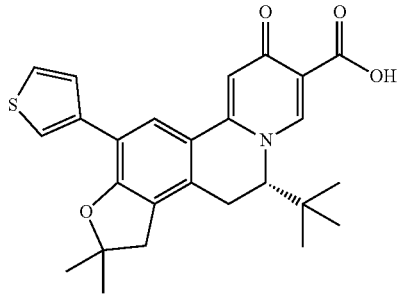

The title compound was prepared following similar procedure as Example 133. ESI MS m/z=450.1 [M+H]⁺.

Example 150: (S)-5-(tert-butyl)-2,2-dimethyl-12-(1-methyl-1H-pyrazol-5-yl)-9-oxo-2,3,4,9-tetrahydro-5H-furo[3,2-f]pyrido[2,1-a]isoquinoline-8-carboxylic Acid

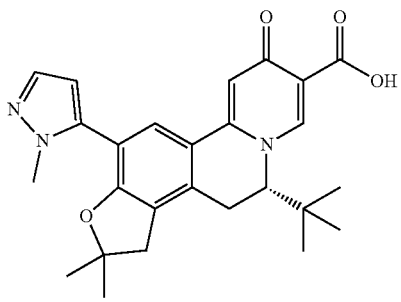 [SMILES: Cn1nccc1-c1cc2c(c3c1OC(C)(C)C3)C[C@@H](C(C)(C)C)n1cc(C(=O)O)c(=O)cc1-2]

The title compound was prepared following similar procedure as Example 133. ESI MS m/z=448.1 [M+H]⁺.

Example 151: (S)-5-(tert-butyl)-2,2-dimethyl-12-(1-methyl-1H-pyrazol-4-yl)-9-oxo-2,3,4,9-tetrahydro-5H-furo[3,2-f]pyrido[2,1-a]isoquinoline-8-carboxylic Acid

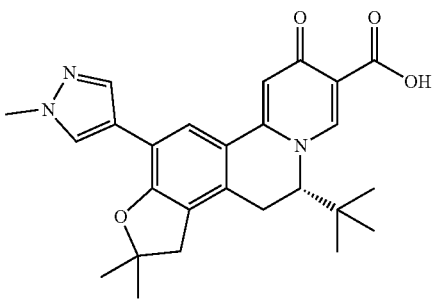 [SMILES: Cn1cc(-c2cc3c(c4c2OC(C)(C)C4)C[C@@H](C(C)(C)C)n2cc(C(=O)O)c(=O)cc2-3)cn1]

The title compound was prepared following similar procedure as Example 133. ESI MS m/z=448.1 [M+H]⁺.

Example 152: (S)-5-(tert-butyl)-2,2-dimethyl-9-oxo-12-(thiophen-2-yl)-2,3,4,9-tetrahydro-5H-furo[3,2-f]pyrido[2,1-a]isoquinoline-8-carboxylic Acid

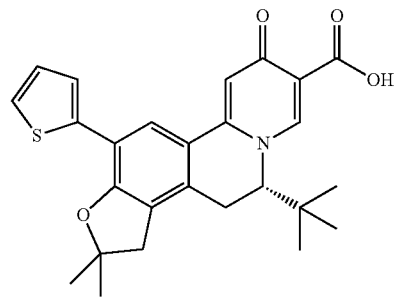 [SMILES: CC1(C)Cc2c3c(cc(-c4cccs4)c2O1)-c1cc(=O)c(C(=O)O)cn1[C@H](C(C)(C)C)C3]

The title compound was prepared following similar procedure as Example 30. ESI MS m/z=450.1 [M+H]⁺.

Example 153: (S)-6-(tert-butyl)-10-(3,3-difluoroazetidin-1-yl)-9-(4-methoxybutyl)-2-oxo-6,7-dihydro-2H-pyrido[2,1-a]isoquinoline-3-carboxylic Acid

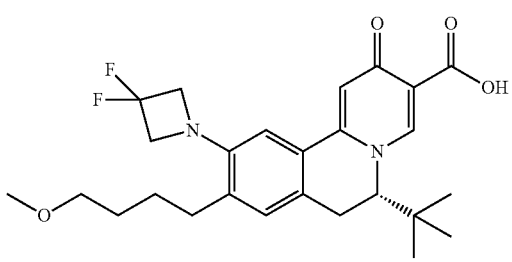 [SMILES: COCCCCc1cc2c(cc1N1CC(F)(F)C1)-c1cc(=O)c(C(=O)O)cn1[C@H](C(C)(C)C)C2]

Step 1: An oven-dried vial was charged with (S)-6-(tert-butyl)-10-chloro-9-(4-methoxybutyl)-2-oxo-6,7-dihydro-2H-pyrido[2,1-a]isoquinoline-3-carboxylic acid (50 mg, 0.12 mmol), 3,3-difluoroazetidine hydrochloride (47 mg, 0.359 mmol), Pd'BuXPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 10 h at 110° C. After cooling to room temperature, the reaction mixture was filtered and concentrated. The crude product was dissolved in DMSO (2 mL) and purified by RPHPLC to provide the product as a white solid (1 mg, 2% yield). ESI MS m/z=475.1 [M+H]⁺.

Example 154: (S)-6-(tert-butyl)-10-(3,3-difluoroazetidin-1-yl)-2-oxo-6,7-dihydro-2H-pyrido[2,1-a]isoquinoline-3-carboxylic Acid

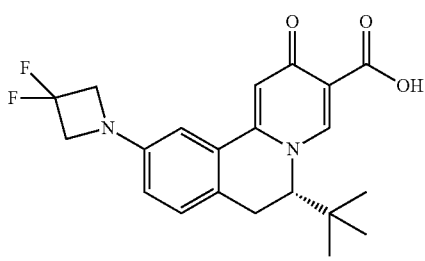 [SMILES: CC(C)(C)[C@@H]1Cc2ccc(N3CC(F)(F)C3)cc2-c2cc(=O)c(C(=O)O)cn21]

Step 1: To a stirred mixture of 4-bromoanisole (220.00 g, 1.78 mol, 1.00 equiv.) and pinacolone (117.45 g, 2.67 mol, 1.50 equiv.) in THF (2200.00 mL) were added t-BuONa (227.00 g, 3.56 mol, 2.00 equiv.), Xantphos (68.5 g, 0.18 mol, 0.1 equiv.) and $Pd_2(dba)_3$ (54 g, 0.089 mol, 0.05 equiv.) at room temperature under nitrogen atmosphere. The resulting mixture was stirred for 14 h at 50° C. under nitrogen atmosphere. The mixture was allowed to cool down to room temperature. The resulting mixture was filtered and the filter cake was washed with EtOAc (1000 mL). The filtrate was diluted with water (2000 mL). The resulting mixture was extracted with EtOAc (3×2 L). The combined organic layers were washed with brine (2×2 L), dried over anhydrous $Na_2SO_4$. After filtration, the filtrate was concentrated under reduced pressure. The residue was purified by silica gel column chromatography, eluted with PE/EtOAc (10:1) to afford 1-(4-methoxyphenyl)-3,3-dimethylbutan-2-one (140 g, 57.70% yield) as a yellow oil.

Step 2: To a stirred mixture of 1-(4-methoxyphenyl)-3,3-dimethylbutan-2-one (140.00 g, 678.673 mmol, 1.00 equiv.) in methanol (2100 mL) was added $NH_4OAc$ (523.6 g, 6.8 mol, 10 equiv.) at room temperature. The resulting mixture was stirred for 1 h at 70° C. The mixture was allowed to cool down to room temperature. To the above mixture was added $NaBH_3CN$ (85.68 g, 1.36 mol, 2 equiv.). The resulting mixture was stirred for additional 14 h at 70° C. The mixture was allowed to cool down to room temperature. The resulting mixture was concentrated under vacuum. The resulting mixture was diluted with water (2 L). The resulting mixture was extracted with $CH_2Cl_2$ (2×3 L). The combined organic layers were washed with brine (2×2 L), dried over anhydrous $Na_2SO_4$. After filtration, the filtrate was concentrated under reduced pressure. This resulted in 1-(4-methoxyphenyl)-3,3-dimethylbutan-2-amine (130 g, 92.39% yield) as a white semi-solid.

Step 3: To a stirred mixture of 1-(4-methoxyphenyl)-3,3-dimethylbutan-2-amine (130 g, 627.059 mmol, 1.00 equiv.) in 1,4-dioxane (2600.00 mL) was added ethyl formate (2600 mL) at room temperature under nitrogen atmosphere. The resulting mixture was stirred for 14 h at 105° C. under nitrogen atmosphere. The mixture was allowed to cool down to room temperature. The resulting mixture was concentrated under vacuum. The residue was purified by silica gel column chromatography, eluted with PE/EtOAc (4:1) to afford N-[1-(4-methoxyphenyl)-3,3-dimethylbutan-2-yl]formamide (100 g, 67.77% yield) as a white solid.

Step 4: To a stirred solution of N-[1-(4-methoxyphenyl)-3,3-dimethylbutan-2-yl]formamide (100.00 g, 424.941 mmol, 1.00 equiv.) in DCM (2000.00 mL) was added $(COCl)_2$ (80.90 g, 637.379 mmol, 1.50 equiv.) dropwise at 0° C. under nitrogen atmosphere. The resulting mixture was stirred for 1 h at room temperature under nitrogen atmosphere. To the above mixture was added $FeCl_3$ (103.39 g, 637.411 mmol, 1.5 equiv.) at −10° C. The resulting mixture was stirred for additional 2 h at room temperature. The resulting mixture was filtered and the filter cake was washed with DCM (500 mL). The filtrate was diluted with DCM (2 L). The resulting mixture was washed with 2×500 mL of HCl (0.5 N). The combined organic layers were dried over anhydrous $Na_2SO_4$. After filtration, the filtrate was concentrated under reduced pressure. This resulted in 5-tert-butyl-9-methoxy-5H,6H,10bH-[1,3]oxazolo[2,3-a]isoquinoline-2,3-dione (120 g, 97.60% yield) as a yellow solid.

Step 5: To a stirred mixture of 5-tert-butyl-9-methoxy-5H,6H,10bH-[1,3]oxazolo[2,3-a]isoquinoline-2,3-dione (120.00 g, 414.750 mmol, 1.00 equiv.) in MeOH (3420.00 mL) was added $H_2SO_4$ (180.00 mL, 3376.904 mmol, 8.14 equiv.) at room temperature under nitrogen atmosphere. The resulting mixture was stirred for 4 h at 70° C. under nitrogen atmosphere. The mixture was allowed to cool down to room temperature. The mixture was basified to pH 8 with ammonium hydroxide. The resulting mixture was concentrated under vacuum. The resulting mixture was diluted with water (1 L). The resulting mixture was extracted with $CH_2Cl_2$ (3×2 L). The combined organic layers were washed with brine (1×1 L), dried over anhydrous $Na_2SO_4$. After filtration, the filtrate was concentrated under reduced pressure. The residue was purified by silica gel column chromatography, eluted with PE/EtOAc (10:1) to afford 3-tert-butyl-7-methoxy-3,4-dihydroisoquinoline (40 g, 44.38% yield) as a yellow solid.

Step 6: To a stirred mixture of 3-tert-butyl-7-methoxy-3,4-dihydroisoquinoline (40.00 g, 184.067 mmol, 1.00 equiv.) in EtOH (3400.00 mL) was added ethyl 2-(ethoxymethylidene)-3-oxobutanoate (102.82 g, 552.181 mmol, 3.00 equiv.) at room temperature under nitrogen atmosphere. The resulting mixture was stirred for 7 days at 80° C. under nitrogen atmosphere. The mixture was allowed to cool down to room temperature. The resulting mixture was concentrated under vacuum. The residue was purified by silica gel column chromatography, eluted with PE/EtOAc (1:4) to afford ethyl 6-tert-butyl-10-methoxy-2-oxo-1H,6H,7H,11bH-pyrido[2,1-a]isoquinoline-3-carboxylate (31 g, 47.12% yield) as a brown solid.

Step 7: To a stirred solution of ethyl 6-tert-butyl-10-methoxy-2-oxo-1H,6H,7H,11bH-pyrido[2,1-a]isoquinoline-3-carboxylate (31.00 g, 86.725 mmol, 1.00 equiv.) in DME (1550.00 mL) was added p-chloranil (21.32 g, 86.716 mmol, 1.00 equiv.) at room temperature under nitrogen atmosphere. The resulting mixture was stirred for 1 h at 90° C. under nitrogen atmosphere. The mixture was allowed to cool down to room temperature. The resulting mixture was diluted with water (500 mL). The resulting mixture was extracted with $CH_2Cl_2$ (3×500 mL). The combined organic layers were washed with brine (2×500 mL), dried over anhydrous $Na_2SO_4$. After filtration, the filtrate was concentrated under reduced pressure. The residue was purified by silica gel column chromatography, eluted with PE/EtOAc (1:4) and DCM/EtOAc (1:4) to afford a crude residue. The residue was purified by Prep-Chiral-HPLC with the following conditions: column, CHIRAL ART Cellulose-SB2×25 cm, 5 um; mobile phase, Phase A: Hex:DCM=5:1, Phase B: EtOH, Gradient, 0 to 30% B in 7 min; flow rate, 25 mL/min, detector, UV 260 nm. This resulted in ethyl (6S)-6-tert-butyl-10-methoxy-2-oxo-6H,7H-pyrido[2,1-a]isoquinoline-3-carboxylate (9.5 g, 30.2% yield) as a white solid.

Step 8: Into a 500 mL 3-necked round-bottom flask were added ethyl (6S)-6-tert-butyl-10-methoxy-2-oxo-6H,7H-pyrido[2,1-a]isoquinoline-3-carboxylate (9.50 g, 26.728 mmol, 1.00 equiv.) and HBr in water (285.00 mL, 40%) at room temperature. The resulting mixture was stirred for 4 h at 100° C. under nitrogen atmosphere. The mixture was allowed to cool down to room temperature. The resulting mixture was concentrated under reduced pressure. This resulted in (6S)-6-tert-butyl-10-hydroxy-2-oxo-6H,7H-pyrido[2,1-a]isoquinoline-3-carboxylic acid (crude, 10 g) as a brown solid.

Step 9: To a stirred solution of (6S)-6-tert-butyl-10-hydroxy-2-oxo-6H,7H-pyrido[2,1-a]isoquinoline-3-carboxylic acid (crude, 10.00 g) and EtOH (200.00 mL) was added $SOCl_2$ (18.98 g, 159.536 mmol, 5.00 equiv.) dropwise at 0° C. under nitrogen atmosphere. The resulting mixture was stirred for 14 h at 80° C. under nitrogen atmosphere. The mixture was allowed to cool down to room temperature. The resulting mixture was concentrated under reduced pressure. The resulting mixture was diluted with EtOH (1 L) and DCM (4 L). The mixture was basified to pH 8 with saturated NaHCO$_3$(aq.). The aqueous layer was extracted with DCM/EtOH (4/1) (500 mL). The combined organic layers were dried over anhydrous Na$_2$SO$_4$. After filtration, the filtrate was concentrated under reduced pressure. The residue was purified by silica gel column chromatography, eluted with DCM/EtOH (2:3) to afford ethyl (6S)-6-tert-butyl-10-hydroxy-2-oxo-6H,7H-pyrido[2,1-a]isoquinoline-3-carboxylate (5.0683 g, 46.52% yield) as a brown solid. $^1$H NMR (400 MHz, DMSO-d6): δ 9.81 (b, 1H), 8.36 (s, 1H), 7.19-7.13 (m, 2H), 6.87 (d, J=5.1 Hz, 1H), 6.65 (s, 1H), 4.32-4.30 (m, 1H), 4.22 (q, J=6.9 Hz, 2H), 3.33-3.13 (m, 2H), 1.27 (t, J=7.2 Hz, 3H), 0.71 (s, 9H). [α]$_D$=−164.20 (C=0.04 g/100 mL in DCM/EtOH(1/3), T=25° C.). ESI MS m/z=342.1 [M+H]$^+$.

Step 10: A vial was charged with ethyl (6S)-6-tert-butyl-10-hydroxy-2-oxo-6H,7H-pyrido[2,1-a]isoquinoline-3-carboxylate (341 mg, 1 mmol), PhNTf2 (356 mg, 1 mmol), and DCM (15 mL). The vial was cooled to 0° C. and then triethylamine (1 mL) was added. The vial was stirred at room temperature overnight, then evaporated to dryness. The residue was purified on silica gel to provide the product, ethyl (S)-6-(tert-butyl)-2-oxo-10-(((trifluoromethyl)sulfonyl)oxy)-6,7-dihydro-2H-pyrido[2,1-a]isoquinoline-3-carboxylate (142 mg, 30% yield). ESI MS m/z=474.1 [M+H]$^+$.

Step 11: An oven-dried vial was charged with ethyl (S)-6-(tert-butyl)-2-oxo-10-(((trifluoromethyl)sulfonyl)oxy)-6,7-dihydro-2H-pyrido[2,1-a]isoquinoline-3-carboxylate (57 mg, 0.12 mmol), 3,3-difluoroazetidine hydrochloride (47 mg, 0.359 mmol), Pd$^t$BuXPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 24 h at 110° C. After cooling to room temperature, the reaction mixture was filtered and concentrated. The crude product was dissolved in DMSO (2 mL) and purified by RPHPLC to provide the product, (S)-6-(tert-butyl)-10-(3,3-difluoroazetidin-1-yl)-2-oxo-6,7-dihydro-2H-pyrido[2,1-a]isoquinoline-3-carboxylic acid as a tan solid (2 mg, 5% yield). ESI MS m/z=389.1 [M+H]$^+$.

Example 155: (2R,5S)-5-(tert-butyl)-12-(3,3-difluoroazetidin-1-yl)-2-(difluoromethyl)-9-oxo-2,3,4,9-tetrahydro-5H-furo[3,2-f]pyrido[2,1-a]isoquinoline-8-carboxylic Acid

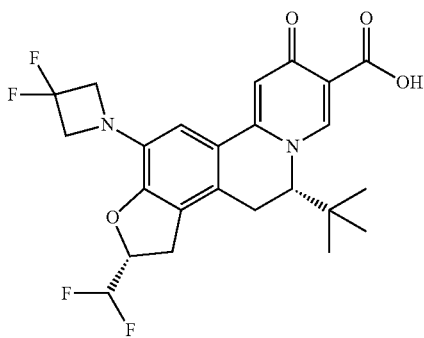 [SMILES: CC(C)(C)[C@@H]1Cc2c(cc(N3CC(F)(F)C3)c3c2C[C@H](C(F)F)O3)-c2cc(=O)c(C(=O)O)cn21]

Step 1: Into a 1000 mL round bottom flask was added 5-bromo-2-chlorophenol (20 g, 97.1 mmol, 1.0 eq), allyl bromide (17.4 g, 145.6 mmol, 1.5 eq), K$_2$CO$_3$ (26.7 g, 194.2 mmol, 2.0 eq) and acetone (500 mL). The mixture was warmed to reflux and stirred for 3 hrs. After completion of reaction indicated by LCMS, the mixture was filtered and rinsed repeatedly with acetone. The combined filtrates were concentrated to afford crude 2-(allyloxy)-4-bromo-1-chlorobenzene (20 g) which was used in next step without further purification.

Step 2: Into a 1000 mL 3-neck round bottom flask was added 2-(allyloxy)-4-bromo-1-chlorobenzene (20 g, 81.3 mmol, 1.0 eq) and hexane (300 mL). The mixture was cooled to 0° C. and Et$_2$AlCl (162 mL, 162.6 mmol, 2.0 eq, 1M solution in hexane) was added dropwise. After complete addition, the mixture was slowly warmed to room temperature and stirred for another 1 hr. After completion of reaction indicated by LCMS, the mixture was quenched with 1N HCl at 0° C. and concentrated. The residue was extracted with EA, the combined organic layers were dried, filtered and concentrated. The resulting residue was purified by silica gel column chromatography to afford 2-allyl-3-bromo-6-chlorophenol (16 g, 67% yield for 2 steps) as a colorless oil.

Step 3: Into a 1000 mL round bottom flask was added 2-allyl-3-bromo-6-chlorophenol (16 g, 65.0 mmol, 1.0 eq) and DCM (320 mL). The mixture was cooled to 0° C. and m-CPBA (19.6 g, 97.5 mmol, 1.5 eq, 85% purity) was added portionwise. The mixture was slowly warmed to room temperature and stirred for overnight. After completion of reaction indicated by TLC, the mixture was quenched by aq. Na$_2$S$_2$O$_3$ solution. The mixture was concentrated and extracted with EA. The combined organic layers were washed sequentially with aq. NaHCO$_3$ solution and brine, then dried, filtered and concentrated. The resulting epoxide, 3-bromo-6-chloro-2-(oxiran-2-ylmethyl)phenol (16 g) was used in next step without further purification.

Step 4: Into a 500 mL round bottom flask was added 3-bromo-6-chloro-2-(oxiran-2-ylmethyl)phenol (16 g, 61.1 mmol, 1 eq) and MeOH (200 mL). K$_2$CO$_3$ (25.3 g, 183.3 mmol, 3.0 eq) was added portionwise at room temperature. The mixture was stirred overnight. After completion of reaction indicated by TLC, the mixture was filtered and the solid cake was rinsed repeatedly with MeOH. The combined filtrates were concentrated to give a residue which was purified by silica gel column chromatography to furnish (4-bromo-7-chloro-2,3-dihydrobenzofuran-2-yl)methanol (12 g, 70% yield for 2 steps) as a white solid.

Step 5: Into a 500 mL round bottom flask was added (4-bromo-7-chloro-2,3-dihydrobenzofuran-2-yl)methanol (12 g, 45.8 mmol, 1.0 eq) and DCM (200 mL). DMP (23.2 g, 54.9 mmol, 1.2 eq) was added portionwise at 0° C. The mixture was slowly warmed to room temperature and stirred for overnight. After completion of reaction indicated by LCMS, the mixture was quenched with aq. NaHCO$_3$ solution and concentrated. The residue was extracted with EA. The combined organic layers were dried, filter and concentrated. The resulting residue was purified by silica gel column chromatography to afford 5.1 g of pure 4-bromo-7-chloro-2,3-dihydrobenzofuran-2-carbaldehyde and an additional 2 g with 80% purity (55% combined yield).

Step 6: Into a 250 mL round bottom flask was added 4-bromo-7-chloro-2,3-dihydrobenzofuran-2-carbaldehyde (5 g, 19.2 mmol, 1.0 eq) and DCM (100 mL). The mixture was cooled to 0° C. and DAST (7.7 g, 48.0 mmol, 2.5 eq) was added dropwise. The mixture was stirred for another 1 hr at 0° C. After completion of reaction indicated by LCMS, the mixture was quenched with H$_2$O carefully and extracted with DCM. The combined organic layers were dried, filtered and concentrated. The resulting crude 4-bromo-7-chloro-2-

(difluoromethyl)-2,3-dihydrobenzofuran (5 g) was used in next step without purification.

Step 7: Into a 100 mL round bottom flask was added 4-bromo-7-chloro-2-(difluoromethyl)-2,3-dihydrobenzofuran (1 g, 3.5 mmol, 1.0 eq), methyl tert-butyl ketone (1.1 g, 10.5 mmol, 3.0 eq), Pd$_2$(dba)$_3$ (91.5 mg, 0.1 mmol, 0.03 eq), Xantphos (115.6 mg, 0.2 mmol, 0.06 eq), t-BuONa (1.0 g, 10.5 mmol, 3.0 eq) and THF (15 mL). The mixture was thoroughly flushed with N$_2$ and stirred for 3 h at 80° C. After completion of reaction indicated by LCMS, the mixture was quenched with aq. NH$_4$Cl solution and extracted with EA. The combined organic layers were dried, filtered and concentrated. The resulting residue was purified by silica gel column chromatography to afford 1-(7-chloro-2-(difluoromethyl)-2,3-dihydrobenzofuran-4-yl)-3,3-dimethylbutan-2-one (0.42 g, 40% yield).

Step 8: Into a 40 mL vial was added 1-(7-chloro-2-(difluoromethyl)-2,3-dihydrobenzofuran-4-yl)-3,3-dimethylbutan-2-one (0.4 g, 1.3 mmol, 1.0 eq), NH$_4$OAc (1.0 g, 13.0 mmol, 10.0 eq) and MeOH (10 mL). NaBH$_3$CN (0.3 g, 5.2 mmol, 4.0 eq) was added portionwise at 0° C. The mixture was warmed to 70° C. and stirred for overnight. After completion of reaction indicated by LCMS, the mixture was concentrated and washed with 1N NaOH solution. The residue was extracted with EA, the combined organic layers were dried, filtered and concentrated. The resulting crude 1-(7-chloro-2-(difluoromethyl)-2,3-dihydrobenzofuran-4-yl)-3,3-dimethylbutan-2-amine (0.4 g) was used in next step without further purification.

Step 9: Into a 20 mL vial was added 1-(7-chloro-2-(difluoromethyl)-2,3-dihydrobenzofuran-4-yl)-3,3-dimethylbutan-2-amine (0.4 g, 1.3 mmol, 1.0 eq), HCOOH (240 mg, 5.2 mmol, 4.0 eq) and dioxane (10 mL). The mixture was warmed to 100° C. and stirred for 3 hrs at this temperature. After completion of reaction indicated by LCMS, the mixture was concentrated. The resulting crude N-(1-(7-chloro-2-(difluoromethyl)-2,3-dihydrobenzofuran-4-yl)-3,3-dimethylbutan-2-yl)formamide (0.41 g) was used in next step without further purification.

Step 10: Into a 20 mL vial was added N-(1-(7-chloro-2-(difluoromethyl)-2,3-dihydrobenzofuran-4-yl)-3,3-dimethylbutan-2-yl)formamide (0.42 g, 1.3 mmol, 1.0 eq) and anhydrous CH$_3$CN (10 mL). POCl$_3$ (0.3 g, 2.0 mmol, 1.5 eq) was added dropwise at 0° C. The mixture was warmed to 70° C. and stirred for 1 hr. After completion of reaction indicated by LCMS, the mixture was cooled, quenched with 30% ammonium hydroxide solution and concentrated. The residue was extracted with EA, the combined organic layers were dried, filtered and concentrated. The resulting crude 8-(tert-butyl)-4-chloro-2-(difluoromethyl)-1,2,8,9-tetrahydrofuro[3,2-f]isoquinoline (0.35 g) was used in next step without further purification.

Step 11: Into a 20 mL vial was added 8-(tert-butyl)-4-chloro-2-(difluoromethyl)-1,2,8,9-tetrahydrofuro[3,2-f]isoquinoline (0.35 g, 1.1 mmol, 1.0 eq), ethyl 2-(ethoxymethylidene)-3-oxobutanoate (0.8 g, 4.4 mmol, 4.0 eq), EtOH (6 mL) and H$_2$O (2 mL). The mixture was warmed to 100° C. and stirred for overnight at this temperature. After completion of reaction indicated by LCMS, the mixture was concentrated and extracted with EA. The combined organic layers were dried, filtered and concentrated. The resulting residue was purified by silica gel column chromatography to afford ethyl 5-(tert-butyl)-12-chloro-2-(difluoromethyl)-9-oxo-2,3,4,9,10,10a-hexahydro-5H-furo[3,2-f]pyrido[2,1-a]isoquinoline-8-carboxylate (0.2 g, 33% yield for 4 steps).

Step 12: Into a 20 mL vial was added ethyl 5-(tert-butyl)-12-chloro-2-(difluoromethyl)-9-oxo-2,3,4,9,10,10a-hexahydro-5H-furo[3,2-f]pyrido[2,1-a]isoquinoline-8-carboxylate (0.2 g, 0.44 mmol, 1.0 eq), p-chloranil (216 mg, 0.88 mmol, 2.0 eq) and DME (5 mL). The mixture was heated to 70° C. and stirred for 60 min at this temperature. After completion of reaction indicated by LCMS, the mixture was cooled and concentrated. The residue was purified by SFC (Column: CHIRAL ART Cellulose-SB, mobile phase: 50% CO$_2$/(2 mM ammonia in EtOH) to provide the product, ethyl (2R,5S)-5-(tert-butyl)-12-chloro-2-(difluoromethyl)-9-oxo-2,3,4,9-tetrahydro-5H-furo[3,2-f]pyrido[2,1-a]isoquinoline-8-carboxylate (67 mg, 34% yield).

Step 13: Into a vial was placed ethyl (2R,5S)-5-(tert-butyl)-12-chloro-2-(difluoromethyl)-9-oxo-2,3,4,9-tetrahydro-5H-furo[3,2-f]pyrido[2,1-a]isoquinoline-8-carboxylate (67 mg, 0.15 mmol), EtOH (5 mL), and 1 M Aq. NaOH (5 mL). The resulting solution was stirred for 5 h at room temperature. Most of the EtOH was removed under vacuum. The resulting solution was diluted with 5 mL of water. The pH value of the solution was adjusted to 3 with 1 M aq. HCl. The solids were collected by filtration to provide the product, (2R,5S)-5-(tert-butyl)-12-chloro-2-(difluoromethyl)-9-oxo-2,3,4,9-tetrahydro-5H-furo[3,2-f]pyrido[2,1-a]isoquinoline-8-carboxylic acid as a off-white solid (59 mg, 93% yield). ESI MS m/z=424.1 [M+H]$^+$.

Step 14: An oven-dried vial was charged with (2R,5S)-5-(tert-butyl)-12-chloro-2-(difluoromethyl)-9-oxo-2,3,4,9-tetrahydro-5H-furo[3,2-f]pyrido[2,1-a]isoquinoline-8-carboxylic acid (51 mg, 0.12 mmol), 3,3-difluoroazetidine hydrochloride (47 mg, 0.359 mmol), Pd$^t$BuXPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 15 h at 110° C. After cooling to room temperature, the reaction mixture was filtered and concentrated. The crude product was dissolved in DMSO (2 mL) and purified by RPHPLC to provide the product, (2R,5S)-5-(tert-butyl)-12-(3,3-difluoroazetidin-1-yl)-2-(difluoromethyl)-9-oxo-2,3,4,9-tetrahydro-5H-furo[3,2-f]pyrido[2,1-a]isoquinoline-8-carboxylic acid as a tan solid (23 mg, 40% yield). ESI MS m/z=481.1 [M+H]$^+$.

Example 156: (2R,5S)-5-(tert-butyl)-2-(difluoromethyl)-12-(furan-3-yl)-9-oxo-2,3,4,9-tetrahydro-5H-furo[3,2-f]pyrido[2,1-a]isoquinoline-8-carboxylic Acid

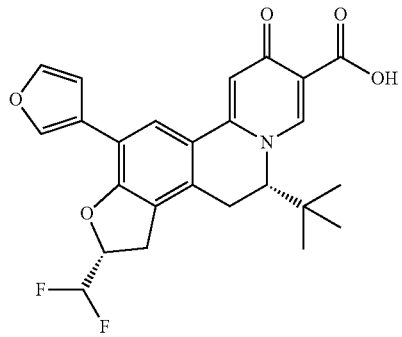 [SMILES: CC(C)(C)[C@@H]1Cc2c(cc(-c3ccoc3)c3c2C[C@H](C(F)F)O3)-c2cc(=O)c(C(=O)O)cn21]

Step 1: An oven-dried vial was charged with (2R,5S)-5-(tert-butyl)-12-chloro-2-(difluoromethyl)-9-oxo-2,3,4,9-tetrahydro-5H-furo[3,2-f]pyrido[2,1-a]isoquinoline-8-carboxylic acid (42 mg, 0.1 mmol), 3-furylboronic acid (56 mg, 0.5 mmol), Pd$^t$BuXPhos G3 (8 mg, 0.01 mmol), and Cs$_2$CO$_3$ (326 mg, 1 mmol). The vial was purged with nitrogen gas for 5 minutes, then DMF:water (8:1) (10 mL) was added via syringe. The reaction mixture was heated under a nitrogen atmosphere for 8 h at 110° C. After cooling to room temperature, the reaction mixture was filtered and concentrated. The crude product was purified by RPHPLC to provide the product, (2R,5S)-5-(tert-butyl)-2-(difluoromethyl)-12-(furan-3-yl)-9-oxo-2,3,4,9-tetrahydro-5H-furo[3,2-f]pyrido[2,1-a]isoquinoline-8-carboxylic acid (25 mg, 56% yield). ESI MS m/z=456.1 [M+H]$^+$.

Example 157: (2S,5S)-5-(tert-butyl)-12-(3,3-difluoroazetidin-1-yl)-2-methyl-9-oxo-2,3,4,9-tetrahydro-5H-furo[3,2-f]pyrido[2,1-a]isoquinoline-8-carboxylic Acid

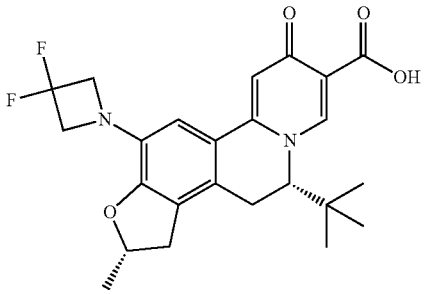 [SMILES: C[C@H]1Cc2c3c(cc(N4CC(F)(F)C4)c2O1)-c1cc(=O)c(C(=O)O)cn1[C@H](C(C)(C)C)C3]

Step 1: An oven-dried vial was charged with (2S,5S)-5-(tert-butyl)-12-chloro-2-methyl-9-oxo-2,3,4,9-tetrahydro-5H-furo[3,2-f]pyrido[2,1-a]isoquinoline-8-carboxylic acid (46 mg, 0.12 mmol), 3,3-difluoroazetidine hydrochloride (47 mg, 0.359 mmol), Pd$^t$BuXPhos G3 (7 mg, 0.008 mmol), and NaOtBu (57 mg, 0.598 mmol). The vial was purged with nitrogen gas for 5 minutes, then toluene (10 mL) was added via syringe. The reaction mixture was heated under a nitrogen atmosphere for 15 h at 110° C. After cooling to room temperature, the reaction mixture was filtered and concentrated. The crude product was dissolved in DMSO (2 mL) and purified by RPHPLC to provide the product, (2S,5S)-5-(tert-butyl)-12-(3,3-difluoroazetidin-1-yl)-2-methyl-9-oxo-2,3,4,9-tetrahydro-5H-furo[3,2-f]pyrido[2,1-a]isoquinoline-8-carboxylic acid as a tan solid (12 mg, 22% yield). ESI MS m/z=445.1 [M+H]$^+$.

Biological Activity

Methods:

2.2.15 cells are passaged upon attaining confluency in DMEM/F12 media in the presence of 10% FBS, Penn/Strep, and 250 ug/mL G418. Novel compounds are 5 fold serially diluted in DMSO and added to 96 well plates containing 35,000 cells/well at a 1:200 dilution so that the final concentration of DMSO is 0.5%. On day 5, post treatment cell lysates and supernatants are harvested for analysis.

Cells are lysed using Agilent Sidestep Lysis buffer, diluted 1:100 and quantified via quantitative real time PCR. Commercially available ELISA kits are used to quantitate the viral proteins HBsAg (Alpco) or HBeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 µM; B 0.1-1 µM; C>1 µM.

Additionally, compound induced cellular toxicity is evaluated by exposing HepG2 cells seeded at 5,000 cells/well to serially diluted compound with a final DMSO concentration of 0.5% for three days. At day 3, post seeding cells are treated with ATPlite 1 Step according to the manufacturer's instructions. Compound concentrations that reduce total ATP levels in wells by 50% relative to no drug controls ($CC_{50}$) are reported; $CC_{50}$ ranges are as follows: A>25 µM; B 10-25 µM; C<10 µM.

TABLE 2

| | Summary of Activities | | | | |
|---|---|---|---|---|---|
| Example Number | 2.2.15 cells $EC_{50}$ (µM) | HepG2 cells $CC_{50}$ (µM) | Example Number | 2.2.15 cells $EC_{50}$ (µM) | HepG2 cells $CC_{50}$ (µM) |
| 1 | A | A | 2 | A | A |
| 3 | A | C | 4 | A | A |
| 5 | A | A | 6 | A | A |
| 7 | A | A | 8 | A | B |
| 9 | A | A | 10 | A | A |
| 11 | A | A | 12 | A | A |
| 13 | A | B | 14 | A | B |
| 15 | A | B | 16 | A | B |
| 17 | A | B | 18 | A | A |
| 19 | B | A | 20 | B | A |
| 21 | B | A | 22 | B | A |
| 23 | B | A | 24 | B | A |
| 25 | B | A | 26 | B | A |
| 27 | B | A | 28 | B | A |
| 29 | B | A | 30 | A | A |
| 31 | A | | 32 | A | |
| 33 | A | | 34 | A | |
| 35 | A | | 36 | A | |
| 37 | C | | 38 | C | |
| 39 | C | | 40 | C | |
| 41 | A | | 42 | A | |
| 43 | A | | 44 | A | |
| 45 | A | | 46 | A | A |
| 47 | C | | 48 | A | |
| 49 | A | | 50 | A | |
| 51 | A | | 52 | A | |
| 53 | A | | 54 | B | |
| 55 | A | | 56 | A | |
| 57 | C | | 58 | C | |
| 59 | A | B | 60 | A | B |
| 61 | A | A | 62 | A | C |
| 63 | A | B | 64 | A | C |
| 65 | A | C | 66 | A | C |
| 67 | A | C | 68 | A | |
| 69 | A | | 70 | A | |
| 71 | A | C | 72 | A | |
| 73 | A | | 74 | A | |
| 75 | A | | 76 | A | |
| 77 | A | C | 78 | A | |
| 79 | A | C | 80 | C | |
| 81 | C | | 82 | A | |
| 83 | A | | 84 | C | |
| 85 | A | | 86 | A | C |
| 87 | A | | 88 | A | |
| 89 | A | | 90 | A | |
| 91 | A | | 92 | A | |
| 93 | A | | 94 | C | |
| 95 | C | | 96 | A | |
| 97 | A | | 98 | C | |
| 99 | A | | 100 | A | C |
| 101 | A | | 102 | A | |
| 103 | A | | 104 | A | |
| 105 | A | | 106 | A | |
| 107 | A | | 108 | A | |
| 109 | C | | 110 | A | |
| 111 | A | | 112 | C | |
| 113 | C | | 114 | C | |
| 115 | C | | 116 | A | |
| 117 | A | | 118 | A | |
| 119 | C | | 120 | C | |
| 121 | A | | 122 | C | |
| 123 | A | | 124 | A | |
| 125 | A | | 126 | A | |

TABLE 2-continued

Summary of Activities

| Example Number | 2.2.15 cells EC$_{50}$ (µM) | HepG2 cells CC$_{50}$ (µM) | Example Number | 2.2.15 cells EC$_{50}$ (µM) | HepG2 cells CC$_{50}$ (µM) |
| --- | --- | --- | --- | --- | --- |
| 127 | A | | 128 | A | |
| 129 | A | | 130 | A | |
| 131 | A | | 132 | A | C |
| 133 | B | | 134 | A | |
| 135 | A | | 136 | A | |
| 137 | C | | 138 | A | |
| 139 | A | | 140 | A | |
| 141 | A | | 142 | A | |
| 143 | A | | 144 | C | |
| 145 | C | | 146 | C | |
| 147 | C | | 148 | C | |
| 149 | C | | 150 | C | |
| 151 | C | | 152 | C | |
| 153 | A | | 154 | C | |
| 155 | C | | | | |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (Va) or Formula (Vb):

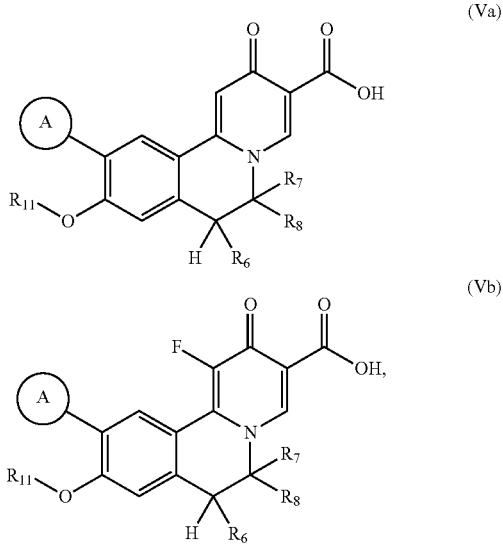

or a pharmaceutically acceptable salt thereof, wherein:
A is optionally substituted 3- to 12-membered heterocyclic;
$R_{11}$ at each occurrence is independently selected from hydrogen, optionally substituted $C_1$-$C_6$ alkyl, optionally substituted $C_3$-$C_6$ cycloalkyl, and optionally substituted 3- to 7-membered heterocyclic;
$R_6$ is hydrogen;
$R_7$ is hydrogen; and
$R_8$ is hydrogen, halo, optionally substituted $C_1$-$C_6$ alkyl, or optionally substituted $C_1$-$C_6$ alkoxy;
Alternatively, $R_8$ is taken together with $R_6$ and the carbon atoms to which they are attached to form a $C_3$-$C_7$ cycloalkyl ring, or a 3- to 7-membered heterocyclic ring; wherein the cycloalkyl or heterocyclic ring is optionally substituted with up to three groups independently selected from R, —OR, —N(R)$_2$, halo, CN, COOR, CON(R)$_2$, and oxo.

2. The compound of claim 1, wherein $R_{11}$ is selected from —CH$_2$R$_{21}$, —CH$_2$CH$_2$R$_{21}$, —CH$_2$CH$_2$CH$_2$R$_{21}$, and —CH$_2$CH$_2$CH$_2$CH$_2$R$_{21}$; and $R_{21}$ is selected from —OH, —OMe, —OEt, phenyl,

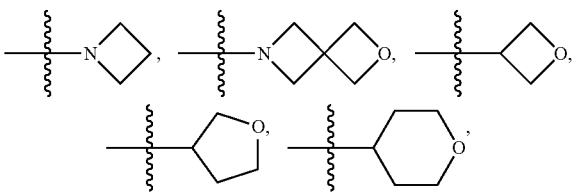

OC(O)R, —C(O)OR, —C(O)NRR, —OC(O)OR, —OC(O)NRR, —NRR, —NRC(O)R, —NRC(O)OR, —NRC(O)—NRR, —S(O)R, —OS(O)$_2$R, —S(O)$_2$OR, —S(O)$_2$R, —S(O)$_2$NRR; —NRS(O)$_2$NRR; —OP(O)(OR)$_2$, —P(O)(OR)$_2$, —NRP(O)(OR)$_2$, and —P(O)(NRR)$_2$.

3. The compound of claim 1, wherein A is selected from the following by removal of one hydrogen atom:

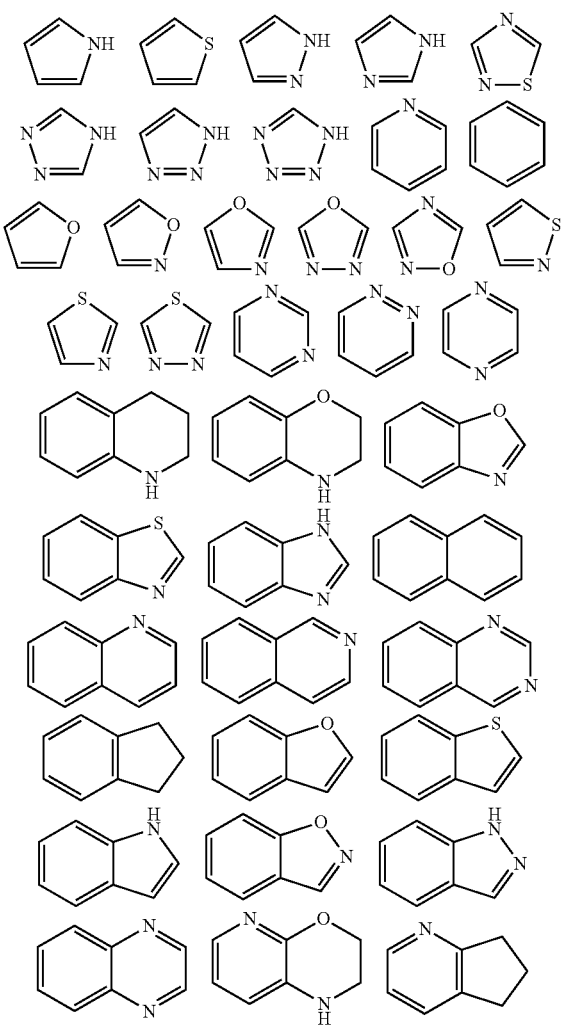

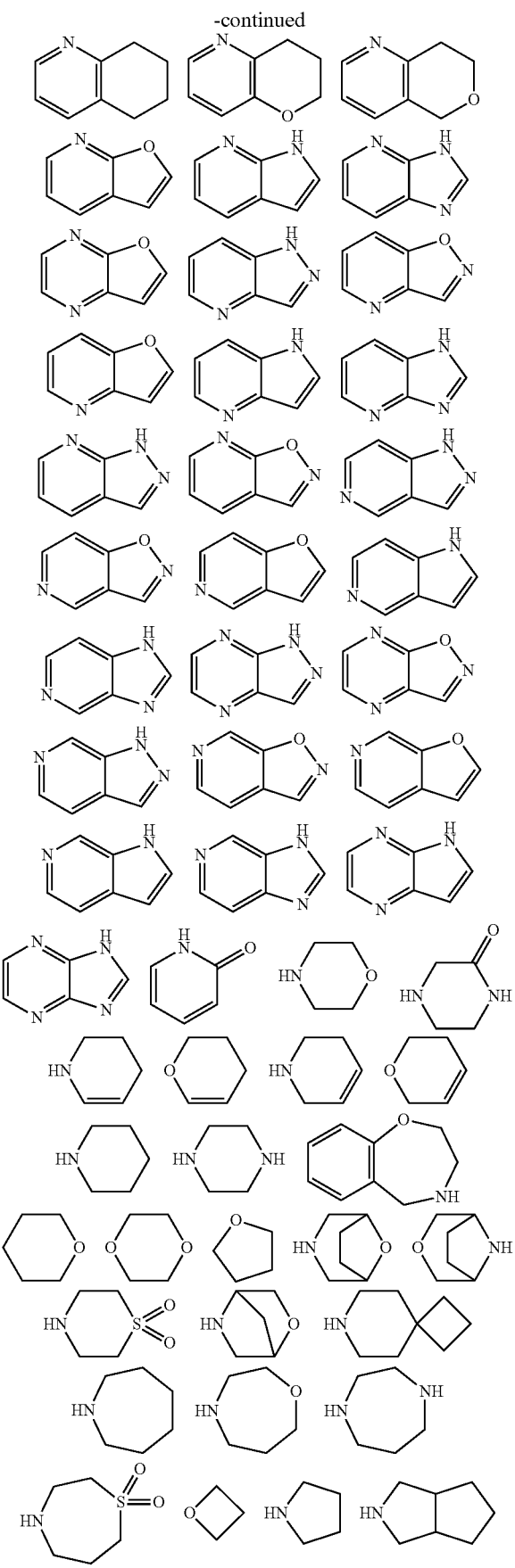

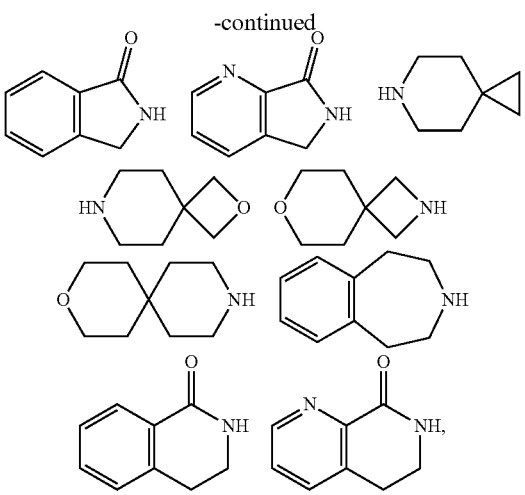

wherein each of these groups is optionally substituted with one to four groups independently selected from halo, CN, —OR, —N(R)$_2$, optionally substituted $C_1$-$C_6$ alkyl, and optionally substituted 3- to 7-membered heterocyclic.

4. A compound represented by Formula (Va) or Formula (Vb):

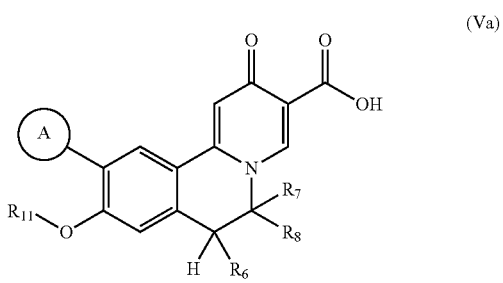

(Va)

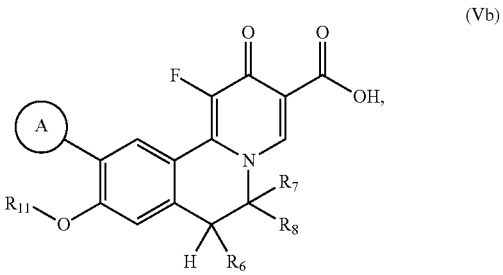

(Vb)

or a pharmaceutically acceptable salt thereof, wherein:
  A is optionally substituted 3- to 12- membered heterocyclic, optionally substituted aryl, or optionally substituted heteroaryl;
  $R_{11}$ at each occurrence is independently selected from hydrogen, optionally substituted $C_1$-$C_6$ alkyl, optionally substituted $C_3$-$C_6$ cycloalkyl, and optionally substituted 3- to 7- membered heterocyclic;
  $R_8$ is taken together with $R_6$ and the carbon atoms to which they are attached to form a $C_3$-$C_7$ cycloalkyl ring, or a 3- to 7- membered heterocyclic ring; wherein the cycloalkyl or heterocyclic ring is optionally substituted with up to three groups independently selected from R, -OR, -N(R)$_2$, halo, CN, COOR, CON(R)$_2$, and oxo; and $R_7$ is hydrogen; or
  $R_8$ is taken together with $R_7$ and the carbon atom to which they are attached to form a $C_3$-$C_7$ cycloalkyl ring, or a 3- to 7-membered heterocyclic ring; wherein the cycloalkyl, or heterocyclic ring is optionally substituted with up to three groups independently selected from R, —OR, —N(R)₂, halo, CN, COOR, CON(R)₂, and oxo; and R₆ is hydrogen; and R is selected from hydrogen and optionally substituted $C_1$-$C_6$ alkyl.

5. The compound of claim 1, represented by Formula (VIIa), (VIIb), (VIIc), or (VIId), or a pharmaceutically acceptable salt thereof,

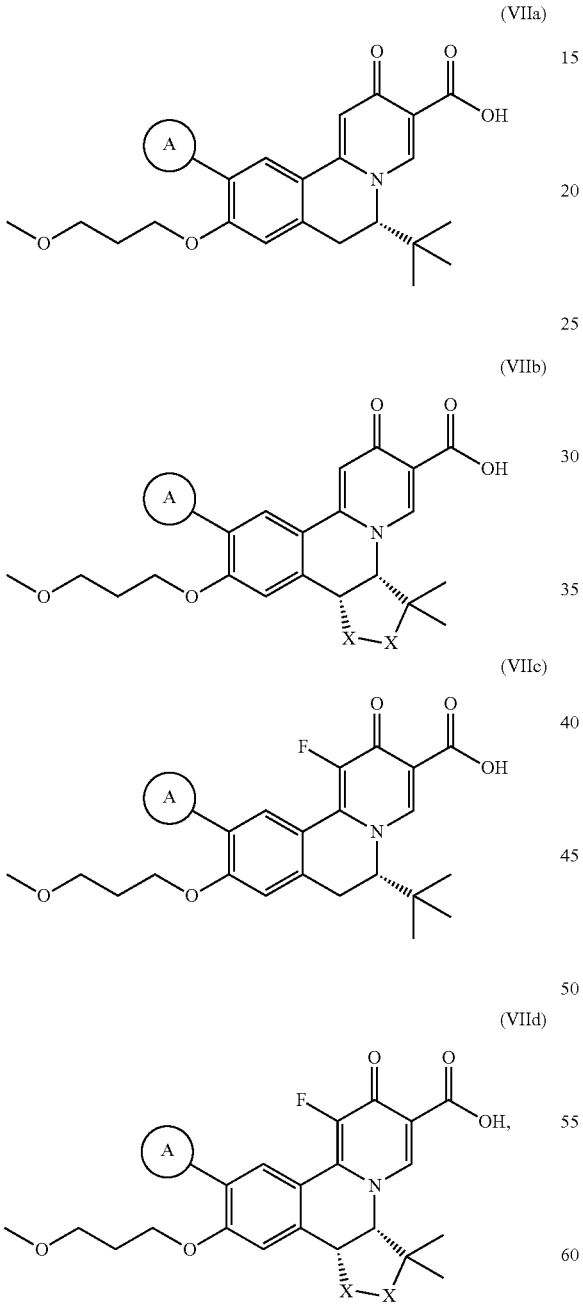

wherein one X is O or $CH_2$, and the other X is $CH_2$; and A is as defined in claim 1.

6. A compound of claim 1, represented by Formula (VIIIa) or (VIIIb), or a pharmaceutically acceptable salt thereof:

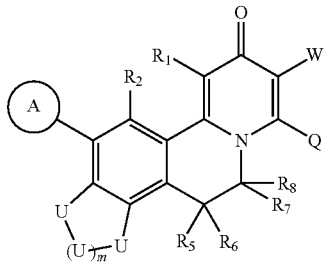

(VIIIa)

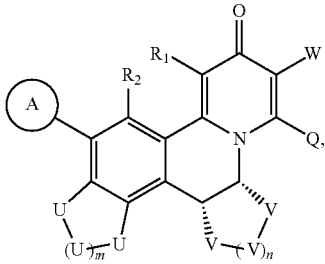

(VIIIb)

wherein A is optionally substituted 3- to 12-membered heterocyclic, optionally substituted aryl, or optionally substituted heteroaryl; $R_1$ is hydrogen, halo, or optionally substituted $C_1$-$C_6$ alkyl; $R_2$ is hydrogen, halo, CN, optionally substituted $C_1$-$C_6$ alkyl, or optionally substituted $C_1$-$C_6$ alkoxy; $R_5$, $R_6$ and $R_7$ are hydrogen; $R_8$ is hydrogen, halo, optionally substituted $C_1$-$C_6$ alkyl, or optionally substituted $C_1$-$C_6$ alkoxy; W is —C(O)OH; Q is hydrogen; one V is —O—, —C(O)—, —S—, —S(O)₂—, —NR₂₂— or —C(R₂₂)₂—, and the another Vs are independently —O—, —NR₂₂— or —C(R₂₂)₂—; one U is —O—, —C(O)—, —S—, —S(O)₂—, —NR₂₂— or —C(R₂₂)₂—, and the other Us are independently —O—, —NR₂₂— or —C(R₂₂)₂—; each R₂₂ is independently hydrogen, optionally substituted —$C_1$-$C_6$ alkyl, optionally substituted —$C_2$-$C_6$ alkenyl, optionally substituted —$C_2$-$C_6$ alkynyl, optionally substituted $C_1$-$C_6$ alkoxy; optionally substituted —$C_3$-$C_7$ cycloalkyl, optionally substituted 3- to 7-membered heterocyclic, optionally substituted aryl or optionally substituted heteroaryl; n is 0, 1, 2 or 3; and m is 0, 1, 2 or 3.

7. The compound of claim 1, represented by Formula (IXa), (IXb), (IXc), or (IXd), or a pharmaceutically acceptable salt thereof:

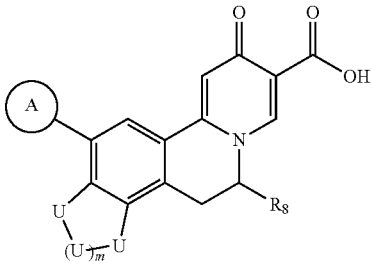

(IXa)

187
-continued

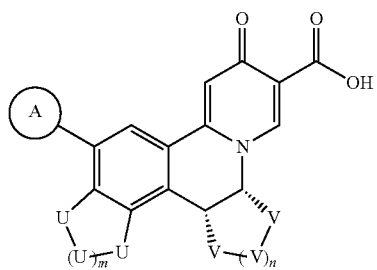
(IXb)

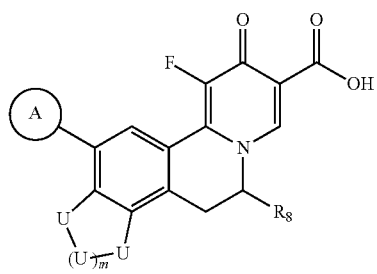
(IXc)

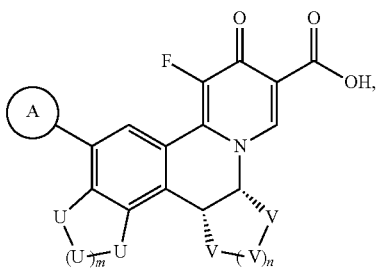
(IXd)

wherein one V is —O—, —C(O)—, —S—, —S(O)₂—, —NR₂₂— or —C(R₂₂)₂—, and the another Vs are independently —O—, —NR₂₂— or —C(R₂₂)₂—; one U is —O—, —C(O)—, —S—, —S(O)₂—, —NR₂₂— or —C(R₂₂)₂—, and the other Us are independently —O—, —NR₂₂— or —C(R₂₂)₂—; each R₂₂ is independently hydrogen, optionally substituted —C₁-C₆ alkyl, optionally substituted —C₂-C₆ alkenyl, optionally substituted —C₂-C₆ alkynyl, optionally substituted C₁-C₆ alkoxy; optionally substituted —C₃-C₇ cycloalkyl, optionally substituted 3- to 7-membered heterocyclic, optionally substituted aryl or optionally substituted heteroaryl; n is 0, 1, 2 or 3; m is 0, 1, 2 or 3; and A and R₈ are as defined in claim 1.

8. The compound of claim 1, wherein A is selected from the groups set forth in Table 1:

188
-continued

| Entry | A |
|---|---|
| 3 | 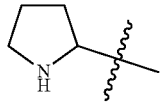 |
| 4 | 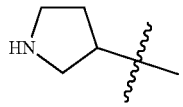 [SMILES: *C1CCNC1] |
| 5 | 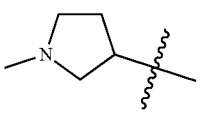 [SMILES: *C1CCN(C)C1] |
| 6 | 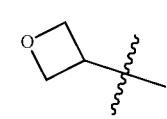 [SMILES: *C1COC1] |
| 7 | 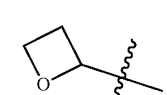 |
| 8 | 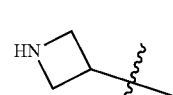 |
| 9 |  |
| 10 |  |
| 11 |  |
| 12 | 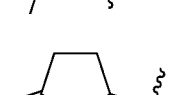 |
| 13 | 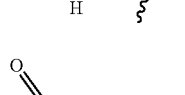 |
| 14 | 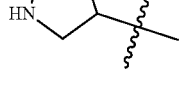 |

| Entry | A |
|---|---|
| 1 | (tetrahydrofuran-2-yl) |
| 2 | (tetrahydrofuran-3-yl) |

-continued

| Entry | A |
|---|---|
| 15 | tetrahydropyran-3-yl |
| 16 | tetrahydropyran-4-yl |
| 17 | piperidin-2-yl (NH) |
| 18 | piperidin-3-yl (NH) |
| 19 | piperidin-4-yl (NH) |
| 20 | piperidin-1-yl |
| 21 | pyrrolidin-1-yl |
| 22 | azetidin-1-yl |
| 23 | 3-fluoropyrrolidin-1-yl |
| 24 | 3-fluoroazetidin-1-yl |
| 25 | furan-2-yl |
| 26 | furan-3-yl |

-continued

| Entry | A |
|---|---|
| 27 | isoxazol-5-yl |
| 28 | isoxazol-4-yl |
| 29 | isoxazol-3-yl |
| 30 | 1,2,5-oxadiazol-3-yl |
| 31 | 1,3,4-oxadiazol-3-yl |
| 32 | oxazol-5-yl |
| 33 | oxazol-2-yl |
| 34 | 1,3,4-oxadiazol-2-yl |
| 35 | thiophen-2-yl |
| 36 | isothiazol-4-yl |
| 37 | isothiazol-5-yl |
| 38 | isothiazol-4-yl |
| 39 | isothiazol-3-yl |

US 11,058,678 B2
| 191 -continued | | | 192 -continued | |
|---|---|---|---|---|
| Entry | A | | Entry | A |
| 40 | 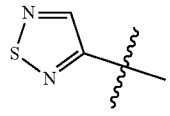 [SMILES: *c1cnsn1] | | 52 | 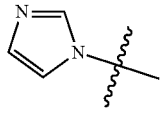 |
| 41 | 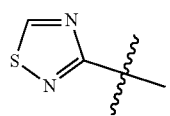 | | 53 | 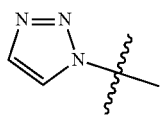 |
| 42 | 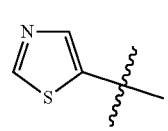 | | 54 | 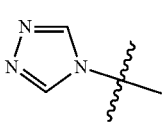 [SMILES: *n1cnnc1] |
| 43 | 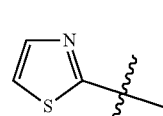 | | 55 | 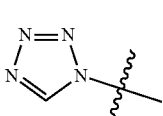 |
| 44 | 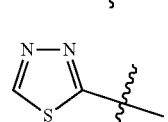 | | 56 | 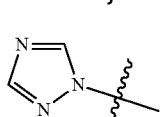 |
| 45 | 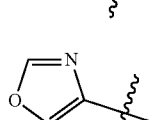 | | 57 | 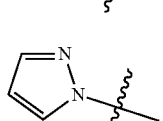 |
| 46 | 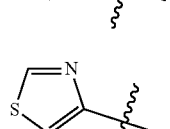 | | 58 | 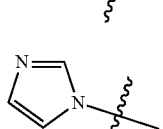 |
| 47 | 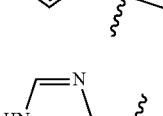 | | 59 |  |
| 48 |  | | 60 | 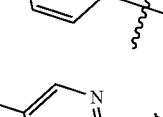 |
| 49 | 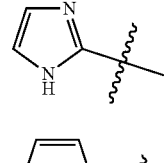 | | 61 | 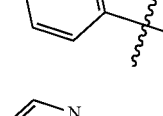 |
| 50 | 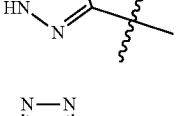 | | 62 | 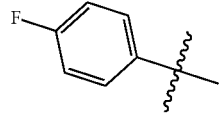 |
| 51 | 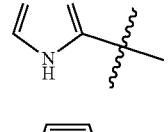 | | 63 | 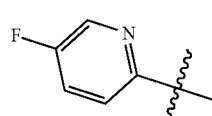 |

| Entry | A |
|---|---|
| 64 | 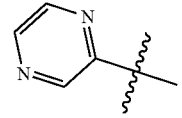 [SMILES: *c1cnccn1] |
| 65 | 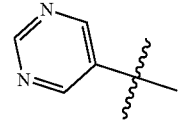 [SMILES: *c1cncnc1] |
| 66 | 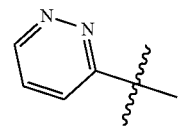 [SMILES: *c1cccnn1] |
| 67 | 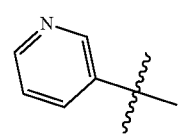 [SMILES: *c1cccnc1] |
| 68 | 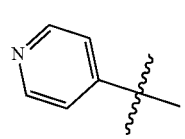 [SMILES: *c1ccncc1] |
| 69 | 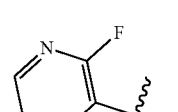 |
| 70 | 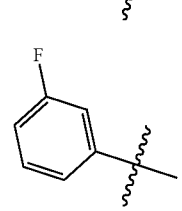 |
| 71 | 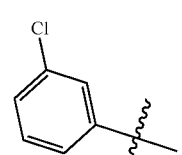 |
| 72 | 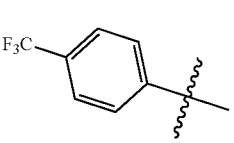 [SMILES: *c1ccc(C(F)(F)F)cc1] |
| 73 | 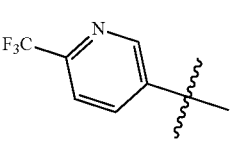 [SMILES: *c1ccc(C(F)(F)F)nc1] |
| 74 | 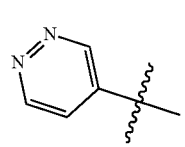 |
| 75 | 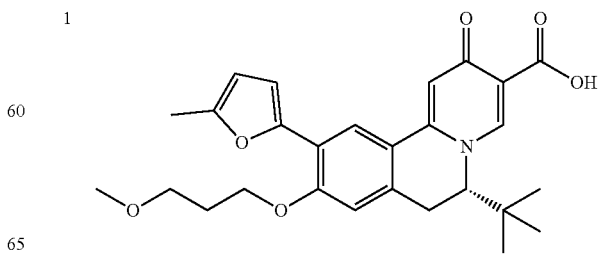 |
| 76 | |
| 77 | |
| 78 | |
| 79 | |
| 80 | |
9. The compound of claim 1, selected from the compounds set forth below, or a pharmaceutically acceptable salt thereof:
| Compound | Structure |
|---|---|
| 1 | 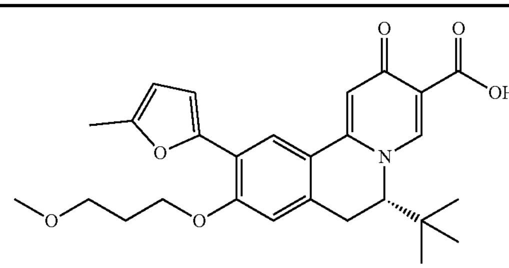 |

| Compound | Structure |
|---|---|
| 2 | 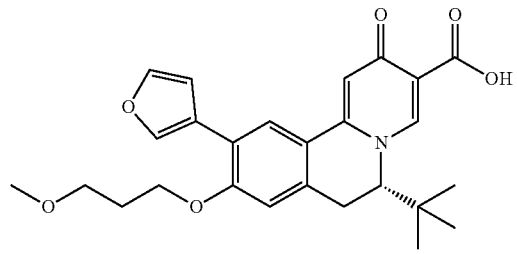 |
| 3 | 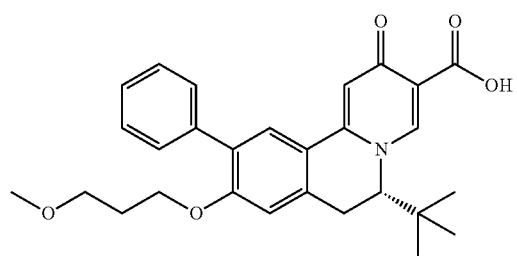 [SMILES: COCCCOc1cc2c(cc1-c1ccccc1)-c1cc(=O)c(C(=O)O)cn1[C@H](C(C)(C)C)C2] |
| 4 | 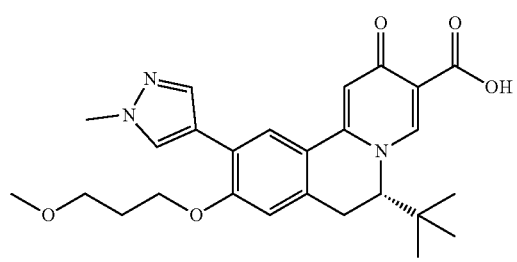 [SMILES: COCCCOc1cc2c(cc1-c1cnn(C)c1)-c1cc(=O)c(C(=O)O)cn1[C@H](C(C)(C)C)C2] |
| 5 | 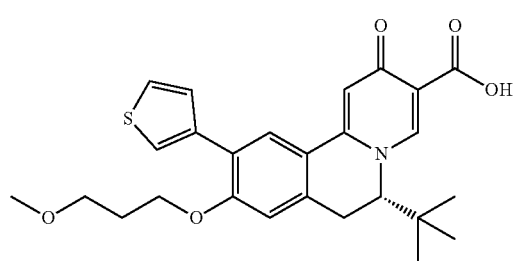 |
| 6 | 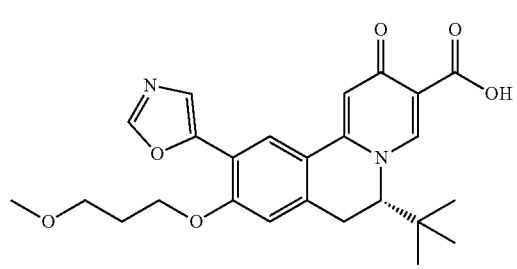 [SMILES: COCCCOc1cc2c(cc1-c1cnco1)-c1cc(=O)c(C(=O)O)cn1[C@H](C(C)(C)C)C2] |
| 7 | 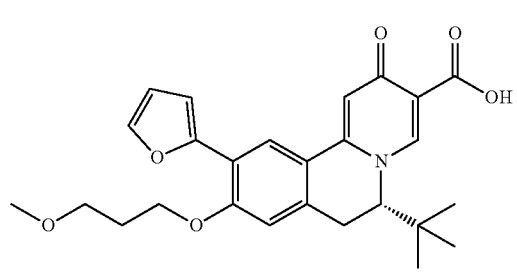 [SMILES: COCCCOc1cc2c(cc1-c1ccco1)-c1cc(=O)c(C(=O)O)cn1[C@H](C(C)(C)C)C2] |
| 8 | 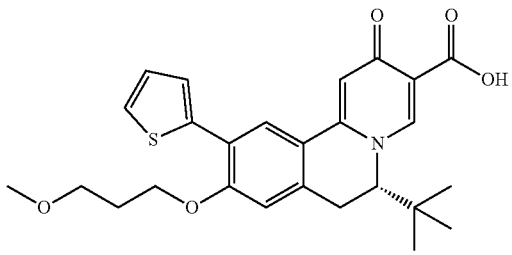 |
| 9 | 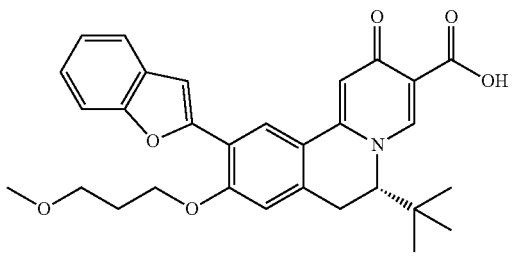 |
| 10 | 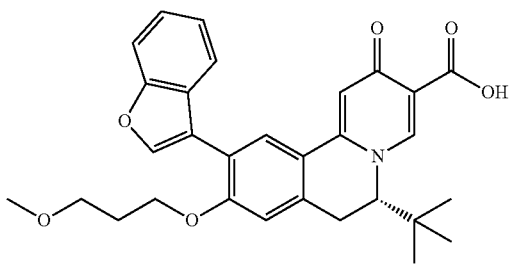 |
| 11 | 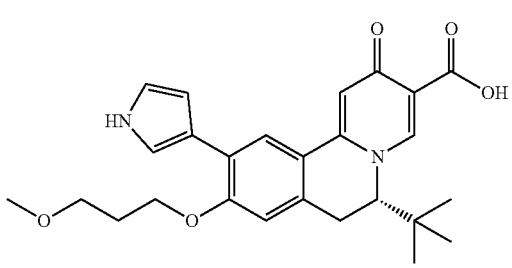 |
| 12 | 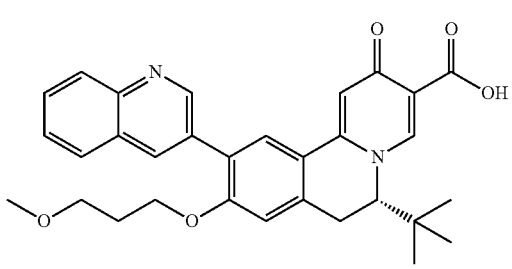 [SMILES: COCCCOc1cc2c(cc1-c1cnc3ccccc3c1)-c1cc(=O)c(C(=O)O)cn1[C@H](C(C)(C)C)C2] |
| 13 | 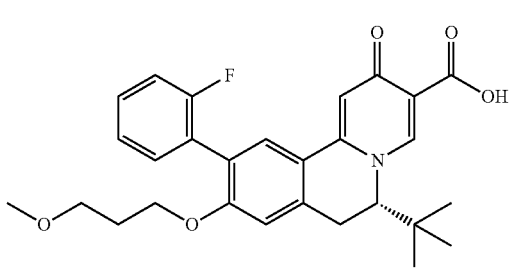 [SMILES: COCCCOc1cc2c(cc1-c1ccccc1F)-c1cc(=O)c(C(=O)O)cn1[C@H](C(C)(C)C)C2] |

| Compound | Structure |
|---|---|
| 14 | 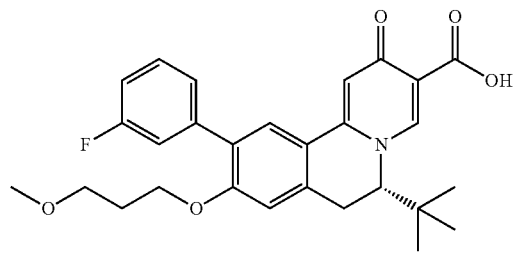 [SMILES: COCCCOc1cc2c(cc1-c1cccc(F)c1)-c1cc(=O)c(C(=O)O)cn1[C@H](C(C)(C)C)C2] |
| 15 | 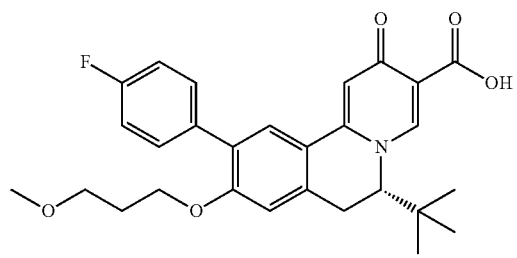 [SMILES: COCCCOc1cc2c(cc1-c1ccc(F)cc1)-c1cc(=O)c(C(=O)O)cn1[C@H](C(C)(C)C)C2] |
| 16 | 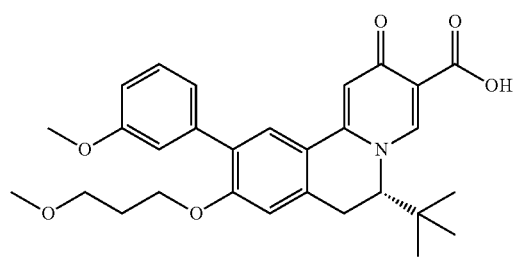 [SMILES: COCCCOc1cc2c(cc1-c1cccc(OC)c1)-c1cc(=O)c(C(=O)O)cn1[C@H](C(C)(C)C)C2] |
| 17 | 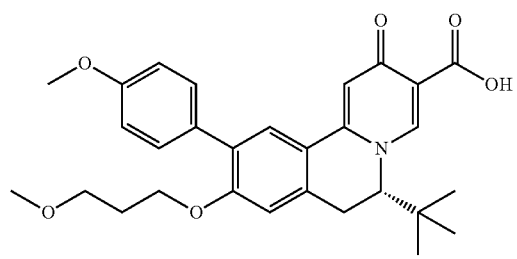 [SMILES: COCCCOc1cc2c(cc1-c1ccc(OC)cc1)-c1cc(=O)c(C(=O)O)cn1[C@H](C(C)(C)C)C2] |
| 18 | 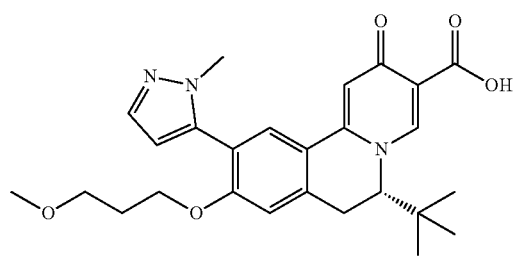 [SMILES: COCCCOc1cc2c(cc1-c1ccnn1C)-c1cc(=O)c(C(=O)O)cn1[C@H](C(C)(C)C)C2] |
| 19 | 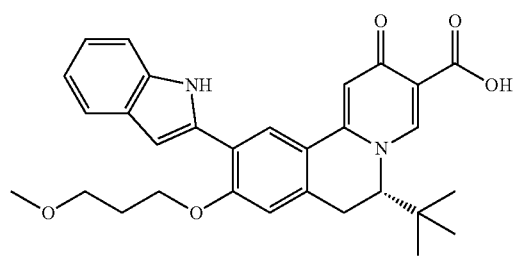 [SMILES: COCCCOc1cc2c(cc1-c1cc3ccccc3[nH]1)-c1cc(=O)c(C(=O)O)cn1[C@H](C(C)(C)C)C2] |
| Compound | Structure |
|---|---|
| 20 | 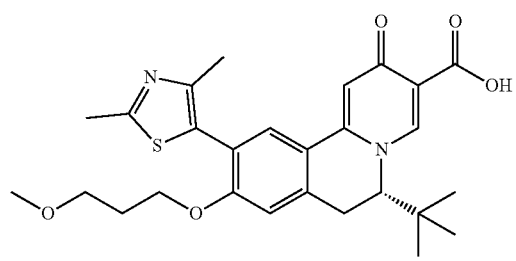 [SMILES: COCCCOc1cc2c(cc1-c1sc(C)nc1C)-c1cc(=O)c(C(=O)O)cn1[C@H](C(C)(C)C)C2] |
| 21 | 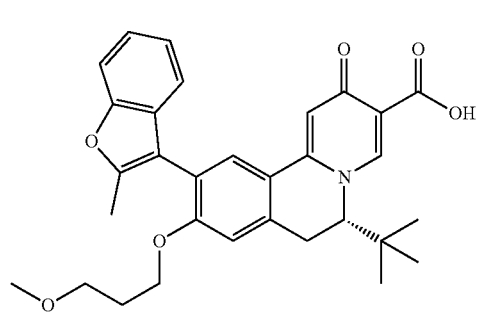 [SMILES: COCCCOc1cc2c(cc1-c1c(C)oc3ccccc13)-c1cc(=O)c(C(=O)O)cn1[C@H](C(C)(C)C)C2] |
| 22 | 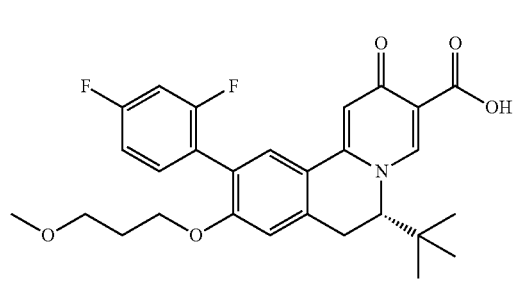 |
| 23 | 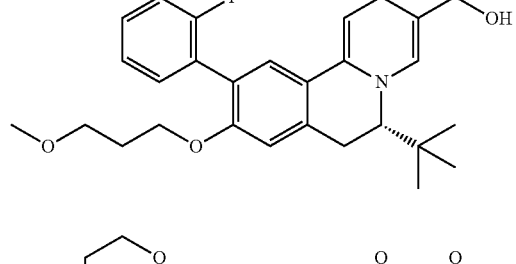 |
| 24 | 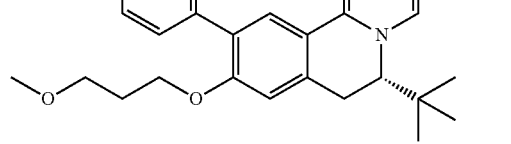 |

| Compound | Structure |
|---|---|
| 25 | 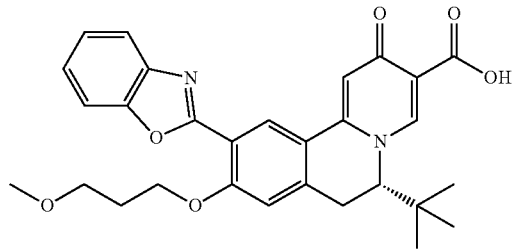 [SMILES: COCCCOc1cc2c(cc1-c1nc3ccccc3o1)-c1cc(=O)c(C(=O)O)cn1[C@H](C(C)(C)C)C2] |
| 26 | 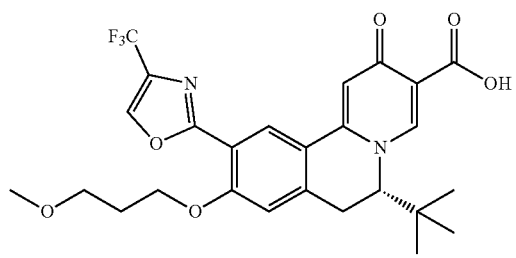 [SMILES: COCCCOc1cc2c(cc1-c1nc(C(F)(F)F)co1)-c1cc(=O)c(C(=O)O)cn1[C@H](C(C)(C)C)C2] |
| 27 | 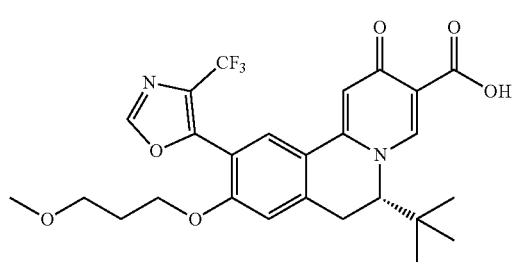 [SMILES: COCCCOc1cc2c(cc1-c1ocnc1C(F)(F)F)-c1cc(=O)c(C(=O)O)cn1[C@H](C(C)(C)C)C2] |
| 28 | 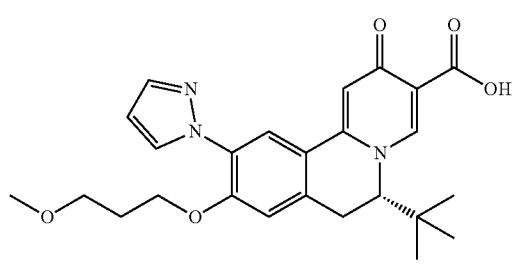 [SMILES: COCCCOc1cc2c(cc1-n1cccn1)-c1cc(=O)c(C(=O)O)cn1[C@H](C(C)(C)C)C2] |
| 29 | 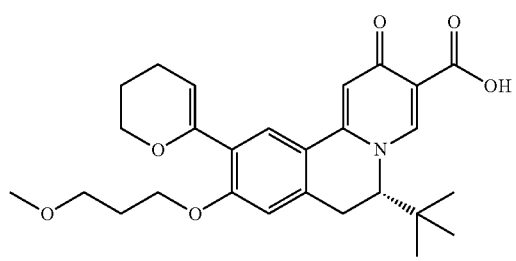 [SMILES: COCCCOc1cc2c(cc1C1=CCCCO1)-c1cc(=O)c(C(=O)O)cn1[C@H](C(C)(C)C)C2] |
| 30 | 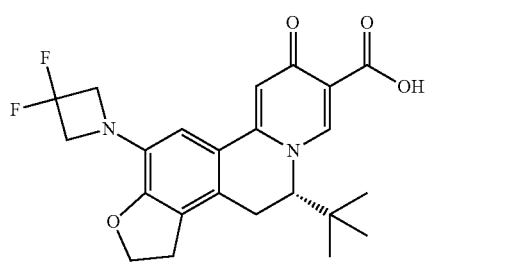 [SMILES: CC(C)(C)[C@@H]1Cc2c(cc(N3CC(F)(F)C3)c3c2CCO3)-c2cc(=O)c(C(=O)O)cn21] |
| Compound | Structure |
|---|---|
| 31 | 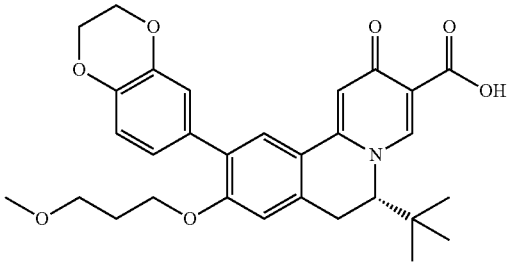 [SMILES: COCCCOc1cc2c(cc1-c1ccc3c(c1)OCCO3)-c1cc(=O)c(C(=O)O)cn1[C@H](C(C)(C)C)C2] |
| 32 | 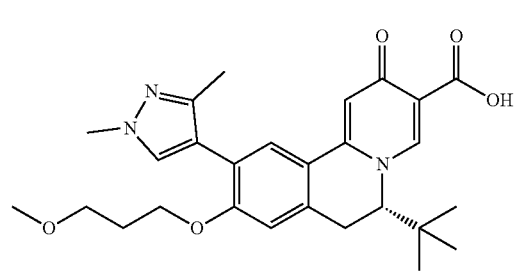 [SMILES: COCCCOc1cc2c(cc1-c1cn(C)nc1C)-c1cc(=O)c(C(=O)O)cn1[C@H](C(C)(C)C)C2] |
| 33 | 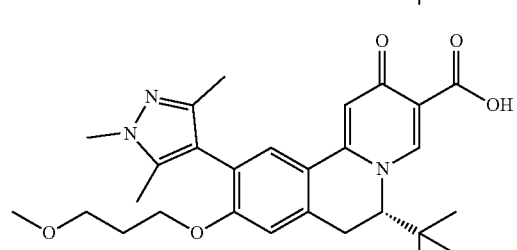 |
| 34 | 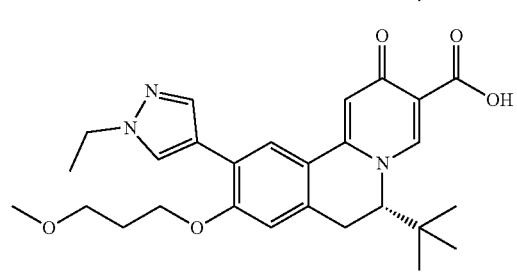 |
| 35 | 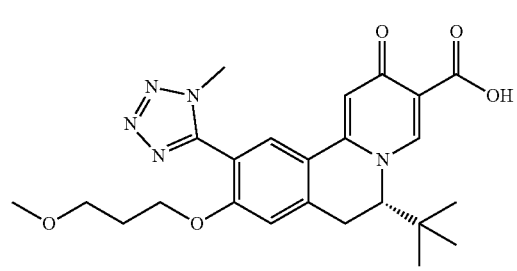 [SMILES: COCCCOc1cc2c(cc1-c1nnnn1C)-c1cc(=O)c(C(=O)O)cn1[C@H](C(C)(C)C)C2] |
| 36 | 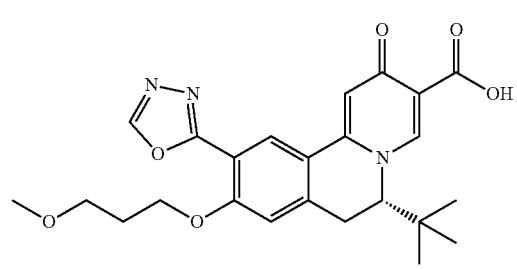 |

| Compound | Structure |
|---|---|
| 37 | 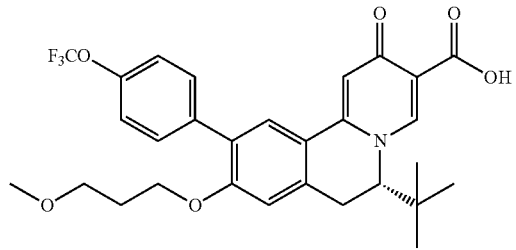 [SMILES: COCCCOc1cc2c(cc1-c1ccc(OC(F)(F)F)cc1)-c1cc(=O)c(C(=O)O)cn1[C@H](C(C)(C)C)C2] |
| 38 | 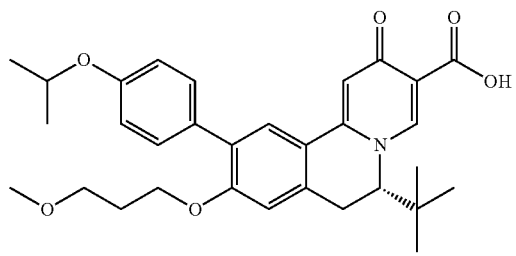 [SMILES: COCCCOc1cc2c(cc1-c1ccc(OC(C)C)cc1)-c1cc(=O)c(C(=O)O)cn1[C@H](C(C)(C)C)C2] |
| 39 | 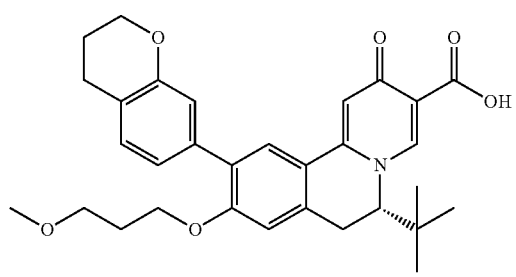 [SMILES: COCCCOc1cc2c(cc1-c1ccc3c(c1)OCCC3)-c1cc(=O)c(C(=O)O)cn1[C@H](C(C)(C)C)C2] |
| 40 | 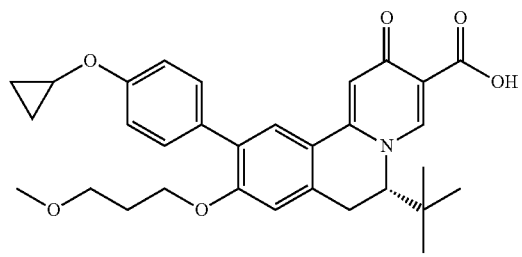 [SMILES: COCCCOc1cc2c(cc1-c1ccc(OC3CC3)cc1)-c1cc(=O)c(C(=O)O)cn1[C@H](C(C)(C)C)C2] |
| 41 | 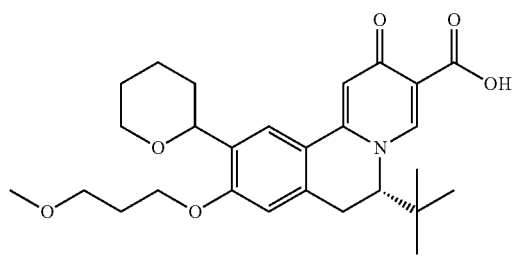 [SMILES: COCCCOc1cc2c(cc1C1CCCCO1)-c1cc(=O)c(C(=O)O)cn1[C@H](C(C)(C)C)C2] |
| 42 | 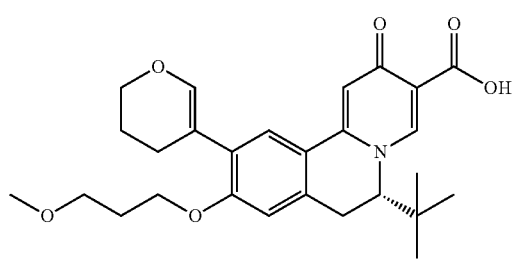 [SMILES: COCCCOc1cc2c(cc1C1=COCCC1)-c1cc(=O)c(C(=O)O)cn1[C@H](C(C)(C)C)C2] |
| Compound | Structure |
|---|---|
| 43 | 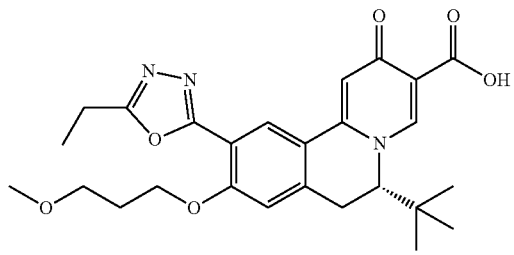 [SMILES: CCc1nnc(-c2cc3c(cc2OCCCOC)C[C@@H](C(C)(C)C)n2cc(C(=O)O)c(=O)cc2-3)o1] |
| 44 | 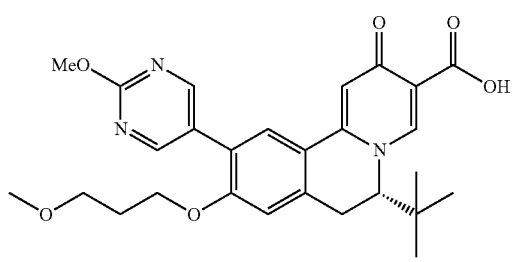 [SMILES: COCCCOc1cc2c(cc1-c1cnc(OC)nc1)-c1cc(=O)c(C(=O)O)cn1[C@H](C(C)(C)C)C2] |
| 45 | 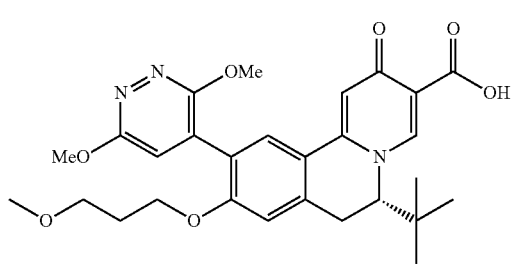 [SMILES: COCCCOc1cc2c(cc1-c1cc(OC)nnc1OC)-c1cc(=O)c(C(=O)O)cn1[C@H](C(C)(C)C)C2] |
| 46 | 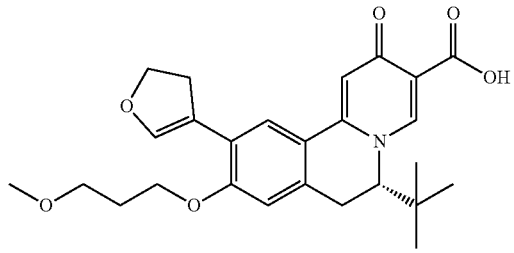 |
| 47 | 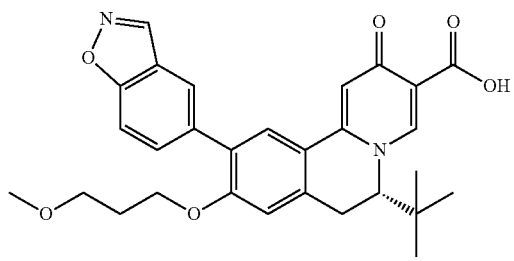 [SMILES: COCCCOc1cc2c(cc1-c1ccc3oncc3c1)-c1cc(=O)c(C(=O)O)cn1[C@H](C(C)(C)C)C2] |
| 48 | 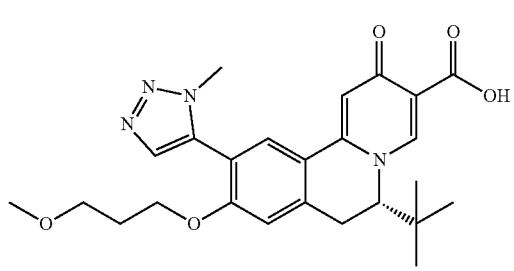 [SMILES: COCCCOc1cc2c(cc1-c1cnnn1C)-c1cc(=O)c(C(=O)O)cn1[C@H](C(C)(C)C)C2] |

| Compound | Structure |
|---|---|
| 49 | 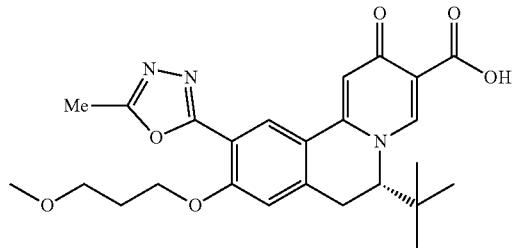 [SMILES: COCCCOc1cc2c(cc1-c1nnc(C)o1)-c1cc(=O)c(C(=O)O)cn1[C@H](C(C)(C)C)C2] |
| 50 | 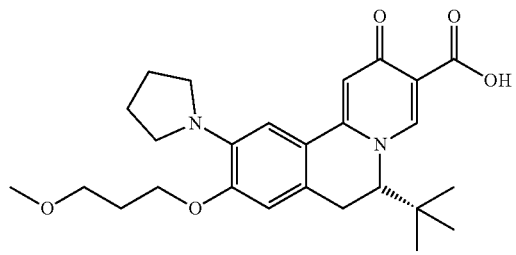 |
| 51 | 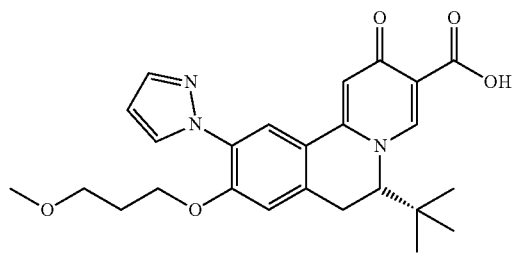 |
| 52 | 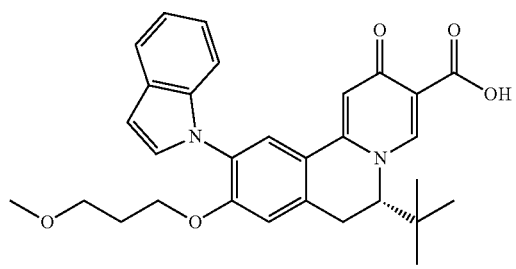 [SMILES: COCCCOc1cc2c(cc1-n1ccc3ccccc31)-c1cc(=O)c(C(=O)O)cn1[C@H](C(C)(C)C)C2] |
| 53 | 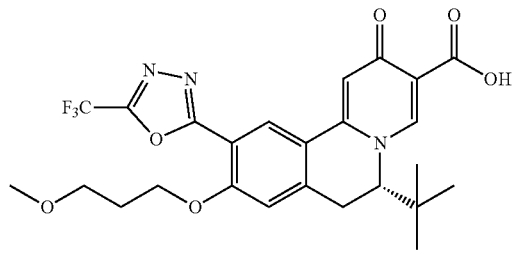 |
| 54 | 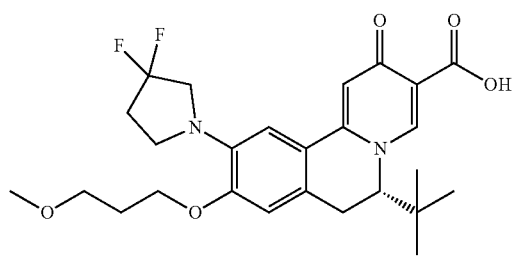 [SMILES: COCCCOc1cc2c(cc1N1CCC(F)(F)C1)-c1cc(=O)c(C(=O)O)cn1[C@H](C(C)(C)C)C2] |
| 55 | 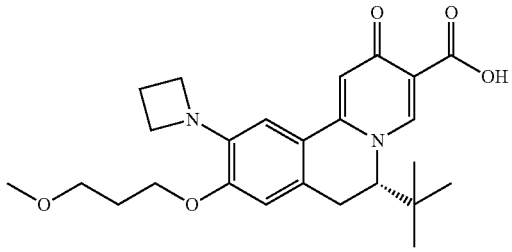 [SMILES: COCCCOc1cc2c(cc1N1CCC1)-c1cc(=O)c(C(=O)O)cn1[C@H](C(C)(C)C)C2] |
| 56 | 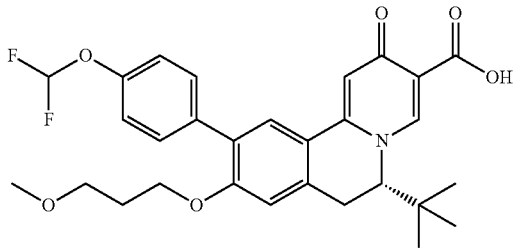 [SMILES: COCCCOc1cc2c(cc1-c1ccc(OC(F)F)cc1)-c1cc(=O)c(C(=O)O)cn1[C@H](C(C)(C)C)C2] |
| 57 | 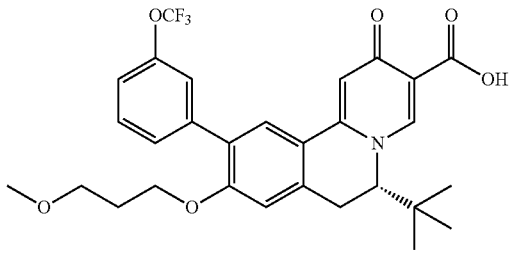 [SMILES: COCCCOc1cc2c(cc1-c1cccc(OC(F)(F)F)c1)-c1cc(=O)c(C(=O)O)cn1[C@H](C(C)(C)C)C2] |
| 58 | 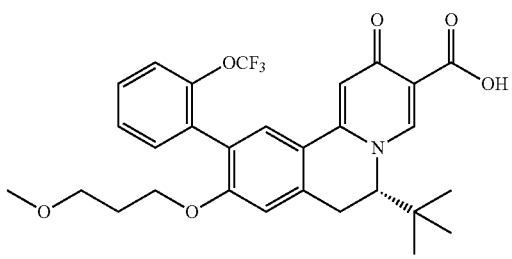 [SMILES: COCCCOc1cc2c(cc1-c1ccccc1OC(F)(F)F)-c1cc(=O)c(C(=O)O)cn1[C@H](C(C)(C)C)C2] |
| 59 | 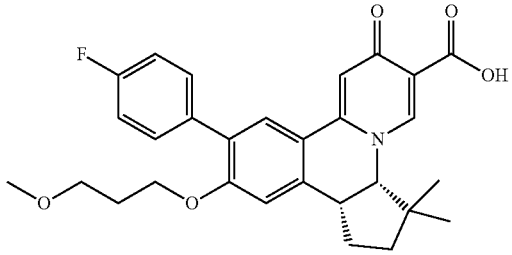 [SMILES: COCCCOc1cc2c(cc1-c1ccc(F)cc1)-c1cc(=O)c(C(=O)O)cn1[C@H]1[C@@H]2CCC1(C)C] |
| 60 | 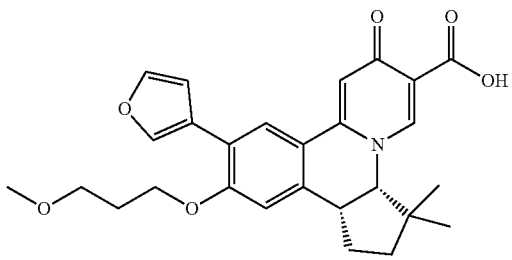 [SMILES: COCCCOc1cc2c(cc1-c1ccoc1)-c1cc(=O)c(C(=O)O)cn1[C@H]1[C@@H]2CCC1(C)C] |

| Compound | Structure |
|---|---|
| 61 | 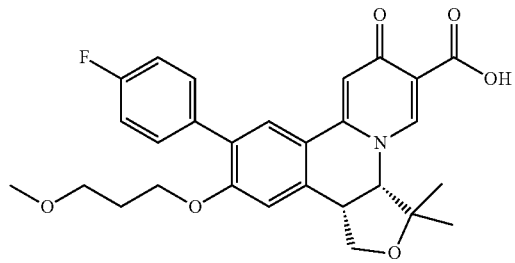 [SMILES: COCCCOc1cc2c(cc1-c1ccc(F)cc1)-c1cc(=O)c(C(=O)O)cn1[C@H]1[C@@H]2COC1(C)C] |
| 62 | 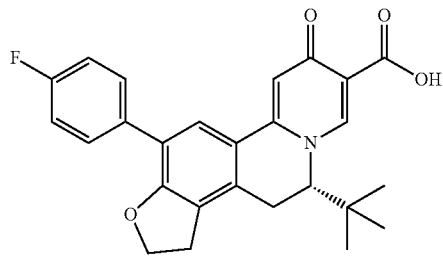 |
| 63 | 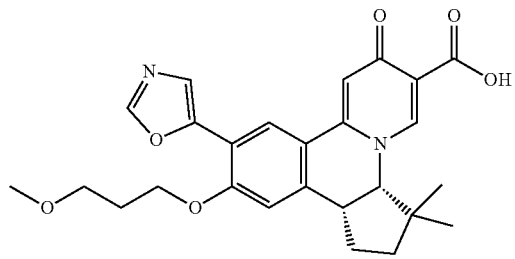 [SMILES: COCCCOc1cc2c(cc1-c1cnco1)-c1cc(=O)c(C(=O)O)cn1[C@H]1[C@@H]2CCC1(C)C] |
| 64 | 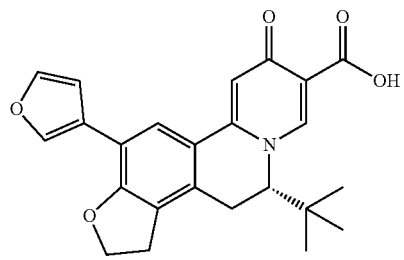 [SMILES: CC(C)(C)[C@@H]1Cc2c(cc(-c3ccoc3)c3c2CCO3)-c2cc(=O)c(C(=O)O)cn21] |
| 65 | 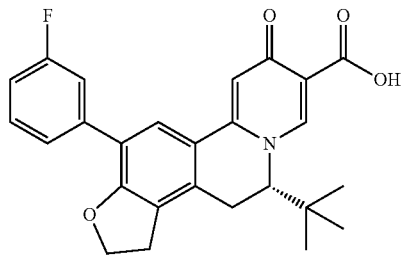 |
| 66 | 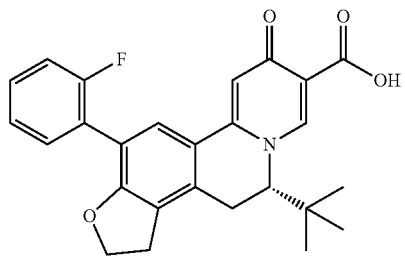 |
| 67 | 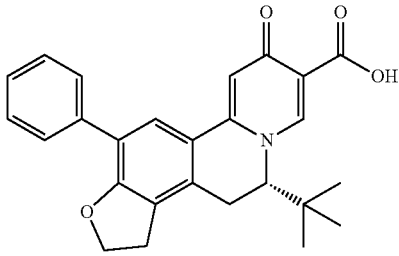 [SMILES: CC(C)(C)[C@@H]1Cc2c(cc(-c3ccccc3)c3c2CCO3)-c2cc(=O)c(C(=O)O)cn21] |
| 68 | 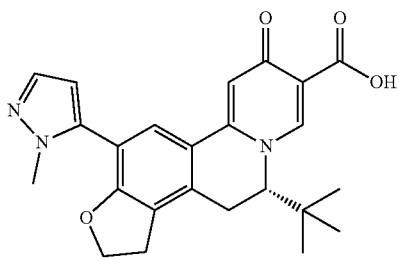 [SMILES: Cn1nccc1-c1cc2c(c3c1OCC3)C[C@@H](C(C)(C)C)n1cc(C(=O)O)c(=O)cc1-2] |
| 69 | 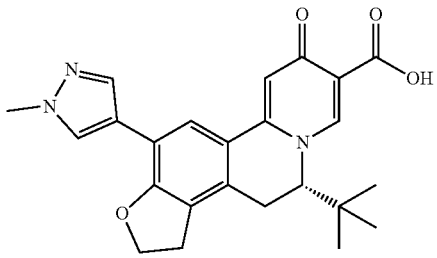 [SMILES: Cn1cc(-c2cc3c(c4c2OCC4)C[C@@H](C(C)(C)C)n2cc(C(=O)O)c(=O)cc2-3)cn1] |
| 70 | 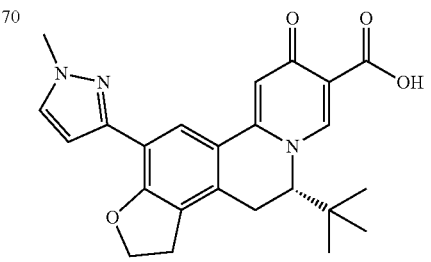 |
| 71 | 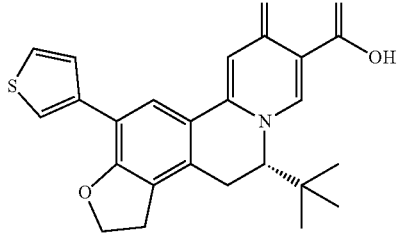 |

207
-continued
| Compound | Structure |
|---|---|
| 72 | 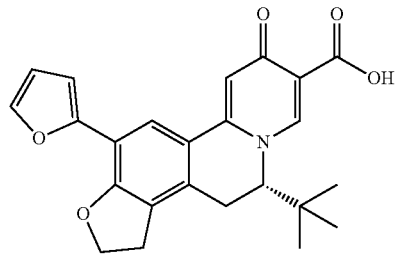 [SMILES: CC(C)(C)[C@@H]1Cc2c(cc(-c3ccco3)c3c2CCO3)-c2cc(=O)c(C(=O)O)cn21] |
| 73 | 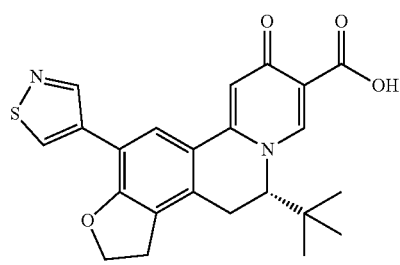 |
| 74 | 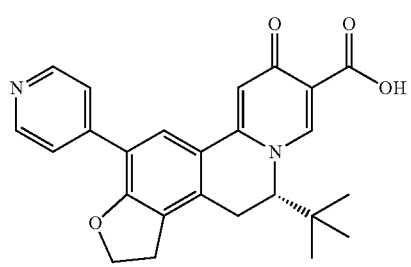 |
| 75 | 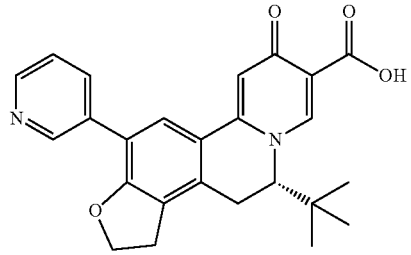 [SMILES: CC(C)(C)[C@@H]1Cc2c(cc(-c3cccnc3)c3c2CCO3)-c2cc(=O)c(C(=O)O)cn21] |
| 76 | 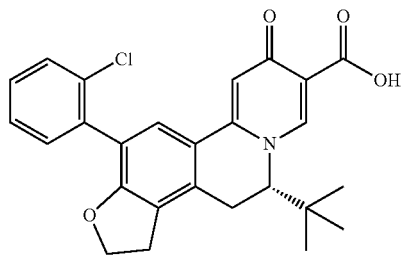 |
| 77 | 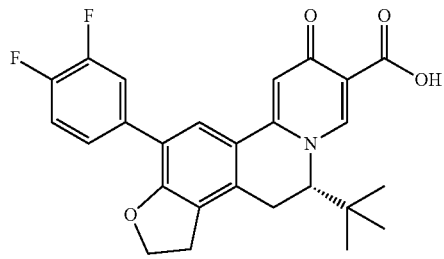 |
208
-continued
| Compound | Structure |
|---|---|
| 78 | 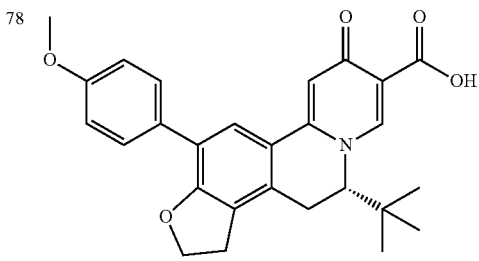 |
| 79 | 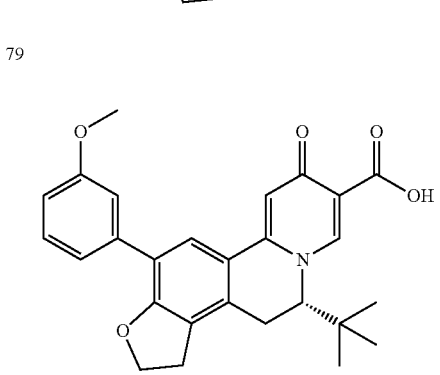 |
| 80 | 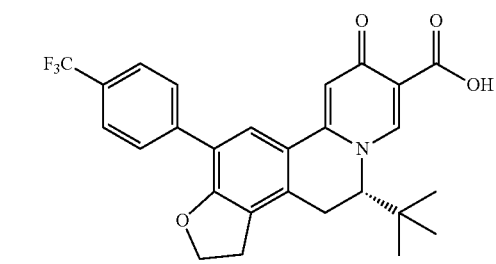 |
| 81 | 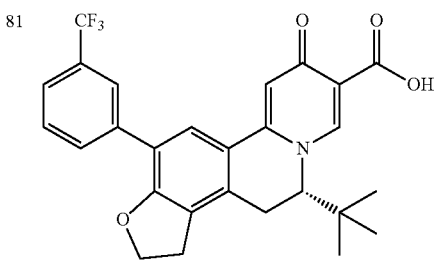 |
| 82 | 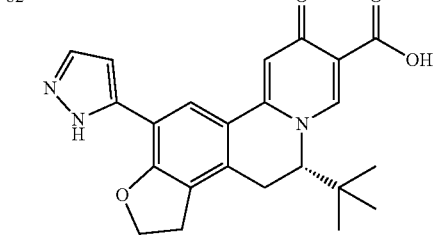 |

| Compound | Structure |
|---|---|
| 83 | 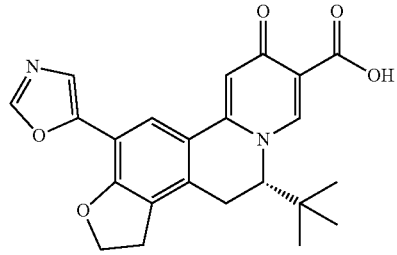 [SMILES: CC(C)(C)[C@@H]1Cc2c(cc(-c3cnco3)c3c2CCO3)-c2cc(=O)c(C(=O)O)cn21] |
| 84 | 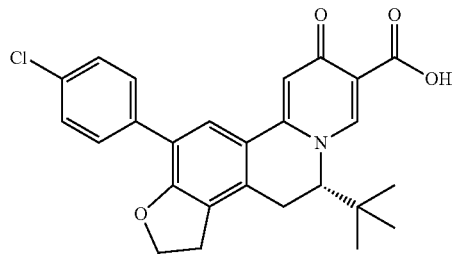 [SMILES: CC(C)(C)[C@@H]1Cc2c(cc(-c3ccc(Cl)cc3)c3c2CCO3)-c2cc(=O)c(C(=O)O)cn21] |
| 85 | 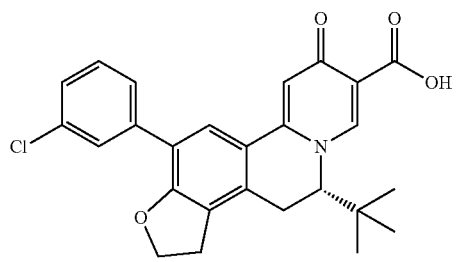 [SMILES: CC(C)(C)[C@@H]1Cc2c(cc(-c3cccc(Cl)c3)c3c2CCO3)-c2cc(=O)c(C(=O)O)cn21] |
| 86 | 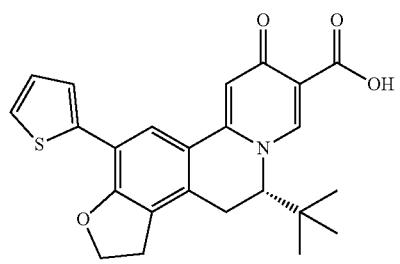 |
| 87 | 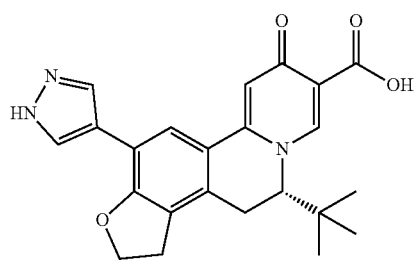 [SMILES: CC(C)(C)[C@@H]1Cc2c(cc(-c3cn[nH]c3)c3c2CCO3)-c2cc(=O)c(C(=O)O)cn21] |
| 88 | 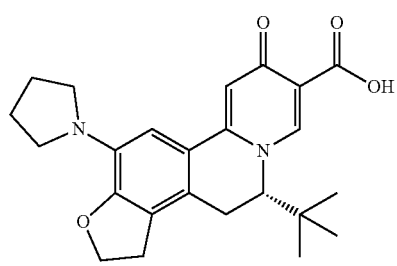 |
| Compound | Structure |
|---|---|
| 89 | 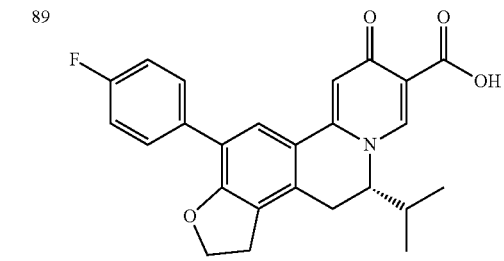 |
| 90 | 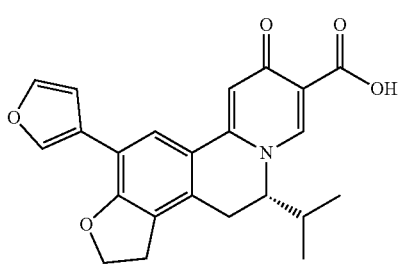 [SMILES: CC(C)[C@@H]1Cc2c(cc(-c3ccoc3)c3c2CCO3)-c2cc(=O)c(C(=O)O)cn21] |
| 91 | 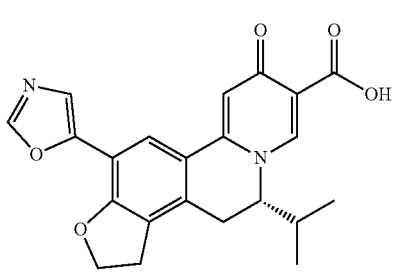 [SMILES: CC(C)[C@@H]1Cc2c(cc(-c3cnco3)c3c2CCO3)-c2cc(=O)c(C(=O)O)cn21] |
| 92 | 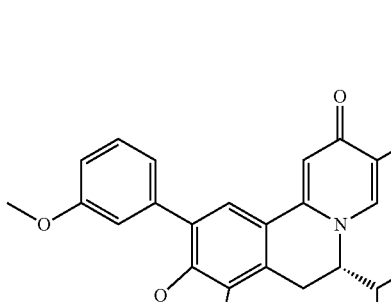 |
| 93 | 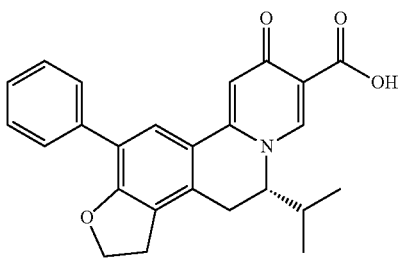 [SMILES: CC(C)[C@@H]1Cc2c(cc(-c3ccccc3)c3c2CCO3)-c2cc(=O)c(C(=O)O)cn21] |

| Compound | Structure |
|---|---|
| 94 | 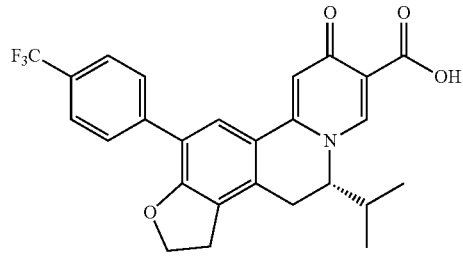 |
| 95 | 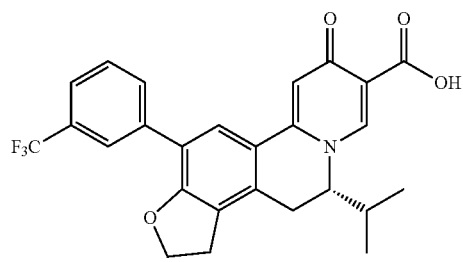 [SMILES: CC(C)[C@@H]1Cc2c(cc(-c3cccc(C(F)(F)F)c3)c3c2CCO3)-c2cc(=O)c(C(=O)O)cn21] |
| 96 | 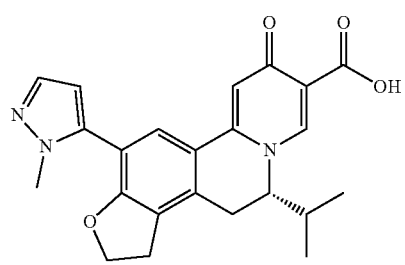 [SMILES: CC(C)[C@@H]1Cc2c(cc(-c3ccnn3C)c3c2CCO3)-c2cc(=O)c(C(=O)O)cn21] |
| 97 | 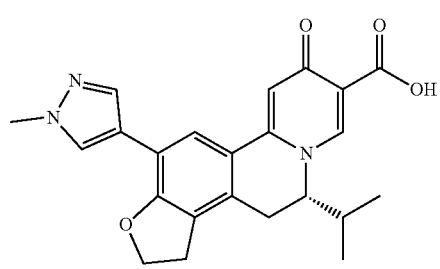 [SMILES: CC(C)[C@@H]1Cc2c(cc(-c3cnn(C)c3)c3c2CCO3)-c2cc(=O)c(C(=O)O)cn21] |
| 98 | 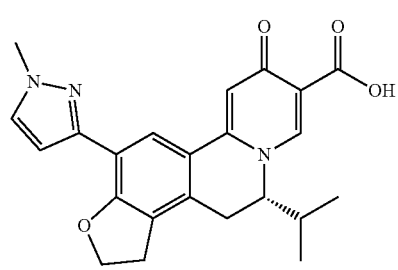 [SMILES: CC(C)[C@@H]1Cc2c(cc(-c3ccn(C)n3)c3c2CCO3)-c2cc(=O)c(C(=O)O)cn21] |
| 99 | 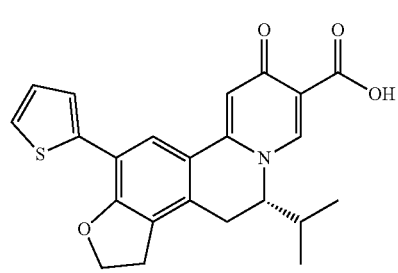 [SMILES: CC(C)[C@@H]1Cc2c(cc(-c3cccs3)c3c2CCO3)-c2cc(=O)c(C(=O)O)cn21] |
| 100 | 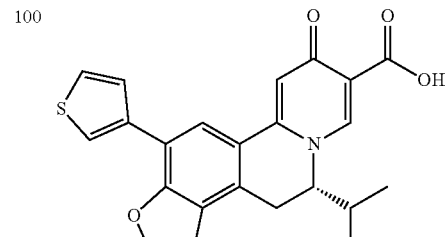 |
| 101 | 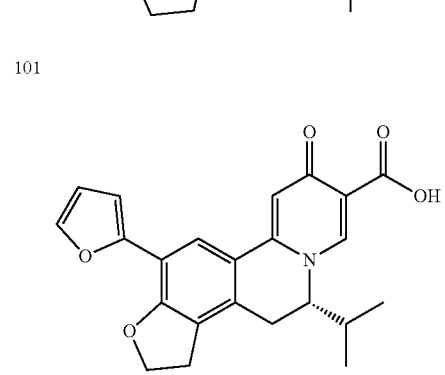 |
| 102 | 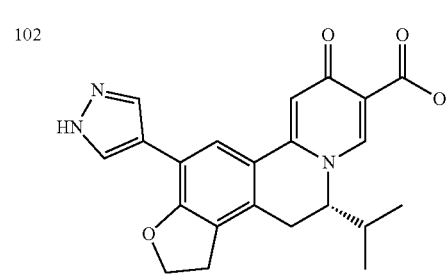 |
| 103 | 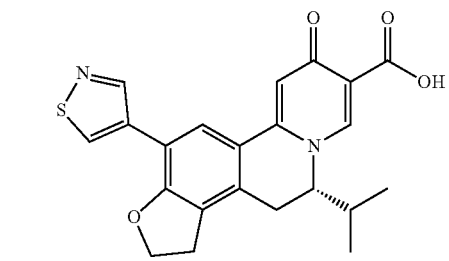 |
| 104 | 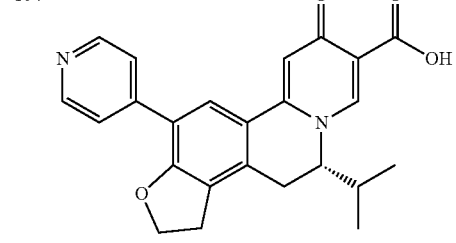 |

| Compound | Structure |
|---|---|
| 105 | 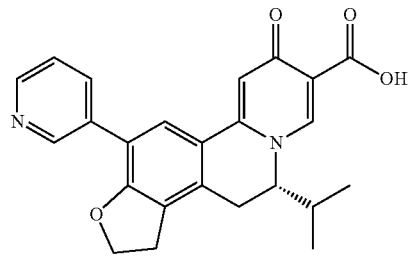 [SMILES: CC(C)[C@@H]1Cc2c(cc(-c3cccnc3)c3c2CCO3)-c2cc(=O)c(C(=O)O)cn21] |
| 106 | 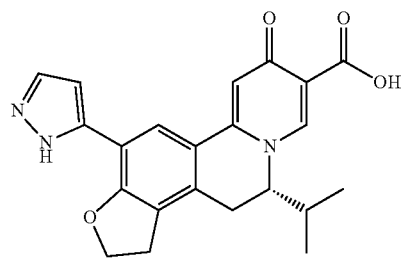 |
| 107 | 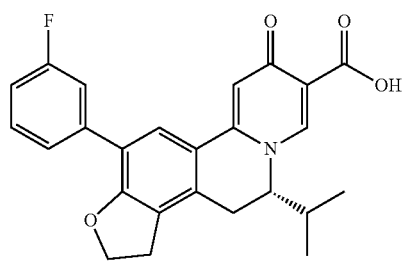 [SMILES: CC(C)[C@@H]1Cc2c(cc(-c3cccc(F)c3)c3c2CCO3)-c2cc(=O)c(C(=O)O)cn21] |
| 108 | 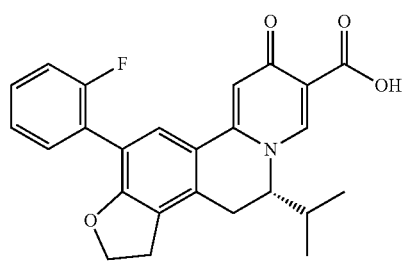 [SMILES: CC(C)[C@@H]1Cc2c(cc(-c3ccccc3F)c3c2CCO3)-c2cc(=O)c(C(=O)O)cn21] |
| 109 | 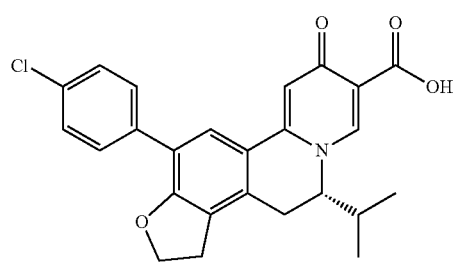 [SMILES: CC(C)[C@@H]1Cc2c(cc(-c3ccc(Cl)cc3)c3c2CCO3)-c2cc(=O)c(C(=O)O)cn21] |
| 110 | 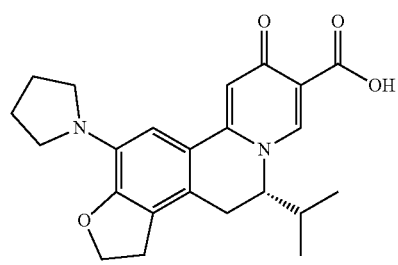 [SMILES: CC(C)[C@@H]1Cc2c(cc(N3CCCC3)c3c2CCO3)-c2cc(=O)c(C(=O)O)cn21] |
| 111 | 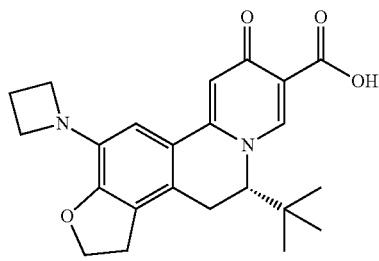 [SMILES: CC(C)(C)[C@@H]1Cc2c(cc(N3CCC3)c3c2CCO3)-c2cc(=O)c(C(=O)O)cn21] |
| 112 | 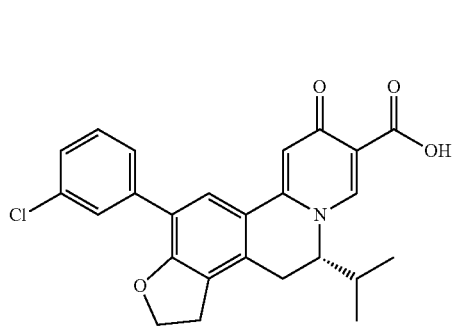 [SMILES: CC(C)[C@@H]1Cc2c(cc(-c3cccc(Cl)c3)c3c2CCO3)-c2cc(=O)c(C(=O)O)cn21] |
| 113 | 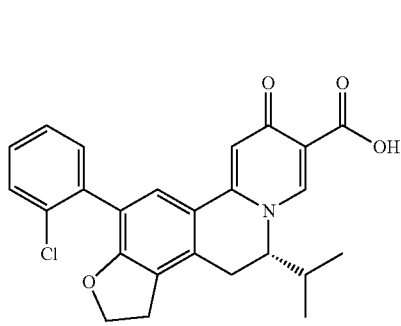 [SMILES: CC(C)[C@@H]1Cc2c(cc(-c3ccccc3Cl)c3c2CCO3)-c2cc(=O)c(C(=O)O)cn21] |
| 114 | 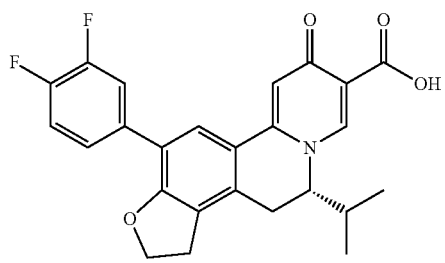 |
| 115 | 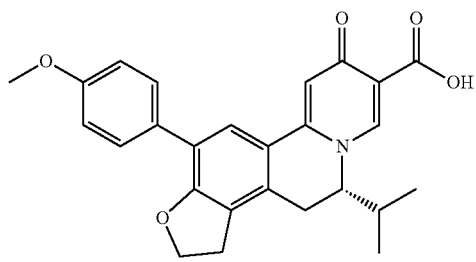 [SMILES: COc1ccc(-c2cc3c(c4c2OCC4)C[C@@H](C(C)C)n2cc(C(=O)O)c(=O)cc2-3)cc1] |

| Compound | Structure |
|---|---|
| 116 | 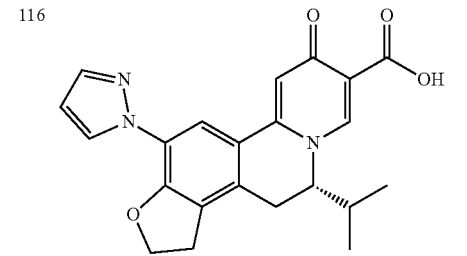 |
| 117 | 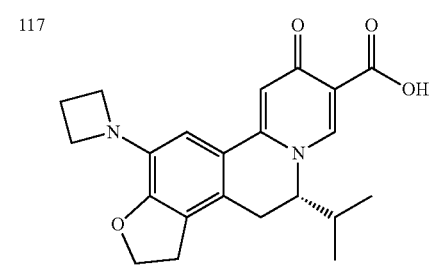 |
| 118 | 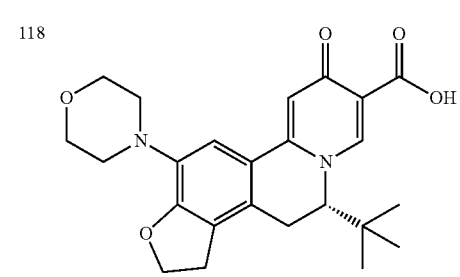 |
| 119 | 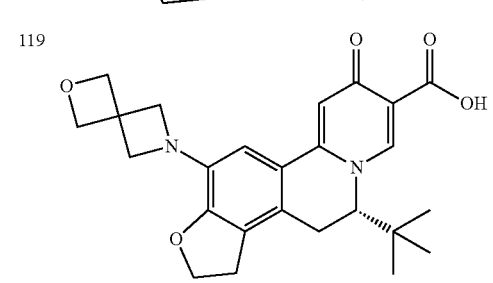 |
| 120 | 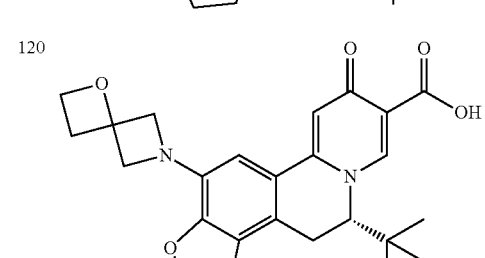 |
| 121 | 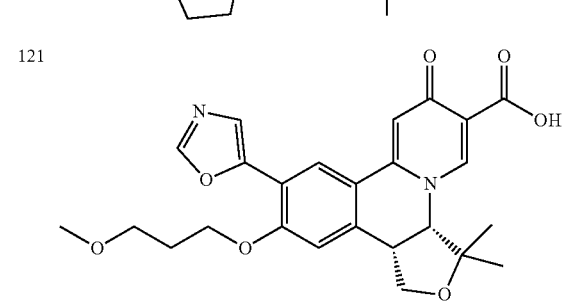 |
| 122 | 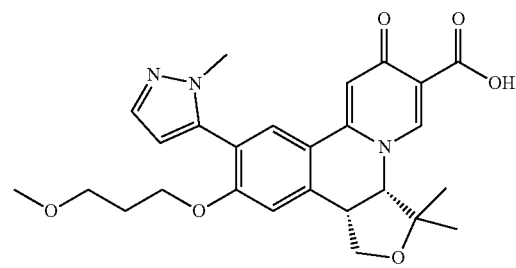 [SMILES: COCCCOc1cc2c(cc1-c1ccnn1C)-c1cc(=O)c(C(=O)O)cn1[C@H]1[C@@H]2COC1(C)C] |
| 123 | 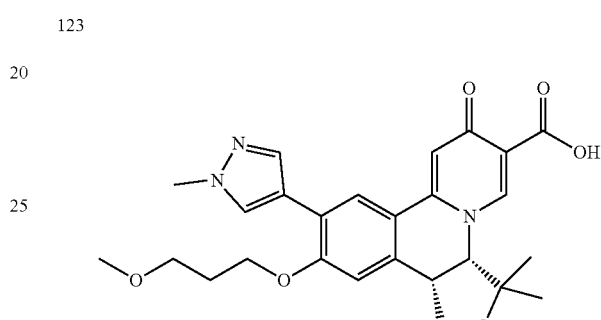 |
| 124 | 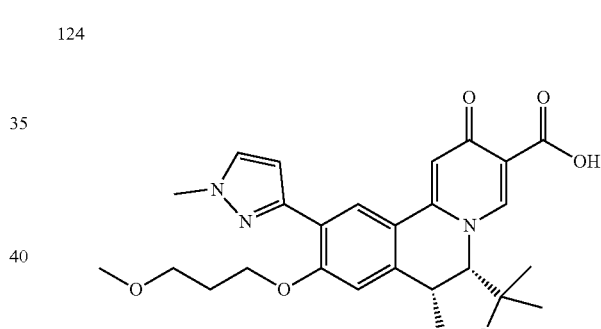 |
| 125 | 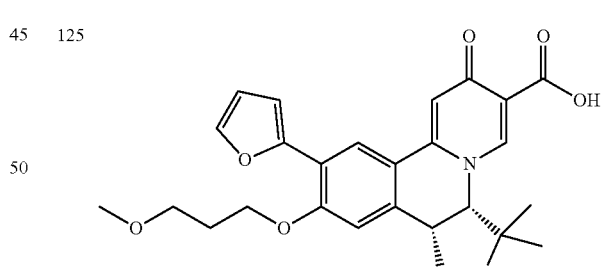 |
| 126 | 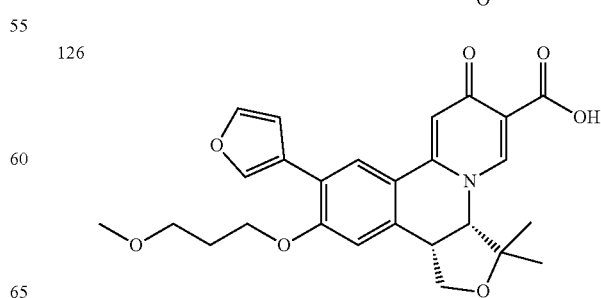 |

| Compound | Structure |
|---|---|
| 127 | 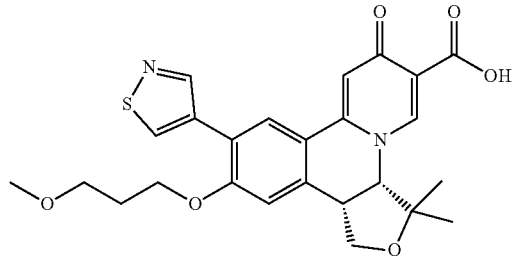 [SMILES: COCCCOc1cc2c(cc1-c1cnsc1)-c1cc(=O)c(C(=O)O)cn1[C@H]1[C@@H]2COC1(C)C] |
| 128 | 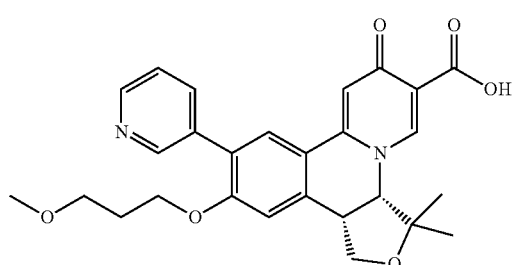 |
| 129 | 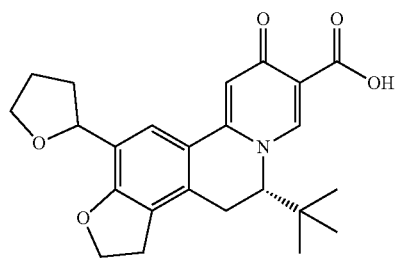 [SMILES: CC(C)(C)[C@@H]1Cc2c(cc(C3CCCO3)c3c2CCO3)-c2cc(=O)c(C(=O)O)cn21] |
| 130 | 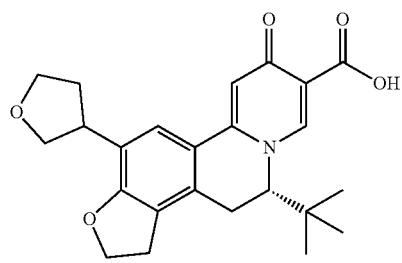 [SMILES: CC(C)(C)[C@@H]1Cc2c(cc(C3CCOC3)c3c2CCO3)-c2cc(=O)c(C(=O)O)cn21] |
| 131 | 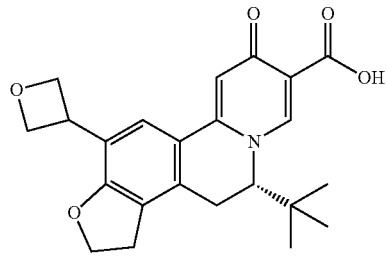 [SMILES: CC(C)(C)[C@@H]1Cc2c(cc(C3COC3)c3c2CCO3)-c2cc(=O)c(C(=O)O)cn21] |
| Compound | Structure |
|---|---|
| 132 | 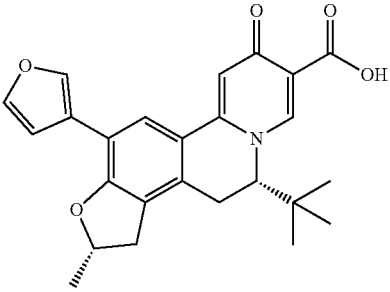 [SMILES: C[C@H]1Cc2c3c(cc(-c4ccoc4)c2O1)-c1cc(=O)c(C(=O)O)cn1[C@H](C(C)(C)C)C3] |
| 133 | 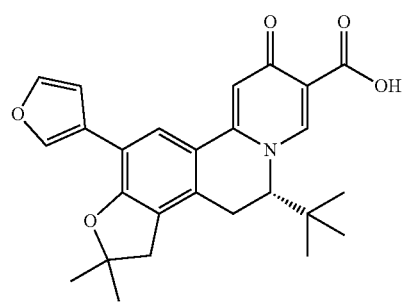 [SMILES: CC1(C)Cc2c3c(cc(-c4ccoc4)c2O1)-c1cc(=O)c(C(=O)O)cn1[C@H](C(C)(C)C)C3] |
| 134 | 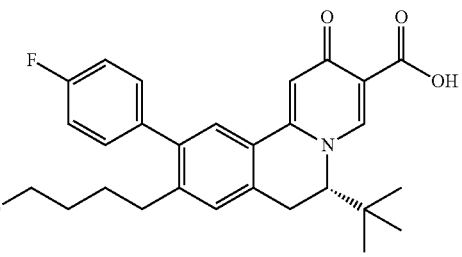 |
| 135 | 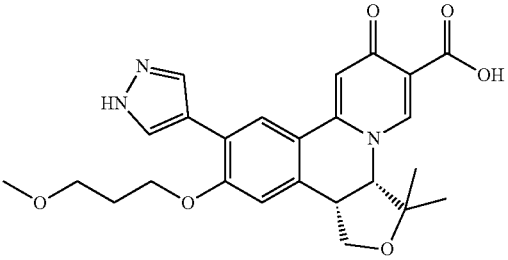 [SMILES: COCCCOc1cc2c(cc1-c1cn[nH]c1)-c1cc(=O)c(C(=O)O)cn1[C@H]1[C@@H]2COC1(C)C] |
| 136 | 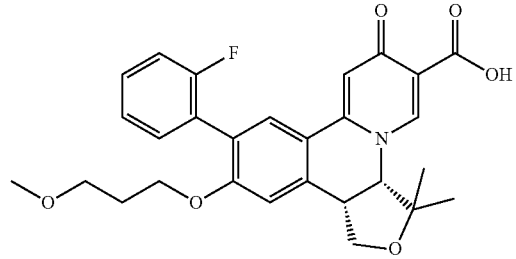 |

-continued
| Compound | Structure |
|---|---|
| 137 | 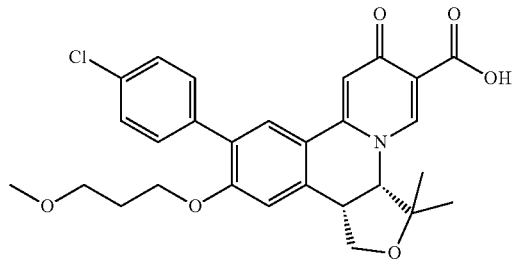 [SMILES: COCCCOc1cc2c(cc1-c1ccc(Cl)cc1)-c1cc(=O)c(C(=O)O)cn1[C@H]1[C@@H]2COC1(C)C] |
| 138 | 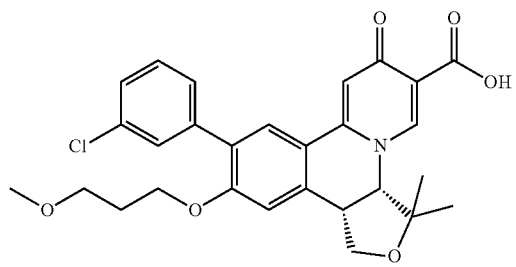 [SMILES: COCCCOc1cc2c(cc1-c1cccc(Cl)c1)-c1cc(=O)c(C(=O)O)cn1[C@H]1[C@@H]2COC1(C)C] |
| 139 | 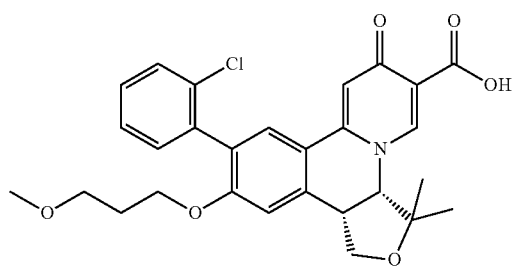 [SMILES: COCCCOc1cc2c(cc1-c1ccccc1Cl)-c1cc(=O)c(C(=O)O)cn1[C@H]1[C@@H]2COC1(C)C] |
| 140 | 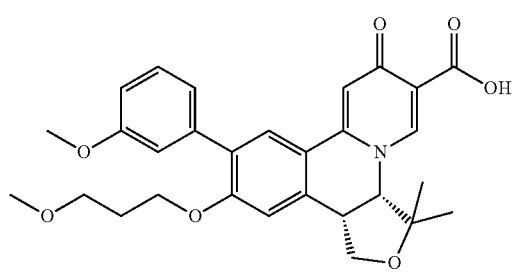 [SMILES: COCCCOc1cc2c(cc1-c1cccc(OC)c1)-c1cc(=O)c(C(=O)O)cn1[C@H]1[C@@H]2COC1(C)C] |
| 141 | 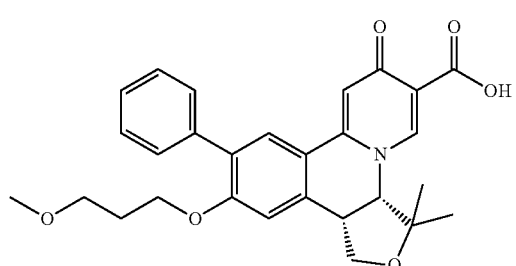 |
-continued
| Compound | Structure |
|---|---|
| 142 | 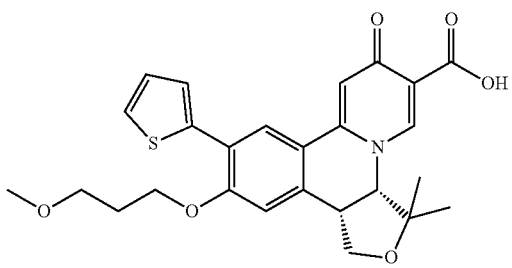 [SMILES: COCCCOc1cc2c(cc1-c1cccs1)-c1cc(=O)c(C(=O)O)cn1[C@H]1[C@@H]2COC1(C)C] |
| 143 | 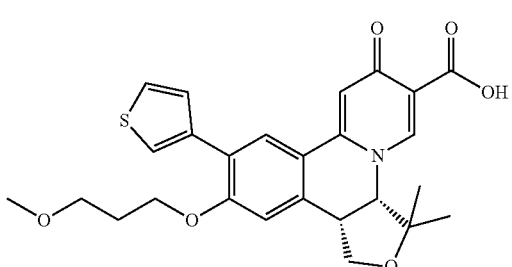 |
| 144 | 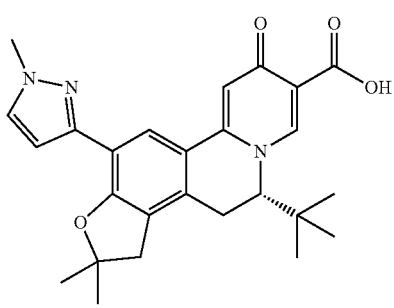 [SMILES: Cn1ccc(-c2cc3c(c4c2OC(C)(C)C4)C[C@@H](C(C)(C)C)n2cc(C(=O)O)c(=O)cc2-3)n1] |
| 145 | 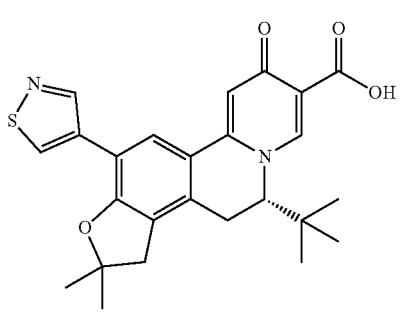 |
| 146 | 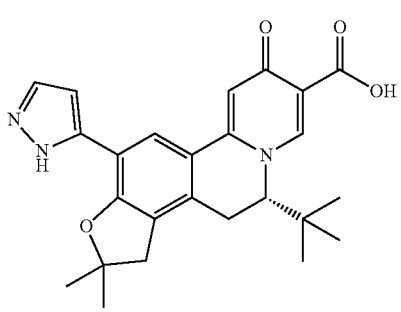 [SMILES: CC1(C)Cc2c3c(cc(-c4ccn[nH]4)c2O1)-c1cc(=O)c(C(=O)O)cn1[C@H](C(C)(C)C)C3] |

| Compound | Structure |
|---|---|
| 147 | 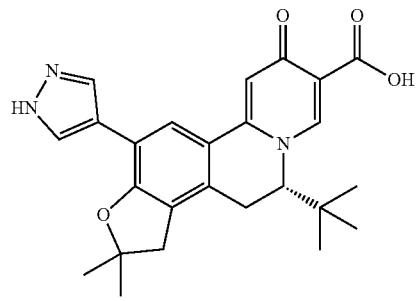 [SMILES: CC1(C)Cc2c3c(cc(-c4cn[nH]c4)c2O1)-c1cc(=O)c(C(=O)O)cn1[C@H](C(C)(C)C)C3] |
| 148 | 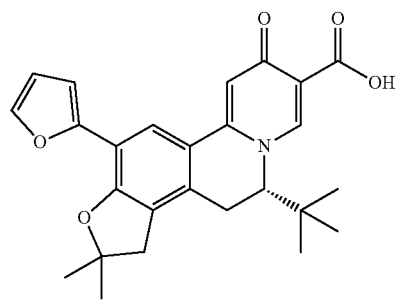 [SMILES: CC1(C)Cc2c3c(cc(-c4ccco4)c2O1)-c1cc(=O)c(C(=O)O)cn1[C@H](C(C)(C)C)C3] |
| 149 | 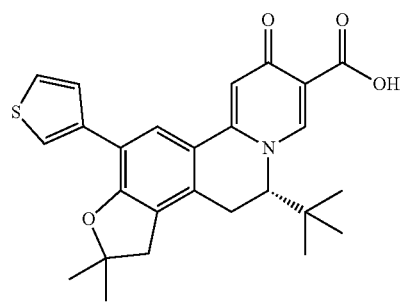 |
| 150 | 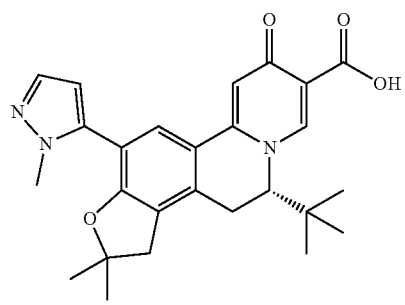 [SMILES: Cn1nccc1-c1cc2c(c3c1OC(C)(C)C3)C[C@@H](C(C)(C)C)n1cc(C(=O)O)c(=O)cc1-2] |
| 151 | 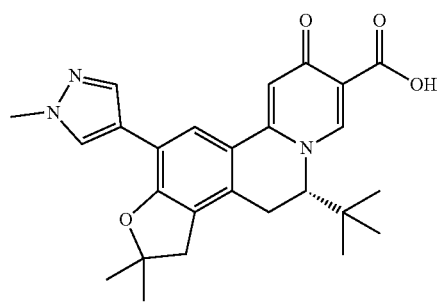 [SMILES: Cn1cc(-c2cc3c(c4c2OC(C)(C)C4)C[C@@H](C(C)(C)C)n2cc(C(=O)O)c(=O)cc2-3)cn1] |
| Compound | Structure |
|---|---|
| 152 | 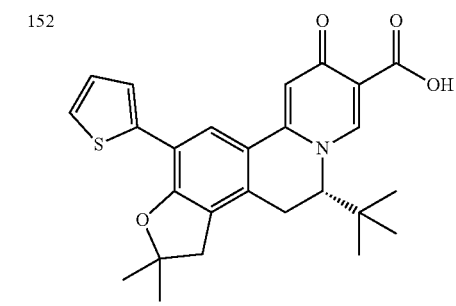 |
| 153 | 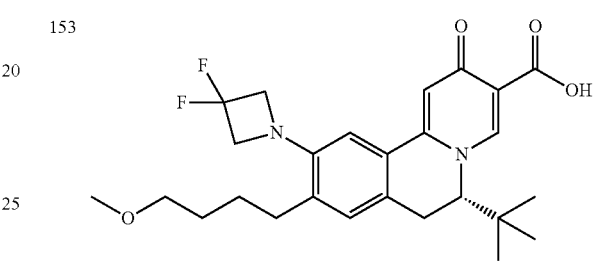 |
| 154 | 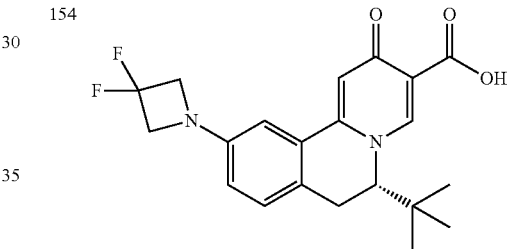 |
| 155 | 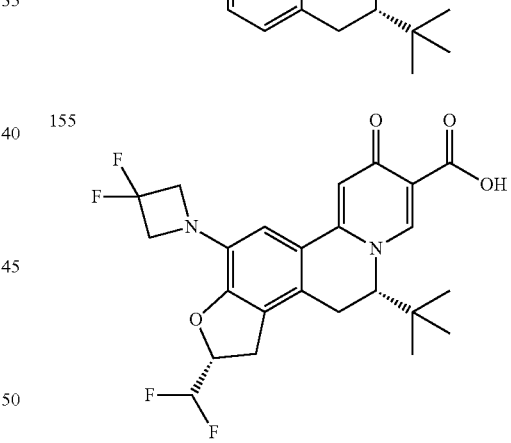 |
| 156 | 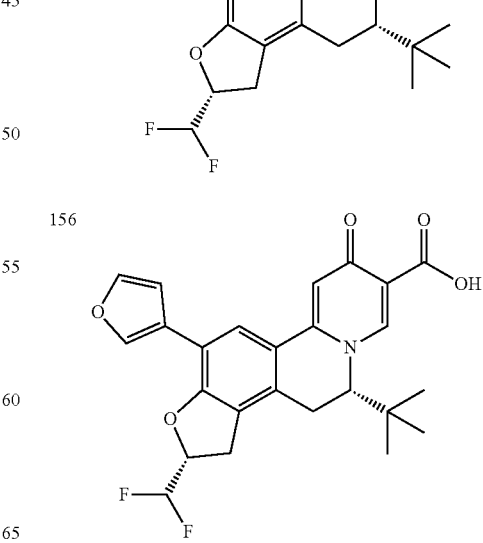 |

| Com-pound | Structure |
|---|---|
| 157 | 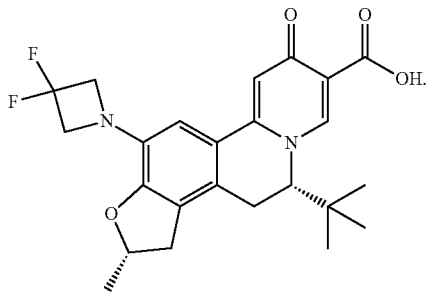 [SMILES: C[C@H]1Cc2c3c(cc(N4CC(F)(F)C4)c2O1)-c1cc(=O)c(C(=O)O)cn1[C@H](C(C)(C)C)C3] |

10. A pharmaceutical composition comprising a compound according to claim 1 and a pharmaceutically acceptable carrier or excipient.

11. A method of treating or preventing an HBV infection in a subject in need thereof, comprising administering to the subject a therapeutically effective amount of a compound or a combination of compounds according to claim 1.

12. The compound of claim 1, wherein A is

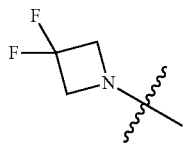 or 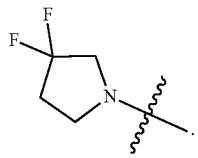.

13. The compound of claim 4, represented by Formula (IVa) or Formula (IVb), or a pharmaceutically acceptable salt thereof,

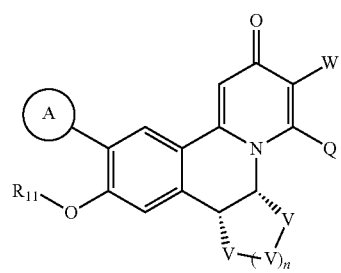 (IVa)

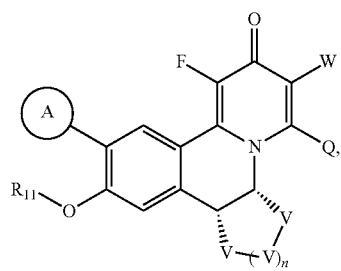 (IVb)

wherein W is —C(O)OH; Q is hyrdogen; one V is —O—, —C(O)—, —S—, —S(O)$_2$—, —NR$_{22}$— or —C(R$_{22}$)$_2$—, and the other Vs are independently —O—, —NR$_{22}$— or —C(R$_{22}$)$_2$—; each R$_{22}$ is independently hydrogen, optionally substituted —C$_1$-C$_6$ alkyl, optionally substituted —C$_2$-C$_6$ alkenyl, optionally substituted —C$_2$-C$_6$ alkynyl, optionally substituted C$_1$-C$_6$ alkoxy; optionally substituted —C$_3$-C$_7$ cycloalkyl, optionally substituted 3- to 7-membered heterocyclic, optionally substituted aryl or optionally substituted heteroaryl; n is 0, 1, 2 or 3; and A and R$_{11}$ are as defined in claim 1.

14. The compound of claim 6, wherein A is selected from the groups set forth in the table below:

| Entry | A |
|---|---|
| 1 | 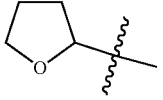 [SMILES: *C1CCCO1] |
| 2 | 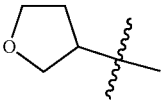 [SMILES: *C1CCOC1] |
| 3 | 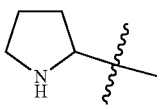 [SMILES: *C1CCCN1] |
| 4 | 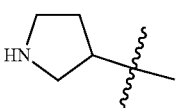 |
| 5 | 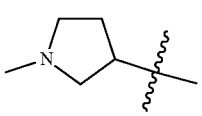 [SMILES: *C1CCN(C)C1] |
| 6 | 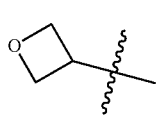 [SMILES: *C1COC1] |
| 7 | 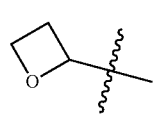 [SMILES: *C1CCO1] |
| 8 | 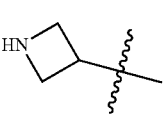 [SMILES: *C1CNC1] |
| 9 | 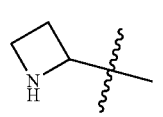 |
| 10 |  |
| 11 | 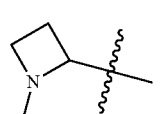 |
| 12 | 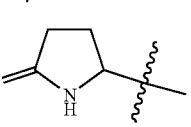 |

225
-continued

| Entry | A |
|---|---|
| 13 | 5-oxopyrrolidin-3-yl |
| 14 | tetrahydro-2H-pyran-2-yl |
| 15 | tetrahydro-2H-pyran-3-yl |
| 16 | tetrahydro-2H-pyran-4-yl |
| 17 | piperidin-2-yl |
| 18 | piperidin-3-yl |
| 19 | piperidin-4-yl |
| 20 | piperidin-1-yl |
| 21 | pyrrolidin-1-yl |
| 22 | azetidin-1-yl |
| 23 | 3-fluoropyrrolidin-1-yl |
| 24 | 3-fluoroazetidin-1-yl |

226
-continued

| Entry | A |
|---|---|
| 25 | furan-2-yl |
| 26 | furan-3-yl |
| 27 | isoxazol-5-yl |
| 28 | isoxazol-4-yl |
| 29 | isoxazol-3-yl |
| 30 | 1,2,5-oxadiazol-3-yl |
| 31 | 1,3,4-oxadiazol-... |
| 32 | oxazol-5-yl |
| 33 | oxazol-2-yl |
| 34 | 1,3,4-oxadiazol-2-yl |
| 35 | thiophen-2-yl |
| 36 | thiophen-3-yl |
| 37 | isothiazol-5-yl |

227
-continued

| Entry | A |
|---|---|
| 38 | isothiazol-4-yl |
| 39 | isothiazol-3-yl |
| 40 | 1,2,5-thiadiazol-3-yl |
| 41 | 1,3,4-thiadiazol-2-yl |
| 42 | thiazol-5-yl |
| 43 | thiazol-2-yl |
| 44 | 1,3,4-thiadiazol-2-yl |
| 45 | oxazol-4-yl |
| 46 | thiazol-4-yl |
| 47 | 1H-imidazol-4-yl |
| 48 | 1H-imidazol-2-yl |
| 49 | 1H-pyrazol-3-yl |

228
-continued

| Entry | A |
|---|---|
| 50 | 4H-1,2,4-triazol-3-yl |
| 51 | 1-methyl-1H-pyrazol-3-yl |
| 52 | 1H-pyrazol-1-yl |
| 53 | 1H-imidazol-1-yl |
| 54 | 1H-1,2,3-triazol-1-yl |
| 55 | 4H-1,2,4-triazol-4-yl |
| 56 | 1H-tetrazol-1-yl |
| 57 | 1H-1,2,4-triazol-1-yl |
| 58 | 1H-pyrazol-1-yl |
| 59 | 1H-imidazol-1-yl |
| 60 | 4-fluorophenyl |
| 61 | 5-fluoropyridin-2-yl |

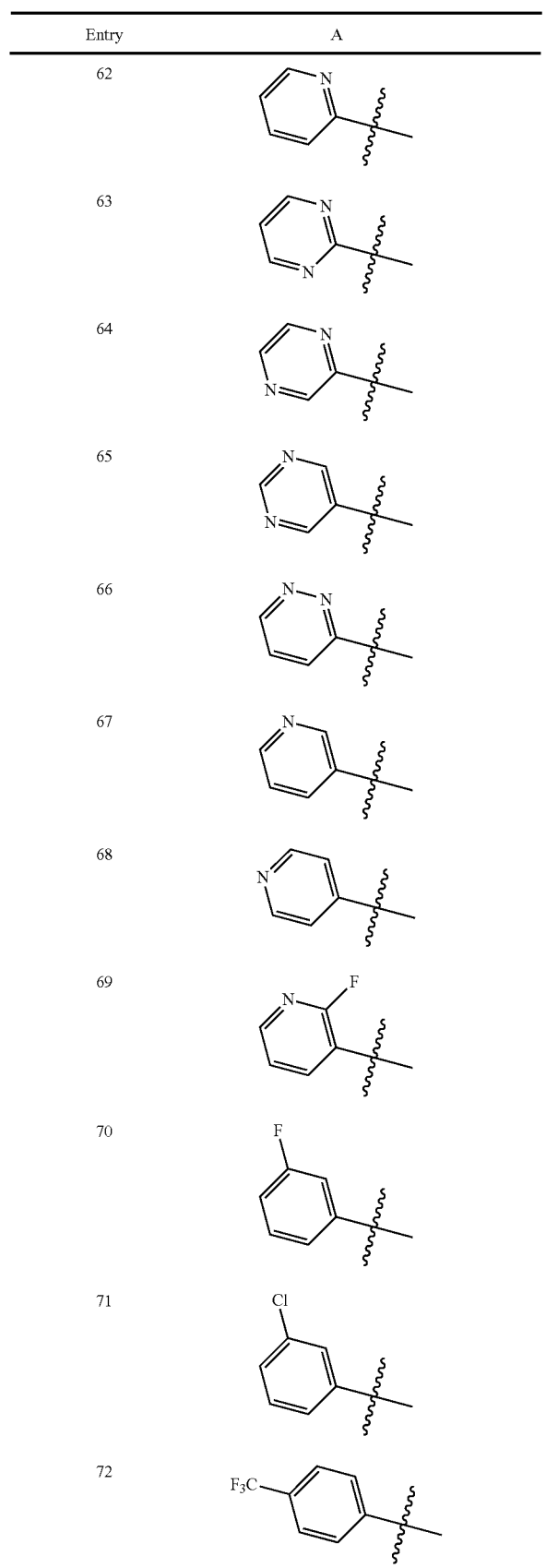
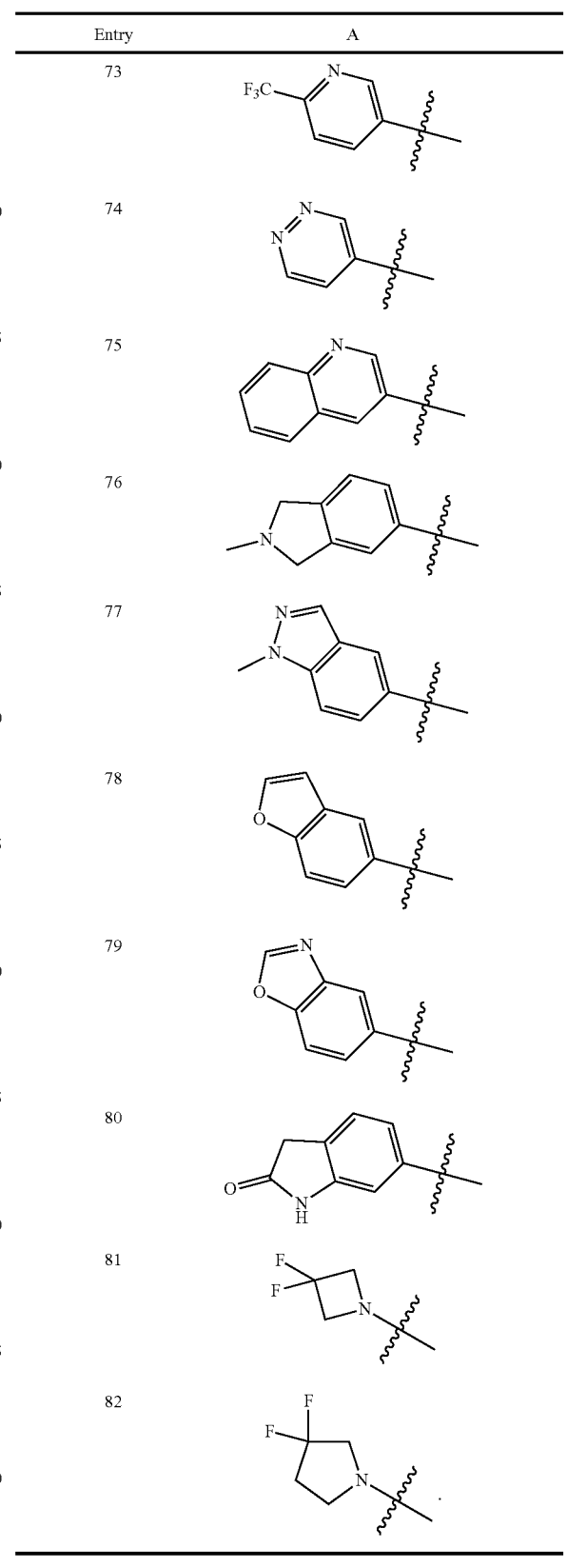
15. A pharmaceutical composition comprising a compound according to claim 6 and a pharmaceutically acceptable carrier or excipient.

16. A method of treating or preventing an HBV infection in a subject in need thereof, comprising administering to the subject a therapeutically effective amount of a compound or a combination of compounds according to claim 6.

17. A pharmaceutical composition comprising a compound according to claim 9 and a pharmaceutically acceptable carrier or excipient.

18. A method of treating or preventing an HBV infection in a subject in need thereof, comprising administering to the subject a therapeutically effective amount of a compound or a combination of compounds according to claim 9.

19. The compound of claim 13, wherein A is selected from the groups set forth in the table below:

| Entry | A |
|---|---|
| 1 | 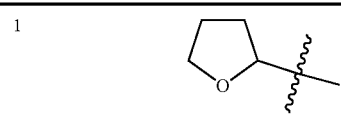 |
| 2 | 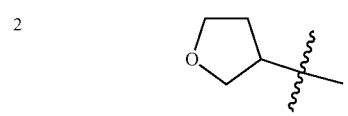 |
| 3 | 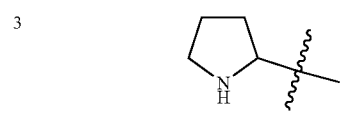 |
| 4 | 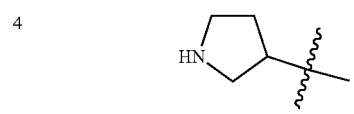 |
| 5 | 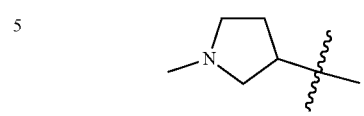 |
| 6 | 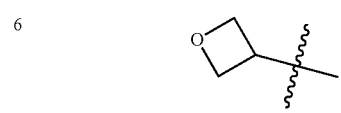 |
| 7 | 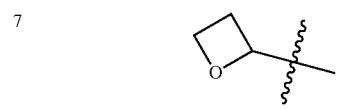 |
| 8 | 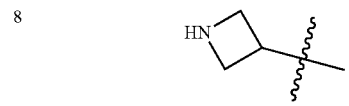 |
| 9 | 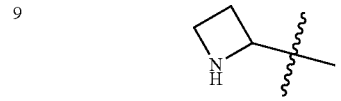 |
| 10 | 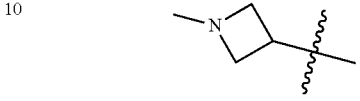 |

-continued

| Entry | A |
|---|---|
| 11 |  |
| 12 | 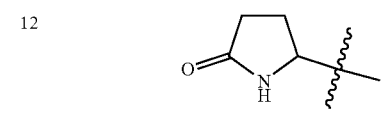 |
| 13 | 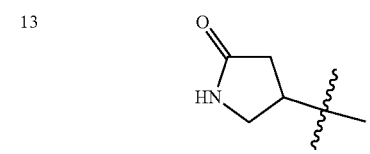 |
| 14 | 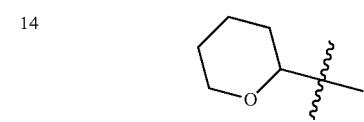 |
| 15 | 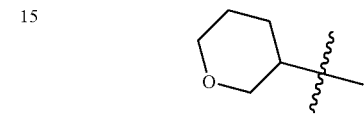 |
| 16 | 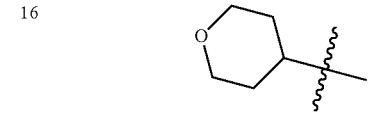 |
| 17 | 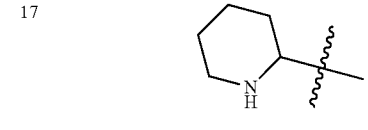 |
| 18 | 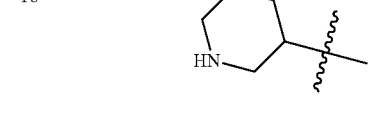 |
| 19 | 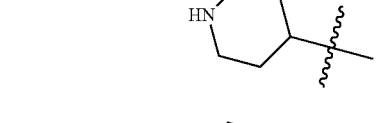 |
| 20 | 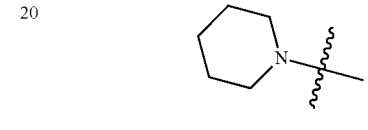 |
| 21 |  |
| 22 |  |

| Entry | A |
|---|---|
| 23 | 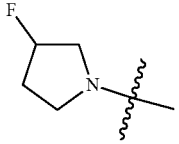 [SMILES: *N1CCC(F)C1] |
| 24 | 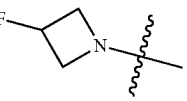 |
| 25 | 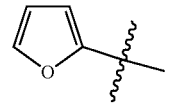 |
| 26 | 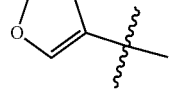 |
| 27 | 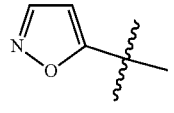 [SMILES: *c1ccno1] |
| 28 | 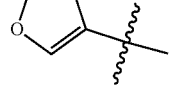 |
| 29 | 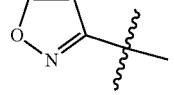 |
| 30 | 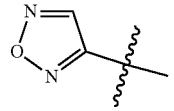 [SMILES: *c1cnon1] |
| 31 | 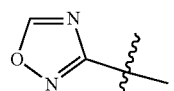 |
| 32 | 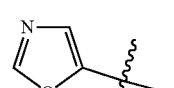 |
| 33 | 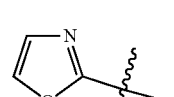 |
| 34 | 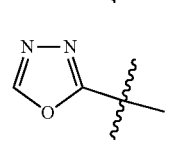 |
| Entry | A |
|---|---|
| 35 | 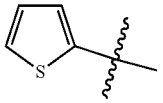 [SMILES: *c1cccs1] |
| 36 | 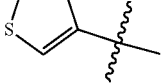 |
| 37 | 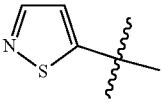 [SMILES: *c1ccns1] |
| 38 | 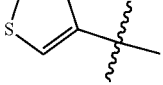 |
| 39 | 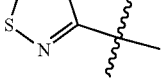 |
| 40 | 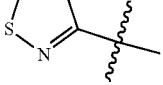 |
| 41 | 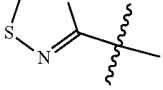 |
| 42 | 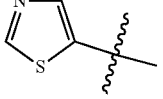 |
| 43 | 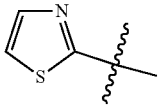 |
| 44 | 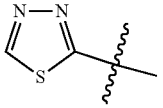 |
| 45 | 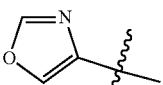 |
| 46 | 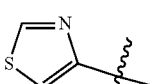 |
| 47 | 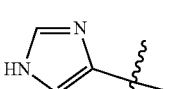 |

| Entry | A |
|---|---|
| 48 | 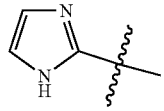 [SMILES: *c1ncc[nH]1] |
| 49 | 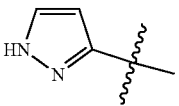 |
| 50 | 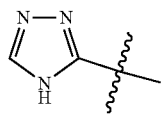 [SMILES: *c1nnc[nH]1] |
| 51 | 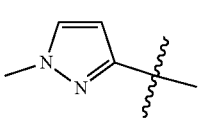 [SMILES: *c1ccn(C)n1] |
| 52 | 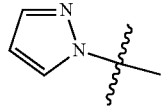 [SMILES: *n1cccn1] |
| 53 | 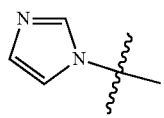 [SMILES: *n1ccnc1] |
| 54 | 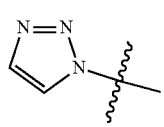 [SMILES: *n1ccnn1] |
| 55 | 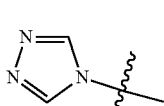 |
| 56 | 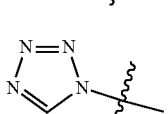 |
| 57 | 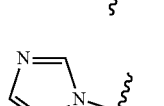 |
| 58 | 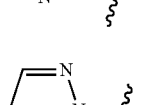 |
| 59 |  |
| 60 | 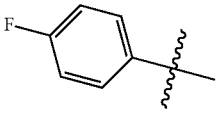 [SMILES: *c1ccc(F)cc1] |
| 61 | 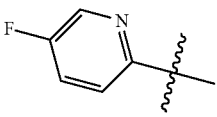 [SMILES: *c1ccc(F)cn1] |
| 62 | 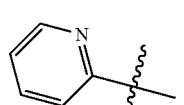 |
| 63 | 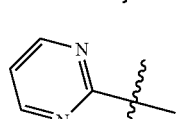 |
| 64 | 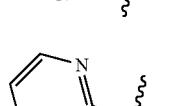 |
| 65 |  |
| 66 | 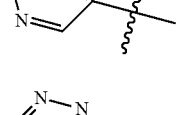 |
| 67 | 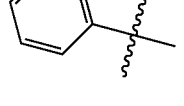 |
| 68 | 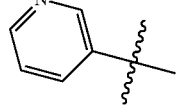 |
| 69 | 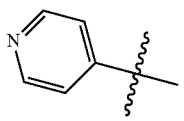 [SMILES: *c1ccncc1] |
| 70 | 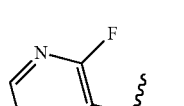 |

| Entry | A |
|---|---|
| 71 | 3-chlorophenyl |
| 72 | 4-(trifluoromethyl)phenyl |
| 73 | 6-(trifluoromethyl)pyridin-3-yl |
| 74 | pyridazin-4-yl |
| 75 | quinolin-3-yl |
| 76 | 2-methylisoindolin-5-yl |
| 77 | 1-methyl-1H-indazol-5-yl |
| 78 | benzofuran-5-yl |
| 79 | benzo[d]oxazol-5-yl |
| 80 | 2-oxoindolin-6-yl |
| 81 | 3,3-difluoroazetidin-1-yl |
| 82 | 3,3-difluoropyrrolidin-1-yl |

20. A pharmaceutical composition comprising a compound according to claim 13 and a pharmaceutically acceptable carrier or excipient.

21. A method of treating or preventing an HBV infection in a subject in need thereof, comprising administering to the subject a therapeutically effective amount of a compound or a combination of compounds according to claim 13.

* * * * *

UNITED STATES PATENT AND TRADEMARK OFFICE
CERTIFICATE OF CORRECTION

PATENT NO. : 11,058,678 B2  
APPLICATION NO. : 16/251386  
DATED : July 13, 2021  
INVENTOR(S) : Joseph Panarese et al.

Page 1 of 4

It is certified that error appears in the above-identified patent and that said Letters Patent is hereby corrected as shown below:

In the Claims

At Column 182

In Claim 3, Lines 27-65 delete " 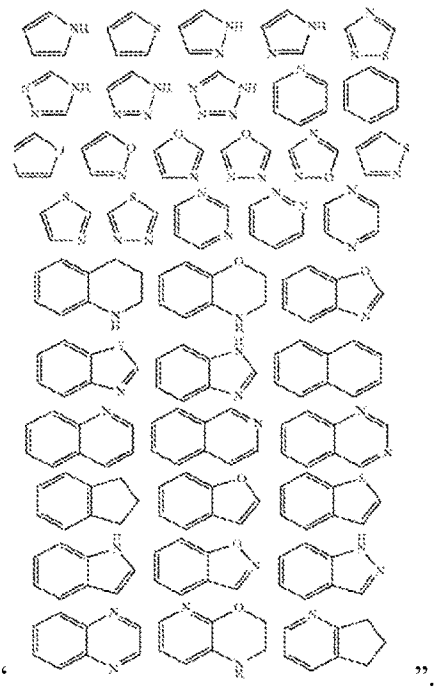 ".

Signed and Sealed this  
Twenty-seventh Day of December, 2022

Katherine Kelly Vidal  
*Director of the United States Patent and Trademark Office*

CERTIFICATE OF CORRECTION (continued)
U.S. Pat. No. 11,058,678 B2

At Column 183

In Claim 3, Lines 1-40 delete " 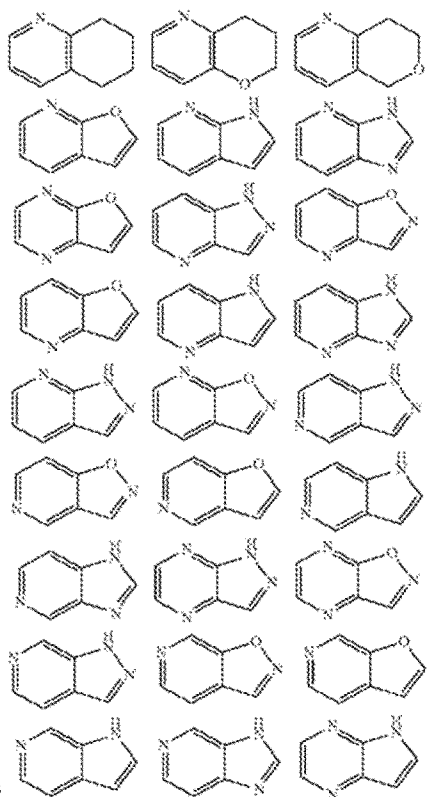 "; and

In Claim 3, Line 50 delete " 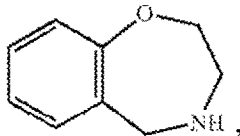 ".

At Columns 184

In Claim 3, Line 5 delete " 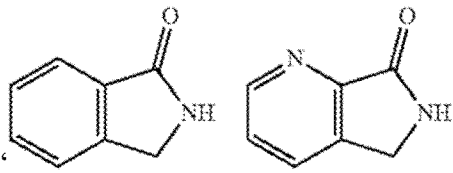 "; and

In Claim 3, Line 10-19 delete " 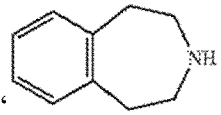

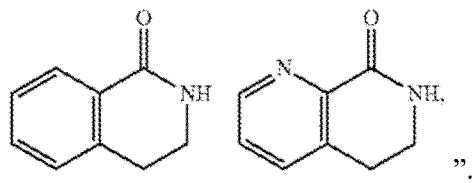 ".

At Column 185
In Claim 6, Line 66 delete "of claim 1,".

At Column 186
In Claim 7, delete "1" and insert -- 6 --.

At Columns 189 and 190
In Claim 8, delete Entries "25 through 39".

At Columns 191 and 192
In Claim 8, delete Entries "40 through 63".

At Columns 193 and 194
In Claim 8, delete Entries "64 through 80".

At Column 194
In Claim 9, Line 49 delete "The" and insert -- A --;
In Claim 9, Line 49 delete "of claim 1,"; and
In Claim 9, delete Compound Structure "1".

At Columns 195 and 196
In Claim 9, delete Compound Structures "2 through 13".

At Columns 197 and 198
In Claim 9, delete Compound Structures "14 through 23".

At Column 199
In Claim 9, delete Compound Structures "25 through 28".

At Column 200
In Claim 9, delete Compound Structures "31 through 36".

At Column 201
In Claim 9, delete Compound Structures "37 through 40", "43 through 46" and "47 through 48".

At Column 202
In Claim 9, delete Compound Structures "43 through 45" and "47 through 48".

At Column 203
In Claim 9, delete Compound Structures "49" and "51 through 53".

At Column 204
In Claim 9, delete Compound Structures "56 through 60".

At Column 205
In Claim 9, delete Compound Structures "61 through 63".

At Column 218
In Claim 9, delete Compound Structure "134".

At Column 231
In Claim 19, Line 14 delete "13" and insert -- 4 --.

At Column 238
In Claim 20, Line 37 delete "13" and insert -- 4 --; and
In Claim 21, Line 43 delete "13" and insert -- 4 --.